(12) United States Patent
Federov et al.

(10) Patent No.: US 8,580,757 B2
(45) Date of Patent: Nov. 12, 2013

(54) METHODS OF MODULATING MESENCHYMAL STEM CELL DIFFERENTIATION

(75) Inventors: Yuriy Federov, Cranberry Township, PA (US); Devin Leake, Denver, CO (US)

(73) Assignee: Thermo Fisher Scientific Biosciences Inc., Lafayette, CO (US)

( * ) Notice: Subject to any disclaimer, the term of this patent is extended or adjusted under 35 U.S.C. 154(b) by 11 days.

(21) Appl. No.: 12/672,881

(22) PCT Filed: Aug. 7, 2008

(86) PCT No.: PCT/US2008/072491
§ 371 (c)(1),
(2), (4) Date: May 12, 2011

(87) PCT Pub. No.: WO2009/023525
PCT Pub. Date: Feb. 19, 2009

(65) Prior Publication Data
US 2011/0263675 A1     Oct. 27, 2011

Related U.S. Application Data

(60) Provisional application No. 61/035,253, filed on Mar. 10, 2008, provisional application No. 61/034,926, filed on Mar. 7, 2008, provisional application No. 60/954,963, filed on Aug. 9, 2007.

(51) Int. Cl.
| | |
|---|---|
| *C12N 15/11* | (2006.01) |
| *C12N 5/00* | (2006.01) |
| *A61K 48/00* | (2006.01) |
| *C12Q 1/68* | (2006.01) |
| *C07H 21/04* | (2006.01) |

(52) U.S. Cl.
USPC ......... 514/44 A; 536/23.1; 536/24.5; 435/6.1; 435/375; 514/44 R

(58) Field of Classification Search
None
See application file for complete search history.

(56) References Cited

U.S. PATENT DOCUMENTS

| | | |
|---|---|---|
| 2004/0087016 A1 | 5/2004 | Keating et al. |
| 2005/0059005 A1* | 3/2005 | Tuschl et al. ............ 435/6 |
| 2006/0166910 A1* | 7/2006 | Tuschl et al. ............ 514/44 |
| 2007/0154563 A1 | 7/2007 | Behnam et al. |

OTHER PUBLICATIONS

Yamaguchi et al., Regulation of osteoblast differentiation mediated by bone morphogenetic proteins, hedgehogs, and Cbfa1, 2000, Endocrine Reviews, vol. 21, pp. 393-411.*
Canalis et al., Bone morphogenetic proteins, their antagonists, and the skeleton, 2003, Endocrine Reviews, vol. 24, pp. 218-235.*
Krek et al., Combinatorial microRNA target predictions, 2005, Nature Genetics, vol. 37, pp. 495-500.*
Stem-loop sequence hsa-mir-489, Accession No. MI0003124 provided by miRBase, accessed http://www.mirbase.org on May 25, 2012.*
Bentwich (2008) Current Topics in Microbiology and Immunology 320:257-69 "Identifying Human MicroRNAs".
Berezikov et al. (2010) Genome Research 16:1289-1298 "Many novel mammalian microRNAs candidates identified by extensive cloning and RAKE analysis".
Freidenstein and Kuralesova (1971) Transplantation 12(2):99-108 "Osteogenic Precursor Cells of Bone Marrow in Radiation Chimeras".
Jaiswal et al. (1997) J. of Cellular Biochemistry 64:295-312 "Osteogenic Differentiation of Purified, Culture-Expanded Human Mesenchymal Stem Cells In Vitro".
Lakshmipathy and Hart (2008) Stem Cells 26:356-63 "Concise Review: MicroRNA Expression in Multipotent Mesenchymal Stromal Cells".
Lim et al. (2005) Nature 433:769-73 "Microarray analysis shows that some microRNAs downregulate large numbers of target mRNAs".
Luzi, published online Oct. 8, 2007, Journal of Bone and Mineral Research, "Osteogenic Differentiation of Human Adipose Tissue-Derived Stem Cells is Modulated by the miR-26a Targeting the SMAD1 Transcription Factor", vol. 23, pp. 287-295.
Palmieri et al. (2007) Journal of Biomedical Science, DOI 10.1007/s11373-007-9193-z "Differences in osteoblast miRNA induced by cell binding domain of collagen and silicate-based synthetic bone".
Palmieri et al. (2008) Bio-Medical Materials and Engineering 18:91-97 "Medpor® regulates osteoblast's MicroRNAs".
Phinney and Prockop (2007) Stem Cells 25:2896-2902 "Concise Review: Mesenchymal Stem/Multipotent Stromal Cells: The State of Transdifferentiation and Modes of Tissue Repair—Current Views".
Tanabe et al. (2008) Stem Cells 144(3):399-408 "Gene Expression Profiling of Human Mesenchymal Stem Cells for Identification of Novel Markers in Early- and Late-Stage Cell Culture".
Chang-Zheng, Chen, et al., MicroRNAs Modulate Hematopoietic Lineage Differentiation, Science, 2, Jan. 2004, pp. 83-86, vol. 303.

* cited by examiner

*Primary Examiner* — Dana Shin
(74) *Attorney, Agent, or Firm* — Dorf & Nelson LLP; Scott D. Locke, Esq.

(57) ABSTRACT

The present disclosure includes compositions and methods for modulating the differentiation of cells having osteogenic differentiation potential (such as mesenchymal stem cells (MSCs)) towards the osteogenic fate, and for obtaining diagnostic and prognostic information relating to diseases and disorders characterized by defects in osteogenic differentiation. The compositions include miRNAs, rm'RNA mimics, miRNA inhibitors, and siRNAs.

1 Claim, 13 Drawing Sheets

SEQUENCE LISTING

```
<160> NUMBER OF SEQ ID NOS: 13

<210> SEQ ID NO 1
<211> LENGTH: 56
<212> TYPE: RNA
<213> ORGANISM: Artificial Sequence
<220> FEATURE:
<223> OTHER INFORMATION: synthetic
<220> FEATURE:
<221> NAME/KEY: modified_base
<222> LOCATION: (1)..(56)
<223> OTHER INFORMATION: bases are 2'-O-methyl modified
```

<400> SEQUENCE: 1
agcucucauc cauggaucua cucuuucuag gagguuguga ugguaccuac ucucga        56

<210> SEQ ID NO 2
<211> LENGTH: 55
<212> TYPE: RNA
<213> ORGANISM: Artificial sequence
<220> FEATURE:
<223> OTHER INFORMATION: synthetic
<220> FEATURE:
<221> NAME/KEY: modified_base
<222> LOCATION: (1)..(55)
<223> OTHER INFORMATION: bases are 2'-O-methyl modified

<400> SEQUENCE: 2
agcucugaaa agagcugcug ccguauaugu gaugucacuu cgagauucgu cucga         55

<210> SEQ ID NO 3
<211> LENGTH: 22
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: 5' phosphate

<400> SEQUENCE: 3
ucagugcauc acagaacuuu gu                                            22

<210> SEQ ID NO 4
<211> LENGTH: 21
<212> TYPE: RNA
<213> ORGANISM: Artificial sequence
<220> FEATURE:
<223> OTHER INFORMATION: synthetic
<220> FEATURE:
<221> NAME/KEY: modified_base
<222> LOCATION: (1)..(2)
<223> OTHER INFORMATION: bases are 2'-O-methyl modifed

<400> SEQUENCE: 4
ugccguauau gugaugucac u                                             21

<210> SEQ ID NO 5
<211> LENGTH: 56
<212> TYPE: RNA
<213> ORGANISM: Artificial sequence
<220> FEATURE:
<223> OTHER INFORMATION: synthetic
<220> FEATURE:
<221> NAME/KEY: modified_base
<222> LOCATION: (1)..(56)
<223> OTHER INFORMATION: bases are 2'-O-methyl modified

<400> SEQUENCE: 5
agcucucauc cauggagaca aaguucugug augcacugac uuguaccuac ucucga       56

<210> SEQ ID NO 6
<211> LENGTH: 22
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: 5' phosphate

```
<400> SEQUENCE: 6
ucagugcauc acagaacuuu gu                                              22

<210> SEQ ID NO 7
<211> LENGTH: 22
<212> TYPE: RNA
<213> ORGANISM: Artificial sequence
<220> FEATURE:
<223> OTHER INFORMATION: synthetic
<220> FEATURE:
<221> NAME/KEY: modified_base
<222> LOCATION: (1)..(2)
<223> OTHER INFORMATION: bases are 2'-O-methyl modified

<400> SEQUENCE: 7
aaaguucugu gaugcacuga uu                                              22

<210> SEQ ID NO 8
<211> LENGTH: 56
<212> TYPE: RNA
<213> ORGANISM: Artificial sequence
<220> FEATURE:
<223> OTHER INFORMATION: synthetic
<220> FEATURE:
<221> NAME/KEY: modified_base
<222> LOCATION: (1)..(56)
<223> OTHER INFORMATION: bases are 2'-O-methyl modified

<400> SEQUENCE: 8
agcucucauc caugggggc ggaacuuagc cacugugaac acguaccuac ucucga          56

<210> SEQ ID NO 9
<211> LENGTH: 21
<212> TYPE: RNA
<213> ORGANISM: Artificial sequence
<220> FEATURE:
<223> OTHER INFORMATION: synthetic
<220> FEATURE:
<221> NAME/KEY: modified_base
<222> LOCATION: (1)..(1)
<223> OTHER INFORMATION: 5' phosphate

<400> SEQUENCE: 9
uucacagugg cuaaguuccg c                                               21

<210> SEQ ID NO 10
<211> LENGTH: 21
<212> TYPE: RNA
<213> ORGANISM: Artificial sequence
<220> FEATURE:
<223> OTHER INFORMATION: synthetic
<220> FEATURE:
<221> NAME/KEY: modified_base
<222> LOCATION: (1)..(2)
<223> OTHER INFORMATION: bases are 2'-O-methyl modified

<400> SEQUENCE: 10
ggaacuuagc cacugugaau u                                               21

<210> SEQ ID NO 11
<211> LENGTH: 56
<212> TYPE: RNA
<213> ORGANISM: Artificial sequence
<220> FEATURE:
<223> OTHER INFORMATION: synthetic
<220> FEATURE:
<221> NAME/KEY: modified_base
<222> LOCATION: (1)..(56)
<223> OTHER INFORMATION: bases are 2'-O-methyl modified
```

```
<400> SEQUENCE: 11
agcucucauc cauggaucua cucuuucuag gagguuguga ugguaccuac ucucga        56

<210> SEQ ID NO 12
<211> LENGTH: 24
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(1)
<223> OTHER INFORMATION: 5' phosphate

<400> SEQUENCE: 12
ucacaaccuc cuagaaagag uaga                                          24

<210> SEQ ID NO 13
<211> LENGTH: 24
<212> TYPE: RNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: bases are 2'-O-methyl modified

<400> SEQUENCE: 13
uacucuuucu aggagguugu gauu                                          24
```

METHODS OF MODULATING MESENCHYMAL STEM CELL DIFFERENTIATION

RELATED APPLICATION INFORMATION

This application is a National Stage Application of PCT/US2008/072491, filed Aug. 7, 2008, and claims the benefit of priority to U.S. Provisional Patent Application Ser. No. 60/954,963, filed Aug. 9, 2007, and also claims the benefit of priority to U.S. Provisional Patent Application Ser. No. 61/034,926, filed Mar. 7, 2008, and also claims the benefit of priority to U.S. Provisional Patent Application Ser. No. 61/035,253, filed Mar. 10, 2008, each of which is entitled "Methods of modulating mesenchymal stem cell differentiation." The disclosures of each prior application are incorporated herein by reference in their entirety. To the extent appropriate, a claim of priority is made to each of the above disclosed applications.

FIELD OF THE DISCLOSURE

The present disclosure relates to the field of mesenchymal stem cell (MSC) differentiation. In particular, the disclosure provides a method of directing MSCs (and other cell type having osteogenic potential) toward osteogenic differentiation, or inhibiting MSCs (and other cell type having osteogenic potential) from osteogenic differentiation, using microRNA (miRNA) inhibitors, mimics, and siRNA.

BACKGROUND

Mesenchymal stem cells (MSCs) are capable of differentiating into a wide range of cell types including those associated with the bone development and maintenance (osteoblasts, osteocytes), cartilage, tendons, muscle, adipose, and more. The pluripotent nature of MSCs makes them a potentially valuable tool in therapeutics, particularly in the fields of disease (e.g. osteogenesis imperfecta), tissue repair and regeneration.

The molecular mechanisms underlying MSC differentiation are poorly understood. Microarray profiling studies have clearly identified genomic profiles that distinguish mother and daughter cell lineages, yet the triggers that orchestrate these processes have not been identified.

RNA interference (RNAi) is a near-ubiquitous pathway involved in post-transcriptional gene modulation. A key effector molecule of RNAi is the microRNA (miRNA or miR). These small, non-coding RNAs are transcribed as primary miRNAs (pri-miRNA) and processed in the nucleus by Drosha (a Type III ribonuclease) to generate short hairpin structures referred to as pre-miRNAs. The resulting molecules are transported to the cytoplasm and processed by a second nuclease (Dicer) before being incorporated into the RNA Induced Silencing Complex (RISC). Interaction between the mature miRNA-RISC complex and messenger RNA (mRNA), particularly between the seed region of the miRNA guide strand (nucleotides 2-7) and regions of the 3' UTR of the mRNA, leads to gene knockdown by transcript cleavage and/or translation attenuation.

SUMMARY

In one aspect, the disclosure provides a method of promoting mesenchymal stem cell (MSC) differentiation towards the osteogenic cell fate. The method comprises introducing into a MSC an effective amount of a composition comprising at least one differentiation promoting agent selected from the group consisting of inhibitors of miR-489, inhibitors of miR-27a, mimics of miR-148b, and siRNAs specific for genes from Tables 6-7.

In another aspect, the disclosure provides a method of inhibiting mesenchymal stem cell (MSC) differentiation towards the osteogenic cell fate. The method comprises introducing into a MSC an effective amount of a composition comprising at least one differentiation inhibitor selected from the group consisting of mimics of miR-489, mimics of miR-27a, siRNA specific for genes from Tables 2-5, and inhibitors of miR-148b.

In another aspect, the disclosure provides a pharmaceutical composition comprising at least one MSC differentiation promoting agent selected from the group consisting of inhibitors of miR-489, inhibitor of miR-27a, siRNAs specific for genes from Tables 6-7, mimics of miR-148b, and further comprising at least one pharmaceutically acceptable excipient.

In another aspect, the disclosure provides a pharmaceutical composition comprising at least one MSC differentiation inhibitor selected from the group consisting of mimics of miR-489, mimics of miR-27a, siRNAs specific for genes from Tables 2-5, and inhibitors of miR-148b, and further comprising at least one pharmaceutically acceptable excipient.

In another aspect, the disclosure discloses the use of at least one of an inhibitor of miR-489, an inhibitor of miR-27a, a mimic of miR-148b, or a siRNA specific for a gene from Tables 6-7 in the manufacture of a medicament for promoting mesenchymal stem cell (MSC) differentiation towards the osteogenic cell fate.

In another aspect, the disclosure discloses the use of at least one of a mimic of miR-489, a mimic of miR-27a, a siRNA specific for a gene from Tables 2-5, or an inhibitor of miR-148b in the manufacture of a medicament for inhibiting mesenchymal stem cell (MSC) differentiation toward the osteogenic cell fate.

In another aspect, the disclosure provides a method for treating an individual suffering from a disease characterized by a decreased degree of mesenchymal stem cell (MSC) differentiation relative to a normal individual. The method comprises administering to an individual in need thereof a pharmaceutically effective amount of a composition comprising at least one differentiation promoting agent selected from the group consisting of inhibitors of miR-489, inhibitors of miR-27a, mimics of miR-148b, and siRNAs specific for genes from Tables 6-7.

In another aspect, the disclosure provides a method for treating an individual suffering from a disease characterized by an increased degree of mesenchymal stem cell (MSC) differentiation relative to a normal individual. The method comprises administering to an individual in need thereof a pharmaceutically effective amount of a composition comprising at least one differentiation inhibitor selected from the group consisting of a mimic of miR-489, a mimic of miR-27a, a siRNA specific for a gene from Tables 2-5, and an inhibitor of miR-148b.

In another aspect, the disclosure provides a method for obtaining diagnostic or prognostic information relating to a disease characterized by an abnormal degree of mesenchymal stem cell (MSC) differentiation. The method comprises 1) determining the expression level of at least one miRNA selected from the group consisting of miR-148b, miR-489, and miR-27a in an individual suspected of having the disease; and 2) comparing the expression level of the at least one miRNA with that observed in a normal individual known to not have the disease, whereby diagnostic or prognostic information may be obtained.

In another aspect, the disclosure provides a method for obtaining diagnostic or prognostic information relating to a disease characterized by an abnormal degree of mesenchymal stem cell (MSC) differentiation. The method comprises 1) determining the expression level of at least one gene from Tables 2-7 in an individual suspected of having the disease; and 2) comparing the expression level of the at least gene with that observed in a normal individual known to not have the disease, whereby diagnostic or prognostic information may be obtained.

In another aspect, the disclosure provides an isolated mesenchymal stem cell (MSC) comprising at least one differentiation modulating agent selected from the group consisting of inhibitors of miR-489, inhibitors of miR-27a, mimics of miR-148b, siRNAs specific for genes from Tables 6-7, mimics of miR-489, mimics of miR-27a, siRNA specific for genes from Tables 2-5, and inhibitors of miR-148b.

In another aspect, the disclosure provides a method for performing a bone graft at a site in an individual in need thereof. The method comprises 1) introducing into a mesenchymal stem cell (MSC) ex vivo an effective amount of a composition comprising at least one differentiation promoting agent selected from the group consisting of inhibitors of miR-489, inhibitors of miR-27a, mimics of miR-148b, and siRNAs specific for genes from Tables 6-7; and 2) transplanting the MSC into the individual at the site.

In another aspect, the disclosure provides a method of promoting mesenchymal stem cell (MSC) differentiation towards the osteogenic cell fate. The method comprises at least partially inhibiting in a MSC the expression of a gene selected from the group consisting of ARSE, COL2A1, FBN1, GHRHR, HOXA2, HOXA5, LECT1, NOG, OSTF1, PAPSS2, TFIP11, and TRPS1 using RNA interference.

In another aspect, the disclosure provides a method of inhibiting mesenchymal stem cell (MSC) differentiation towards the osteogenic cell fate. The method comprises at least partially inhibiting in a MSC the expression of a gene selected from the group consisting of ADAMTS4, AHSG, ALPL, BMI1, CHRD, DLX5, HOXA13, MATN1, MINPP1, PEX7, PRKRA, THRA, AMELY, BMP7, CDH11, CHRD, CHRDL2, EN1, MAPK8, MGP, PAX1, POSTN, SPP1, SUFU, TRAPPC2, TWIST1, GCA, and SLC22A2 using RNA interference.

In another aspect, the disclosure provides a method for increasing osteogenesis in individual. The method comprises administering to an individual in need thereof a pharmaceutically effective amount of at least one mesenchymal stem cell (MSC) differentiation promoting agent selected from the group consisting of inhibitors of miR-489, inhibitors of miR-27a, mimics of miR-148b, and siRNAs specific for genes from Tables 6-7.

In another aspect, the disclosure provides a method of promoting differentiation towards the osteogenic cell fate of a cell having osteogenic potential. The method comprising introducing into the cell an effective amount of a composition comprising at least one differentiation promoting agent selected from the group consisting of inhibitors of miR-489, inhibitors of miR-27a, mimics of miR-148b, and siRNAs specific for genes from Tables 6-7.

In another aspect, the disclosure provides a method of inhibiting differentiation towards the osteogenic cell fate of a cell having osteogenic potential. The method comprises introducing into the cell an effective amount of a composition comprising at least one differentiation inhibitor selected from the group consisting of mimics of miR-489, mimics of miR-27a, siRNA specific for genes from Tables 2-5, and inhibitors of miR-148b.

In another aspect, the disclosure provides mimics and inhibitors of miR-148b, mimics and inhibitors of miR-489, mimics and inhibitors of miR-27a (including, but not limited to, the mimics and inhibitors of Table 1), and siRNAs specific for the genes of Tables 2-7.

Other aspects to the disclosure are provided below.

Approximately 400 human miRNA inhibitors targeting human miRNAs (derived from miRbase, at the http site //microrna/sanger.ac.uk.sequences) were transfected into human MSC cells in differentiation media to assess the importance of various miRNAs to MSC osteogenic differentiation. Cultures that exhibited two-fold greater or lesser levels of alkaline phosphatase expression in this primary screen were identified as playing a role in MSC differentiation. X-axis represents individual miRNA inhibitors tested. Y-axis represents the z-score for each inhibitor relative to controls. Studies were performed in triplicate.

FIGS. 2A-2G. Identification of miRNA Inhibitor and Mimic Pairs that Alter MSC Osteogenic Differentiation.

Figure 2A:
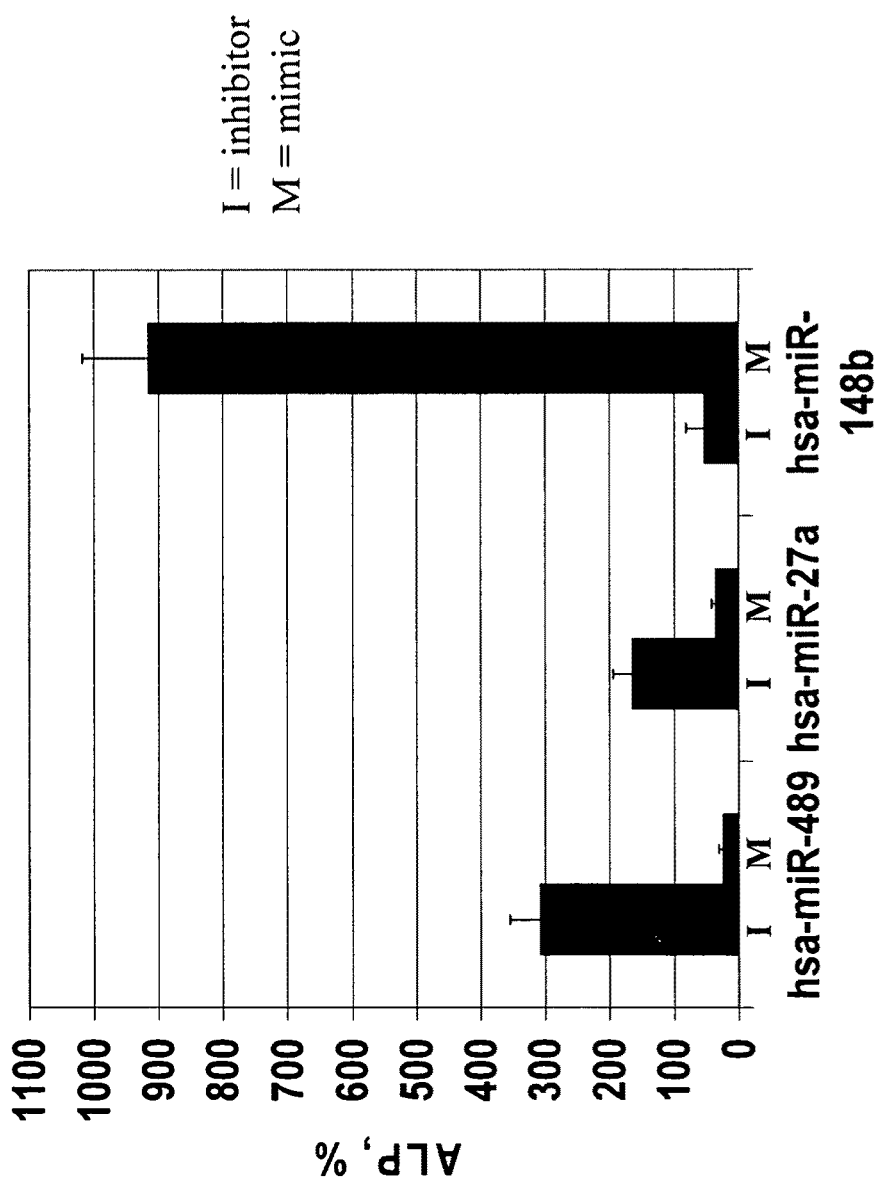
Figure 2B:
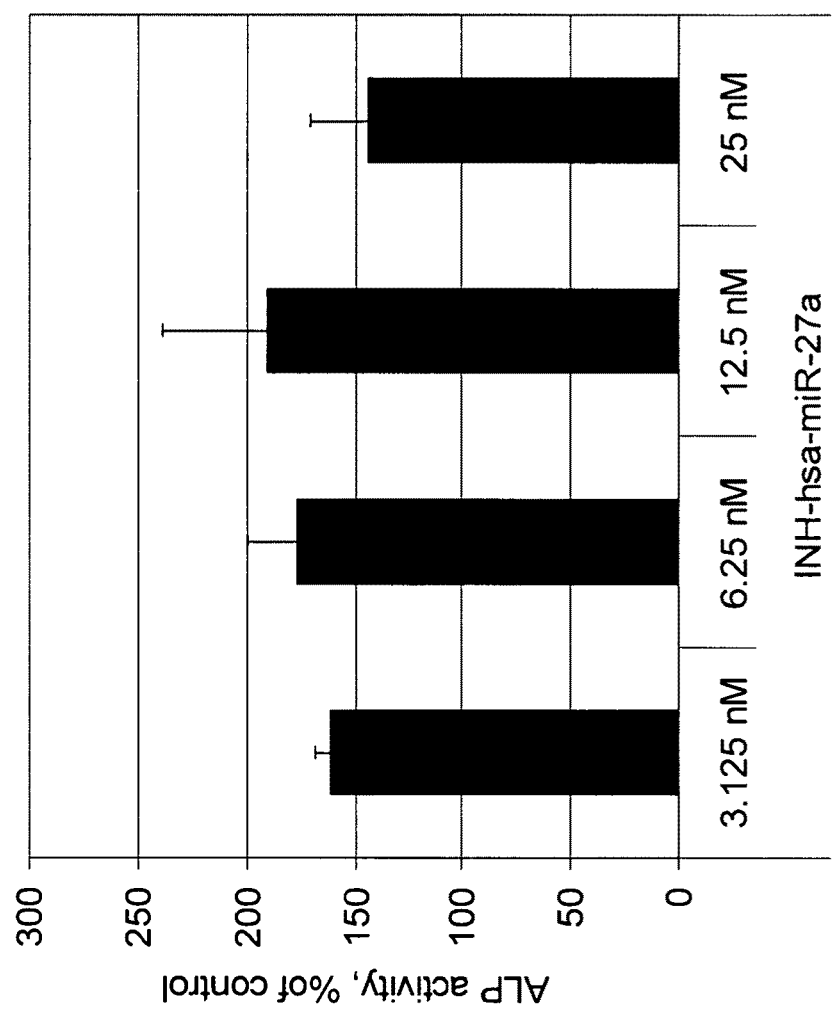
Figure 2C:
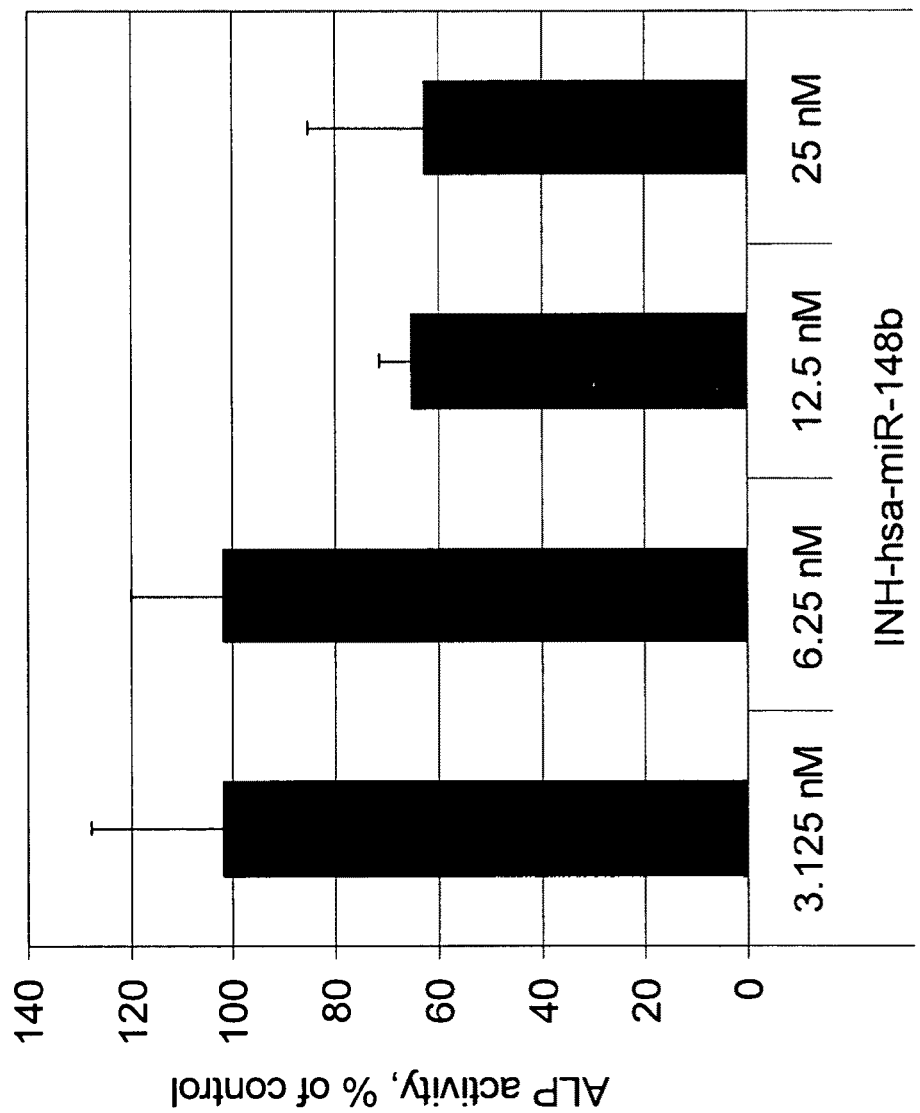
Figure 2D:
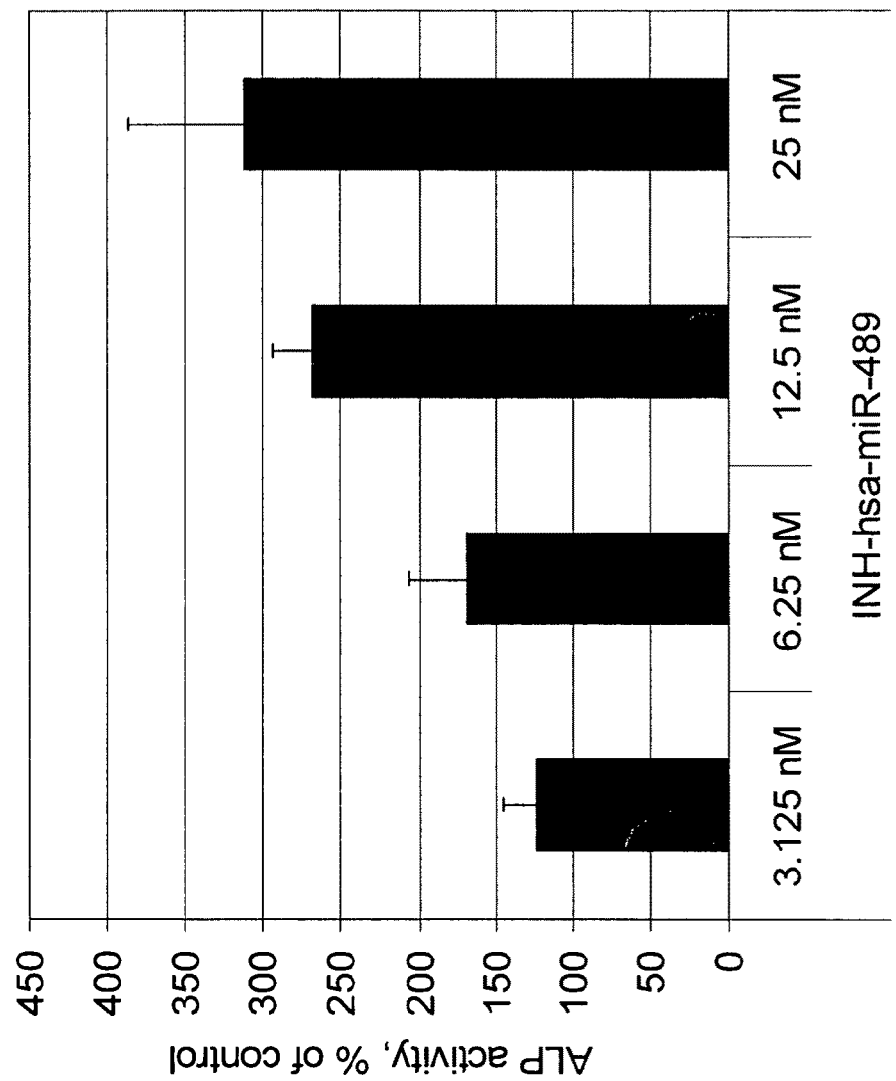
Figure 2E:
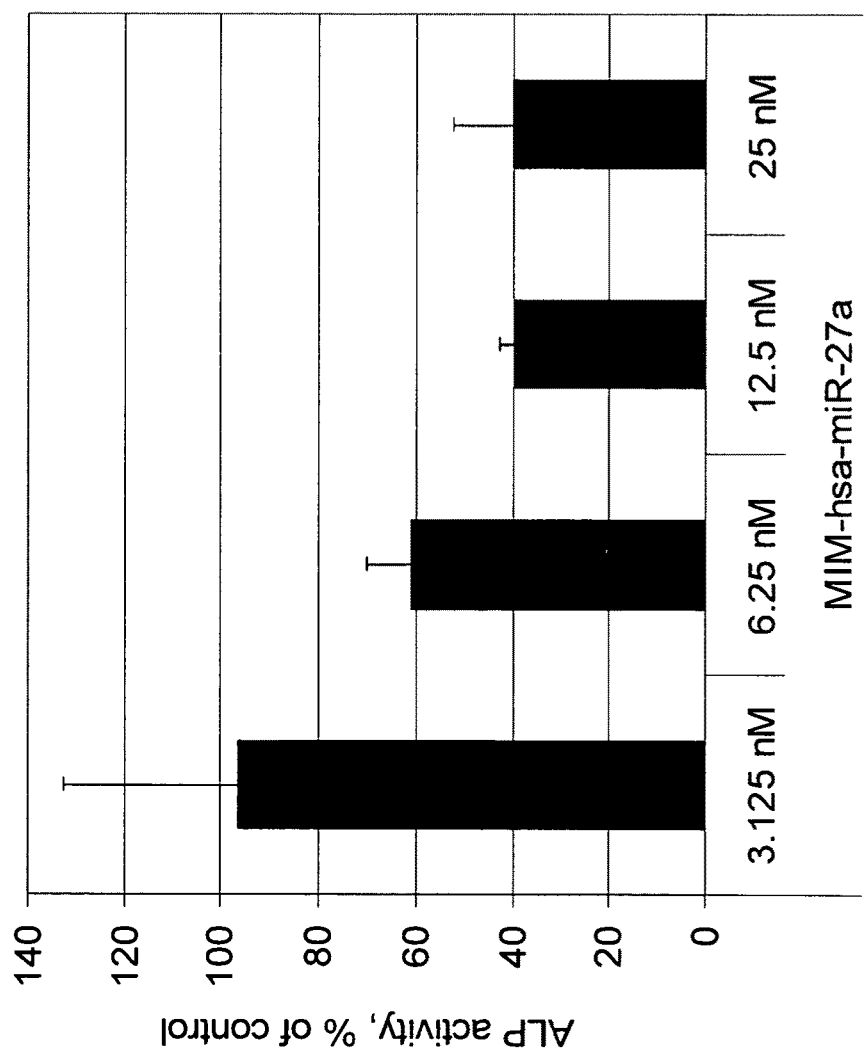
Figure 2F:
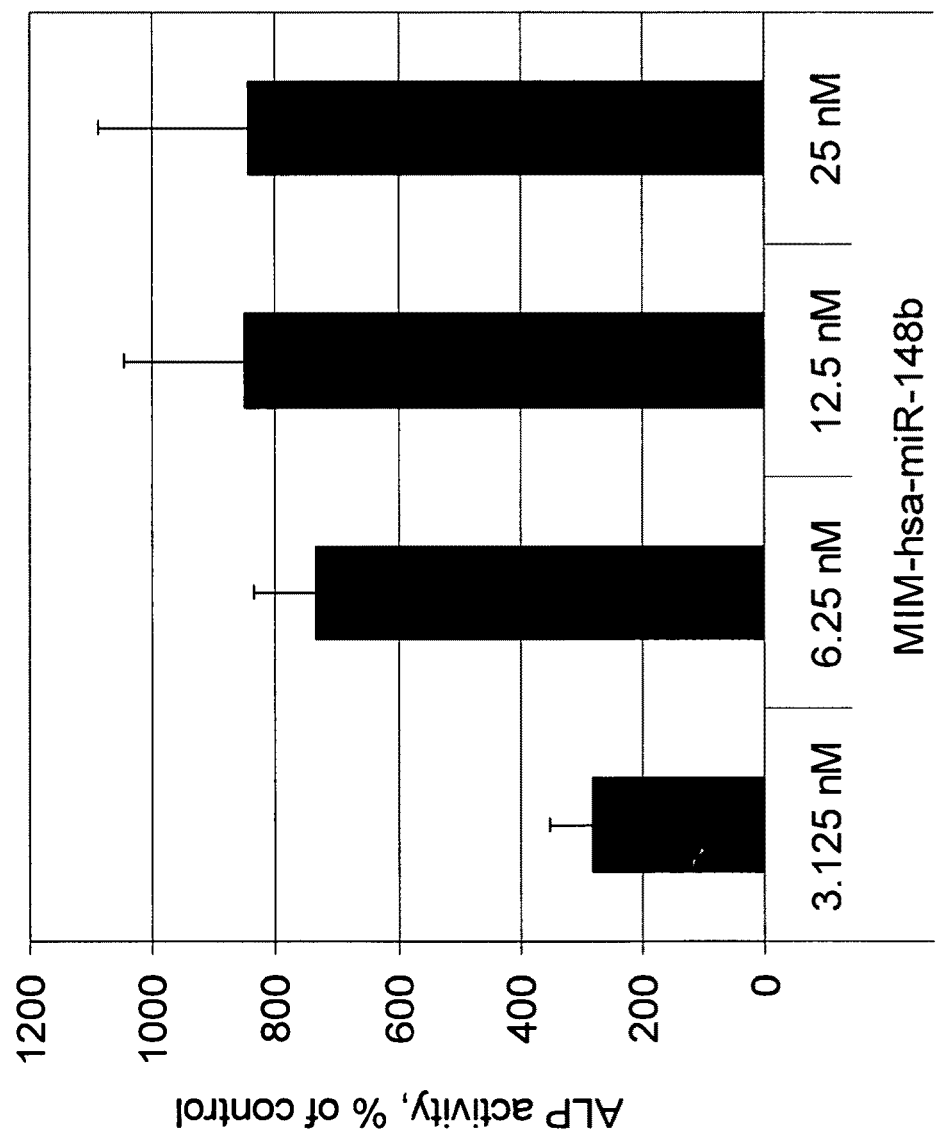
Figure 2G:
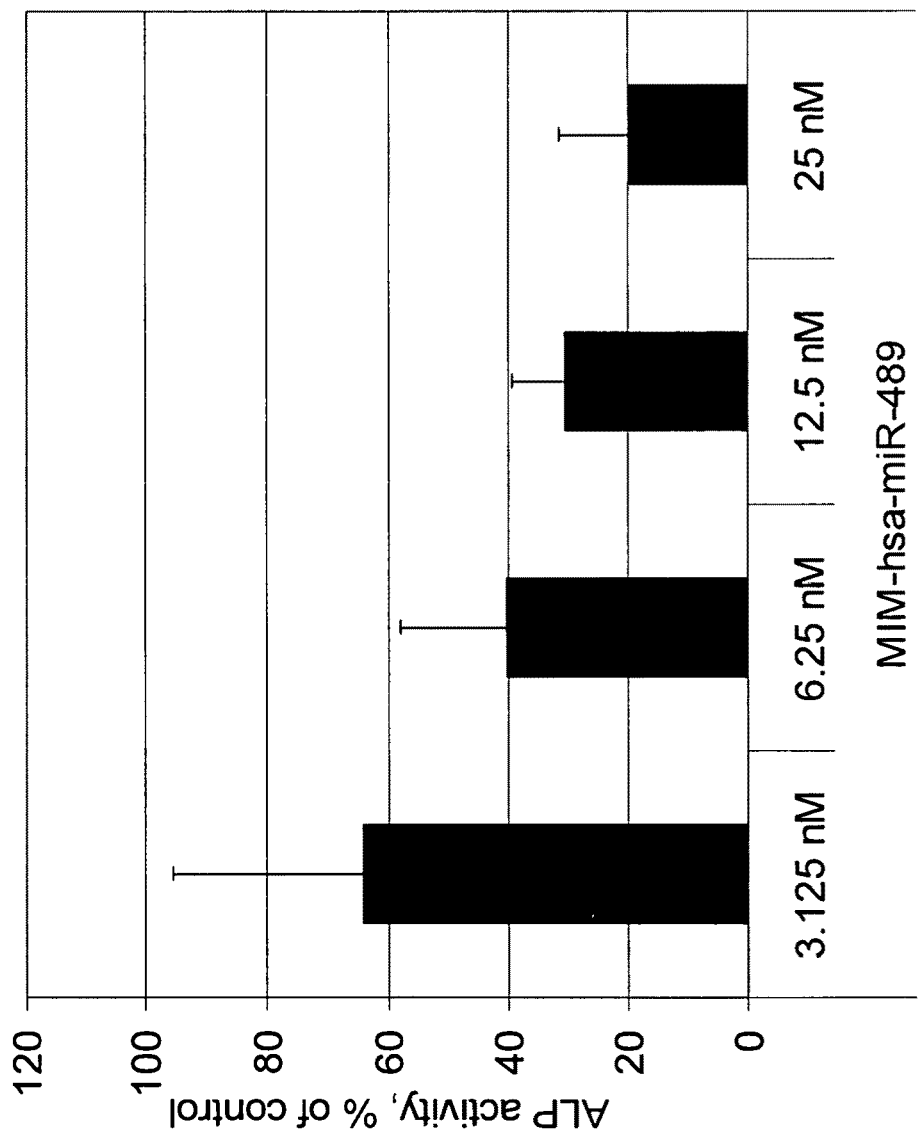

FIG. 2A provides a graph showing inhibitor (I) and mimic (M) pairs that induce opposite effects in the MSC osteogenic differentiation assay. Studies were performed in differentiation media. For hsa-miR-489 and hsa-miR-27a, inhibitors increase alkaline phosphatase (AP) expression and mimics decrease AP expression (Note: 100% represents the amount of activity observed in control experiments). In contrast, an inhibitor of hsa-miR148b decreases alkaline phosphatase expression while a mimic greatly enhances AP expression. FIG. 2B provides a graph showing that the effects of miRNA-27a inhibitors at different doses. FIG. 2C provides a graph showing the effects of miRNA-148b inhibitors at different doses. FIG. 2D provides a graph showing the effects of miRNA-489 inhibitors at different doses. FIG. 2E provides a graph showing the effects of miRNA-27a mimics at different doses. FIG. 2F provides a graph showing the effects of miRNA-148b mimics at different doses. FIG. 2G provides a graph showing the effects of miRNA-489 mimics at different doses. Inhibitors for miR148b and miR 489 exhibit a strong dose dependency. Mimics for miR-27a, miR-148b, and miR-489 all exhibit dose dependency. All experiments were performed in triplicate.

Figure 3A:
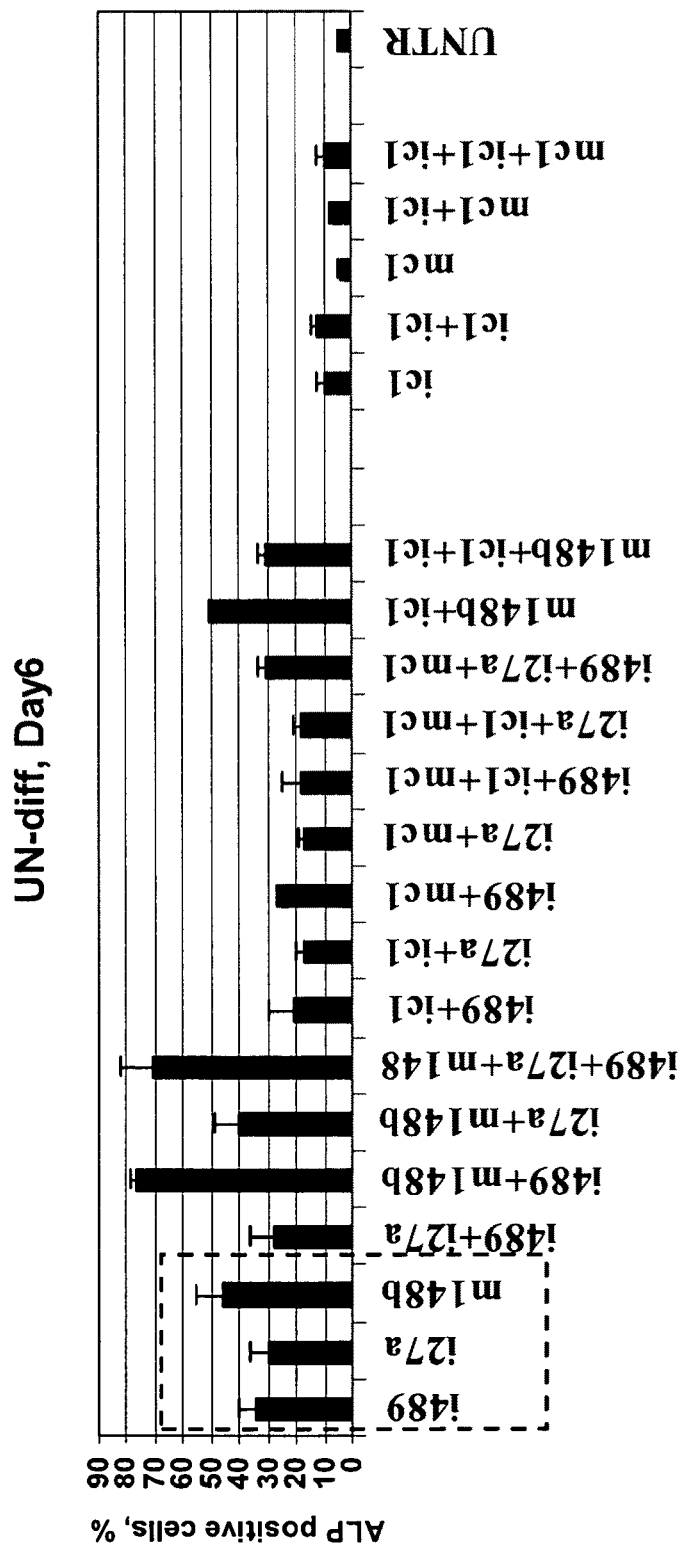
Figure 3B:
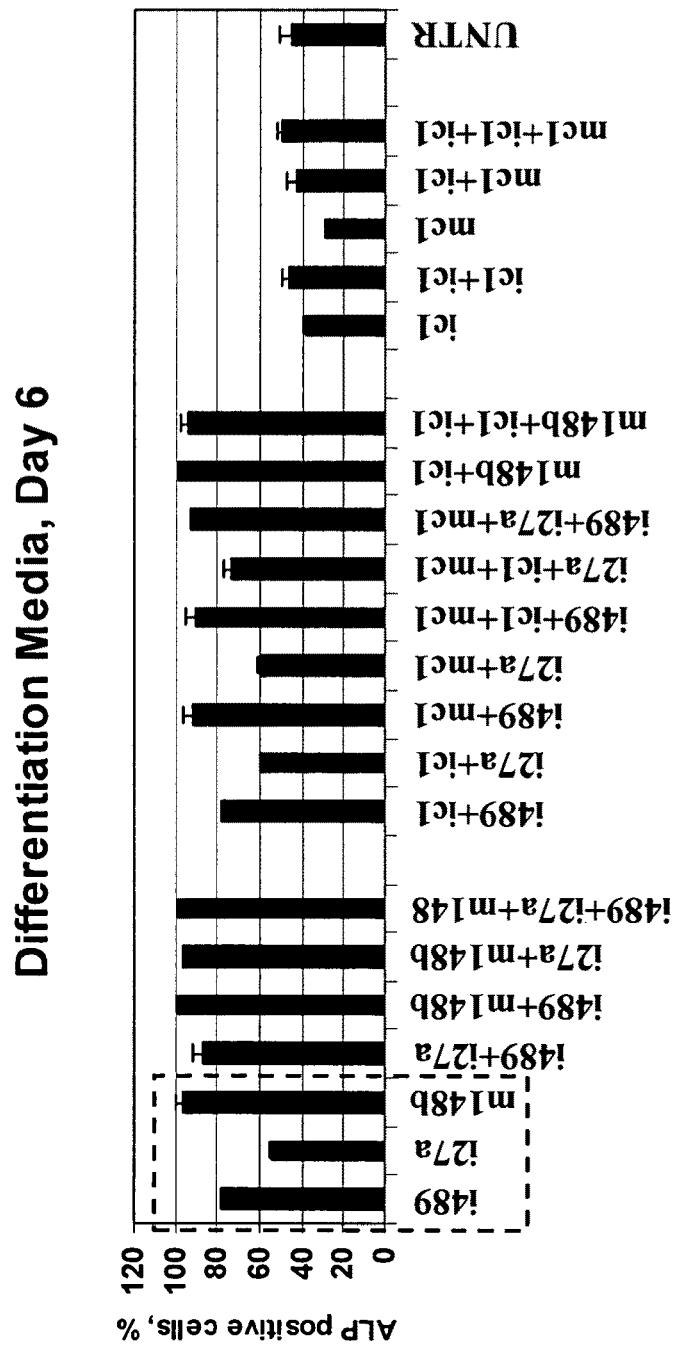

FIGS. 3A-3B. Induction of Osteocyte Differentiation from MSC can Take Place in Both Differentiation Media and Propagation Media.

FIGS. 3A-3B depict graphs that show the percentage of alkaline phosphatase positive cells (Y axes) obtained using various combinations of inhibitors and mimics in the presence of differentiation media and propagation media ("UN-Diff"). The boxed regions shows the ability of miR489 and miR27a inhibitors ("i489" and "i27" respectively), as well as miR148b mimics ("m148b") to induce osteogenic differentiation in propagation media (FIG. 3A) and differentiation media (FIG. 3B). See control inhibitors ("ic1") and control mimics ("mc1") for comparison. FIGS. 3A and 3B demonstrate the ability of these molecules to induce differentiation under both conditions. FIG. 3A also demonstrates the ability of various combinations of molecules to act additively to provide enhanced levels of osteogenic differentiation. Pairs of molecules including 1) i489+i27a, 2) i489+m148b, and 3) i27a+m148b (25 nM of each, 50 nM total), or a combination of all three molecules (i489+i27a+m148b, 25 nM each, 75 nM total) were compared with the effects of individual inhibitors or mimics (i489, i27a, or m148b, 25 nM). The results show that one combination of molecules (i489+m148b) induces greater number of cells to undergo osteogenic differentiation than either of the individual molecule treatments (i.e. i489 or m148b). In FIGS. 3A-3B, the letters "i", "m", and "c" symbolize "inhibitor", "mimic", and "control", respectively.

Figure 4:
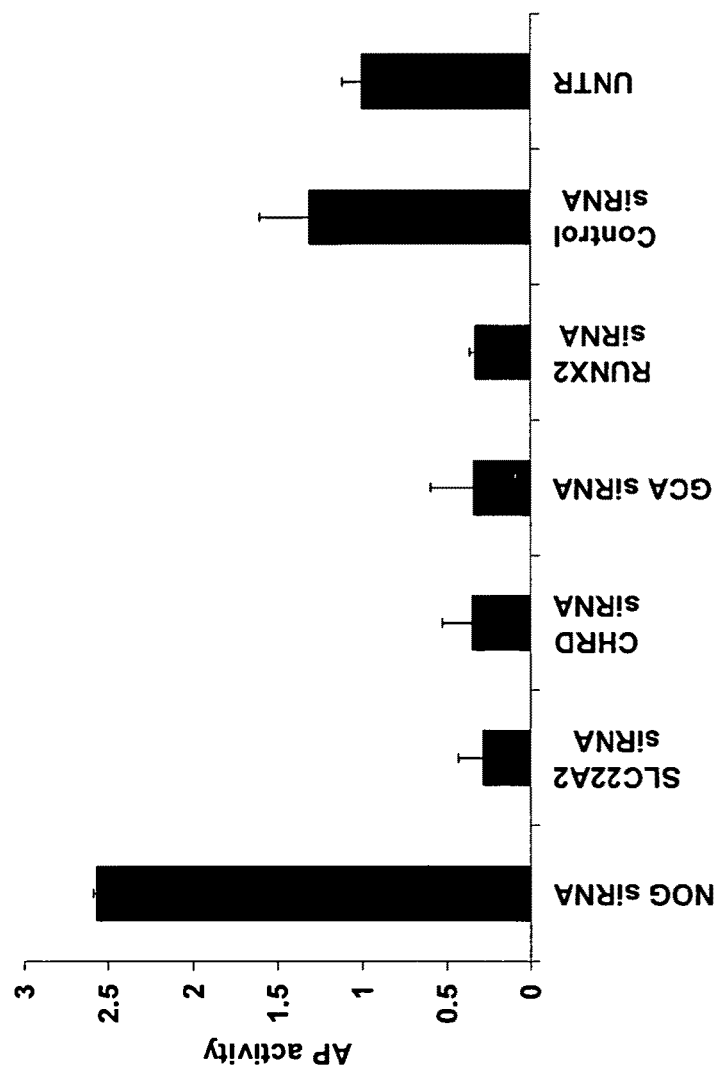

FIG. 4. siRNA-Mediated Knockdown of Genes Targeted By miR-27a, miR-489, and miR-148b.

FIG. 4 provides a graphical representation of the effects of siRNA mediated knockdown of genes targeted by miRNAs of the disclosure. siRNAs targeting CHRD, GCA and SLC22A2 (targets of miRNAs 27a and 489) leads to a decrease in MSC differentiation as measured by AP expression. In contrast, siRNA mediated knockdown of NOG leads to an increase in MSC differentiation as measured by AP expression. UNTR indicates untreated cells.

Figure 5A:
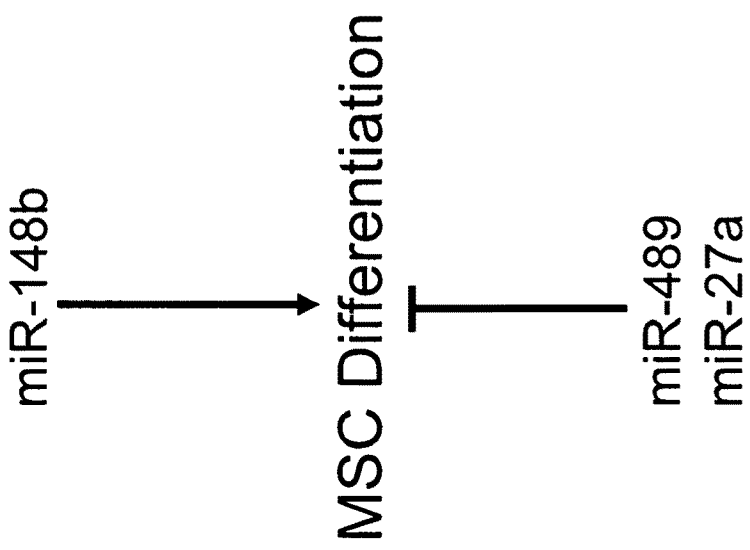
Figure 5B:
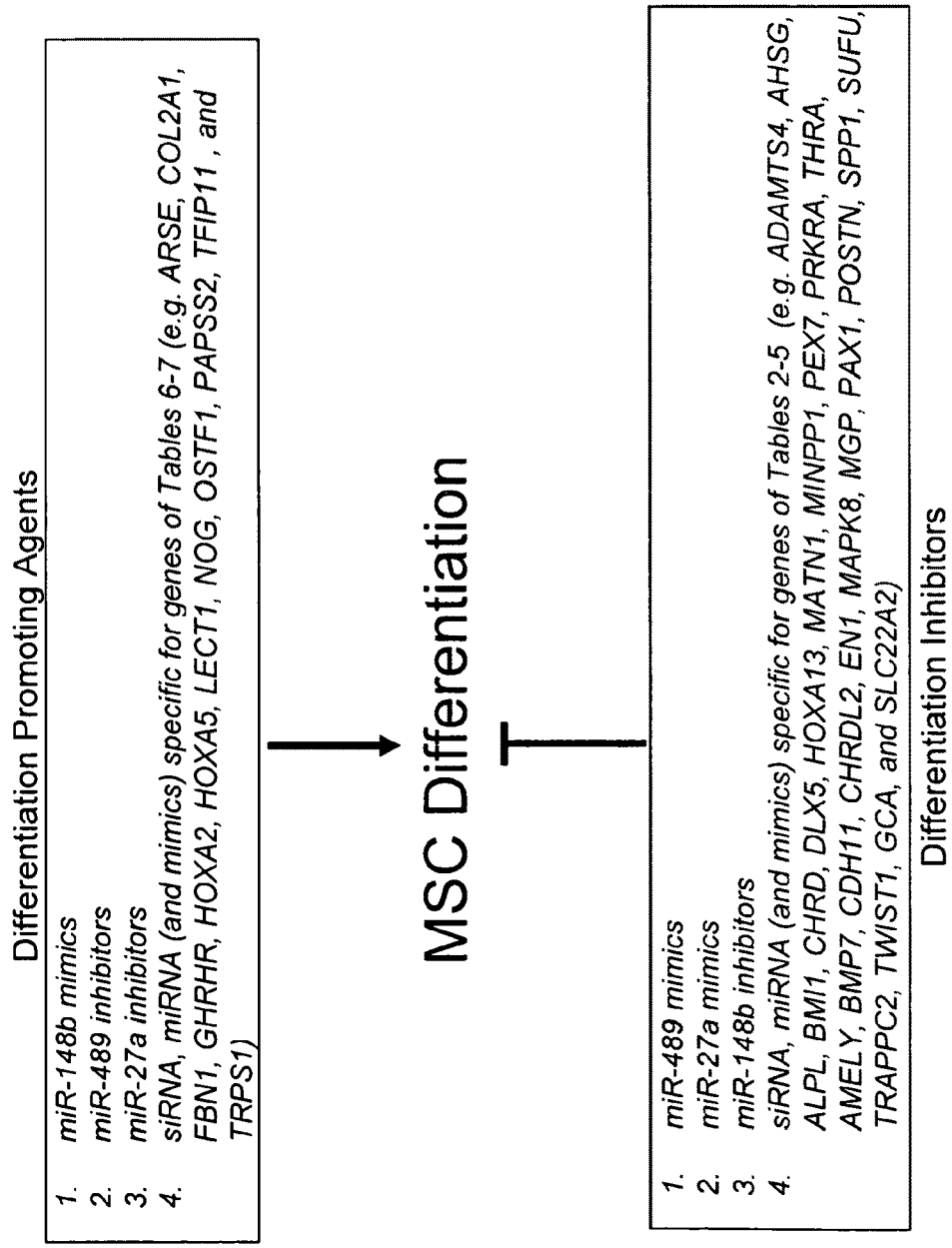

FIGS. 5A-5B. Summary of the Activity of miRs, miR Mimics, siRNAs, miRNA Inhibitors, and Genes in Modulating MSC Differentiation.

FIG. 5A depicts schematically the roles of the miRs identified by the disclosure (miR-148b, miR-489, miR-27a) in MSC differentiation. Specifically, MSC differentiation towards the osteogenic cell fate is promoted by miR-148b and is inhibited by miR-489 and miR-27a. FIG. 5B depicts schematically the MSC differentiation promoting or inhibiting activity of various agents identified in the disclosure. Specifically, MSC differentiation is promoted by miR-148b mimics, miR-489 inhibitors, miR-27a inhibitors, and by siRNAs and miRNAs (and other mediators of RNAi) specific for the genes of Tables 6-7. MSC differentiation is inhibited by miR-489 mimics, miR-27a mimics, miR-148b inhibitors, and by siRNAs and miRNAs (and other mediators of RNAi) specific for the genes of Tables 2-5.

DETAILED DESCRIPTION

All references referred to herein are specifically incorporated herein in their entirety.

DEFINITIONS

The terms "alkaline phosphatase," "ALP," or "AP" are interchangeable and refer to a hydrolase enzyme responsible for removing phosphate groups from many types of molecules. As the name suggests, alkaline phosphatases are most effective in an alkaline environment.

The term "differentiate" refers to the process cells undergo to become a more specialized cell type.

The term "gene silencing" refers to a process by which the expression of a specific gene product is lessened or attenuated by RNA interference. The level of gene silencing (also sometimes referred to as the degree of "knockdown") can be measured by a variety of means, including, but not limited to, measurement of transcript levels by Northern Blot Analysis, B-DNA techniques, transcription-sensitive reporter constructs, expression profiling (e.g. DNA chips), qRT-PCR and related technologies. Alternatively, the level of silencing can be measured by assessing the level of the protein encoded by a specific gene. This can be accomplished by performing a number of studies including Western Analysis, measuring the levels of expression of a reporter protein that has e.g. fluorescent properties (e.g., GFP) or enzymatic activity (e.g. alkaline phosphatases), or several other procedures.

The term "mesenchymal stem cell" or "MSC" refers to pluripotent stem cells that can be derived from a variety of species (e.g. human, mouse, rat) and that can differentiate into osteoblasts, chondrocytes, myocytes, adipocytes and more. Typical MSC molecular markers can vary considerably depending upon the tissue origin of the cells, but can include CD29 and CD105. MSCs can be derived from a number of tissues including, but not limited to, bone marrow, cartilage, tendon, muscle, and adipose tissues.

The term "microRNA", "miRNA", and "miR" are synonymous and refer to a collection of non-coding single-stranded RNA molecules of about 19-28 nucleotides in length, which regulate gene expression. miRNAs are found in a wide range of organisms (from viruses to humans) and have been shown to play a role in development, homeostasis, and disease etiology. MicroRNAs are processed from single stranded primary transcripts known as pri-miRNA to short stem-loop structures (hairpins) called pre-miRNA and finally to mature miRNA. One or both strands of the mature miRNA molecules are partially complementary to one or more messenger RNA (mRNA) molecules, and function to downregulate gene expression by either cleavage or translation attenuation mechanisms.

The term "mature strand" refers to the strand of a fully processed miRNA, or an siRNA that enters RISC. In some cases, miRNAs have a single mature strand that can vary in length between about 17-28 nucleotides in length. In other instances, miRNAs can have two mature strands (i.e. two unique strands that can enter RISC), and the length of the strands can vary between about 17 and 28 nucleotides. In the present disclosure, the terms "mature strand," "guide strand" and "antisense strand" are used interchangeably.

The term "miRNA seed" or "seed" refers to a region of the mature strand(s) of a microRNA or microRNA mimic. The region generally includes nucleotides 2-6 or 2-7 counting from the 5' end of the mature strand.

The term "miRNA seed complement" or "seed complement" refers to a sequence of nucleotides in a target gene, preferably in the 3' UTR of a target gene, that is complementary to some or all of the miRNA seed.

The term "nucleotide" refers to a ribonucleotide or a deoxyribonucleotide or modified form thereof, as well as an analog thereof. Nucleotides include species that comprise purines, e.g., adenine, hypoxanthine, guanine, and their derivatives and analogs, as well as pyrimidines, e.g., cytosine, uracil, thymine, and their derivatives and analogs. Nucleotide analogs include nucleotides having modifications in the chemical structure of the base, sugar and/or phosphate, including, but not limited to, 5-position pyrimidine modifications, 8-position purine modifications, modifications at cytosine exocyclic amines, and substitution of 5-bromouracil; and 2'-position sugar modifications, including but not limited to, sugar-modified ribonucleotides in which the 2'-OH is replaced by a group such as an H, OR, R, halo, SH, SR, $NH_2$, NHR, $NR_2$, or CN, wherein R is an alkyl moiety. Nucleotide analogs are also meant to include nucleotides with bases such as inosine, queuosine, xanthine, sugars such as 2'-methyl ribose, non-natural phosphodiester linkages such as in ethylphosphonates, phosphorothioates and peptides.

Modified bases refer to nucleotide bases such as, for example, adenine, guanine, cytosine, thymine, uracil, xanthine, inosine, and queuosine that have been modified by the replacement or addition of one or more atoms or groups. Some examples of types of modifications that can comprise nucleotides that are modified with respect to the base moieties include but are not limited to, alkylated, halogenated, thiolated, aminated, amidated, or acetylated bases, individually or in combination. More specific examples include, for example, 5-propynyluridine, 5-propynylcytidine, 6-methyladenine, 6-methylguanine, N,N,-dimethyladenine, 2-propyladenine, 2-propylguanine, 2-aminoadenine, 1-methylinosine, 3-methyluridine, 5-methylcytidine, 5-methyluridine and other nucleotides having a modification at the 5 position, 5-(2-amino)propyl uridine, 5-halocytidine, 5-halouridine, 4-acetylcytidine, 1-methyladenosine, 2-methyladenosine, 3-methylcytidine, 6-methyluridine, 2-methylguanosine, 7-methylguanosine, 2,2-dimethylguanosine, 5-methylaminoethyluridine, 5-methyloxyuridine, deazanucleotides such as 7-deaza-adenosine, 6-azouridine, 6-azocytidine, 6-azothymidine, 5-methyl-2-thiouridine, other thio bases such as 2-thiouridine and 4-thiouridine and 2-thiocytidine, dihydrouridine, pseudouridine, queuosine, archaeosine, naphthyl and substituted naphthyl groups, any O- and N-alkylated purines and pyrimidines such as N6-methyladenosine, 5-methylcarbonylmethyluridine, uridine 5-oxyacetic acid, pyridine-4-one, pyridine-2-one, phenyl and modified phenyl groups such as aminophenol or 2,4,6-trimethoxy benzene, modified cytosines that act as G-clamp nucleotides, 8-substituted adenines and guanines, 5-substituted uracils and thymines, azapyrimidines, carboxyhydroxyalkyl nucleotides, carboxyalkylaminoainleotides, and alkylcarbonylalkylated nucleotides. Modified nucleotides also include those nucleotides that are modified with respect to the sugar moiety, as well as nucleotides having sugars or analogs thereof that are not ribosyl. For example, the sugar moieties may be, or be based on, mannoses, arabinoses, glucopyranoses, galactopyranoses, 4'-thioribose, and other sugars, heterocycles, or carbocycles.

The term nucleotide is also meant to include what are known in the art as universal bases. By way of example, universal bases include, but are not limited to, 3-nitropyrrole, 5-nitroindole, or nebularine. The term "nucleotide" is also meant to include the N3' to P5' phosphoramidate, resulting from the substitution of a ribosyl 3'-oxygen with an amine group. Further, the term nucleotide also includes those species that have a detectable label, such as for example a radioactive or fluorescent moiety, or mass label attached to the nucleotide.

As used herein, the term "osteogenic differentiation" refers to processes by which cells become progressively more specialized and adopt attributes typically associated with cells of an osteoblast/osteocyte cell lineage. Typically, this process of specialization for the cell comes at the expense of its breadth of differentiation potential and can be monitored by following the expression of a number of molecular markers including, but not limited to, alkaline phosphatase.

The term "osteoblast" and "osteocyte" refers to abundant cell types found in bone.

The term "pluripotent" refers to a cell's ability to differentiate into multiple cell types.

The term "polynucleotide" refers to polymers of two or more nucleotides, and includes, but is not limited to, DNA, RNA, DNA/RNA hybrids including polynucleotide chains of regularly and/or irregularly alternating deoxyribosyl moieties and ribosyl moieties (i.e., wherein alternate nucleotide units have an —OH, then and —H, then an —OH, then an —H, and so on at the 2' position of a sugar moiety), and modifications of these kinds of polynucleotides, wherein the attachment of various entities or moieties to the nucleotide units at any position are included.

The term "ribonucleotide" and the term "ribonucleic acid" (RNA), refer to a modified or unmodified nucleotide or polynucleotide comprising at least one ribonucleotide unit. A ribonucleotide unit comprises an hydroxyl group attached to the 2' position of a ribosyl moiety that has a nitrogenous base attached in N-glycosidic linkage at the 1' position of a ribosyl moiety, and a moiety that either allows for linkage to another nucleotide or precludes linkage.

The term "RNA interference" and the term "RNAi" are synonymous and refer to the process by which a polynucleotide (a miRNA or siRNA) comprising at least one polyribonucleotide unit exerts an effect on a biological process. The process includes, but is not limited to, gene silencing by degrading mRNA, attenuating translation, interactions with tRNA, rRNA, hnRNA, cDNA and genomic DNA, as well as methylation of DNA with ancillary proteins.

The term "siRNA" and the phrase "short interfering RNA" refer to unimolecular nucleic acids and to nucleic acids comprised of two separate strands that are capable of performing RNAi and that have a duplex region that is between 14 and 30 base pairs in length. Additionally, the term siRNA and the phrase "short interfering RNA" include nucleic acids that also contain moieties other than ribonucleotide moieties, including, but not limited to, modified nucleotides, modified internucleotide linkages, non-nucleotides, deoxynucleotides and analogs of the aforementioned nucleotides.

siRNAs can be duplexes, and can also comprise short hairpin RNAs, RNAs with loops as long as, for example, 4 to 23 or more nucleotides, RNAs with stem loop bulges, microRNAs, and short temporal RNAs. RNAs having loops or hairpin loops can include structures where the loops are connected to the stem by linkers such as flexible linkers. Flexible linkers can be comprised of a wide variety of chemical structures, as long as they are of sufficient length and materials to enable effective intramolecular hybridization of the stem elements. Typically, the length to be spanned is at least about 10-24 atoms. When the siRNAs are hairpins, the sense strand and antisense strand are part of one longer molecule.

Detailed descriptions of the criteria for the rational design of siRNA antisense strands for efficient gene silencing can be found in WO 2004/045543, WO 2006/006948, WO 2005/078095, WO 2005/097992, and WO 2005/090606, each of which is incorporated herein by reference in its entirety.

siRNAs can target any sequence including protein encoding sequences (e.g., open reading frames, ORFs), and non-coding sequences (e.g., 3' UTRs, 5' UTRs, intronic regions, promoter regions, microRNAs, piRNAs, enhancer regions, repetitive sequences, and more). In contrast, microRNA and piRNA mimics of the disclosure generally target a subset of genes and tools for predicting miRNA targets can be found in any number of publications including but not limited to Griffith-Jones, S. et al., Nucleic Acids Research, 2007.

The term "piRNAs" refers to Piwi-interacting RNAs, a class of small RNAs that are believed to be involved in transcriptional silencing (see Lau, N. C. et al (2006) Science, 313:305-306).

The term "z score" refers to a statistical measurement that quantifies the distance (measured in standard deviations) a data point is from the mean of a data set. A z score is a dimensionless quantity derived by subtracting the sample mean from an individual (raw) score and then dividing the difference by the sample standard deviation.

The inventors have identified several microRNAs that participate in determining whether or not MSCs differentiate toward cells of an osteogenic cell fate. In addition, it has been discovered by the inventors that inhibitors and mimics of these microRNAs can be used (singularly or in combination) to induce or inhibit MSC osteogenic differentiation or to prevent MSC differentiation into other cell identities (e.g. adipocytes). In addition, the target genes of those microRNAs have been identified by the inventors (see Tables 2-7), and the inventors have further demonstrated that siRNA-mediated knockdown of those target genes can induce or inhibit MSC osteogenic differentiation in the manner predicted by the microRNA results. Thus, modulation of the expression of those target genes by any method known in the art (e.g., siRNA, piRNA, antisense, antibodies, and aptamers against the proteins produced by the target genes etc), or by using the miRNAs, miRNA mimics, and inhibitors of the disclosure can be used to modulate MSC differentiation, including in a therapeutic or prophylactic context. Moreover, measuring the expression level of the target genes of Tables 2-7 and/or the miRNAs identified herein can yield diagnostic or prognostic medical information relating to diseases or disorders characterized by abnormal degrees of MSC differentiation.

The sequences of currently known human, mouse, and rat miRNAs are available at miRBase which is maintained by the Wellcome Trust Sanger Institute see the http site //microrna.sanger.ac.uk/sequences/. As such, a person of ordinary skill in the art can select a sequence from the database for a desired miRNA and design a mimic useful for the methods disclosed herein.

The miRNAs of the disclosure can be identified as single stranded pri-miRNA or pre-miRNA hairpin structures (wherein a hairpin is defined as an oligonucleotide that is 40-150 nucleotides in length and contains secondary structures that result in regions of duplex and loops) or characterized as mature double stranded miRNAs. The miRNAs are capable of entering the RNAi pathway, being processed by gene products associated with the pathway (e.g., Drosha, Dicer, and the RNA interference Silencing Complex, RISC), and inhibiting gene expression by translation attenuation or message (mRNA) cleavage. As such, all of the miRNAs of the invention can be described by multiple labels depicting the level of processing.

With respect to the sequence of pri-, pre-, and mature miRNA sequences, it is worth noting that the field of RNAi and thus the sequences and structures associated with human, mouse and rat miRNAs varies slightly as versions of the miRNA database evolve. Though these newer versions of e.g. miRbase can have sequences that are extended and/or truncated on either the 5' or 3' end of the mature and passenger sequences, the changes do not alter the overall identity of the miRNA nor the ability to utilize these sequences in the context of the described embodiments.

In a first aspect, the present disclosure provides a method of modulating (e.g. inducing/promoting or inhibiting) mesenchymal stem cell osteogenic differentiation by using microRNA inhibitors and/or mimics. The methods of the disclosure may be performed ex vivo or in vivo.

MCS cells can be obtained commercially (e.g. Lonza, Inc) and cultured in vitro using medium (also referred to as a "pro-osteogenic cocktails" or "differentiation media") that sensitize cells to differentiate. Such media often comprise standard constituents plus dexamethasone, ascorbic acid-2-phosphate, beta-glycerophosphate, or other factors that enhance MSC differentiation. Alternatively, MSCs can be cultured on one or more media that do not sensitize cells toward osteogenic differentiation. Relevant references that pertain to characterization and differentiation of MSCs include: Baksh, D et al. (2004) *J. Cell. Mol. Med.* 8(3): 301-316; Aggarwal, S. et al. (2005) *Blood* 105: 1815-22; Akino, K. et al. (2006) *Wound Repair Regen.* 14:343-9; Jian, H. et al. (2006) *Genes Dev.* 20:666-74, each of which is incorporated herein by reference in its entirety.

The terms "microRNA inhibitor", "miR inhibitor", or "inhibitor" are synonymous and refer to oligonucleotides or modified oligonucleotides that interfere with the ability of specific miRNAs, or siRNAs to silence their intended targets. In general, the inhibitors are nucleic acid or modified nucleic acids in nature including oligonucleotides comprising RNA, modified RNA, DNA, modified DNA, locked nucleic acids (LNAs), or any combination of the above. Modifications include 2' modifications (including 2'-O alkyl modifications and 2' F modifications) and internucleotide modifications (e.g. phosphorothioate modifications) that can affect delivery, stability, specificity, intracellular compartmentalization, or potency. In addition, miRNA inhibitors can comprise conjugates that can affect delivery, intracellular compartmentalization, stability, and/or potency.

Inhibitors can adopt a variety of configurations including single stranded, double stranded (RNA/RNA or RNA/DNA duplexes), and hairpin designs. In general, microRNA inhibitors comprise contain one or more sequences or portions of sequences that are complementary or partially complementary with the mature strand (or strands) of the miRNA to be targeted. In addition, the miRNA inhibitor may also comprise additional sequences located 5' and 3' to the sequence that is the reverse complement of the mature miRNA. The additional sequences may be the reverse complements of the sequences that are adjacent to the mature miRNA in the pri-miRNA from which the mature miRNA is derived, or the additional sequences may be arbitrary sequences (having a mixture of A, G, C, or U). In some embodiments, one or both of the additional sequences are arbitrary sequences capable of forming hairpins. Thus, in some embodiments, the sequence that is the reverse complement of the miRNA is flanked on the 5' side and on the 3' side by hairpin structures. Micro-RNA inhibitors, when double stranded, may include mismatches between nucleotides on opposite strands. Furthermore, micro-RNA inhibitors may be linked to conjugate moieties in order to facilitate uptake of the inhibitor into a cell. For example, a micro-RNA inhibitor may be linked to cholesteryl 5-(bis(4-methoxyphenyl)(phenyl)methoxy)-3 hydroxypentylcarbamate) which allows passive uptake of a micro-RNA inhibitor into a cell. Micro-RNA inhibitors, including hairpin miRNA inhibitors, are described in detail in Vermeulen et al., "Double-Stranded Regions Are Essential Design Components Of Potent Inhibitors of RISC Function," RNA 13: 723-730 (2007) and in WO2007/095387 and WO 2008/036825 each of which is incorporated herein by reference in its entirety. A person of ordinary skill in the art can select a sequence from the database for a desired miRNA and design an inhibitor useful for the methods disclosed herein. The sequences of known human, mouse, and rat miRNAs discovered by wet-lab experimentation or bioinformatic methods are available at miRBase which is maintained by the Wellcome Trust Sanger Institute (http://microma.sanger.ac.uk/sequences/).

The miRNA inhibitors used in the Examples of this disclosure consisted of single stranded, 54 nucleotides, fully 2'-O-methylated, oligonucleotides having a central region that is complementary to the mature miRNA target sequence and 5' and 3' flanking sequences of equivalent length.

Exemplified herein are the inhibitors designed to target hsa-miR-489, hsa-miR-27a, hsa-miR-148b, or any of the closely related family members (see Table 1). As shown in Example 1, transfection of microRNA inhibitors individually targeting the majority of human miRNAs has little or no effect on MSCs osteogenic differentiation. In contrast, transfection of inhibitors targeting hsa-miR-489 or hsa-miR-27a into mesenchymal stem cells enhances the production of alkaline phosphatase, a key cellular marker of osteoblasts. The differentiation is highly specific to osteogenic differentiation and does not include differentiation into other cell types (e.g.

adipose cell, hematopoietic cells). Of equal importance, the inventors have discovered that inhibitors of hsa-miR-489, hsa-miR-27a and related family members induce osteogenic differentiation both in the presence and absence of pro-osteogenic cocktails being added to the media (see Example 4). Moreover, inhibitors of hsa-miR-148b (unlike inhibitors of hsa-miR-489 and hsa-miR-27a) are capable of inhibiting osteogenic differentiation.

miRNA mimics represent a class of molecules that can be used to imitate the gene silencing ability of one or more miRNAs. Thus, the term "microRNA mimic" refers to synthetic non-coding RNAs (i.e. the miRNA is not obtained by purification from a source of the endogenous miRNA) that are capable of entering the RNAi pathway and regulating gene expression. miRNA mimics can be designed as mature molecules (e.g. single stranded) or mimic precursors (e.g., pri- or pre-miRNAs). miRNA mimics can be comprised of nucleic acid (modified or modified nucleic acids) including oligonucleotides comprising, without limitation, RNA, modified RNA, DNA, modified DNA, locked nucleic acids, or 2'-O,4'-C-ethylene-bridged nucleic acids (ENA), or any combination of the above (including DNA-RNA hybrids). In addition, miRNA mimics can comprise conjugates that can affect delivery, intracellular compartmentalization, stability, specificity, functionality, strand usage, and/or potency.

In one design, miRNA mimics are double stranded molecules (e.g., with a duplex region of between about 16 and about 31 nucleotides in length) and contain one or more sequences that have identity with the mature strand of a given miRNA. Modifications can comprise 2' modifications (including 2'-O methyl modifications and 2' F modifications) on one or both strands of the molecule and internucleotide modifications (e.g. phorphorthioate modifications) that enhance nucleic acid stability and/or specificity. In addition, miRNA mimics can include overhangs. The overhangs can consist of 1-6 nucleotides on either the 3' or 5' end of either strand and can be modified to enhance stability or functionality.

In one embodiment, a miRNA mimic comprises a duplex region of between 16 and 31 nucleotides and one or more of the following chemical modification patterns: the sense strand contains 2'-O-methyl modifications of nucleotides 1 and 2 (counting from the 5' end of the sense oligonucleotide), and all of the Cs and Us; the antisense strand modifications can comprise 2' F modification of all of the Cs and Us, phosphorylation of the 5' end of the oligonucleotide, and stabilized internucleotide linkages associated with a 2 nucleotide 3' overhang.

The mimics used in the Examples of this disclosure are 19-28 bp, double stranded RNA molecules comprising a 5' phosphorylated antisense strand that is identical to the mature strand of the miRNA under study. In addition, all mimics used in the Examples contain 2'-O-methyl modifications on the first two nucleotides of the 5' end of the non-targeting strand (also referred to as the passenger strand or the star strand).

In one aspect, the mimic is a mimic of hsa-miR-148b and related family members (see Table 1). As shown in Example 2, transfection of a mimic of hsa-miR-148b into mesenchymal stem cells enhances the production of alkaline phosphatase, a key cellular marker of osteoblasts. Again, the differentiation process is specific to osteogenic differentiation (i.e. cells do not differentiate into other cell lineages). And, as was the case with miRNA inhibitors targeting hsa-miR-489, hsa-miR-27a and related family members, the hsa-miR-148b mimic can induce osteogenic differentiation in the presence and absence of pro-osteogenic cocktails being added to the culture media. Simultaneously, the inventors have discovered that mimics of hsa-miR-489 and hsa-miR27a inhibit MSC osteogenic differentiation.

Thus, in one aspect the disclosure provides a method of promoting MSC differentiation towards the osteogenic cell fate, the method comprising introducing into a MSC (ex vivo or in vivo) a composition comprising at least one differentiation promoting agent selected from the group consisting of inhibitors of miR-489, inhibitors of miR-27a, and mimics of miR-148b. The miRs, mimics and inhibitors can be used singly or in any combination to promote MSC differentiation. By way of non-limiting example, MSC differentiation may be promoted by introducing (e.g., by transfection, passive uptake etc) into a MSC a composition comprising:

1. at least one miR-489 inhibitor (e.g. 1, 2, 3, or more different miR-489 inhibitors);
2. at least one miR-27a inhibitor (e.g. 1, 2, 3, or more different miR-27a inhibitors);
3. at least one miR-148b mimic (e.g. 1, 2, 3, or more different miR-148b mimics);
4. at least one miR-489 inhibitor in combination with at least one miR-27a inhibitor and at least one miR-148b mimic; or
5. at least one miR-489 inhibitor in combination with at least one miR-148b mimic.

In another aspect the disclosure provides a method of inhibiting MSC differentiation toward the osteogenic cell fate, the method comprising introducing into a MSC (ex vivo or in vivo) a composition comprising at least one differentiation inhibitor selected from the group consisting of mimics of miR-489, mimics of miR-27a, and inhibitors of miR-148b. The mimics and inhibitors can be used singly or in any combination to inhibit MSC differentiation. By way of non-limiting example, MSC differentiation may be inhibited by introducing (e.g., by transfection, passive uptake etc) into a MSC a composition comprising:

1. at least one miR-489 mimic (e.g. 1, 2, 3, or more different miR-489 mimics);
2. at least one miR-27a mimic (e.g. 1, 2, 3, or more different miR-27a mimics);
3. at least one miR-148b inhibitor (e.g. 1, 2, 3, or more different miR-148b inhibitors);
4. at least one miR-489 mimic in combination with at least one miR-27a mimic and at least one miR-148b inhibitor; or
5. at least one miR-489 mimic in combination with at least one miR-148b inhibitor.

Given the similarities in miRNAs amongst mammalian systems, equivalent mimic and inhibitor molecules derived from different species are expected to have similar effects on their respective organisms.

In another aspect, the disclosure provides inhibitors and mimics of miR-489, miR-27a, and miR-148b including, but not limited to, the mimics and inhibitors of Table 1. In view of the utility of such mimics and inhibitors disclosed herein by the inventors, the design of other mimics and inhibitors of miR-489, miR-27a, and miR-148b is within the skill of the ordinary artisan.

Synthetic mimics and inhibitors can be delivered to cells to influence MSC differentiation by a variety of methods including, but not limited to, lipid (e.g. DharmaFECT1, Thermo Fisher Scientific) or chemical (e.g. calcium phosphate) mediated transfection, electroporation, lipid-independent delivery via conjugation to one or more entities that mediate lipid- or chemical-independent delivery (e.g. conjugation of cholesterol), or any other method that has been identified or will be identified for nucleic acid transfer to target cells. In addition, mimics and inhibitors can be delivered to a cell using a plasmid vector that expresses the sequence(s) that encode the mimic or inhibitor of choice. Such expression vectors can be introduced into cells (including cells within an organism such as a human being) by art-recognized transfection methods (e.g. Lipofectamine 2000, Invitrogen) or via viral-mediated delivery (e.g. lentiviral, adenoviral). One preferred expression system is described in PCT/US2008/64462, which is incorporated herein by reference in its entirety Studies have demonstrated that not all miRNAs are processed with equal efficiency. For that reason, incorporation of the therapeutic miRNAs (e.g. mimics and inhibitors) of the disclosure into a highly processed scaffold (e.g., miR-196a-2) would ensure efficient processing and expression.

Synthetic mimics and inhibitors may be modified with a wide range of chemical modifications to enhance stability, functionality, cellular uptake, and specificity, and strand usage. For instance, studies presented in U.S. patent application Ser. No. 11/051,195, which is incorporated herein by reference in its entirety, and other documents have identified multiple chemical modification patterns, including 2'-O-methyl modifications, locked nucleic acids (LNAs), morpholinos, ethylene-bridged analogs (ENAs), 2'-F modifications, and phosphorothioate modifications, that greatly enhance the stability of double stranded RNAs in serum. Similarly, addition of 2'-O-methyl modifications to positions 1 and 2 (counting from the 5' end of the molecule) in the passenger strand can enhance functionality and specificity (see patent application Ser. No. 11/019,831, which is incorporated herein by reference in its entirety).

In some embodiments, the miRNA inhibitor or mimic is conjugated to a lipid molecule such as cholesterol (preferably using a linker) in order to allow passive delivery of the inhibitor to a MSC (in vivo or ex vivo). See WO 2008/036825 which is incorporated herein by reference in its entirety. In preferred embodiments, the mimics and inhibitors contain the modification patterns and conjugate moieties disclosed in WO 2008/036825. For example, in one embodiment, a miRNA mimic of the disclosure comprises an RNA duplex having:
1. a sense strand that ranges in size from about 18 to about 30 nucleotides wherein nucleotides 1 and 2 (numbered from the 5' end) are 2' O-methyl modified and wherein all C nucleotides and all U nucleotides are 2'O-methyl modified;
2. an antisense strand that ranges in size from about 18 to about 30 nucleotides, wherein all C nucleotides and all U nucleotides are 2' F modified, and wherein the antisense strand has significant levels of complementarity to the sense strand as well as to the target gene of the endogenous miR;
3. a 2 nucleotide overhang at the 3' end of the antisense strand comprising phosphorothioate linkages;
4. a cholesterol molecule attached to the 3' end of the sense strand via a C5 linker molecule wherein the cholesterol-linker-sense strand can have the structure:

5. optionally a phosphate group at the 5' end of the antisense strand; and
6. optionally, a mismatch between at least one of nucleotides 1, 7, and 14 on the antisense strand (numbered from the 5' end) and the opposite nucleotide on the sense strand. The cholesterol molecule allows passive uptake of the mimic into cells.

The mimics and inhibitors of the disclosure can be generated using a range of art-recognized techniques (e.g. ACE chemistry, see U.S. Pat. Nos. 6,111,086; 6,590,093; 5,889,136; and 6,008,400, each of which is incorporated herein by reference in its entirety).

Mimics and inhibitors can be introduced into MSCs either ex vivo (e.g. in vitro) or in vivo (e.g., within a whole organism such as a human being or any other mammal). Thus, in another aspect the disclosure provides isolated cells and isolated tissues comprising the inhibitors and mimics of the disclosure, and also provides isolated, cells and isolated tissues comprising siRNAs specific for the genes disclosed below. Moreover, as detailed below, the mimics and inhibitors of the disclosure can be formulated as pharmaceutical compositions for the treatment (e.g. therapeutic or prophylactic use) of diseases or disorders in which MSC differentiation (or lack thereof) is implicated (e.g. osteogenesis imperfecta) or for the treatment of disease, conditions, and disorders in which increased osteogenesis or decreased osteogenesis is desirable.

The level of osteogenic differentiation by MSCs can be assessed by a variety of methods including 1) measuring alkaline phosphatase activity by one or more enzymatic assays, 2) staining cells with Alizarin-Red S solution or silver nitrate which identifies calcium phosphate deposits, or 3) measuring expression of osteogenic marker genes including osterix, cbfa1, osteopontin, osteocalcin, or bone sialoprotein, which can be performed at the RNA or protein level.

Small molecule compounds that have effects on osteogenesis have been shown to exhibit effects in in vivo systems (e.g. TAK-778 [(2R,4S)-(–)-N-(4-diethoxyphosphorylmethylphenyl)-1,2,4,5-tetrahydro-4-methyl-7,8-methylenedioxy-5-oxo-3-benzothiepin-2-carboxyamide, see, Notoya, K. et al. (1999) J Pharmacol Exp Ther. 290:1054-64). Thus, the mimics and inhibitors described here will also prove efficacious in whole animal (human and non-human) systems as therapeutic and/or prophylactic agents. Methods for the delivery of miRNA mimics and inhibitors to an organism are known in the art.

In another aspect, the level of expression of one or more of miR-489, miR-27a, and miR-148b (and/or the level(s) of any corresponding pri-miRNA and/or pre-miRNA) is measured. The results of measurements can be used for disease detection, disease diagnosis, disease prognosis (e.g. an estimate of disease outcome), and to determine or predict the efficacy of a therapeutic treatment. For example, because an inhibitor of miR-489 promotes MSC differentiation towards the osteogenic cell fate, then this suggests that individuals with a high

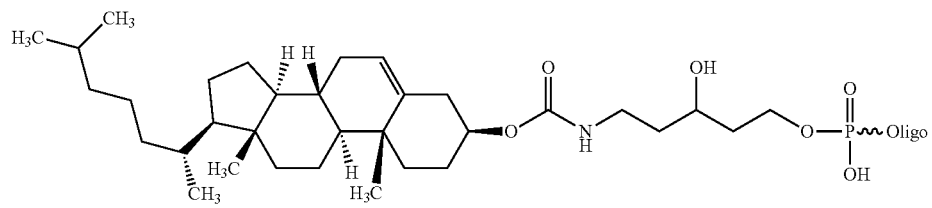

level of expression of miR-489 may have a reduced degree of MSC differentiation compared to individuals with a relatively lower level of miR-489 expression. Conversely, because a mimic of miR-148b promotes MSC differentiation towards the osteogenic cell fate, then this suggests that individuals with a high level of expression of miR-148b may have a higher degree of MSC differentiation compared to individuals with a relatively lower level of miR-489 expression. In one embodiment, the method comprises the steps of 1) determining the expression level of one or more of the miRNAs of the disclosure from an individual suspected of having a disease or disorder characterized by abnormal MSC differentiation (e.g., osteogenesis imperfecta) and 2) comparing the level of the one or more miRNAs with that observed in a normal individual known to not have the disease or disorder, whereby diagnostic or prognostic information may be obtained.

The miRNAs used as diagnostic or prognostic markers may be utilized individually or in combination with other molecular markers for bone disorders, including without limitation other miRNAs, mRNAs, proteins, and nucleotide polymorphisms.

A range of techniques well known in the art can be used to quantitate amounts of one or more miRNA sequences of the disclosure from e.g., a biological sample. For instance, complements of the mature miRNA sequences of the disclosure can be associated with a solid support (e.g., a microarray) and purified RNA from e.g., clinical or control samples can be fluorescently labeled and profiled to determine whether the patient is suffering from a disease resulting from improper osteogenic differentiation (see Baskerville, S. et al. RNA 11:241-7). One preferred microarray platform is described in the document in WO/2008/048342 (filed as PCT/US2007/003116) which is incorporated herein by reference in its entirety. Alternatively, Northern blotting and/or quantitative PCR-based techniques can be used to assess the relative amounts of any of the miRNAs of the disclosure derived from e.g., control and/or test samples (Duncan, D. D. et al. 2006 Anal. Biochem. 359:268-70). In addition, affinity matrices, in situ hybridization, and in situ PCR may be used. These techniques are all well known in the art.

Preferably, statistical methods are used to identify significant changes in miRNA levels for the aforementioned prognostic and diagnostic assays. For example, in one embodiment, p values are calculated using known methods to determine the significance in the change of the level of expression of a miRNA. In some embodiments, a value of $p<0.05$ is used as a threshold value for significance.

Samples for the prognostic and diagnostic assays of the disclosure may be obtained from an individual (e.g., a human or animal subject) suspected of having a disease or disorder characterized by abnormal MSC differentiation (e.g., osteogenesis imperfecta) using any technique known in the art. For example, the sample may be obtained from an individual who is manifesting clinical symptoms that are consistent with the existence of a disease or disorder characterized by abnormal MSC differentiation, or from an individual with no clinical symptoms but with a predisposition towards developing a disease or disorder characterized by abnormal MSC differentiation due to genetic or environmental factors. Samples may be obtained by extracting a small portion of bone tissue from an individual using, for example, a biopsy needle.

In some instances, genomic amplification of a sequence encoding a miRNA in a tissue may result in a higher level of expression of that miRNA relative to tissues in which the sequence encoding the miRNA has not undergone amplification. Thus, in another embodiment, the copy number of miR-489, miR-27a, and miR-148b is measured in a tissue which comprises MSCs. Methods suitable for determining the genomic copy number of a sequence encoding a miRNA include Southern blotting, fluorescence in situ hybridization, comparative genomic hybridization, and amplification based methods such as quantitative PCR (for example, using Taqman probes).

The methods of the disclosure can also be used to identify genes that play a role in enhancing osteogenesis and/or limit MSC differentiation into other cell types (e.g. adipocytes). The terms "miRNA target gene", "miRNA target", and "target gene" are used interchangeably herein to refer to genes that are directly modulated by specific miRNA(s). Extensive studies into the mechanism of miRNA action have identified characteristic features of miRNA target genes. These include the presence of the 3' UTR target sites (e.g. seed complements), the number and positioning of seed complements within a 3' UTR, preferences for local AU-rich sequences and more (see, for instance, Grimson, A. et al 2007. Mol Cell 27:91-105). As such, miRNA target genes can be identified bioinformatically (e.g., see the miRNA target prediction site at the http site on the world-wide-web: russell.embl-heidelberg.de/miRNAs; Targetscan, the http site on the world-wide-web: targetscan.org/mam_31/), by microarray analysis (Huang et. al., 2007, Nature Methods 4:1045-9), and by biochemical methods (Karginov, F. V., 2007, PNAS 104:19291-6). Using the procedures described in Example 5, the inventors have determined target genes that are regulated by miRs-27a, 489, and 148b, including but not limited to the target genes disclosed in Tables 2-7. Thus, in another aspect, the disclosure provides a collection of target genes that are modulated by miRs-27a, 489, and 148b, including the genes in Tables 2-7. The nucleotide sequences of the genes in Tables 2-7 are well known in the art. For example, gene sequences may be obtained through http site//www.ncbi.nlm.nih.gov/sites/entrez?db=gene using the gene names, target names, Transcript Id. Numbers and ReqSeq Accession Numbers provided in Tables 2-7. For each gene of Tables 2-7, the most recent version of the sequence associated with the recited accession number as of the filing date of this application is specifically incorporated herein by reference.

It will be recognized by one skilled in the art that knowledge of the target genes that are modulated by miRs-27a, 489, and 148b enables other methods for modulating mesenchymal stem cell differentiation both ex vivo (e.g. in vitro) and in vivo. In general, a decrease in the expression level of a gene from Tables 2-3 or Tables 4-5 (e.g. CHRD, GCA, and SLC22A2) will inhibit mesenchymal stem cell (MSC) differentiation towards the osteogenic cell fate, whereas an increase in the expression level of a gene from Tables 2-3 or Tables 4-5 will promote mesenchymal stem cell (MSC) differentiation towards the osteogenic cell fate. Similarly, a decrease in the expression level of a gene from Tables 6-7 (e.g. NOG) will promote mesenchymal stem cell (MSC) differentiation towards the osteogenic cell fate, whereas an increase in the expression level of a gene from Tables 6-7 will inhibit mesenchymal stem cell (MSC) differentiation towards the osteogenic cell fate.

In addition to using the miRNAs, miRNA mimics, and miRNA inhibitors disclosed above, modulation of the expression level of the target genes provided in Tables 2-7 can also be achieved using miRNA mimics that hybridize to a different site in the target gene than the site recognized by the endogenous miRs-27a, 489, and 148b.

Modulation of the expression level of the target genes provide in Tables 2-7 can also be achieved using siRNAs that can be designed using techniques well known in the art. Non-limiting examples demonstrating the siRNA-mediated modulation of the target genes of Tables 2-7 are provided in Example 5. For example, in one embodiment, the disclosure provides a method of promoting mesenchymal stem cell (MSC) differentiation towards the osteogenic cell fate, the method comprising introducing into a MSC at least one siRNA or miRNA mimic specific for at least one of the target genes of Tables 6-7 (e.g. a siRNA specific for NOG). In another embodiment, the disclosure provides a method of inhibiting mesenchymal stem cell (MSC) differentiation towards the osteogenic cell fate, the method comprising introducing into a MSC at least one siRNA or miRNA mimic specific for at least one of the target genes of Tables 2-5 (e.g. CHRD, GCA, and SLC22A2). In preferred embodiments, the expression level of one or more genes from Table 3, 5, and/or 7 (e.g. ARSE, COL2A1, FBN1, GHRHR, HOXA2, HOXA5, LECT1, NOG, OSTF1, PAPSS2, TFIP11, TRPS1, ADAMTS4, AHSG, ALPL, BMI1, CHRD, DLX5, HOXA13, MATN1, MINPP1, PEX7, PRKRA, THRA, AMELY, BMP7, CDH11, CHRD, CHRDL2, EN1, MAPK8, MGP, PAX1, POSTN, SPP1, SUFU, TRAPPC2, TWIST1, GCA, and SLC22A2) is modulated in an MSC in vivo or ex vivo (e.g. in vitro) using miRNAs, miRNA mimics, miRNA inhibitors, siRNA, and/or any other mediator of RNAi or transcriptional silencing known in the art.

It is expressly contemplated that combinations of two or more agents of the disclosure (miRNAs, miRNA mimics, miRNA inhibitors, and siRNAs) are used to modulate MSC differentiation in vivo or ex vivo.

The identification of the target genes of Tables 2-7 that are induced and/or suppressed by the miRNA mimics and inhibitors described herein can also lead to the identification of small molecules that can modulate this critical step in cellular differentiation. Small molecules can be identified, for example, using conventional High Throughput Screening (HTS) methodology.

All of the agents identified in the instant disclosure (miRNAs, miRNA mimics, miRNA inhibitors, and siRNAs) that modulate MSC differentiation have utility in the fields of tissue transplantation/grafting (e.g. bone formation, tissue mineralization, osteochondral repair, fracture repair including non-union fracture repair), treatment of disease (e.g. osteogenesis imperfecta), bioprocessing, 3D culture, and biomarker development (see, for instance, Reiker, J. et al. (2005) *Expert Opin. Biol. Ther.* 5(12): 1572-1584). For example, using a differentiation promoting agent(s) of the disclosure (e.g., a miR-148b mimic, a miR-489 inhibitor, a miR-27a inhibitor, or siRNA or an miRNA mimic specific for a gene from Tables 6-7, such as NOG, or any combination of two or more of these agents such as two miR-489 inhibitors, or such as a miR-489 inhibitor plus a siRNA specific for NOG, or such as a miR-27a inhibitor plus a miRNA mimic for NOG etc), a MSC cultured ex vivo may be induced to differentiate towards the osteogenic cell fate and may then be transplanted into an individual in need of a bone graft along with an appropriate matrix or implant, if required. The MSC may be obtained from the same individual that receives the bone graft (autograft) or from a different individual (allograft).

Pharmaceutical compositions comprising the inhibitors, mimics, siRNAs, and small molecules of the disclosure, are also expressly contemplated and may be used for the treatment (e.g. therapy—ranging from alleviation of one or more symptoms to a complete cure—or prophylaxis) of any disease, condition, or disorder in which MSC differentiation (or lack thereof) is implicated (e.g. osteogenesis imperfecta) or where increased osteogenesis is desirable (e.g. osteoporosis or any other disease, condition, or disorder where increasing bone density and growth is desirable such as, without limitation, osteoarthritis, periodontal disease, bone fractures of any type or etiology, bone loss from surgery, reconstructive surgery, osteomylitis, and idiopathic bone loss) or where decreased osteogenesis is desirable (e.g. fibrodysplasia ossificans progressiva). For example, a pharmaceutical formulation comprising at least one siRNA or miRNA mimic specific for a gene from Tables 6-7 (e.g. NOG) can be used to treat an individual suffering from a disease characterized by a decreased degree of MSC differentiation relative to a normal individual, or to treat a disease or disorder in which increasing bone growth, mass, or density is desirable. Similarly, a pharmaceutical formulation comprising at least one siRNA or miRNA mimic specific for a gene from Tables 2-5 (e.g. CHRD, GCA, and SLC22A2) can be used to treat an individual suffering from a disease characterized by a increased degree of MSC differentiation relative to a normal individual. Preferably, the target gene whose expression level is modulated by a siRNA or miRNA mimic is a gene from Table 3, 5, or 7. By way of another example, a pharmaceutical formulation comprising at least one miR-148b mimic and/or at least one miR-489 inhibitor and/or at least one miR-27a inhibitor and/or at least one siRNA specific for a gene from Tables 6-7 can be used to treat an individual suffering from a disease characterized by a decreased degree of MSC differentiation relative to a normal individual. By way of another example, a pharmaceutical formulation comprising at least one miR-489 mimic and/or least one miR-27a mimic and/or at least one miR-148b inhibitor and/or at least one siRNA specific for a gene from Tables 2-5 can be used to treat an individual suffering from a disease characterized by a increased degree of MSC differentiation relative to a normal individual. In all cases, a pharmaceutically effective amount of the composition is administered to an individual in need thereof, such as a human patient i.e. an amount that is sufficient to induce a response in the individual that is clinically relevant and significant.

In addition to the siRNA(s), miRNA mimic(s), and miRNA inhibitor(s), the pharmaceutical formulations preferably also comprise one or more pharmaceutically acceptable carriers or excipients, and may be formulated for a variety of routes of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the therapeutic compositions of the invention can be formulated in liquid solutions; preferably in physiologically compatible buffers such as Hank's solution or Ringer's solution. In addition, the therapeutic compositions may be formulated in solid form and redissolved or suspended immediately prior to use. Lyophilized forms are also included. Preparations for oral administration are also contemplated, and may be formulated in a conventional manner to give either immediate or controlled release.

The pharmaceutical compositions of the disclosure may also include an additional active ingredient(s) for the treatment of bone disease e.g. TAK-778 R2R,4S)-(−)-N-(4-diethoxyphosphorylmethylphenyl)-1,2,4,5-tetrahydro-4-methyl-7,8-methylenedioxy-5-oxo-3-benzothiepin-2-carboxyamide.

In another aspect, the level of expression of one or more of the target genes of Tables 2-7 is measured. The results of measurements can be used for disease detection, disease diagnosis, disease prognosis, and to determine or predict the efficacy of a therapeutic treatment. For example, individuals with a high level of expression of a gene from Tables 6-7 (e.g. NOG) may have a reduced degree of MSC differentiation compared to individuals with a relatively lower level of expression of the same gene(s). Conversely, individuals with a low level of expression of a gene from Tables 6-7 may have a higher degree of MSC differentiation compared to individuals with a relatively higher level of expression of the same genes. Similarly, individuals with a high level of expression of a gene from Tables 2-5 (e.g. CHRD, GCA, SLC22A2) may have a higher degree of MSC differentiation compared to individuals with a relatively lower level of expression of the same gene(s); individuals with a low level of expression of a gene from Tables 2-5 may have a reduced degree of MSC differentiation compared to individuals with a relatively higher level of expression of the same gene(s). Methods for the measurement of the expression level of the target genes of Table 2-7 are well-known in the art, and include Northern blotting and quantitative PCR-based methods and microarray analysis (see also the methods disclosed above for measuring miRNA levels which are generally applicable to the measurement of mRNA also). In other embodiments, the level of the protein encoded by a gene from Tables 2-7 is measured using, for example, western blots, antibody arrays, ELISA assays, or any other technique known in the art.

The assays can be performed on biological samples taken from the individual. In one embodiment, the method comprises the steps of 1) determining the expression level of one or more of the target genes of Tables 2-7 from an individual suspected of having a disease or disorder characterized by abnormal MSC differentiation (e.g., osteogenesis imperfecta) and 2) comparing the level of the one or more target genes with that observed in a normal individual known to not have the disease or disorder, whereby diagnostic or prognostic information may be obtained. Preferably, the target gene whose expression level is determined is a gene from Table 3, 5, or 7 (e.g. ARSE, COL2A1, FBN1, GHRHR, HOXA2, HOXA5, LECT1, NOG, OSTF1, PAPSS2, TFIP11, TRPS1, ADAMTS4, AHSG, ALPL, BMI1, CHRD, DLX5, HOXA13, MATN1, MINPP1, PEX7, PRKRA, THRA, AMELY, BMP7, CDH11, CHRD, CHRDL2, EN1, MAPK8, MGP, PAX1, POSTN, SPP1, SUFU, TRAPPC2, TWIST1, GCA, and SLC22A2). The targets genes of Tables 2-7 may be used as diagnostic or prognostic markers either individually or in combination with other molecular markers disclosed herein or identified in previous or future studies (e.g., other miRNAs, proteins, nucleotide polymorphisms).

In another embodiment, the miRNAs and target genes described herein can be used as molecular markers in drug screening assays during drug development. Typically, in the early stages of drug development, in vitro studies involving cultured cells that often mimic one or more aspects of diseased tissue are performed to identify molecules that induce desirable phenotypes. As up or down regulation of miRNAs or target genes described herein are indicative of e.g. osteogenic differentiation, they can be used as markers during drug development to identify agents that positively effect clinical outcomes. In one preferred example, one or more of the miRNAs described herein are used to screen a collection of small molecules to identify agents that modulate the expression of the target gene sequences listed in the enclosed tables. Agents that cause e.g., miRNA(s) expression levels to return to a level that is more normal would be considered potential therapeutic candidates.

In another example, one or more of the miRNAs described herein are used as prognostic indicators to judge the effectiveness of drug treatment regimes. For example, the levels of miRNAs of the disclosure can be assessed in osteogenesis imperfecta patients receiving a particular treatment to determine the effectiveness of the treatment in lessening one or more phenotypes of the disease.

In another aspect, an exogenous vector construct comprising at least part of the coding sequence of a gene from Tables 2-7 is expressed in cells ex vivo or in vivo in order to modulate MSC differentiation. For example, in one embodiment, MSC differentiation towards the osteogenic cell fate is promoted by expressing an expression construct comprising at least part of the coding sequence of a gene from Tables 2-5 (e.g. at least part of the coding sequence of CHRD, GCA, or SLC22A2) operationally linked to sequences that allow the expression of the coding sequence. In another embodiment, MSC differentiation towards the osteogenic cell fate is inhibited by expressing an expression construct comprising at least part of the coding sequence of a gene from Tables 6-7 (e.g. at least part of the coding sequence of NOG) operationally linked to sequences that allow the expression of the coding sequence. Methods for generating and expressing expression constructs, including methods for expressing such constructs in vivo in humans, are well known in the art.

The aforementioned treatment and diagnostic methods are preferably carried out using human subjects; however, one skilled in the art will recognize that the methods of the disclosure can also be carried out in other animal species which possess orthologs of the genes of the Table 2-7 and/or of miR-148b, miR-489, and miR-27a. Determining orthologs of the genes and miRs of the disclosure in other animal species is within the skill of the ordinary worker in the field.

Note that while the invention has been described with reference to the differentiation of MSCs, the inventors have also recognized that the methods and agents provided herein may be used to modulate the differentiation of any other cell type that has osteogenic potential. Thus, in another series of embodiments, the disclosure provides methods of promoting differentiation towards the osteogenic cell fate of a cell having osteogenic potential, the methods comprising introducing into the cell (in vivo or ex vivo) an effective amount of a composition comprising at least one differentiation promoting agent selected from the group consisting of inhibitors of miR-489, inhibitors of miR-27a, mimics of miR-148b, and siRNAs specific for genes from Tables 6-7. Similarly, in another series of embodiments, the disclosure provides methods of inhibiting differentiation towards the osteogenic cell fate of a cell having osteogenic potential, the methods comprising introducing into the cell (in vivo or ex vivo) an effective amount of a composition comprising at least one differentiation inhibitor selected from the group consisting of mimics of miR-489, mimics of miR-27a, siRNAs specific for genes from Tables 2-5, and inhibitors of miR-148b.

Given the general applicability of the methods and agents of the disclosure in modulating the differentiation of cells having osteogenic potential (not just MSCs), it will be clear that any disease or condition that is characterized by either inadequate or inappropriate osteogenesis (e.g. ectopic osteogenesis or increased osteogenesis) may be treated using the methods and agents of the disclosure i.e. the methods of the disclosure are not restricted to the treatment of diseases or conditions in which MSC differentiation (or lack thereof) plays a pathological role. Similarly, using the diagnostic methods disclosed herein, diagnostic and prognostic information may be obtained regarding any disease or condition characterized by either inadequate or inappropriate osteogenesis (e.g. ectopic osteogenesis or increased osteogenesis) i.e. the diagnostic methods of the disclosure are not restricted to the diagnosis of diseases or conditions in which MSC differentiation (or lack thereof) plays a pathological role.

By way of non-limiting example, it is known that certain vascular cells, namely vascular smooth muscle cells (VSMS), calcifying vascular cells (CVC), and pericytes have the ability to differentiate into osteoblasts (or osteoblast-type cell). With respect to VSMCs, it is known that these cells have the ability to differentiate into osteoblasts (or osteoblast-type cell) in response to several stimuli including oxidative stress, bone morphogenetic proteins, or changes in pyrophosphate levels. It has been suggested that the ability of VSMSs, CVCs, and/or pericytes to differentiate into osteoblasts may explain the development of vascular calcifications, such as atherosclerotic calcification, medial artery calcification, and cardiac valve calcification. Johnson et al., Circulation Research 99:1044-1059 (2006). Thus, the methods and agents of the disclosure may be used in the treatment or prevention of vascular calcification. In particular, the agents of the disclosure that inhibit the differentiation towards the osteogenic cell fate of cells having osteogenic differentiation potential (mimics of miR-489, mimics of miR-27a, siRNA specific for genes from Tables 2-5, and inhibitors of miR-148b) may be administered (e.g. in pharmaceutical compositions) to a patient to treat or prevent vascular calcification.

The following examples are non-limiting.

EXAMPLES

General Reagents and Techniques

Mesenchymal stem cells, propagation media, and differentiation media were obtained from Lonza, Inc (Basel, Switzerland). Total alkaline phosphatase was determined using an osteogenesis assay kit from Biomedical Research Service Center (SUNY, Buffalo, N.Y.). To detect alkaline phosphatase expression in individual cells, ELF kits were purchased from ATCC (Manassas, Va.). Cells were then analyzed for alkaline phosphatase activity using an ArrayScan VTi (Thermo Fisher).

In most assays, cells (2,500 cells per well, 96 well plate) were transfected with miRNA mimics and inhibitors (25 nM, DharmaFECT1 Lipid) and incubated for approximately six days before assessing the level of osteogenic differentiation.

Example 1

Primary Screen for microRNAs that Alter MSC Differentiation Using miRNA Inhibitors To identify microRNAs that play an important role in MSC osteogenic differentiation, a screen using microRNA inhibitors targeting over 400 human miRNAs (miR database) was performed in adult human mesenchymal stem cells. To achieve this, MSC cells (Lonza, Inc) were plated in propagation media (Lonza, Inc) at a density of 2.5K cells per well in a 96-well plate (Nunc). At t=24 h, cells were transfected with miRNA inhibitors (miRIDIAN inhibitors, Thermo Fisher Scientific, 25 nM) and cultured for 6 days in differentiation media (Lonza, Inc). Subsequently, cells were lysed, the level of alkaline phosphatase (a classic osteogenic marker) was measured (osteogenesis assay kit, Biomedical Research Service Center, Cat # A-104) and normalized to total protein to determine the relative level of alkaline phosphatase expression in each culture. Untreated cells, cells treated with a negative control inhibitor (5' mAmGmCmUmCmUmCmA-mUm CmCmAmUmGmGmAmUmCmUmAmCmUmC-mUmUmUmCmUmAmGmGmAmGm GmUmUmG-mUmGmAmUmGmGmUmAmCmCmUmAmCmUmCm UmCmGmA, fully 2'-O-methylated, inhibitor of C. elegans miR-67) (SEQ ID NO:1), and cells treated with siRNA targeting the RUNX2 transcription factor which has been identified as being important in MSC cell differentiation into osteocytes were used as controls in the primary screen. Results were assessed using Excel software (Microsoft, Inc.) and standard statistical tools common to the art (e.g. z score).

Figure 1:
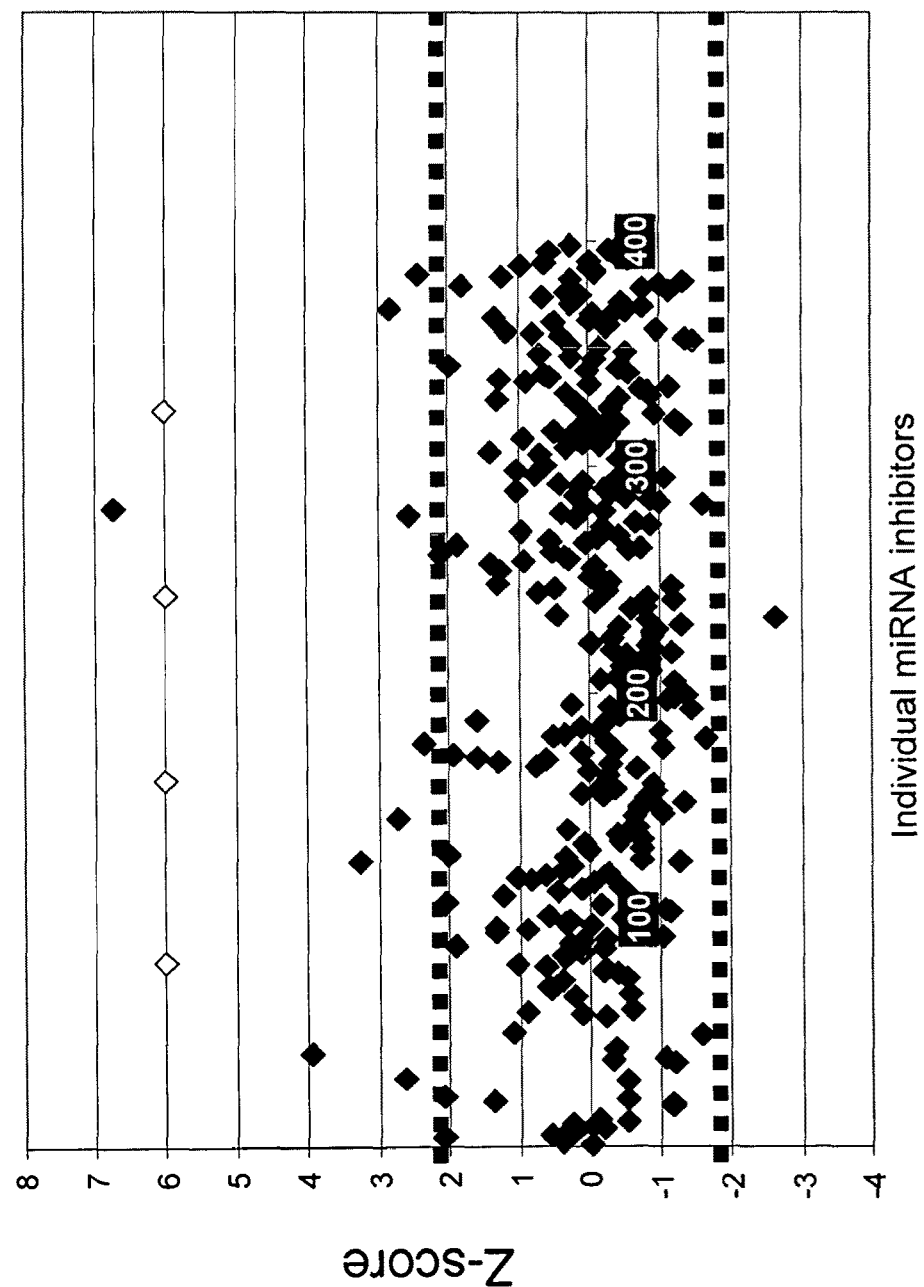
FIG. 1. Inhibitor Screen.

Results of these experiments are presented in FIG. 1. While the majority of inhibitors failed to significantly alter the level of osteogenic differentiation in the culture, a subset (including all of the miRNA inhibitors listed in Table 1) had significant effects on the expression levels of alkaline phosphatase. In particular, transfection of cells with inhibitors targeting hsa-miR-489 and hsa-miR-27a increased alkaline phosphatase levels by as much as 300% over control (non-targeting) miRNA inhibitors. In contrast, treating the cells with inhibitors to hsa-miR148b decreased alkaline phosphatase levels by approximately two-fold (as compared to inhibitor control molecules). These results were confirmed with a second inhibitor design that utilized hairpin flanking regions to enhance functionality of the molecule.

TABLE 1

Lists of miRNAs that when targeted with an inhibitor molecule, increase or decrease MSC osteogenic differentiation. The identity of the miRNA, as well as the sequence of the inhibitor and mimic used in the experiments described in this document are provided.

| Molecule | Sequence: "m" = methylated, "p" = phosphorylated. All sequences reported as 5'→3' | SEQ ID NO: |
|---|---|---|
| hsa-miR-489 inhibitor | mAmGmCmUmCmUmGmAmAmAmAmG mAmGmCmUmGmCmUmGmCmCmGmUm AmUmAmUmGmUmGmAmUmGmUmCm AmCmUmUmCmGmAmGmAmUmCmG mUmCmUmCmGmA | 2 |
| hsa-miR-489 mimic sequence (AS strand) | pUCAGUGCAUCACAGAACUUUGU | 3 |
| hsa-miR-489 mimic sequence (S strand) | mUmGCCGUAUAUGUGAUGUCACU | 4 |

TABLE 1-continued

Lists of miRNAs that when targeted with an inhibitor molecule, increase or decrease MSC osteogenic differentiation. The identity of the miRNA, as well as the sequence of the inhibitor and mimic used in the experiments described in this document are provided.

| Molecule | Sequence: "m" = methylated, "p" = phosphorylated. All sequences reported as 5'→3' | SEQ ID NO: |
|---|---|---|
| hsa-miR-148b inhibitor | mAmGmCmUmCmUmCmAmUmCmCmAm UmGmGmAmGmAmCmAmAmAmGmUm UmCmUmGmUmGmAmUmGmCmAmCmU mGmAmCmUmUmGmUmAmCmCmUmA mCmUmCmUmCmGmA | 5 |
| hsa-miR-148b mimic (AS strand) | pUCAGUGCAUCACAGAACUUUGU | 6 |
| hsa-miR-148b mimic (S strand) | mAmAAGUUCUGUGAUGCACUGAUU | 7 |
| hsa-miR-27a inhibitor | mAmGmCmUmCmUmCmAmUmCmCmAm UmGmGmGmGmGmCmGmGmAmAm CmUmUmAmGmCmCznAmCmUmGmUmG mAmAmCznAmCmGmUmAmCmCmUmAm CmUmCmUmCmGmA | 8 |
| hsa-miR-27a mimic (AS strand) | pUUCACAGUGGCUAAGLTUCCGC | 9 |
| hsa-miR-27a mimic (S strand) | mGmGAACUUAGCCACUGUGAAUU | 10 |
| Control inhibitor | mAmGmCmUmCmUmCmAmUmCmCmAm UmGmGmAmUmCmUmAmCmUmCmUmU mUmCmUmAmGmGmAmGmGmUmUmG mUmGmAmUmGmGmUmAmCmCmUmA mCmUmCmUmCmGmA | 11 |
| Control mimic (AS strand) | pUCACAACCUCCUAGAAAGAGUAGA | 12 |
| Control mimic (S strand) | mUmACUCUUUCUAGGAGGUUGUGAUU | 13 |

Example 2

Test of microRNA Mimics in MSC Differentiation

If an miRNA inhibitor increases differentiation, it was predicted that a miRNA mimic of the same microRNA would decrease differentiation. Conversely, if an miRNA inhibitor decreased differentiation, it was predicted that treatment of cells with the mimic for that miRNA would amplify differentiation. To that end, miRNA mimics that corresponded to the positive hits observed in the primary (inhibitor) screen were synthesized and transfected into MSCs (2.5K cells per well, 25 nM miRNA mimic, Thermo Fisher Scientific).

Only three of the miRNAs identified in the primary inhibitor screen exhibited the predicted effects in the mimic screen (see Table 1). While transfection of cells with inhibitors targeting hsa-miR-489 and hsa-miR-27a increased alkaline phosphatase levels, introduction of the corresponding mimics significantly decreased overall differentiation (see FIG. 2a). While treating the cells with inhibitors to hsa-miR148b decreased alkaline phosphatase levels, treatment with the corresponding mimic induced the opposite phenotype, elevating alkaline phosphatase expression by over 800%. Both inhibitor and mimic results were dose-dependent (see FIGS. 2B-G). These results indicate that hsa-miR-489, hsa-miR-27a, and hsa-miR148b play a role in MSCs osteogenic differentiation and that mimics and inhibitors for these miRNAs can be used to modulate differentiation.

Example 3

Identification of Combinations of miRNA Inhibitors and/or Mimics that Provide Additive Effects.

Transfection of 1) hsa-miR-489 inhibitors, 2) hsa-miR-27a inhibitors, or 3) hsa-miR148b mimics enhanced expression of alkaline phosphatase and thus osteogenic differentiation by MSCs. To determine whether any combination of these reagents acted in an additive fashion, the action of individual inhibitor or mimic molecules (e.g. inhibitor 489, inhibitor 27a, or mimic 148b) was compared with various combinations including 1) i489+i27a, 2) i489+m148b, 3) i27a+m148b, and 4) i489+i27a+m148b in the differentiation assay. To achieve this, MCS cells were plated at standard cell densities (2.5K per well, standard propagation media) and either individual, pairs, or trios of inhibitors, or inhibitors and mimics were transfected. In this instance, alkaline phosphatase expression was assessed on a cell-by-cell basis using an ELF kit purchased from ATCC (Cat. # SCRR-3010). Briefly, following transfection, cells were incubated in propagation media for 6 days and then fixed in 4% paraformaldehyde. Subsequently, cultures were stained with ELF97 fluorogenic substrate to detect alkaline phosphatase, and counterstained with SYTO Green to label nuclei. Cells were then analyzed for alkaline phosphatase activity using an ArrayScan VTi (Thermo Fisher).

The results of these experiments along with the appropriate controls are presented in FIG. 3A. Only two combinations (i489+m148b and i489+i27a+m148b) significantly enhanced the expression of alkaline phosphatase (and thus osteogenic differentiation.) in this assay. As a single pairing (i489+m148b) is common in both data sets, this indicates that the i489+m148b combination acts additively to enhance osteogenic differentiation by MSCs.

Example 4 miRNA Inhibitors and Mimics Induce Differentiation in Standard Propagation Media Initial studies designed to identify miRNA inhibitors and mimics that enhanced osteogenic differentiation were performed in differentiation media. To determine whether the inhibitors and mimics identified in Examples 1 and 2 could induce their effects in propagation media, differentiation studies were performed in both differentiation media and standard propagation media (Lonzo Biologics, Inc).

The results of these experiments are presented in FIGS. 3A and 3B, which show that hsa-miR-489, and hsa-miR-27a inhibitors, as well as hsa-miR148b mimics induce alkaline phosphatase expression in both media conditions. This finding indicates that the inhibitors and mimics listed induce MSC osteogenic differentiation in the absence of other signals.

Example 5

Identifying Targets of miRs-27a, 489, and 148b.

To identify targets of the preferred miRNAs identified in previous examples, the sequence of each miRNA was entered into miRanda (the http site: //www.mircoma.org/microrna/home.do) and a list of potential targets was generated based on the presence of 3' UTR seed complements and additional parameters (see, Lewis et al, (2005) Cell, 120:15-20). For miR-27a, 956 target genes were predicted, for miR-489, 888 target genes, and 327 target genes were predicted for miR-148b. See Tables 2, 4, and 6. Interestingly, roughly 80 of the bioinformatically identified targets were common to both miR-27a and miR-489, the two miRNAs that when introduced into MSCs, inhibited osteogenic differentiation. Additional in silico techniques were then employed to further narrow the list of targets provided by miRanda. Specifically, the genes identified by miRanda were analyzed using the gene ontology tool L2L (the http site: //depts.washington.edu/121/database.html) to identify members that were associated with "skeletal development". From this study, 15 of the 956 target genes initially identified for miR-27a, 12 of the 888 target genes for miR-489, and 12 of the 827 target genes for miR-148b were identified (see Tables 3, 5, and 7).

In order to confirm the target genes identified herein are indeed functionally linked with the miRNAs identified, siRNAs were developed to a subset of the selected target genes to assess the involvement of the gene in osteogenic differentiation. We predicted that if these genes are truly targets of the respective miRNAs, then knockdown of those genes by siRNAs should mimic the effects of the respective miRNA. Four genes exemplified below represent this scenario; three that were predicted to be targeted by both miR-27a and miR-489 and one that was predicted to be targeted by miR-148b.

For these experiments, pools of siRNAs targeting NOG, CHRD, GCA, SLC22A2, RUNX2 (a positive control), or a non-targeting siRNA (a negative control, "control siRNA") were introduced into hMSCs. Cells were then transferred to differentiation media (48 hr after transfection) and assessed for the expression of AP 6 days after osteogenic induction.

The results of these studies are presented in FIG. 4 and demonstrate that knockdown of the respective targets mimics the phenotypes associated with the respective miRNAs. Specifically, in cultures treated with siRNA targeting CHRD, GCA and SLC22A2, expression of AP was similar to that observed in cultures where RUNX2 (a known modulator of osteogenic differentiation) was targeted (i.e. less than 50% of the controls). This phenotype is similar to that induced by miR-27a and miR-489 which are predicted to target the CHRD, GCA and SLC22A2 gene. In contrast, cultures treated with siRNA targeting NOG exhibited AP levels that were 2.5 times those observed in control (non-targeting siRNA) cultures. Again, this phenotype parallels that observed when cells were treated with miR148b, the miRNA that targets NOG. Together these studies validate 1) the function of miRs-27a, 489, and 148b in their role as regulators of osteogenic differentiation, and 2) the methods used to identify targets of the preferred miRNAs.

Tables 2, 4, and 6 represent miRNA target gene lists as determined by miRanda alone. Tables 3, 5, and 7 represent miRNA target gene lists as determined by miRanda followed by L2L bioinformatic procedures.

TABLE 2

All targets of miR-27a.

| Transcript ID | RefSeq Accession Number | Target Name | Gene Name |
| --- | --- | --- | --- |
| ENST00000229384 | | 15E2_HUMAN | |
| ENST00000382381 | NM_001089 | ABCA3 | ATP-binding cassette, sub-family A (ABC1), member 3 |
| ENST00000375538 | NM_007168 | ABCA8 | ATP-binding cassette, sub-family A (ABC1), member 8 |
| ENST00000382075 | NM_178559 | ABCB5 | ATP-binding cassette, sub-family B (MDR/TAP), member 5 |
| ENST00000339447 | | ABCB7 | ATP-binding cassette, sub-family B (MDR/TAP), member 7 |
| ENST00000347800 | NM_004915 NM_016818.2 NM_207174 NM_207627.1 | ABCG1 | ATP-binding cassette, sub-family G (WHITE), member 1 |

TABLE 2-continued

All targets of miR-27a.

| Transcript ID | RefSeq Accession Number | Target Name | Gene Name |
|---|---|---|---|
| ENST00000360937 | NM_207628.1<br>NM_207629<br>NM_001091.2 | ABP1 | Amiloride binding protein 1 (amine oxidase (copper-containing)) |
| ENST00000285093 | NM_001080467.1 | ACAA2 | Acetyl-Coenzyme A acyltransferase 2 (mitochondrial 3-oxoacyl-Coenzyme A thiolase) |
| ENST00000373695 | NM_052957 | ACRC | Acidic repeat containing |
| ENST00000289416 | | ACSM3 | Acyl-CoA synthetase medium-chain family member 3 |
| ENST00000224784 | | ACTA2 | Actin, alpha 2, smooth muscle, aorta |
| ENST00000188312 | NM_022496 | ACTR6 | ARP6 actin-related protein 6 homolog (yeast) |
| ENST00000265708 | NM_001464 | ADAM2 | ADAM metallopeptidase domain 2 (fertilin beta) |
| ENST00000367995 | NM_005099 | ADAMTS4 | ADAM metallopeptidase with thrombospondin type 1 motif, 4 |
| ENST00000381052 | NM_197941 | ADAMTS6 | ADAM metallopeptidase with thrombospondin type 1 motif, 6 |
| ENST00000383707 | NM_182920 | ADAMTS9 | ADAM metallopeptidase with thrombospondin type 1 motif, 9 |
| ENST00000358680 | | ADC | Arginine decarboxylase |
| ENST00000380823 | | ADCY3 | Adenylate cyclase 3 |
| ENST00000304222 | | ADORA2B | Adenosine A2b receptor |
| ENST00000380572 | NM_000680<br>NM_033302<br>NM_033303<br>NM_033304 | ADRA1A | Adrenergic, alpha-1A-, receptor |
| ENST00000269143 | NM_006796 | AFG3L2 | AFG3 ATPase family gene 3-like 2 (yeast) |
| ENST00000375826 | | AGMAT | Agmatine ureohydrolase (agmatinase) |
| ENST00000264167 | NM_003659 | AGPS | Alkylglycerone phosphate synthase |
| ENST00000273784 | NM_001622 | AHSG | Alpha-2-HS-glycoprotein |
| ENST00000375341 | NM_003748<br>NM_170726 | ALDH4A1 | Aldehyde dehydrogenase 4 family, member A1 |
| ENST00000302708 | | ALKBH3 | AlkB, alkylation repair homolog 3 (*E. coli*) |
| ENST00000374832 | NM_000478 | ALPL | Alkaline phosphatase, liver/bone/kidney |
| ENST00000330330 | | AMY2B | Amylase, alpha 2B (pancreatic) |
| ENST00000255667 | NM_032290 | ANKRD32 | Ankyrin repeat domain 32 |
| ENST00000265224 | | ANKRD7 | |
| ENST00000375109 | | ANP32B | Acidic (leucine-rich) nuclear phosphoprotein 32 family, member B |
| ENST00000374368 | NM_174890 | ANUBL1 | AN1, ubiquitin-like, homolog (*Xenopus laevis*) |
| ENST00000296511 | NM_001154 | ANXA5 | Annexin A5 |
| ENST00000258749 | NM_001637 | AOAH | Acyloxyacyl hydrolase (neutrophil) |
| ENST00000246149 | NM_015013 | AOF2 | Amine oxidase (flavin containing) domain 2 |
| ENST00000346661 | NM_007247<br>NM_080550 | AP1GBP1 | AP1 gamma subunit binding protein 1 |
| ENST00000359032 | NM_014203.2<br>NM_130787.2 | AP2A1 | Adaptor-related protein complex 2, alpha 1 subunit |
| ENST00000316757 | | APBA3 | Amyloid beta (A4) precursor protein-binding, family A, member 3 (X11-like 2) |
| ENST00000355285 | NM_153000 | APCDD1 | Adenomatosis polyposis coli down-regulated 1 |
| ENST00000257254 | | APJ_HUMAN | |
| ENST00000244669 | NM_006789 | APOBEC2 | Apolipoprotein B mRNA editing enzyme, catalytic polypeptide-like 2 |
| ENST00000313578 | NM_173039 | AQP11 | Aquaporin 11 |
| ENST00000320481 | NM_020824 | ARHGAP21 | Rho GTPase activating protein 21 |
| ENST00000374872 | NM_015185 | ARHGEF9 | Cdc42 guanine nucleotide exchange factor (GEF) 9 |
| ENST00000320767 | NM_025047 | ARL14 | ADP-ribosylation factor-like 14 |

TABLE 2-continued

All targets of miR-27a.

| Transcript ID | RefSeq Accession Number | Target Name | Gene Name |
|---|---|---|---|
| ENST00000379532 | | ARMC6_HUMAN | |
| ENST00000263634 | NM_016115 NM_145863 | ASB3 | Ankyrin repeat and SOCS box-containing 3 |
| ENST00000380920 | NM_001671 | ASGR1 | Asialoglycoprotein receptor 1 |
| ENST00000215906 | | ASPHD2 | Aspartate beta-hydroxylase domain containing 2 |
| ENST00000372393 | | ASS | |
| ENST00000378759 | | ATAD3A | ATPase family, AAA domain containing 3A |
| ENST00000378737 | | ATAD3B | ATPase family, AAA domain containing 3B |
| ENST00000373673 | NM_145178 | ATOH7 | Atonal homolog 7 (Drosophila) |
| ENST00000218008 | NM_012069 | ATP1B4 | ATPase, (Na+)/K+ transporting, beta 4 polypeptide |
| ENST00000284727 | NM_001002258 NM_001689 | ATP5G3 | ATP synthase, H+ transporting, mitochondrial F0 complex, subunit C3 (subunit 9) |
| ENST00000369762 | NM_001183 | ATP6AP1 | ATPase, H+ transporting, lysosomal accessory protein 1 |
| ENST00000264649 | | ATP6V0A1 | ATPase, H+ transporting, lysosomal V0 subunit a1 |
| ENST00000374133 | | ATPBD1B | ATP binding domain 1 family, member B |
| ENST00000270637 | | ATPBD3 | ATP binding domain 3 |
| ENST00000378853 | | AURKAIP1 | Aurora kinase A interacting protein 1 |
| ENST00000358927 | NM_000054 | AVPR2 | Arginine vasopressin receptor 2 (nephrogenic diabetes insipidus) |
| ENST00000320865 | | B3GNTL1 | UDP-GlcNAc:betaGal beta-1,3-N-acetylglucosaminyltransferase-like 1 |
| ENST00000367998 | | B4GALT3 | UDP-Gal:betaGlcNAc beta 1,4-galactosyltransferase, polypeptide 3 |
| ENST00000370693 | NM_004282 | BAG2 | BCL2-associated athanogene 2 |
| ENST00000286639 | NM_006399 | BATF | Basic leucine zipper transcription factor, ATF-like |
| ENST00000359924 | | BBC3_HUMAN | |
| ENST00000371608 | | BCAS4 | Breast carcinoma amplified sequence 4 |
| ENST00000310512 | | BCDIN3 | |
| ENST00000164227 | NM_005178 | BCL3 | B-cell CLL/lymphoma 3 |
| ENST00000361907 | NM_017745 NM_020926 | BCOR | BCL6 co-repressor |
| ENST00000372677 | | BEX2 | Brain expressed X-linked 2 |
| ENST00000372645 | | BEX3_HUMAN | |
| ENST00000376719 | NM_005180 | BMI1 | BMI1 polycomb ring finger oncogene |
| ENST00000368636 | | BNIP3 | BCL2/adenovirus E1B 19 kDa interacting protein 3 |
| ENST00000336049 | NM_033030 NM_197970 | BOLL | Bol, boule-like (Drosophila) |
| ENST00000382392 | NM_001002760.1 NM_001002761.1 NM_004678.1 | BPY2C | Basic charge, Y-linked, 2C |
| ENST00000324096 | | BPY2IP1 | |
| ENST00000303498 | NM_000060 | BTD | Biotinidase |
| ENST00000290551 | NM_006763 | BTG2 | BTG family, member 2 |
| ENST00000368859 | | BUB3 | BUB3 budding uninhibited by benzimidazoles 3 homolog (yeast) |
| ENST00000222969 | | BUD31 | BUD31 homolog (S. cerevisiae) |
| ENST00000370654 | | BXDC5 | Brix domain containing 5 |
| ENST00000372996 | | BYSL | Bystin-like |
| ENST00000369286 | NM_018017 | C10orf118 | Chromosome 10 open reading frame 118 |
| ENST00000368815 | NM_015608 | C10orf137 | Chromosome 10 open reading frame 137 |
| ENST00000378605 | | C10orf30 | Chromosome 10 open reading frame 30 |
| ENST00000373279 | NM_145306 | C10orf35 | Chromosome 10 open reading frame 35 |
| ENST00000278064 | NM_025145 | C10orf79 | Chromosome 10 open reading frame 79 |

TABLE 2-continued

All targets of miR-27a.

| Transcript ID | RefSeq Accession Number | Target Name | Gene Name |
|---|---|---|---|
| ENST00000264020 | NM_020153 | C11orf60 | Chromosome 11 open reading frame 60 |
| ENST00000381047 | NM_018169 | C12orf35 | Chromosome 12 open reading frame 35 |
| ENST00000305457 | NM_152335 | C15orf27 | Chromosome 15 open reading frame 27 |
| ENST00000268138 | NM_152259 | C15orf42 | Chromosome 15 open reading frame 42 |
| ENST00000340827 | NM_152448 | C15orf43 | Chromosome 15 open reading frame 43 |
| ENST00000329410 | NM_175900 | C16orf54 | Chromosome 16 open reading frame 54 |
| ENST00000323355 | NM_152728 | C18orf20 | Chromosome 18 open reading frame 20 |
| ENST00000382462 | | C19orf24 | Chromosome 19 open reading frame 24 |
| ENST00000317292 | | C19orf30 | Chromosome 19 open reading frame 30 |
| ENST00000374526 | NM_020362 | C1orf128 | Chromosome 1 open reading frame 128 |
| ENST00000371007 | NM_001013674 | C1orf141 | Chromosome 1 open reading frame 141 |
| ENST00000366760 | | C1orf142 | Chromosome 1 open reading frame 142 |
| ENST00000370574 | NM_017953 | C1orf181 | Chromosome 1 open reading frame 181 |
| ENST00000367974 | | C1orf192 | Chromosome 1 open reading frame 192 |
| ENST00000368369 | NM_006589 NM_198264 | C1orf2 | Chromosome 1 open reading frame 2 |
| ENST00000369095 | NM_018997 NM_031901 NM_144697 | C1orf51 | Chromosome 1 open reading frame 51 |
| ENST00000366628 | | C1orf57 | Chromosome 1 open reading frame 57 |
| ENST00000367723 | NM_014283 NM_016227.1 | C1orf9 | Chromosome 1 open reading frame 9 |
| ENST00000251071 | | C1QDC1 | |
| ENST00000304189 | | C20orf55 | |
| ENST00000370351 | | C20orf59 | Chromosome 20 open reading frame 59 |
| ENST00000354932 | NM_080574 | C20orf70 | Chromosome 20 open reading frame 70 |
| ENST00000378239 | NM_015701 | C2orf30 | Chromosome 2 open reading frame 30 |
| ENST00000245907 | NM_000064 | C3 | Complement component 3 |
| ENST00000383793 | | C3orf20 | Chromosome 3 open reading frame 20 |
| ENST00000383805 | NM_173472 | C3orf24 | Chromosome 3 open reading frame 24 |
| ENST00000344697 | NM_032806 | C3orf39 | Chromosome 3 open reading frame 39 |
| ENST00000367070 | NM_000715 | C4BPA | Complement component 4 binding protein, alpha |
| ENST00000367659 | NM_021243.2 | C6orf115 | Chromosome 6 open reading frame 115 |
| ENST00000275228 | NM_052831 | C6orf192 | Chromosome 6 open reading frame 192 |
| ENST00000331399 | NM_152738 | C6orf218 | Chromosome 6 open reading frame 218 |
| ENST00000368475 | NM_001100411.1 NM_024581.4 | C6orf60 | Chromosome 6 open reading frame 60 |
| ENST00000368596 | | C6orf78 | |
| ENST00000289989 | NM_001013842 | C8orf58 | Chromosome 8 open reading frame 58 |
| ENST00000378956 | NM_148178 NM_148179 | C9orf23 | Chromosome 9 open reading frame 23 |
| ENST00000338437 | NM_001014435.1 NM_005182 | CA7 | Carbonic anhydrase VII |
| ENST00000378357 | NM_001216 | CA9 | Carbonic anhydrase IX |
| ENST00000316803 | NM_001033677 NM_004276 NM_031205 | CABP1 | Calcium binding protein 1 |

TABLE 2-continued

All targets of miR-27a.

| Transcript ID | RefSeq Accession Number | Target Name | Gene Name |
|---|---|---|---|
| ENST00000360228 | NM_000068.3<br>NM_023035.2 | CACNA1A | Calcium channel, voltage-dependent, P/Q type, alpha 1A subunit |
| ENST00000288197 | NM_018398.2 | CACNA2D3 | Calcium channel, voltage-dependent, alpha 2/delta 3 subunit |
| ENST00000252729 | NM_031897<br>NM_145814<br>NM_145815 | CACNG6 | Calcium channel, voltage-dependent, gamma subunit 6 |
| ENST00000296742 | | CAGE1 | Cancer antigen 1 |
| ENST00000339300 | NM_138793 | CANT1 | Calcium activated nucleotidase 1 |
| ENST00000270361 | | CAPN10 | Calpain 10 |
| ENST00000354537 | NM_006615<br>NM_016452 | CAPN9 | Calpain 9 |
| ENST00000380525 | NM_001014437.1<br>NM_001014438.1<br>NM_001751<br>NM_139273.2 | CARS | Cysteinyl-tRNA synthetase |
| ENST00000264645 | | CASC3 | Cancer susceptibility candidate 3 |
| ENST00000356473 | NM_001080124.1<br>NM_001080125.1<br>NM_001228.4<br>NM_033355<br>NM_033356<br>NM_033358 | CASP8 | Caspase 8, apoptosis-related cysteine peptidase |
| ENST00000382436 | | CBWD1 | COBW domain containing 1 |
| ENST00000377349 | | CBWD3 | |
| ENST00000303601 | NM_145020 | CCDC11 | Coiled-coil domain containing 11 |
| ENST00000370276 | NM_206886.2 | CCDC18 | Coiled-coil domain containing 18 |
| ENST00000373602 | | CCDC28B | Coiled-coil domain containing 28B |
| ENST00000284400 | NM_001037325<br>NM_145036 | CCDC46 | Coiled-coil domain containing 46 |
| ENST00000321895 | | CCDC71 | Coiled-coil domain containing 71 |
| ENST00000377638 | | CCDC88 | |
| ENST00000219244 | NM_002987 | CCL17 | Chemokine (C-C motif) ligand 17 |
| ENST00000368261 | NM_001008800<br>NM_001008883.1<br>NM_005998 | CCT3 | Chaperonin containing TCP1, subunit 3 (gamma) |
| ENST00000322008 | | CD151 | CD151 molecule (Raph blood group) |
| ENST00000367063 | NM_000574 | CD55 | CD55 molecule, decay accelerating factor for complement (Cromer blood group) |
| ENST00000381845 | NM_017913 | CDC37L1 | Cell division cycle 37 homolog (*S. cerevisiae*)-like 1 |
| ENST00000361246 | NM_006035 | CDC42BPB | CDC42 binding protein kinase beta (DMPK-like) |
| ENST00000341529 | NM_001795 | CDH5 | Cadherin 5, type 2, VE-cadherin (vascular epithelium) |
| ENST00000268383 | NM_001802 | CDR2 | Cerebellar degeneration-related protein 2, 62 kDa |
| ENST00000382279 | | CDY1_HUMAN | |
| ENST00000306882 | NM_004680<br>NM_170723<br>NM_001003894<br>NM_001003895 | CDY1B | Chromodomain protein, Y-linked, 1B |
| ENST00000372927 | | CENPI | Centromere protein I |
| ENST00000381884 | NM_018451 | CENPJ | Centromere protein J |
| ENST00000262127 | | CEP76 | Centrosomal protein 76 kDa |
| ENST00000355558 | | CFLAR | CASP8 and FADD-like apoptosis regulator |
| ENST00000372833 | | CHCH1_HUMAN | |
| ENST00000290913 | | CHCHD6 | Coiled-coil-helix-coiled-coil-helix domain containing 6 |
| ENST00000342610 | | CHRD | Chordin |
| ENST00000289957 | NM_000749 | CHRNB3 | Cholinergic receptor, nicotinic, beta 3 |
| ENST00000308064 | NM_003654 | CHST1 | Carbohydrate (keratan sulfate Gal-6) sulfotransferase 1 |
| ENST00000358237 | | CI068_HUMAN | |
| ENST00000287159 | | CI070_HUMAN | |
| ENST00000269878 | NM_054113 | CIB3 | Calcium and integrin binding family member 3 |

TABLE 2-continued

All targets of miR-27a.

| Transcript ID | RefSeq Accession Number | Target Name | Gene Name |
|---|---|---|---|
| ENST00000323319 | | CLDN22 | |
| ENST00000355690 | NM_138337 NM_201623 NM_205852 | CLEC12A | C-type lectin domain family 12, member A |
| ENST00000261340 | NM_001004419 NM_013269 | CLEC2D | C-type lectin domain family 2, member D |
| ENST00000316308 | | CLK4 | CDC-like kinase 4 |
| ENST00000245816 | | CLPP | ClpP caseinolytic peptidase, ATP-dependent, proteolytic subunit homolog (*E. coli*) |
| ENST00000281129 | | CN145_HUMAN | |
| ENST00000272602 | NM_001079878.1 NM_001298 | CNGA3 | Cyclic nucleotide gated channel alpha 3 |
| ENST00000356162 | NM_001008225.1 NM_013316.2 | CNOT4 | CCR4-NOT transcription complex, subunit 4 |
| ENST00000307431 | NM_033401.3 NM_138994 | CNTNAP4 | Contactin associated protein-like 4 |
| ENST00000307149 | | COG7 | Component of oligomeric golgi complex 7 |
| ENST00000373668 | NM_001856.3 | COL16A1 | Collagen, type XVI, alpha 1 |
| ENST00000370819 | NM_030820.3 | COL21A1 | Collagen, type XXI, alpha 1 |
| ENST00000328333 | NM_000094 | COL7A1 | Collagen, type VII, alpha 1 (epidermolysis bullosa, dystrophic, dominant and recessive) |
| ENST00000261037 | | COL8A1 | Collagen, type VIII, alpha 1 |
| ENST00000333188 | | COPB2 | Coatomer protein complex, subunit beta 2 (beta prime) |
| ENST00000253484 | NM_001866 | COX7B | Cytochrome c oxidase subunit VIIb |
| ENST00000314133 | NM_004074 | COX8A | Cytochrome c oxidase subunit 8A (ubiquitous) |
| ENST00000264193 | NM_000097 | CPOX | Coproporphyrinogen oxidase |
| ENST00000378951 | | CPSF3L | Cleavage and polyadenylation specific factor 3-like |
| ENST00000294997 | | CR1L | Complement component (3b/4b) receptor 1-like |
| ENST00000367401 | NM_201253 | CRB1 | Crumbs homolog 1 (*Drosophila*) |
| ENST00000339139 | | CRISP2 | Cysteine-rich secretory protein 2 |
| ENST00000262982 | NM_001316 | CSE1L | CSE1 chromosome segregation 1-like (yeast) |
| ENST00000331769 | NM_000759 NM_172219.1 NM_172220 | CSF3 | Colony stimulating factor 3 (granulocyte) |
| ENST00000383738 | NM_006574 | CSPG5 | Chondroitin sulfate proteoglycan 5 (neuroglycan C) |
| ENST00000311083 | | CSRP2 | Cysteine and glycine-rich protein 2 |
| ENST00000201961 | | CT112_HUMAN | |
| ENST00000361944 | NM_014633 | CTR9 | Ctr9, Paf1/RNA polymerase II complex component, homolog (*S. cerevisiae*) |
| ENST00000368980 | NM_000396 | CTSK | Cathepsin K |
| ENST00000217131 | NM_001336 | CTSZ | Cathepsin Z |
| ENST00000310126 | | CU058_HUMAN | |
| ENST00000372453 | NM_173494 | CXorf41 | Chromosome X open reading frame 41 |
| ENST00000285949 | | CYP26C1 | Cytochrome P450, family 26, subfamily C, polypeptide 1 |
| ENST00000371364 | NM_016593 | CYP39A1 | Cytochrome P450, family 39, subfamily A, polypeptide 1 |
| ENST00000336411 | NM_017460 | CYP3A4 | Cytochrome P450, family 3, subfamily A, polypeptide 4 |
| ENST00000379654 | NM_022820 NM_057095 NM_057096 | CYP3A43 | Cytochrome P450, family 3, subfamily A, polypeptide 43 |
| ENST00000368336 | NM_004632 NM_033657 | DAP3 | Death associated protein 3 |
| ENST00000250863 | NM_001351.2 | DAZL | Deleted in azoospermia-like |
| ENST00000355857 | | DBI | Diazepam binding inhibitor (GABA receptor modulator, acyl-Coenzyme A binding protein) |
| ENST00000339452 | NM_017639 | DCHS2 | Dachsous 2 (*Drosophila*) |

TABLE 2-continued

All targets of miR-27a.

| Transcript ID | RefSeq Accession Number | Target Name | Gene Name |
|---|---|---|---|
| ENST00000378278 | NM_001033855 NM_001033857 NM_001033858 NM_022487 | DCLRE1C | DNA cross-link repair 1C (PSO2 homolog, *S. cerevisiae*) |
| ENST00000368419 | NM_152494 | DCST1 | DC-STAMP domain containing 1 |
| ENST00000378601 | | DDB2 | Damage-specific DNA binding protein 2, 48 kDa |
| ENST00000378233 | | DDX3X_HUMAN | |
| ENST00000258772 | | DDX56 | DEAD (Asp-Glu-Ala-Asp) box polypeptide 56 |
| ENST00000381131 | NM_018369 | DEPDC1B | DEP domain containing 1B |
| ENST00000025429 | NM_015954.2 | DERA | 2-deoxyribose-5-phosphate aldolase homolog (*C. elegans*) |
| ENST00000374057 | NM_001083885.1 NM_015404 | DFNB31 | Deafness, autosomal recessive 31 |
| ENST00000284688 | NM_018180 | DHX32 | DEAH (Asp-Glu-Ala-His) box polypeptide 32 |
| ENST00000266070 | NM_022105 NM_033081 NM_080796 NM_080797 | DIDO1 | Death inducer-obliterator 1 |
| ENST00000366636 | | DISC1 | Disrupted in schizophrenia 1 |
| ENST00000373347 | | DLGP3_HUMAN | |
| ENST00000222598 | | DLX5 | Distal-less homeobox 5 |
| ENST00000379075 | NM_001035516.1 NM_033317 | DMKN | Dermokine |
| ENST00000373718 | NM_021800 NM_201262 | DNAJC12 | DnaJ (Hsp40) homolog, subfamily C, member 12 |
| ENST00000382564 | NM_145261 | DNAJC19 | DnaJ (Hsp40) homolog, subfamily C, member 19 |
| ENST00000276570 | | DNAJC5B | DnaJ (Hsp40) homolog, subfamily C, member 5 beta |
| ENST00000367732 | NM_015569.2 | DNM3 | Dynamin 3 |
| ENST00000268793 | NM_022357 | DPEP3 | Dipeptidase 3 |
| ENST00000263084 | | DPH1 | DPH1 homolog (*S. cerevisiae*) |
| ENST00000370107 | | DPH5_HUMAN | |
| ENST00000242158 | | DRC1A_HUMAN | |
| ENST00000305784 | | DTYMK | Deoxythymidylate kinase (thymidylate kinase) |
| ENST00000358896 | NM_017803 | DUS2L | Dihydrouridine synthase 2-like, SMM1 homolog (*S. cerevisiae*) |
| ENST00000380838 | NM_004422 | DVL2 | Dishevelled, dsh homolog 2 (*Drosophila*) |
| ENST00000260605 | NM_001012665.1 NM_016008 | DYNC2LI1 | Dynein, cytoplasmic 2, light intermediate chain 1 |
| ENST00000367089 | NM_006519 | DYNLT1 | Dynein, light chain, Tctex-type 1 |
| ENST00000250024 | NM_024680 | E2F8 | E2F transcription factor 8 |
| ENST00000221847 | | EBI3 | Epstein-Barr virus induced gene 3 |
| ENST00000378284 | NM_032565 | EBPL | Emopamil binding protein-like |
| ENST00000264205 | NM_001397 | ECE1 | Endothelin converting enzyme 1 |
| ENST00000351385 | NM_001037324 NM_001100120.1 NM_001100121.1 NM_014693 NM_032331 | ECE2 | Endothelin converting enzyme 2 |
| ENST00000304546 | | ECEL1 | Endothelin converting enzyme-like 1 |
| ENST00000220959 | | EDD1 | |
| ENST00000264263 | | EFG1_HUMAN | |
| ENST00000333845 | NM_005155 NM_030652 NM_138717 | EGFL8 | EGF-like-domain, multiple 8 |
| ENST00000253108 | | EIF3S4 | |
| ENST00000381683 | | EIF3S6IP | |
| ENST00000228741 | NM_005230 | ELK3 | ELK3, ETS-domain protein (SRF accessory protein 2) |
| ENST00000319359 | | ELL3 | Elongation factor RNA polymerase II-like 3 |
| ENST00000163344 | NM_022821 | ELOVL1 | Elongation of very long chain fatty acids (FEN1/Elo2, SUR4/Elo3, yeast)-like 1 |
| ENST00000334192 | NM_001008707 NM_004434 | EML1 | Echinoderm microtubule associated protein like 1 |
| ENST00000372642 | | ENDOG | Endonuclease G |
| ENST00000376666 | | ENTPD6 | Ectonucleoside triphosphate |

TABLE 2-continued

All targets of miR-27a.

| Transcript ID | RefSeq Accession Number | Target Name | Gene Name |
|---|---|---|---|
| | | | diphosphohydrolase 6 (putative function) |
| ENST00000374311 | | ERGIC3 | ERGIC and golgi 3 |
| ENST00000355449 | | EVL | Enah/Vasp-like |
| ENST00000370902 | NM_016046 | EXOSC1 | Exosome component 1 |
| ENST00000320356 | | EZH2 | Enhancer of zeste homolog 2 (*Drosophila*) |
| ENST00000375551 | NM_000504 | F10 | Coagulation factor X |
| ENST00000355910 | NM_001007524 | F8A3 | Coagulation factor VIII-associated (intronic transcript) 3 |
| ENST00000301838 | NM_003824 | FADD | Fas (TNFRSF6)-associated via death domain |
| ENST00000338446 | NM_001033030 NM_001033031 NM_001033032 NM_018147 | FAIM | Fas apoptotic inhibitory molecule |
| ENST00000216214 | NM_017911 | FAM118A | Family with sequence similarity 118, member A |
| ENST00000336378 | | FAM21D | |
| ENST00000359512 | | FAM39A | |
| ENST00000357985 | | FAM3B | Family with sequence similarity 3, member B |
| ENST00000298575 | NM_152421 | FAM69B | Family with sequence similarity 69, member B |
| ENST00000373736 | | FAM77C | |
| ENST00000357809 | | FAM82A | Family with sequence similarity 82, member A |
| ENST00000300030 | | FAM96A | Family with sequence similarity 96, member A |
| ENST00000314606 | | FARSLA | |
| ENST00000367721 | NM_000639 | FASLG | Fas ligand (TNF superfamily, member 6) |
| ENST00000369956 | | FBX37_HUMAN | |
| ENST00000258200 | | FBXL8 | |
| ENST00000382824 | NM_012173 NM_183420 NM_183421 | FBXO25 | F-box protein 25 |
| ENST00000368176 | | FCRL1 | Fc receptor-like 1 |
| ENST00000368181 | NM_030764 NM_138738 | FCRL2 | Fc receptor-like 2 |
| ENST00000339348 | NM_001004310 | FCRL6 | Fc receptor-like 6 |
| ENST00000371489 | NM_013451.2 NM_133337.1 | FER1L3 | Fer-1-like 3, myoferlin (*C. elegans*) |
| ENST00000343958 | | FGD6_HUMAN | |
| ENST00000370603 | NM_004114 NM_033642 | FGF13 | Fibroblast growth factor 13 |
| ENST00000341420 | NM_013281 NM_198391 | FLRT3 | Fibronectin leucine rich transmembrane protein 3 |
| ENST00000357867 | NM_002026 NM_054034.2 NM_212474 NM_212476.1 NM_212482.1 | FN1 | Fibronectin 1 |
| ENST00000379745 | NM_022823 | FNDC4 | Fibronectin type III domain containing 4 |
| ENST00000370019 | NM_173532 | FNDC7 | Fibronectin type III domain containing 7 |
| ENST00000302177 | NM_004497 | FOXA3 | Forkhead box A3 |
| ENST00000354663 | NM_005479 | FRAT1 | Frequently rearranged in advanced T-cell lymphomas |
| ENST00000373018 | NM_006653 | FRS3 | Fibroblast growth factor receptor substrate 3 |
| ENST00000166139 | NM_005860 | FSTL3 | Follistatin-like 3 (secreted glycoprotein) |
| ENST00000250113 | NM_004860.2 | FXR2 | Fragile X mental retardation, autosomal homolog 2 |
| ENST00000342879 | | FXYD5 | FXYD domain containing ion transport regulator 5 |
| ENST00000367029 | | G0S2 | G0/G1switch 2 |
| ENST00000269097 | | G6PC3 | Glucose 6 phosphatase, catalytic, 3 |
| ENST00000259056 | | GALNT5 | UDP-N-acetyl-alpha-D-galactosamine:polypeptide N-acetylgalactosaminyltransferase 5 (GalNAc-T5) |

TABLE 2-continued

All targets of miR-27a.

| Transcript ID | RefSeq Accession Number | Target Name | Gene Name |
|---|---|---|---|
| ENST00000227756 | | GALNTL4 | UDP-N-acetyl-alpha-D-galactosamine:polypeptide N-acetylgalactosaminyltransferase-like 4 |
| ENST00000373387 | | GARNL3 | GTPase activating Rap/RanGAP domain-like 3 |
| ENST00000265296 | NM_002047.2 | GARS | Glycyl-tRNA synthetase |
| ENST00000357389 | | GAS6 | Growth arrest-specific 6 |
| ENST00000341105 | | GATA2 | GATA binding protein 2 |
| ENST00000372043 | | GBGT1 | Globoside alpha-1,3-N-acetylgalactosaminyltransferase 1 |
| ENST00000233612 | NM_012198 | GCA | Grancalcin, EF-hand calcium binding protein |
| ENST00000379596 | NM_001491 NM_145649 NM_145655 | GCNT2 | Glucosaminyl (N-acetyl) transferase 2, I-branching enzyme (I blood group) |
| ENST00000322348 | NM_016591 | GCNT4 | Glucosaminyl (N-acetyl) transferase 4, core 2 (beta-1,6-N-acetylglucosaminyltransferase) |
| ENST00000378673 | NM_005260 | GDF9 | Growth differentiation factor 9 |
| ENST00000253778 | NM_005110.2 | GFPT2 | Glutamine-fructose-6-phosphate transaminase 2 |
| ENST00000313543 | | GIMAP7 | GTPase, IMAP family member 7 |
| ENST00000357424 | NM_004123 | GIP | Gastric inhibitory polypeptide |
| ENST00000241125 | NM_021954 | GJA3 | Gap junction protein, alpha 3, 46 kDa |
| ENST00000331334 | | GLRX5 | Glutaredoxin 5 |
| ENST00000318348 | NM_016433 | GLTP | Glycolipid transfer protein |
| ENST00000303210 | | GNB2 | Guanine nucleotide binding protein (G protein), beta polypeptide 2 |
| ENST00000354540 | NM_014366 NM_206825.1 NM_206826.1 | GNL3 | Guanine nucleotide binding protein-like 3 (nucleolar) |
| ENST00000225567 | NM_004287.3 NM_054022 | GOSR2 | Golgi SNAP receptor complex member 2 |
| ENST00000334304 | NM_145290 | GPR125 | G protein-coupled receptor 125 |
| ENST00000267015 | NM_020370 | GPR84 | G protein-coupled receptor 84 |
| ENST00000315614 | | GPS2 | G protein pathway suppressor 2 |
| ENST00000309731 | NM_001012642 | GRAMD2 | GRAM domain containing 2 |
| ENST00000347612 | | GRIN2C | Glutamate receptor, ionotropic, N-methyl D-aspartate 2C |
| ENST00000369106 | | GRK5 | G protein-coupled receptor kinase 5 |
| ENST00000296479 | | GRM2 | Glutamate receptor, metabotropic 2 |
| ENST00000319065 | NM_000843 | GRM6 | Glutamate receptor, metabotropic 6 |
| ENST00000256857 | NM_001012512.1 NM_001012513.1 NM_002091 | GRP | Gastrin-releasing peptide |
| ENST00000086933 | | GSCL | |
| ENST00000219627 | NM_002094.2 | GSPT1 | G1 to S phase transition 1 |
| ENST00000340438 | NM_018094 | GSPT2 | G1 to S phase transition 2 |
| ENST00000221130 | NM_000637 | GSR | Glutathione reductase |
| ENST00000267869 | NM_004492 | GTF2A2 | General transcription factor IIA, 2, 12 kDa |
| ENST00000376329 | | GTF2H4 | General transcription factor IIH, polypeptide 4, 52 kDa |
| ENST00000332377 | NM_207118 | GTF2H5 | General transcription factor IIH, polypeptide 5 |
| ENST00000372108 | NM_012087 | GTF3C5 | General transcription factor IIIC, polypeptide 5, 63 kDa |
| ENST00000323798 | NM_002103 | GYS1 | Glycogen synthase 1 (muscle) |
| ENST00000296417 | | H2AFZ | H2A histone family, member Z |
| ENST00000375852 | NM_002110 | HCK | Hemopoietic cell kinase |
| ENST00000314583 | | HCLS1 | Hematopoietic cell-specific Lyn substrate 1 |
| ENST00000373705 | | HCRTR1 | Hypocretin (orexin) receptor 1 |
| ENST00000262069 | NM_014707.1 NM_058176.2 NM_058177.2 NM_178423.1 NM_178425.2 | HDAC9 | Histone deacetylase 9 |

TABLE 2-continued

All targets of miR-27a.

| Transcript ID | RefSeq Accession Number | Target Name | Gene Name |
|---|---|---|---|
| ENST00000300605 | | HDHD2 | Haloacid dehalogenase-like hydrolase domain containing 2 |
| ENST00000374178 | NM_031219 | HDHD3 | Haloacid dehalogenase-like hydrolase domain containing 3 |
| ENST00000303775 | | HEMK2_HUMAN | |
| ENST00000329138 | | HGS | Hepatocyte growth factor-regulated tyrosine kinase substrate |
| ENST00000370940 | NM_001031693 NM_001036645 NM_001036646 NM_007071 | HHLA3 | HERV-H LTR-associating 3 |
| ENST00000229633 | NM_138571 | HINT3 | Histidine triad nucleotide binding protein 3 |
| ENST00000336926 | NM_005338 | HIP1 | Huntingtin interacting protein 1 |
| ENST00000360010 | | HKR1 | GLI-Kruppel family member HKR1 |
| ENST00000366903 | | HLX1 | |
| ENST00000380749 | | HMGN1 | High-mobility group nucleosome binding domain 1 |
| ENST00000376263 | NM_002140 NM_031262 NM_031263 | HNRPK | Heterogeneous nuclear ribonucleoprotein K |
| ENST00000336726 | NM_152510.2 | HORMAD2 | HORMA domain containing 2 |
| ENST00000222753 | NM_000522 | HOXA13 | Homeobox A13 |
| ENST00000239144 | NM_024016 | HOXB8 | Homeobox B8 |
| ENST00000243108 | | HOXC6 | |
| ENST00000306324 | NM_014621 | HOXD4 | Homeobox D4 |
| ENST00000299671 | | HSBP1 | Heat shock factor binding protein 1 |
| ENST00000225929 | NM_000413 | HSD17B1 | Hydroxysteroid (17-beta) dehydrogenase 1 |
| ENST00000373024 | | I5P2_HUMAN | |
| ENST00000235971 | | ID3 | Inhibitor of DNA binding 3, dominant negative helix-loop-helix protein |
| ENST00000370747 | | IFI44 | Interferon-induced protein 44 |
| ENST00000276927 | NM_024013 | IFNA1 | Interferon, alpha 1 |
| ENST00000380205 | NM_002170 | IFNA8 | Interferon, alpha 8 |
| ENST00000229135 | NM_000619 | IFNG | Interferon, gamma |
| ENST00000296266 | NM_018262 NM_052985 NM_052989 NM_052990 | IFT122 | Intraflagellar transport 122 homolog (Chlamydomonas) |
| ENST00000198587 | | IGSF9 | Immunoglobulin superfamily, member 9 |
| ENST00000367120 | NM_014002 | IKBKE | Inhibitor of kappa light polypeptide gene enhancer in B-cells, kinase epsilon |
| ENST00000290200 | | IL10RB | Interleukin 10 receptor, beta |
| ENST00000305579 | | IL12A | Interleukin 12A (natural killer cell stimulatory factor 1, cytotoxic lymphocyte maturation factor 1, p35) |
| ENST00000322153 | NM_005535.1 NM_153701 | IL12RB1 | Interleukin 12 receptor, beta 1 |
| ENST00000264260 | NM_003853 | IL18RAP | Interleukin 18 receptor accessory protein |
| ENST00000367095 | NM_005449 | IL24 | Interleukin 24 |
| ENST00000276110 | | IL2RG | Interleukin 2 receptor, gamma (severe combined immunodeficiency) |
| ENST00000368485 | NM_000565 NM_181359 | IL6R | Interleukin 6 receptor |
| ENST00000259239 | | IMP4 | IMP4, U3 small nucleolar ribonucleoprotein, homolog (yeast) |
| ENST00000269159 | | IMPA2 | Inositol(myo)-1(or 4)-monophosphatase 2 |
| ENST00000322522 | NM_002194 | INPP1 | Inositol polyphosphate-1-phosphatase |
| ENST00000265239 | | IQCG | IQ motif containing G |
| ENST00000356669 | NM_016123 | IRAK4 | Interleukin-1 receptor-associated kinase 4 |

TABLE 2-continued

All targets of miR-27a.

| Transcript ID | RefSeq Accession Number | Target Name | Gene Name |
|---|---|---|---|
| ENST00000258886 | NM_004136 | IREB2 | Iron-responsive element binding protein 2 |
| ENST00000303389 | | IRF2 | Interferon regulatory factor 2 |
| ENST00000268638 | NM_002163 | IRF8 | Interferon regulatory factor 8 |
| ENST00000379231 | | ISG20L1 | Interferon stimulated exonuclease gene 20 kDa-like 1 |
| ENST00000249842 | NM_005545 NM_201526 | ISLR | Immunoglobulin superfamily containing leucine-rich repeat |
| ENST00000268297 | NM_005353 | ITGAD | Integrin, alpha D |
| ENST00000335404 | NM_198510 | ITIH5L | Inter-alpha (globulin) inhibitor H5-like |
| ENST00000380883 | NM_006277 NM_019595 NM_147152.1 | ITSN2 | Intersectin 2 |
| ENST00000383816 | | JAGN1 | Jagunal homolog 1 (*Drosophila*) |
| ENST00000327520 | | JHD2C_HUMAN | |
| ENST00000335080 | NM_018039 | JMJD2D | Jumonji domain containing 2D |
| ENST00000335647 | NM_007044 | KATNA1 | Katanin p60 (ATPase-containing) subunit A 1 |
| ENST00000328224 | NM_002233.2 | KCNA4 | Potassium voltage-gated channel, shaker-related subfamily, member 4 |
| ENST00000316071 | NM_002241 | KCNJ10 | Potassium inwardly-rectifying channel, subfamily J, member 10 |
| ENST00000233826 | NM_002242 | KCNJ13 | Potassium inwardly-rectifying channel, subfamily J, member 13 |
| ENST00000295101 | NM_002239 | KCNJ3 | Potassium inwardly-rectifying channel, subfamily J, member 3 |
| ENST00000366621 | | KCNK1 | Potassium channel, subfamily K, member 1 |
| ENST00000353172 | | KCTD14 | |
| ENST00000379108 | NM_198404 | KCTD4 | Potassium channel tetramerisation domain containing 4 |
| ENST00000360029 | NM_198353 | KCTD8 | Potassium channel tetramerisation domain containing 8 |
| ENST00000297423 | NM_001080394.1 | KIAA0146 | KIAA0146 |
| ENST00000370992 | | KIAA0690 | |
| ENST00000287546 | | KIAA0804 | |
| ENST00000283351 | NM_014939 | KIAA1012 | KIAA1012 |
| ENST00000264501 | NM_015312.2 | KIAA1109 | KIAA1109 |
| ENST00000296121 | | KIAA1143 | KIAA1143 |
| ENST00000328839 | NM_020958 NM_058237 | KIAA1622 | KIAA1622 |
| ENST00000369271 | | KIAA1914 | |
| ENST00000378843 | NM_022113.3 | KIF13A | Kinesin family member 13A |
| ENST00000353409 | NM_015074 NM_183416 | KIF1B | Kinesin family member 1B |
| ENST00000378746 | NM_007054 | KIF3A | Kinesin family member 3A |
| ENST00000332780 | NM_173546 | KLHDC8B | Kelch domain containing 8B |
| ENST00000378222 | NM_002267 | KPNA3 | Karyopherin alpha 3 (importin alpha 4) |
| ENST00000329122 | NM_181602 | KRTAP6-1 | Keratin associated protein 6-1 |
| ENST00000251646 | | KRTHA3B | |
| ENST00000293670 | | KRTHB3 | |
| ENST00000264170 | NM_001032998 NM_003937 | KYNU | Kynureninase (L-kynurenine hydrolase) |
| ENST00000373134 | | L3MBTL | |
| ENST00000381167 | | LAPTM4A | Lysosomal-associated protein transmembrane 4 alpha |
| ENST00000357788 | | LCN8 | Lipocalin 8 |
| ENST00000371103 | | LCOR_HUMAN | |
| ENST00000280706 | NM_144972 | LDHAL6A | Lactate dehydrogenase A-like 6A |
| ENST00000254301 | | LGALS3 | Lectin, galactoside-binding, soluble, 3 |
| ENST00000263726 | NM_033343 | LHX4 | LIM homeobox 4 |
| ENST00000261203 | | LIN7A | Lin-7 homolog A (*C. elegans*) |
| ENST00000267102 | | LMBR1L | Limb region 1 homolog (mouse)-like |

TABLE 2-continued

All targets of miR-27a.

| Transcript ID | RefSeq Accession Number | Target Name | Gene Name |
|---|---|---|---|
| ENST00000296603 | NM_001007527 | LMBRD2 | LMBR1 domain containing 2 |
| ENST00000368300 | NM_005572 NM_170707 NM_170708 | LMNA | Lamin A/C |
| ENST00000376633 | NM_002335 | LRP5 | Low density lipoprotein receptor-related protein 5 |
| ENST00000261349 | NM_002336 | LRP6 | Low density lipoprotein receptor-related protein 6 |
| ENST00000373324 | NM_001005373 NM_001005374 NM_138361 | LRSAM1 | Leucine rich repeat and sterile alpha motif containing 1 |
| ENST00000379953 | | LY86 | Lymphocyte antigen 86 |
| ENST00000244333 | | LYPD3 | LY6/PLAUR domain containing 3 |
| ENST00000374505 | NM_007260 NR_001444.3 | LYPLA2 | Lysophospholipase II |
| ENST00000215739 | NM_006767 | LZTR1 | Leucine-zipper-like transcription regulator 1 |
| ENST00000372173 | NM_001003690.1 NM_014628 | MAD2L1BP | MAD2L1 binding protein |
| ENST00000285879 | NM_005462 | MAGEC1 | Melanoma antigen family C, 1 |
| ENST00000261483 | | MAN2A1 | Mannosidase, alpha, class 2A, member 1 |
| ENST00000366920 | NM_005922 NM_006724 | MAP3K4 | Mitogen-activated protein kinase kinase kinase 4 |
| ENST00000357955 | NM_004635 | MAPKAPK3 | Mitogen-activated protein kinase-activated protein kinase 3 |
| ENST00000294506 | | MATN1 | Matrilin 1, cartilage matrix protein |
| ENST00000359787 | | MB | Myoglobin |
| ENST00000271648 | NM_021960 NM_182763 | MCL1 | Myeloid cell leukemia sequence 1 (BCL2-related) |
| ENST00000230321 | NM_005586 | MDFI | MyoD family inhibitor |
| ENST00000267984 | NM_022566 | MESDC1 | Mesoderm development candidate 1 |
| ENST00000372811 | | MFSD2 | Major facilitator superfamily domain containing 2 |
| ENST00000312952 | NM_004668.1 | MGAM | Maltase-glucoamylase (alpha-glucosidase) |
| ENST00000371994 | NM_004897 | MINPP1 | Multiple inositol polyphosphate histidine phosphatase, 1 |
| ENST00000231790 | NM_000249 | MLH1 | MutL homolog 1, colon cancer, nonpolyposis type 2 (*E. coli*) |
| ENST00000338530 | NM_001042467.1 NM_024101 | MLPH | Melanophilin |
| ENST00000182377 | NM_018099 | MLSTD1 | Male sterility domain containing 1 |
| ENST00000345114 | NM_032951 NM_032952.2 NM_032953.2 NM_032954 | MLXIPL | MLX interacting protein-like |
| ENST00000262065 | NM_012329 | MMD | Monocyte to macrophage differentiation-associated |
| ENST00000368141 | NM_002432 | MNDA | Myeloid cell nuclear differentiation antigen |
| ENST00000296473 | | MON1A | MON1 homolog A (yeast) |
| ENST00000333676 | | MRPL12 | Mitochondrial ribosomal protein L12 |
| ENST00000306185 | | MRPL13 | Mitochondrial ribosomal protein L13 |
| ENST00000379666 | | MRPL33 | Mitochondrial ribosomal protein L33 |
| ENST00000309352 | NM_032478 | MRPL38 | Mitochondrial ribosomal protein L38 |
| ENST00000370234 | NM_032112 NM_176792 NM_176793 NM_176794 | MRPL43 | Mitochondrial ribosomal protein L43 |
| ENST00000312513 | NM_032351 | MRPL45 | Mitochondrial ribosomal protein L45 |
| ENST00000372940 | NM_016065 | MRPS16 | Mitochondrial ribosomal protein S16 |
| ENST00000313608 | | MRPS23 | Mitochondrial ribosomal protein S23 |
| ENST00000276585 | | MRPS28 | Mitochondrial ribosomal protein S28 |
| ENST00000322684 | | MSI2 | Musashi homolog 2 (*Drosophila*) |

TABLE 2-continued

All targets of miR-27a.

| Transcript ID | RefSeq Accession Number | Target Name | Gene Name |
|---|---|---|---|
| ENST00000314404 | NM_017762.2 | MTMR10 | Myotubularin related protein 10 |
| ENST00000323456 | NM_004687 | MTMR4 | Myotubularin related protein 4 |
| ENST00000374852 | NM_017677 | MTMR8 | Myotubularin related protein 8 |
| ENST00000381954 | | MUC20 | Mucin 20, cell surface associated |
| ENST00000303270 | | MXD3 | MAX dimerization protein 3 |
| ENST00000252102 | | NDUFA2 | NADH dehydrogenase (ubiquinone) 1 alpha subcomplex, 2, 8 kDa |
| ENST00000381417 | | NDUFS4 | NADH dehydrogenase (ubiquinone) Fe—S protein 4, 18 kDa (NADH-coenzyme Q reductase) |
| ENST00000375569 | | NECAP2 | NECAP endocytosis associated 2 |
| ENST00000250495 | | NEDD8 | Neural precursor cell expressed, developmentally down-regulated 8 |
| ENST00000379072 | NM_012224.1 | NEK1 | NIMA (never in mitosis gene a)-related kinase 1 |
| ENST00000366999 | NM_002497 | NEK2 | NIMA (never in mitosis gene a)-related kinase 2 |
| ENST00000356175 | NM_000267 NM_001042492.1 | NF1 | Neurofibromin 1 (neurofibromatosis, von Recklinghausen disease, Watson disease) |
| ENST00000355469 | NM_145912 | NFAM1 | NFAT activating protein with ITAM motif 1 |
| ENST00000361004 | NM_006164.2 | NFE2L2 | Nuclear factor (erythroid-derived 2)-like 2 |
| ENST00000375724 | NM_005384 | NFIL3 | Nuclear factor, interleukin 3 regulated |
| ENST00000368009 | NM_005600 | NIT1 | Nitrilase 1 |
| ENST00000285279 | | NM_030796.3 | |
| ENST00000360476 | NM_021077 NM_205858.1 | NMB | Neuromedin B |
| ENST00000255262 | NM_020167 | NMUR2 | Neuromedin U receptor 2 |
| ENST00000382421 | | NOL1 | Nucleolar protein 1, 120 kDa |
| ENST00000328848 | NM_018648 | NOLA3 | Nucleolar protein family A, member 3 (H/ACA small nucleolar RNPs) |
| ENST00000375043 | NM_004557 | NOTCH4 | Notch homolog 4 (*Drosophila*) |
| ENST00000367158 | NM_015718 | NOX3 | NADPH oxidase 3 |
| ENST00000301284 | | NP_001001520.1 | |
| ENST00000389349 | | NP_001001671.1 | |
| ENST00000304823 | | NP_001004341.1 | |
| ENST00000351071 | | NP_001005751.1 | |
| ENST00000333305 | | NP_001007190.1 | |
| ENST00000370732 | | NP_001007552.1 | |
| ENST00000341942 | | NP_001008396.1 | |
| ENST00000298943 | | NP_001010908.1 | |
| ENST00000378704 | | NP_001012457.1 | |
| ENST00000370494 | | NP_001013007.1 | |
| ENST00000344380 | | NP_001013646.1 | |
| ENST00000378909 | | NP_001017363.1 | |
| ENST00000370743 | | NP_001017417.1 | |
| ENST00000370737 | | NP_001017435.1 | |
| ENST00000381461 | | NP_001017969.1 | |
| ENST00000295220 | | NP_001025167.1 | |
| ENST00000374412 | | NP_001034934.1 | |
| ENST00000294916 | | NP_001035043.2 | |
| ENST00000382142 | | NP_001035536.1 | |
| ENST00000329687 | | NP_001111.2 | |
| ENST00000355848 | | NP_006324.1 | |
| ENST00000323199 | | NP_031375.3 | |
| ENST00000357765 | | NP_054763.2 | |
| ENST00000357899 | | NP_054874.3 | |
| ENST00000377264 | | NP_055919.1 | |
| ENST00000381237 | | NP_056174.1 | |
| ENST00000296444 | | NP_057563.3 | |
| ENST00000313565 | | NP_060000.1 | |
| ENST00000321489 | | NP_060028.2 | |
| ENST00000367501 | | NP_060143.3 | |
| ENST00000265154 | | NP_060170.1 | |
| ENST00000238788 | | NP_060197.3 | |
| ENST00000357242 | | NP_060222.2 | |
| ENST00000379207 | | NP_060463.1 | |

TABLE 2-continued

All targets of miR-27a.

| Transcript ID | RefSeq Accession Number | Target Name | Gene Name |
|---|---|---|---|
| ENST00000358591 | | NP_060741.2 | |
| ENST00000358867 | | NP_060950.2 | |
| ENST00000329540 | | NP_061930.1 | |
| ENST00000359236 | | NP_061959.2 | |
| ENST00000270066 | | NP_061981.1 | |
| ENST00000263657 | | NP_064528.1 | |
| ENST00000336353 | | NP_064580.1 | |
| ENST00000319688 | | NP_065789.1 | |
| ENST00000368842 | | NP_071409.2 | |
| ENST00000317623 | | NP_071940.3 | |
| ENST00000295079 | | NP_078796.1 | |
| ENST00000371410 | | NP_078804.1 | |
| ENST00000358067 | | NP_078896.3 | |
| ENST00000238936 | | NP_079065.2 | |
| ENST00000278886 | | NP_079452.3 | |
| ENST00000272521 | | NP_085054.1 | |
| ENST00000369218 | | NP_110423.3 | |
| ENST00000263776 | | NP_115981.1 | |
| ENST00000367003 | | NP_116094.2 | |
| ENST00000376396 | | NP_296375.1 | |
| ENST00000300079 | | NP_542392.2 | |
| ENST00000290894 | | NP_612365.1 | |
| ENST00000341392 | | NP_620134.2 | |
| ENST00000355682 | | NP_653178.1 | |
| ENST00000301037 | | NP_653211.1 | |
| ENST00000002125 | | NP_653337.1 | |
| ENST00000335360 | | NP_689552.2 | |
| ENST00000281961 | | NP_689603.1 | |
| ENST00000282259 | | NP_689618.2 | |
| ENST00000367136 | | NP_689704.3 | |
| ENST00000370720 | | NP_689795.2 | |
| ENST00000296468 | | NP_689991.1 | |
| ENST00000292616 | | NP_690852.1 | |
| ENST00000304584 | | NP_699196.1 | |
| ENST00000296953 | | NP_705835.1 | |
| ENST00000265453 | | NP_775795.2 | |
| ENST00000329378 | | NP_775936.1 | |
| ENST00000378660 | | NP_775966.1 | |
| ENST00000335211 | | NP_840059.1 | |
| ENST00000380814 | | NP_861450.1 | |
| ENST00000334588 | | NP_872620.1 | |
| ENST00000285718 | | NP_878908.1 | |
| ENST00000383694 | | NP_878913.1 | |
| ENST00000340369 | | NP_919269.2 | |
| ENST00000343063 | | NP_919288.1 | |
| ENST00000275053 | | NP_940870.1 | |
| ENST00000306862 | | NP_940968.1 | |
| ENST00000237186 | | NP_944602.1 | |
| ENST00000317449 | | NP_981967.1 | |
| ENST00000354805 | | NP_982273.1 | |
| ENST00000377137 | | NP_997211.1 | |
| ENST00000357485 | | NP_997646.1 | |
| ENST00000339255 | NM_020448 | NPAL3 | NIPA-like domain containing 3 |
| ENST00000269228 | NM_000271 | NPC1 | Niemann-Pick disease, type C1 |
| ENST00000265634 | NM_002523 | NPTX2 | Neuronal pentraxin II |
| ENST00000242152 | | NPY | Neuropeptide Y |
| ENST00000358384 | | NR_002822.1 | |
| ENST00000332894 | | NR2F2 | Nuclear receptor subfamily 2, group F, member 2 |
| ENST00000291442 | NM_005234 | NR2F6 | Nuclear receptor subfamily 2, group F, member 6 |
| ENST00000314171 | NM_030759 | NRBF2 | Nuclear receptor binding factor 2 |
| ENST00000382740 | | NSG1_HUMAN | |
| ENST00000219066 | | NTHL1 | Nth endonuclease III-like 1 (*E. coli*) |
| ENST00000231498 | | NU155_HUMAN | |
| ENST00000361681 | | NU6M_HUMAN | |
| ENST00000367157 | | NUAK2 | NUAK family, SNF1-like kinase, 2 |
| ENST00000262302 | | NUBP2 | Nucleotide binding protein 2 (MinD homolog, *E. coli*) |
| ENST00000334513 | | NUD17_HUMAN | |
| ENST00000339154 | | NUDT6 | Nudix (nucleoside diphosphate linked moiety X)-type motif 6 |
| ENST00000366680 | NM_018230 | NUP133 | Nucleoporin 133 kDa |

TABLE 2-continued

All targets of miR-27a.

| Transcript ID | RefSeq Accession Number | Target Name | Gene Name |
|---|---|---|---|
| ENST00000294172 | | NXF1 | Nuclear RNA export factor 1 |
| ENST00000372107 | NM_018698 | NXT2 | Nuclear transport factor 2-like export factor 2 |
| ENST00000324607 | | OACT1 | |
| ENST00000366706 | | OBSCN | Obscurin, cytoskeletal calmodulin and titin-interacting RhoGEF |
| ENST00000334011 | NM_152635 | OIT3 | Oncoprotein induced transcript 3 |
| ENST00000371797 | NM_006334 NM_014279 | OLFM1 | Olfactomedin 1 |
| ENST00000333973 | NM_001004738 | OR5L1 | Olfactory receptor, family 5, subfamily L, member 1 |
| ENST00000297431 | NM_002553 NM_181747.1 | ORC5L | Origin recognition complex, subunit 5-like (yeast) |
| ENST00000313733 | NM_014835 NM_144498 | OSBPL2 | Oxysterol binding protein-like 2 |
| ENST00000263650 | NM_020896 NM_145638 | OSBPL5 | Oxysterol binding protein-like 5 |
| ENST00000378500 | NM_000531 | OTC | Ornithine carbamoyltransferase |
| ENST00000339475 | NM_021728 NM_172337.1 | OTX2 | Orthodenticle homeobox 2 |
| ENST00000378434 | NM_005767 | P2RY5 | Purinergic receptor P2Y, G-protein coupled, 5 |
| ENST00000360935 | | P54762-4 | |
| ENST00000318607 | NM_002568 | PABPC1 | Poly(A) binding protein, cytoplasmic 1 |
| ENST00000381859 | NM_030979 | PABPC3 | Poly(A) binding protein, cytoplasmic 3 |
| ENST00000374284 | NM_000437 | PAFAH2 | Platelet-activating factor acetylhydrolase 2, 40 kDa |
| ENST00000265192 | | PAIP2 | Poly(A) binding protein interacting protein 2 |
| ENST00000378466 | NM_018216 | PANK4 | Pantothenate kinase 4 |
| ENST00000045065 | NM_001003931.1 NM_001003935.1 NM_005485.3 | PARP3 | Poly (ADP-ribose) polymerase family, member 3 |
| ENST00000368465 | NM_020524 | PBXIP1 | Pre-B-cell leukemia homeobox interacting protein 1 |
| ENST00000376286 | | PCCA | Propionyl Coenzyme A carboxylase, alpha polypeptide |
| ENST00000377922 | NM_001040429 | PCDH17 | Protocadherin 17 |
| ENST00000297529 | NM_006197.3 | PCM1 | Pericentriolar material 1 |
| ENST00000282096 | | PDE3B | Phosphodiesterase 3B, cGMP-inhibited |
| ENST00000227868 | | PDHX | Pyruvate dehydrogenase complex, component X |
| ENST00000219406 | NM_006849.2 | PDIA2 | Protein disulfide isomerase family A, member 2 |
| ENST00000005178 | NM_002612 | PDK4 | Pyruvate dehydrogenase kinase, isozyme 4 |
| ENST00000340532 | NM_003687 | PDLIM4 | PDZ and LIM domain 4 |
| ENST00000261313 | | PEBP1 | Phosphatidylethanolamine binding protein 1 |
| ENST00000367756 | NM_000288 | PEX7 | Peroxisomal biogenesis factor 7 |
| ENST00000296029 | NM_002619 | PF4 | Platelet factor 4 (chemokine (C-X-C motif) ligand 4) |
| ENST00000226524 | NM_002620 | PF4V1 | Platelet factor 4 variant 1 |
| ENST00000340802 | | PFKM | Phosphofructokinase, muscle |
| ENST00000321327 | NM_024554 | PGBD5 | PiggyBac transposable element derived 5 |
| ENST00000300408 | | PHB | Prohibitin |
| ENST00000361895 | | PHF15_HUMAN | |
| ENST00000327906 | | PHF7 | PHD finger protein 7 |
| ENST00000369409 | NM_006623 | PHGDH | Phosphoglycerate dehydrogenase |
| ENST00000328273 | | PHKG2 | Phosphorylase kinase, gamma 2 (testis) |
| ENST00000369604 | | PHTF1 | Putative homeodomain transcription factor 1 |
| ENST00000331075 | NM_001002837.1 NM_014422.2 | PIB5PA | Phosphatidylinositol (4,5) bisphosphate 5-phosphatase, A |
| ENST00000026218 | | PIGQ | Phosphatidylinositol glycan anchor biosynthesis, class Q |
| ENST00000291009 | NM_002652 | PIP | Prolactin-induced protein |
| ENST00000230643 | NM_014386.2 | PKD2L2 | Polycystic kidney disease 2-like 2 |

TABLE 2-continued

All targets of miR-27a.

| Transcript ID | RefSeq Accession Number | Target Name | Gene Name |
|---|---|---|---|
| ENST00000368452 | | PKIB | Protein kinase (cAMP-dependent, catalytic) inhibitor beta |
| ENST00000372764 | NM_002658 | PLAU | Plasminogen activator, urokinase |
| ENST00000325234 | NM_000932 | PLCB3 | Phospholipase C, beta 3 (phosphatidylinositol-specific) |
| ENST00000326631 | | PLEKHJ1 | Pleckstrin homology domain containing, family J member 1 |
| ENST00000381170 | NM_006622 | PLK2 | Polo-like kinase 2 (*Drosophila*) |
| ENST00000380965 | | PM14_HUMAN | |
| ENST00000368276 | | PMF1 | Polyamine-modulated factor 1 |
| ENST00000369216 | | PNLIPRP1 | Pancreatic lipase-related protein 1 |
| ENST00000254508 | | PO210_HUMAN | |
| ENST00000265465 | NM_002689 | POLA2 | Polymerase (DNA directed), alpha 2 (70 kD subunit) |
| ENST00000222572 | | PON2 | Paraoxonase 2 |
| ENST00000264231 | | POPDC2 | Popeye domain containing 2 |
| ENST00000229003 | | PP11_HUMAN | |
| ENST00000373232 | | PPA1 | Pyrophosphatase (inorganic) 1 |
| ENST00000269812 | | PPAP2C | Phosphatidic acid phosphatase type 2C |
| ENST00000309576 | NM_005037 NM_015869 NM_138711 NM_138712 | PPARG | Peroxisome proliferator-activated receptor gamma |
| ENST00000225174 | NM_005729 | PPIF | Peptidylprolyl isomerase F (cyclophilin F) |
| ENST00000367437 | NM_139126 | PPIL4 | Peptidylprolyl isomerase (cyclophilin)-like 4 |
| ENST00000295908 | | PPM1K | Protein phosphatase 1K (PP2C domain containing) |
| ENST00000328257 | | PPME1_HUMAN | |
| ENST00000376745 | | PPP1CA | Protein phosphatase 1, catalytic subunit, alpha isoform |
| ENST00000279387 | | PPP4C | Protein phosphatase 4 (formerly X), catalytic subunit |
| ENST00000229430 | NM_002726 | PREP | Prolyl endopeptidase |
| ENST00000296800 | NM_006251 NM_206907 | PRKAA1 | Protein kinase, AMP-activated, alpha 1 catalytic subunit |
| ENST00000378567 | NM_001033581.1 NM_001033582.1 NM_002744 | PRKCZ | Protein kinase C, zeta |
| ENST00000325748 | | PRKRA | Protein kinase, interferon-inducible double stranded RNA dependent activator |
| ENST00000361340 | NM_001536.3 NM_198318.2 NM_198319 | PRMT1 | Protein arginine methyltransferase 1 |
| ENST00000374477 | | PROCR | Protein C receptor, endothelial (EPCR) |
| ENST00000375547 | NM_003891 | PROZ | Protein Z, vitamin K-dependent plasma glycoprotein |
| ENST00000227524 | NM_014502 | PRPF19 | PRP19/PSO4 pre-mRNA processing factor 19 homolog (*S. cerevisiae*) |
| ENST00000360614 | | PRSS15 | |
| ENST00000376376 | NM_020200 | PRTFDC1 | Phosphoribosyl transferase domain containing 1 |
| ENST00000291752 | NM_002784 | PSG9 | Pregnancy specific beta-1-glycoprotein 9 |
| ENST00000322215 | | PSMA1 | Proteasome (prosome, macropain) subunit, alpha type, 1 |
| ENST00000261303 | | PSMC1 | Proteasome (prosome, macropain) 26S subunit, ATPase, 1 |
| ENST00000219313 | | PSMD7 | Proteasome (prosome, macropain) 26S subunit, non-ATPase, 7 |
| ENST00000215071 | NM_002812 | PSMD8 | Proteasome (prosome, macropain) 26S subunit, non-ATPase, 8 |
| ENST00000338910 | | PSPC1 | Paraspeckle component 1 |
| ENST00000375275 | | PTCH | |

TABLE 2-continued

All targets of miR-27a.

| Transcript ID | RefSeq Accession Number | Target Name | Gene Name |
|---|---|---|---|
| ENST00000261266 | | PTPRB | Protein tyrosine phosphatase, receptor type, B |
| ENST00000354705 | NM_002840<br>NM_130440 | PTPRF | Protein tyrosine phosphatase, receptor type, F |
| ENST00000281171 | NM_002848<br>NM_030667<br>NM_030668.1<br>NM_030669.1<br>NM_030670.1<br>NM_030671.1 | PTPRO | Protein tyrosine phosphatase, receptor type, O |
| ENST00000335223 | | PTRH1 | Peptidyl-tRNA hydrolase 1 homolog (*S. cerevisiae*) |
| ENST00000329875 | NM_006907<br>NM_153824 | PYCR1 | Pyrroline-5-carboxylate reductase 1 |
| ENST00000382759 | | Q15379_HUMAN | |
| ENST00000300167 | | Q15885_HUMAN | |
| ENST00000389664 | | Q3B8N5_HUMAN | |
| ENST00000377441 | | Q4V339_HUMAN | |
| ENST00000284630 | | Q5H9U9_HUMAN | |
| ENST00000371125 | | Q5JQE8_HUMAN | |
| ENST00000358745 | | Q5JTY0_HUMAN | |
| ENST00000377380 | | Q5RIA9_HUMAN | |
| ENST00000355876 | | Q5SNT8_HUMAN | |
| ENST00000376284 | | Q5STD0_HUMAN | |
| ENST00000369586 | | Q5T5W8_HUMAN | |
| ENST00000377523 | | Q5T7N8_HUMAN | |
| ENST00000382086 | | Q5TI84_HUMAN | |
| ENST00000374801 | | Q5VW05_HUMAN | |
| ENST00000357846 | | Q6DRA6_HUMAN | |
| ENST00000357858 | | Q6IPT3_HUMAN | |
| ENST00000330280 | | Q6P1K8_HUMAN | |
| ENST00000376153 | | Q6P6C6_HUMAN | |
| ENST00000258884 | | Q6PCB6_HUMAN | |
| ENST00000293695 | | Q6PIF2_HUMAN | |
| ENST00000310694 | | Q6UTX4_HUMAN | |
| ENST00000371751 | | Q6ZP22_HUMAN | |
| ENST00000329807 | | Q6ZQP9_HUMAN | |
| ENST00000373364 | | Q6ZRV4_HUMAN | |
| ENST00000381934 | | Q6ZSM7_HUMAN | |
| ENST00000342355 | | Q6ZU04_HUMAN | |
| ENST00000377696 | | Q6ZUF0_HUMAN | |
| ENST00000375548 | | Q6ZUP0_HUMAN | |
| ENST00000370590 | | Q6ZUQ1_HUMAN | |
| ENST00000371863 | | Q6ZVB9_HUMAN | |
| ENST00000382314 | | Q86SG3-2 | |
| ENST00000334298 | | Q86TT0_HUMAN | |
| ENST00000307823 | | Q8N467_HUMAN | |
| ENST00000322053 | | Q8N675_HUMAN | |
| ENST00000356176 | | Q8N7L3_HUMAN | |
| ENST00000313294 | | Q8NA31_HUMAN | |
| ENST00000380816 | | Q8NA85_HUMAN | |
| ENST00000327685 | | Q8NBD7_HUMAN | |
| ENST00000277491 | | Q8NDA2_HUMAN | |
| ENST00000313807 | | Q8TAS2_HUMAN | |
| ENST00000358148 | | Q8TEB0_HUMAN | |
| ENST00000268314 | | Q96C12_HUMAN | |
| ENST00000339359 | | Q9BVY2_HUMAN | |
| ENST00000253461 | | Q9H693_HUMAN | |
| ENST00000261651 | | Q9H7M0_HUMAN | |
| ENST00000321536 | | Q9P188_HUMAN | |
| ENST00000267328 | NM_017817 | RAB20 | RAB20, member RAS oncogene family |
| ENST00000344445 | NM_016277<br>NM_183227 | RAB23 | RAB23, member RAS oncogene family |
| ENST00000375836 | | RAB3GAP1 | RAB3 GTPase activating protein subunit 1 (catalytic) |
| ENST00000373826 | | RAB42 | RAB42, member RAS oncogene family |
| ENST00000373538 | NM_005833 | RABEPK | Rab9 effector protein with kelch motifs |
| ENST00000337432 | | RAD51C | RAD51 homolog C (*S. cerevisiae*) |
| ENST00000368404 | | RAG1AP1 | Recombination activating gene 1 activating protein 1 |
| ENST00000372062 | | RALGDS | Ral guanine nucleotide dissociation stimulator |

TABLE 2-continued

All targets of miR-27a.

| Transcript ID | RefSeq Accession Number | Target Name | Gene Name |
|---|---|---|---|
| ENST00000374757 | NM_002885 | RAP1GAP | RAP1 GTPase activating protein |
| ENST00000319149 | NM_000964 NM_001024809.2 NM_001033603 | RARA | Retinoic acid receptor, alpha |
| ENST00000231572 | NM_002887 | RARS | Arginyl-tRNA synthetase |
| ENST00000220062 | NM_016563 | RASL12 | RAS-like, family 12 |
| ENST00000319715 | NM_006910 NM_018703 | RBBP6 | Retinoblastoma binding protein 6 |
| ENST00000369784 | NM_022768 | RBM15 | RNA binding motif protein 15 |
| ENST00000367006 | | RCOR3 | REST corepressor 3 |
| ENST00000367664 | | REPS1 | RALBP1 associated Eps domain containing 1 |
| ENST00000355710 | NM_020630.4 NM_020975 | RET | Ret proto-oncogene |
| ENST00000380071 | | RFC3 | Replication factor C (activator 1) 3, 38 kDa |
| ENST00000374596 | | RGL2 | Ral guanine nucleotide dissociation stimulator-like 2 |
| ENST00000367459 | NM_002922 | RGS1 | Regulator of G-protein signaling 1 |
| ENST00000206262 | NM_012419 | RGS17 | Regulator of G-protein signaling 17 |
| ENST00000343854 | NM_004296 | RGS6 | Regulator of G-protein signaling 6 |
| ENST00000268125 | NM_000326 | RLBP1 | Retinaldehyde binding protein 1 |
| ENST00000340900 | | RNASE1 | Ribonuclease, RNase A family, 1 (pancreatic) |
| ENST00000344624 | | RNASEN | Ribonuclease III, nuclear |
| ENST00000375734 | NM_005168 | RND3 | Rho family GTPase 3 |
| ENST00000311269 | | RNF190 | |
| ENST00000358395 | NM_007219 | RNF24 | Ring finger protein 24 |
| ENST00000339626 | NM_005977 NM_183043 NM_183044 NM_183045 | RNF6 | Ring finger protein (C3H2C3 type) 6 |
| ENST00000369485 | | RNGTT | RNA guanylyltransferase and 5'-phosphatase |
| ENST00000296255 | NM_002950 | RPN1 | Ribophorin I |
| ENST00000341844 | | RPS12 | Ribosomal protein S12 |
| ENST00000372360 | | RPS24 | Ribosomal protein S24 |
| ENST00000334205 | NM_001006944.1 NM_003942 | RPS6KA4 | Ribosomal protein S6 kinase, 90 kDa, polypeptide 4 |
| ENST00000261991 | | RPS6KA5 | Ribosomal protein S6 kinase, 90 kDa, polypeptide 5 |
| ENST00000312629 | | RPS6KB2 | Ribosomal protein S6 kinase, 70 kDa, polypeptide 2 |
| ENST00000358328 | NM_031464 | RPS6KL1 | Ribosomal protein S6 kinase-like 1 |
| ENST00000246792 | | RRAS | Related RAS viral (r-ras) oncogene homolog |
| ENST00000258955 | NM_018346 | RSAD1 | Radical S-adenosyl methionine domain containing 1 |
| ENST00000276659 | NM_178565 | RSPO2 | R-spondin 2 homolog (*Xenopus laevis*) |
| ENST00000368317 | NM_032784 | RSPO3 | R-spondin 3 homolog (*Xenopus laevis*) |
| ENST00000369724 | | RWDD2 | |
| ENST00000367891 | NM_001009598 NM_006917 | RXRG | Retinoid X receptor, gamma |
| ENST00000367469 | NM_015278 | SASH1 | SAM and SH3 domain containing 1 |
| ENST00000368363 | NM_005698 NM_052837 | SCAMP3 | Secretory carrier membrane protein 3 |
| ENST00000019103 | NM_002980 | SCTR | Secretin receptor |
| ENST00000247020 | | SDF2 | Stromal cell-derived factor 2 |
| ENST00000360001 | | SDF4 | Stromal cell derived factor 4 |
| ENST00000215812 | | SEC14L3 | SEC14-like 3 (*S. cerevisiae*) |
| ENST00000264454 | | SEC22C | SEC22 vesicle trafficking protein homolog C (*S. cerevisiae*) |
| ENST00000379041 | | SEC61A2 | Sec61 alpha 2 subunit (*S. cerevisiae*) |
| ENST00000368868 | NM_003944 | SELENBP1 | Selenium binding protein 1 |
| ENST00000355853 | | SEMA4G | Sema domain, immunoglobulin domain (Ig), transmembrane domain (TM) and short cytoplasmic domain, (semaphorin) 4G |

TABLE 2-continued

All targets of miR-27a.

| Transcript ID | RefSeq Accession Number | Target Name | Gene Name |
|---|---|---|---|
| ENST00000357599 | NM_001031702 | SEMA5B | Sema domain, seven thrombospondin repeats (type 1 and type 1-like), transmembrane domain (TM) and short cytoplasmic domain, (semaphorin) 5B |
| ENST00000367516 | | SEN15_HUMAN | |
| ENST00000004980 | | SENP1_HUMAN | |
| ENST00000367104 | | SERAC1 | Serine active site containing 1 |
| ENST00000372563 | NM_000354 | SERPINA7 | Serpin peptidase inhibitor, clade A (alpha-1 antiproteinase, antitrypsin), member 7 |
| ENST00000221455 | NM_007056 | SFRS16 | Splicing factor, arginine/serine-rich 16 |
| ENST00000229390 | | SFRS9 | Splicing factor, arginine/serine-rich 9 |
| ENST00000355697 | | SFXN4_HUMAN | |
| ENST00000373277 | NM_005489 NM_170600 | SH2D3C | SH2 domain containing 3C |
| ENST00000350336 | NM_016009 | SH3GLB1 | SH3-domain GRB2-like endophilin B1 |
| ENST00000359782 | | SIRT5 | Sirtuin (silent mating type information regulation 2 homolog) 5 (*S. cerevisiae*) |
| ENST00000354161 | | SLC12A9 | Solute carrier family 12 (potassium/chloride transporters), member 9 |
| ENST00000318989 | | SLC16A10 | Solute carrier family 16, member 10 (aromatic amino acid transporter) |
| ENST00000308453 | NM_001098486.1 NM_006632 | SLC17A3 | Solute carrier family 17 (sodium phosphate), member 3 |
| ENST00000273173 | | SLC22A14 | Solute carrier family 22 (organic cation transporter), member 14 |
| ENST00000345033 | NM_003058 | SLC22A2 | Solute carrier family 22 (organic cation transporter), member 2 |
| ENST00000317881 | | SLC25A5 | Solute carrier family 25 (mitochondrial carrier; adenine nucleotide translocator), member 5 |
| ENST00000361193 | NM_173626 | SLC26A11 | Solute carrier family 26, member 11 |
| ENST00000356119 | NM_052961 NM_138718 | SLC26A8 | Solute carrier family 26, member 8 |
| ENST00000306873 | | SLC30A1 | Solute carrier family 30 (zinc transporter), member 1 |
| ENST00000379343 | | SLC30A6 | Solute carrier family 30 (zinc transporter), member 6 |
| ENST00000217420 | NM_080552 | SLC32A1 | Solute carrier family 32 (GABA vesicular transporter), member 1 |
| ENST00000298681 | NM_014579 | SLC39A2 | Solute carrier family 39 (zinc transporter), member 2 |
| ENST00000380059 | NM_032034 | SLC4A11 | Solute carrier family 4, sodium borate transporter, member 11 |
| ENST00000260126 | | SLCO5A1 | Solute carrier organic anion transporter family, member 5A1 |
| ENST00000359345 | NM_144990 | SLFNL1 | Schlafen-like 1 |
| ENST00000332281 | | SNAI3 | Snail homolog 3 (*Drosophila*) |
| ENST00000348795 | NM_003087 | SNCG | Synuclein, gamma (breast cancer-specific protein 1) |
| ENST00000354725 | | SND1_HUMAN | |
| ENST00000290330 | | SNF8 | SNF8, ESCRT-II complex subunit, homolog (*S. cerevisiae*) |
| ENST00000374015 | | SNRPC | Small nuclear ribonucleoprotein polypeptide C |
| ENST00000244227 | | SNUT3_HUMAN | |
| ENST00000379516 | NM_003100 | SNX2 | Sorting nexin 2 |
| ENST00000344780 | | SNX21_HUMAN | |
| ENST00000251847 | | SNX23_HUMAN | |
| ENST00000264694 | NM_031953 | SNX25 | Sorting nexin 25 |
| ENST00000306121 | NM_015976 NM_152238 | SNX7 | Sorting nexin 7 |
| ENST00000302056 | NM_004232 | SOCS6 | Suppressor of cytokine signaling 6 |
| ENST00000373645 | NM_001005176 NM_007237.3 | SP140 | SP140 nuclear body protein |

TABLE 2-continued

All targets of miR-27a.

| Transcript ID | RefSeq Accession Number | Target Name | Gene Name |
|---|---|---|---|
| ENST00000282470 | NM_004684 | SPARCL1 | SPARC-like 1 (mast9, hevin) |
| ENST00000351008 | NM_031955 | SPATA16 | Spermatogenesis associated 16 |
| ENST00000289431 | NM_006038 | SPATA2 | Spermatogenesis associated 2 |
| ENST00000282074 | | SPBC25 | |
| ENST00000377104 | | SPRY2 | Sprouty homolog 2 (*Drosophila*) |
| ENST00000372739 | NM_003127 | SPTAN1 | Spectrin, alpha, non-erythrocytic 1 (alpha-fodrin) |
| ENST00000379648 | | SRP19 | Signal recognition particle 19 kDa |
| ENST00000343379 | NM_015558 NM_198935 | SS18L1 | Synovial sarcoma translocation gene on chromosome 18-like 1 |
| ENST00000278742 | NM_021978 | ST14 | Suppression of tumorigenicity 14 (colon carcinoma) |
| ENST00000382009 | NM_020860 | STIM2 | Stromal interaction molecule 2 |
| ENST00000368625 | | STK32C | Serine/threonine kinase 32C |
| ENST00000220876 | | STMN2 | Stathmin-like 2 |
| ENST00000378577 | | STOML2 | Stomatin (EPB72)-like 2 |
| ENST00000298596 | NM_152709.3 | STOX1 | Storkhead box 1 |
| ENST00000374263 | NM_022486 | SUSD1 | Sushi domain containing 1 |
| ENST00000342784 | | SYDE1 | Synapse defective 1, Rho GTPase, homolog 1 (*C. elegans*) |
| ENST00000360448 | | SYTL3 | Synaptotagmin-like 3 |
| ENST00000369958 | | TAF13 | TAF13 RNA polymerase II, TATA box binding protein (TBP)-associated factor, 18 kDa |
| ENST00000380818 | NM_001015892 NM_003187 | TAF9 | TAF9 RNA polymerase II, TATA box binding protein (TBP)-associated factor, 32 kDa |
| ENST00000374895 | NM_000544.3 NM_018833 | TAP2 | Transporter 2, ATP-binding cassette, sub-family B (MDR/TAP) |
| ENST00000040877 | NM_005646 | TARBP1 | TAR (HIV-1) RNA binding protein 1 |
| ENST00000375371 | NM_152232 | TAS1R2 | Taste receptor, type 1, member 2 |
| ENST00000331710 | NM_013254 | TBK1 | TANK-binding kinase 1 |
| ENST00000230354 | NM_003194 | TBP | TATA box binding protein |
| ENST00000247219 | NM_199047 | TBPL2 | TATA box binding protein like 2 |
| ENST00000369431 | NM_152380 | TBX15 | T-box 15 |
| ENST00000309889 | NM_003673 | TCAP | Titin-cap (telethonin) |
| ENST00000282111 | NM_031283 | TCF7L1 | Transcription factor 7-like 1 (T-cell specific, HMG-box) |
| ENST00000373977 | NM_001093728.1 NM_018679 | TCP11 | T-complex 11 (mouse) |
| ENST00000335725 | NM_001008744 NM_018319 | TDP1 | Tyrosyl-DNA phosphodiesterase 1 |
| ENST00000372578 | NM_031274.3 | TEX13A | Testis expressed 13A |
| ENST00000274400 | | TF2H2_HUMAN | |
| ENST00000222543 | NM_006528 | TFPI2 | Tissue factor pathway inhibitor 2 |
| ENST00000261600 | | THOC1 | THO complex 1 |
| ENST00000264637 | | THRA | Thyroid hormone receptor, alpha (erythroblastic leukemia viral (v-erb-a) oncogene homolog, avian) |
| ENST00000297347 | | THRAP6 | |
| ENST00000288014 | | THTPA | Thiamine triphosphatase |
| ENST00000287814 | NM_003256 | TIMP4 | TIMP metallopeptidase inhibitor 4 |
| ENST00000296802 | | TIP1_HUMAN | |
| ENST00000311912 | NM_016610 NM_138636 | TLR8 | Toll-like receptor 8 |
| ENST00000370196 | | TLX1_HUMAN | |
| ENST00000294613 | NM_032027.2 | TM2D1 | TM2 domain containing 1 |
| ENST00000299705 | | TMED3 | Transmembrane emp24 protein transport domain containing 3 |
| ENST00000206380 | | TMEM101 | Transmembrane protein 101 |
| ENST00000216080 | | TMEM153 | |
| ENST00000292246 | NM_018075 | TMEM16K | Transmembrane protein 16K |
| ENST00000336702 | NM_014807 | TMEM24 | Transmembrane protein 24 |
| ENST00000297459 | NM_153015 | TMEM74 | Transmembrane protein 74 |
| ENST00000307216 | NM_015497 | TMEM87A | Transmembrane protein 87A |
| ENST00000300433 | NM_153229 | TMEM92 | Transmembrane protein 92 |
| ENST00000335572 | NM_182559.2 | TMPRSS12 | Transmembrane protease, serine 12 |
| ENST00000233143 | NM_021103 | TMSB10 | Thymosin, beta 10 |
| ENST00000297533 | | TMUB1 | Transmembrane and ubiquitin-like domain containing 1 |

TABLE 2-continued

All targets of miR-27a.

| Transcript ID | RefSeq Accession Number | Target Name | Gene Name |
|---|---|---|---|
| ENST00000264331 | NM_001068.2 | TOP2B | Topoisomerase (DNA) II beta 180 kDa |
| ENST00000373284 | NM_001085347.1 NM_130459 | TOR2A | Torsin family 2, member A |
| ENST00000301057 | | TP53I13 | Tumor protein p53 inducible protein 13 |
| ENST00000308422 | NM_000547 NM_175719 NM_175720 NM_175721 NM_175722 | TPO | Thyroid peroxidase |
| ENST00000367478 | NM_003292.2 | TPR | Translocated promoter region (to activated MET oncogene) |
| ENST00000340513 | NM_012112 | TPX2 | TPX2, microtubule-associated, homolog (*Xenopus laevis*) |
| ENST00000373887 | NM_005658 | TRAF1 | TNF receptor-associated factor 1 |
| ENST00000367023 | | TRAF3IP3 | TRAF3 interacting protein 3 |
| ENST00000297221 | | TRERF1 | Transcriptional regulating factor 1 |
| ENST00000357105 | | TREX1 | Three prime repair exonuclease 1 |
| ENST00000311762 | NM_003301 | TRHR | Thyrotropin-releasing hormone receptor |
| ENST00000274327 | NM_001656 NM_033227.2 NM_033228 | TRIM23 | Tripartite motif-containing 23 |
| ENST00000357530 | NM_024114 | TRIM48 | Tripartite motif-containing 48 |
| ENST00000380027 | | TRIM5 | Tripartite motif-containing 5 |
| ENST00000333149 | NM_178125 | TRIM50 | Tripartite motif-containing 50 |
| ENST00000360177 | | TRIM59 | Tripartite motif-containing 59 |
| ENST00000379705 | NM_016179 | TRPC4 | Transient receptor potential cation channel, subfamily C, member 4 |
| ENST00000277065 | NM_001007470.1 NM_001007471.2 NM_020952.4 NM_024971 NM_206945.3 NM_206946 NM_206947 NM_206948 | TRPM3 | Transient receptor potential cation channel, subfamily M, member 3 |
| ENST00000333213 | NM_207346 | TSEN54 | TRNA splicing endonuclease 54 homolog (*S. cerevisiae*) |
| ENST00000307180 | NM_145003 | TSNARE1 | T-SNARE domain containing 1 |
| ENST00000372003 | NM_005727 | TSPAN1 | Tetraspanin 1 |
| ENST00000375442 | | TSPYL2 | TSPY-like 2 |
| ENST00000382110 | | TTC15 | Tetratricopeptide repeat domain 15 |
| ENST00000334974 | | TUBGCP2 | Tubulin, gamma complex associated protein 2 |
| ENST00000216185 | | TXN2 | Thioredoxin 2 |
| ENST00000371626 | NM_015913 | TXNDC12 | Thioredoxin domain containing 12 (endoplasmic reticulum) |
| ENST00000369317 | NM_006472 | TXNIP | Thioredoxin interacting protein |
| ENST00000301944 | | TXNL6 | |
| ENST00000367926 | NM_003115 | UAP1 | UDP-N-acetylglucosamine pyrophosphorylase 1 |
| ENST00000340573 | NM_004223 NM_198183 | UBE2L6 | Ubiquitin-conjugating enzyme E2L 6 |
| ENST00000371076 | NM_152489 | UBE2U | Ubiquitin-conjugating enzyme E2U (putative) |
| ENST00000381764 | | UCHL1 | Ubiquitin carboxyl-terminal esterase L1 (ubiquitin thiolesterase) |
| ENST00000337130 | | UGP2 | UDP-glucose pyrophosphorylase 2 |
| ENST00000268159 | NM_001039675.1 NM_018671 | UNC45A | Unc-45 homolog A (*C. elegans*) |
| ENST00000340926 | NM_025154.3 | UNC84A | Unc-84 homolog A (*C. elegans*) |
| ENST00000366829 | NM_018974 | UNC93A | Unc-93 homolog A (*C. elegans*) |
| ENST00000262946 | NM_006830 | UQCR | Ubiquinol-cytochrome c reductase, 6.4 kDa subunit |
| ENST00000335373 | NM_006677.1 | USP19 | Ubiquitin specific peptidase 19 |
| ENST00000304076 | NM_005428 | VAV1 | Vav 1 guanine nucleotide exchange factor |
| ENST00000313132 | | VDAC2 | Voltage-dependent anion channel 2 |

TABLE 2-continued

All targets of miR-27a.

| Transcript ID | RefSeq Accession Number | Target Name | Gene Name |
|---|---|---|---|
| ENST00000309422 | | VEGFB | Vascular endothelial growth factor B |
| ENST00000280193 | NM_005429.2 | VEGFC | Vascular endothelial growth factor C |
| ENST00000249330 | NM_003378 | VGF | VGF nerve growth factor inducible |
| ENST00000367244 | NM_003381 NM_194435 | VIP | Vasoactive intestinal peptide |
| ENST00000301774 | | VMD2 | |
| ENST00000331471 | | VMDL3_HUMAN | |
| ENST00000355155 | | VP13B_HUMAN | |
| ENST00000220509 | NM_020857 | VPS18 | Vacuolar protein sorting 18 homolog (*S. cerevisiae*) |
| ENST00000324849 | | VPS37A | Vacuolar protein sorting 37 homolog A (*S. cerevisiae*) |
| ENST00000369456 | NM_024626 | VTCN1 | V-set domain containing T cell activation inhibitor 1 |
| ENST00000233615 | | WBP1 | WW domain binding protein 1 |
| ENST00000381329 | NM_014023 | WDR37 | WD repeat domain 37 |
| ENST00000330317 | | WDR4 | WD repeat domain 4 |
| ENST00000378322 | | WDR8 | WD repeat domain 8 |
| ENST00000368664 | | WISP3 | WNT1 inducible signaling pathway protein 3 |
| ENST00000366753 | NM_033131 | WNT3A | Wingless-type MMTV integration site family, member 3A |
| ENST00000380713 | | WRB | Tryptophan rich basic protein |
| ENST00000313620 | | XP_292836.3 | |
| ENST00000372288 | | XP_931110.1 | |
| ENST00000383005 | | XP_932040.1 | |
| ENST00000309582 | | XP_935270.1 | |
| ENST00000255845 | | XP_937394.1 | |
| ENST00000388939 | | XP_937526.1 | |
| ENST00000378263 | | XP_942691.1 | |
| ENST00000378260 | | XP_942710.1 | |
| ENST00000323562 | | XP_943634.1 | |
| ENST00000331993 | | XP_944689.1 | |
| ENST00000303979 | | XP_944836.1 | |
| ENST00000367014 | | XR_000991.1 | |
| ENST00000380885 | | XR_001064.1 | |
| ENST00000282268 | NM_003401 NM_022406 NM_022550 | XRCC4 | X-ray repair complementing defective repair in Chinese hamster cells 4 |
| ENST00000300145 | NM_033276.2 | XRCC6BP1 | XRCC6 binding protein 1 |
| ENST00000339413 | NM_001039671.1 NM_001039672 NM_001039673.1 NM_033557 | YIF1B | Yip1 interacting factor homolog B (*S. cerevisiae*) |
| ENST00000204279 | | YPEL3 | Yippee-like 3 (*Drosophila*) |
| ENST00000317012 | NM_024508 | ZBED2 | Zinc finger, BED-type containing 2 |
| ENST00000291374 | | ZBTB8_HUMAN | |
| ENST00000218506 | NM_144969 | ZDHHC15 | Zinc finger, DHHC-type containing 15 |
| ENST00000216602 | | ZFYVE21 | Zinc finger, FYVE domain containing 21 |
| ENST00000339296 | | ZN621_HUMAN | |
| ENST00000358296 | NM_173531.2 | ZNF100 | Zinc finger protein 100 |
| ENST00000360371 | | ZNF124 | Zinc finger protein 124 |
| ENST00000343499 | | ZNF177 | Zinc finger protein 177 |
| ENST00000300823 | NM_001032372.1 NM_001032373.1 NM_001032374.1 NM_001032375.1 NM_015919.3 | ZNF226 | Zinc finger protein 226 |
| ENST00000377255 | | ZNF306 | |
| ENST00000361328 | | ZNF31 | |
| ENST00000372167 | | ZNF334 | Zinc finger protein 334 |
| ENST00000243644 | NM_021632 | ZNF350 | Zinc finger protein 350 |
| ENST00000361807 | NM_145312 | ZNF485 | Zinc finger protein 485 |
| ENST00000361113 | NM_145295.2 | ZNF627 | Zinc finger protein 627 |
| ENST00000358785 | NM_024804 | ZNF669 | Zinc finger protein 669 |
| ENST00000341976 | NM_021916 | ZNF70 | Zinc finger protein 70 |
| ENST00000293068 | | ZNFN1A3 | |
| ENST00000233331 | | ZNHIT4 | Zinc finger, HIT type 4 |

TABLE 3 miR-27a targets identified by miRanda and L2L.

| Target Gene | Accession No: | Gene Name |
|---|---|---|
| ADAMTS4 | NM_005099.4 GI: 157427674 | ADAM metallopeptidase with thrombospondin type 1 motif, 4 |
| AHSG | NM_001622.2 GI: 156523969 | alpha-2-HS-glycoprotein |
| ALPL | NM_000478.3 GI: 116734716 | alkaline phosphatase, liver/bone/kidney |
| BMI1 | NM_005180.5 GI: 39725706 | BMI1 polycomb ring finger oncogene |
| CHRD | NM_003741.2 GI: 30089979 | chordin |
| DLX5 | NM_005221.5 GI: 84043959 | distal-less homeobox 5 |
| HOXA13 | NM_000522.3 GI: 84452162 | homeobox A13 |
| MATN1 | NM_002379.2 GI: 13518035 | matrilin 1, cartilage matrix protein |
| MINPP1 | NM_004897.2 GI: 19923760 | multiple inositol polyphosphate histidine phosphatase, 1 |
| PEX7 | NM_000288.1 GI: 4505730 | peroxisomal biogenesis factor 7 |
| PRKRA | NM_003690.3 GI: 32261293 | protein kinase, interferon-inducible double stranded RNA dependent activator |
| THRA | NM_199334.2 GI: 46255056 | thyroid hormone receptor, alpha (erythroblastic leukemia viral (v-erb-a) oncogene homolog, avian) |
| THRA | NM_003250.4 GI: 40806158 | thyroid hormone receptor, alpha (erythroblastic leukemia viral (v-erb-a) oncogene homolog, avian) |

TABLE 4

All targets of miR-489.

| Transcript ID | RefSeq Accession Number | Target Name | Gene Name |
|---|---|---|---|
| ENST00000263100 | NM_130786 | A1BG | Alpha-1-B glycoprotein |
| ENST00000389663 | NM_015657 NM_173076 | ABCA12 | ATP-binding cassette, sub-family A (ABC1), member 12 |
| ENST00000382055 | NM_178559 | ABCB5 | ATP-binding cassette, sub-family B (MDR/TAP), member 5 |
| ENST00000339718 | NM_033226 | ABCC12 | ATP-binding cassette, sub-family C (CFTR/MRP), member 12 |
| ENST00000334444 | NM_001023587 NM_005688.2 | ABCC5 | ATP-binding cassette, sub-family C (CFTR/MRP), member 5 |
| ENST00000295962 | | ABHD6 | Abhydrolase domain containing 6 |
| ENST00000308982 | | ACAD9 | Acyl-Coenzyme A dehydrogenase family, member 9 |
| ENST00000231909 | NM_022899 | ACTR8 | ARP8 actin-related protein 8 homolog (yeast) |
| ENST00000303536 | | ACYP2 | Acylphosphatase 2, muscle type |
| ENST00000256389 | NM_003814 | ADAM20 | ADAM metallopeptidase domain 20 |
| ENST00000335595 | NM_003817 | ADAM7 | ADAM metallopeptidase domain 7 |
| ENST00000352040 | NM_030955 | ADAMTS12 | ADAM metallopeptidase with thrombospondin type 1 motif, 12 |
| ENST00000299164 | NM_139055 | ADAMTS15 | ADAM metallopeptidase with thrombospondin type 1 motif, 15 |
| ENST00000380559 | NM_001040272.4 NM_052866 NM_139238 NM_139264 | ADAMTSL1 | ADAMTS-like 1 |
| ENST00000238561 | | ADCK1 | AarF domain containing kinase 1 |
| ENST00000349243 | | AGTR1 | Angiotensin II receptor, type 1 |
| ENST00000273784 | NM_001622 | AHSG | Alpha-2-HS-glycoprotein |
| ENST00000367601 | NM_016108 | AIG1 | Androgen-induced 1 |
| ENST00000373176 | NM_000476 | AK1 | Adenylate kinase 1 |
| ENST00000267584 | NM_152327 | AK7 | Adenylate kinase 7 |
| ENST00000228850 | NM_006422 | AKAP3 | A kinase (PRKA) anchor protein 3 |
| ENST00000358526 | NM_003886 NM_139289 | AKAP4 | A kinase (PRKA) anchor protein 4 |
| ENST00000285930 | | AKR1B1 | Aldo-keto reductase family 1, member B1 (aldose reductase) |
| ENST00000339618 | NM_000382 NM_001031806 | ALDH3A2 | Aldehyde dehydrogenase 3 family, member A2 |
| ENST00000007633 | NM_000694.2 NM_001030010.1 | ALDH3B1 | Aldehyde dehydrogenase 3 family, member B1 |
| ENST00000338110 | | ALDOA_HUMAN | |
| ENST00000374978 | NM_033087 | ALG2 | Asparagine-linked glycosylation 2 homolog (S. cerevisiae, alpha-1,3-mannosyltransferase) |

TABLE 4-continued

All targets of miR-489.

| Transcript ID | RefSeq Accession Number | Target Name | Gene Name |
|---|---|---|---|
| ENST00000239891 | | ALG5 | Asparagine-linked glycosylation 5 homolog (*S. cerevisiae*, dolichyl-phosphate beta-glucosyltransferase) |
| ENST00000216489 | NM_006020 | ALKBH1 | AlkB, alkylation repair homolog 1 (*E. coli*) |
| ENST00000378840 | | ALKBH3 | AlkB, alkylation repair homolog 3 (*E. coli*) |
| ENST00000380490 | | ALOX5AP | Arachidonate 5-lipoxygenase-activating protein |
| ENST00000383037 | NM_001143 | AMELY | Amelogenin, Y-linked |
| ENST00000338852 | | AMY2B | Amylase, alpha 2B (pancreatic) |
| ENST00000354910 | NM_015391 | ANAPC13 | Anaphase promoting complex subunit 13 |
| ENST00000304704 | NM_002937 NM_194430 NM_194431 | ANG | Angiogenin, ribonuclease, RNase A family, 5 |
| ENST00000367629 | NM_004673 | ANGPTL1 | Angiopoietin-like 1 |
| ENST00000373815 | NM_001149 NM_020987 | ANK3 | Ankyrin 3, node of Ranvier (ankyrin G) |
| ENST00000357927 | | ANKRD18A | Ankyrin repeat domain 18A |
| ENST00000322980 | NM_173505 | ANKRD29 | Ankyrin repeat domain 29 |
| ENST00000296511 | NM_001154 | ANXA5 | Annexin A5 |
| ENST00000291439 | | AP1M1 | Adaptor-related protein complex 1, mu 1 subunit |
| ENST00000250244 | NM_005498.3 | AP1M2 | Adaptor-related protein complex 1, mu 2 subunit |
| ENST00000337619 | NM_001283.3 NM_057089.2 | AP1S1 | Adaptor-related protein complex 1, sigma 1 subunit |
| ENST00000334271 | NM_001039569.1 | AP1S3 | Adaptor-related protein complex 1, sigma 3 subunit |
| ENST00000263270 | | AP2S1 | Adaptor-related protein complex 2, sigma 1 subunit |
| ENST00000278359 | | APIP | APAF1 interacting protein |
| ENST00000375918 | NM_019101 | APOM | Apolipoprotein M |
| ENST00000315596 | | APRIN | |
| ENST00000368087 | | ARG1 | Arginase, liver |
| ENST00000300901 | | ARHGAP23 | Rho GTPase activating protein 23 |
| ENST00000273258 | NM_006407 | ARL6IP5 | ADP-ribosylation-like factor 6 interacting protein 5 |
| ENST00000305242 | NM_018076 | ARMC4 | Armadillo repeat containing 4 |
| ENST00000349321 | | ART3 | ADP-ribosyltransferase 3 |
| ENST00000389601 | NM_130387 | ASB14 | Ankyrin repeat and SOCS box-containing 14 |
| ENST00000263634 | NM_016115 NM_145863 | ASB3 | Ankyrin repeat and SOCS box-containing 3 |
| ENST00000266744 | | ASCL1 | Achaete-scute complex homolog 1 (*Drosophila*) |
| ENST00000375689 | NM_015338 | ASXL1 | Additional sex combs like 1 (*Drosophila*) |
| ENST00000264110 | | ATF2 | Activating transcription factor 2 |
| ENST00000317868 | NM_032852 NM_178221 | ATG4C | ATG4 autophagy related 4 homolog C (*S. cerevisiae*) |
| ENST00000309469 | NM_032885 | ATG4D | ATG4 autophagy related 4 homolog D (*S. cerevisiae*) |
| ENST00000286371 | | ATP1B3 | ATPase, Na+/K+ transporting, beta 3 polypeptide |
| ENST00000349466 | NM_001001344 NM_021949 | ATP2B3 | ATPase, Ca++ transporting, plasma membrane 3 |
| ENST00000284727 | NM_001002258 NM_001689 | ATP5G3 | ATP synthase, H+ transporting, mitochondrial F0 complex, subunit C3 (subunit 9) |
| ENST00000330342 | NM_012463 | ATP6V0A2 | ATPase, H+ transporting, lysosomal V0 subunit a2 |
| ENST00000290949 | | ATP6V0D1 | ATPase, H+ transporting, lysosomal 38 kDa, V0 subunit d1 |
| ENST00000335514 | | ATPIF1 | ATPase inhibitory factor 1 |
| ENST00000377526 | | AUP1 | Ancient ubiquitous protein 1 |
| ENST00000382956 | | AXIN1 | Axin 1 |
| ENST00000367998 | | B4GALT3 | UDP-Gal:betaGlcNAc beta 1,4-galactosyltransferase, polypeptide 3 |
| ENST00000375372 | | BARX1 | BARX homeobox 1 |

TABLE 4-continued

All targets of miR-489.

| Transcript ID | RefSeq Accession Number | Target Name | Gene Name |
|---|---|---|---|
| ENST00000375842 | | BAT5 | HLA-B associated transcript 5 |
| ENST00000378455 | NM_017745 | BCOR | BCL6 co-repressor |
| ENST00000296424 | NM_020926 NM_020139 | BDH2 | 3-hydroxybutyrate dehydrogenase, type 2 |
| ENST00000372677 | | BEX2 | Brain expressed X-linked 2 |
| ENST00000372645 | | BEX3_HUMAN | |
| ENST00000227758 | NM_001166 | BIRC2 | Baculoviral IAP repeat-containing 2 |
| ENST00000367807 | NM_003666 | BLZF1 | Basic leucine zipper nuclear factor 1 (JEM-1) |
| ENST00000265624 | | BMP7 | Bone morphogenetic protein 7 (osteogenic protein 1) |
| ENST00000349552 | NM_174897 | BPIL3 | Bactericidal/permeability-increasing protein-like 3 |
| ENST00000354807 | NM_006085.4 | BPNT1 | 3'(2'), 5'-bisphosphate nucleotidase 1 |
| ENST00000220659 | | BRF2 | BRF2, subunit of RNA polymerase III transcription initiation factor, BRF1-like |
| ENST00000339775 | NM_006806 | BTG3 | BTG family, member 3 |
| ENST00000289361 | | BTN3A1 | Butyrophilin, subfamily 3, member A1 |
| ENST00000244519 | | BTN3A3 | Butyrophilin, subfamily 3, member A3 |
| ENST00000230340 | | BYSL | Bystin-like |
| ENST00000337623 | NM_015608 | C10orf137 | Chromosome 10 open reading frame 137 |
| ENST00000331772 | NM_001031709 NM_018363 | C10orf59 | Chromosome 10 open reading frame 59 |
| ENST00000374157 | | C10orf73 | Chromosome 10 open reading frame 73 |
| ENST00000368887 | | C10orf89 | |
| ENST00000333254 | NM_198515 | C10orf96 | Chromosome 10 open reading frame 96 |
| ENST00000378615 | | C11orf49 | Chromosome 11 open reading frame 49 |
| ENST00000261191 | NM_018164 | C12orf11 | Chromosome 12 open reading frame 11 |
| ENST00000261700 | | C14orf166 | Chromosome 14 open reading frame 166 |
| ENST00000256545 | | C15orf24 | Chromosome 15 open reading frame 24 |
| ENST00000311880 | | C17orf66 | Chromosome 17 open reading frame 66 |
| ENST00000389005 | NM_018553 | C17orf85 | Chromosome 17 open reading frame 85 |
| ENST00000333234 | NM_031446 | C18orf21 | Chromosome 18 open reading frame 21 |
| ENST00000300227 | NM_198995 | C18orf34 | Chromosome 18 open reading frame 34 |
| ENST00000367910 | NM_178550.4 | C1orf110 | Chromosome 1 open reading frame 110 |
| ENST00000371760 | | C1orf185 | Chromosome 1 open reading frame 185 |
| ENST00000371980 | NM_001013615 | C1orf190 | Chromosome 1 open reading frame 190 |
| ENST00000368790 | | C1orf42 | |
| ENST00000331283 | | C21orf119 | Chromosome 21 open reading frame 119 |
| ENST00000266155 | NM_031444 | C22orf13 | Chromosome 22 open reading frame 13 |
| ENST00000295049 | | C2orf11 | |
| ENST00000273037 | | C3orf31 | Chromosome 3 open reading frame 31 |
| ENST00000318887 | NM_173824 | C3orf38 | Chromosome 3 open reading frame 38 |
| ENST00000344697 | NM_032806 | C3orf39 | Chromosome 3 open reading frame 39 |
| ENST00000341199 | | C5orf25 | Chromosome 5 open reading frame 25 |
| ENST00000244558 | | C6orf130 | Chromosome 6 open reading frame 130 |

TABLE 4-continued

All targets of miR-489.

| Transcript ID | RefSeq Accession Number | Target Name | Gene Name |
|---|---|---|---|
| ENST00000369552 | NM_001031743 NM_178823 | C6orf165 | Chromosome 6 open reading frame 165 |
| ENST00000316149 | | C6orf66 | Chromosome 6 open reading frame 66 |
| ENST00000368596 | | C6orf78 | |
| ENST00000234643 | NM_000066 | C8B | Complement component 8, beta polypeptide |
| ENST00000375117 | | C9orf156 | Chromosome 9 open reading frame 156 |
| ENST00000256925 | | CABL1_HUMAN | |
| ENST00000325656 | NM_145200 | CABP4 | Calcium binding protein 4 |
| ENST00000350061 | NM_000720 | CACNA1D | Calcium channel, voltage-dependent, L type, alpha 1D subunit |
| ENST00000263942 | NM_000069 | CACNA1S | Calcium channel, voltage-dependent, L type, alpha 1S subunit |
| ENST00000329008 | NM_001017440 NM_031468 | CALN1 | Calneuron 1 |
| ENST00000359414 | | CAPN13 | Calpain 13 |
| ENST00000251973 | NM_014550 | CARD10 | Caspase recruitment domain family, member 10 |
| ENST00000309710 | | CARD14 | Caspase recruitment domain family, member 14 |
| ENST00000296777 | | CART_HUMAN | |
| ENST00000247026 | | CCDC55 | Coiled-coil domain containing 55 |
| ENST00000320516 | NM_033124 | CCDC65 | Coiled-coil domain containing 65 |
| ENST00000321945 | NM_139076 | CCDC98 | Coiled-coil domain containing 98 |
| ENST00000358813 | NM_004591 | CCL20 | Chemokine (C-C motif) ligand 20 |
| ENST00000250151 | | CCL4 | Chemokine (C-C motif) ligand 4 |
| ENST00000378569 | | CCL7 | Chemokine (C-C motif) ligand 7 |
| ENST00000225840 | | CCL8 | Chemokine (C-C motif) ligand 8 |
| ENST00000376042 | NM_033031 NM_033670 | CCNB3 | Cyclin B3 |
| ENST00000360054 | NM_001039577 NM_030937 | CCNL2 | Cyclin L2 |
| ENST00000299300 | NM_006431 | CCT2 | Chaperonin containing TCP1, subunit 2 (beta) |
| ENST00000258091 | NM_001009570.1 NM_006429.2 | CCT7 | Chaperonin containing TCP1, subunit 7 (eta) |
| ENST00000368169 | NM_001765 | CD1C | CD1c molecule |
| ENST00000354397 | NM_021155 | CD209 | CD209 molecule |
| ENST00000368034 | NM_016382 | CD244 | CD244 molecule, natural killer cell receptor 2B4 |
| ENST00000262262 | NM_001082618.1 NM_001772 | CD33 | CD33 molecule |
| ENST00000226279 | | CD38 | CD38 molecule |
| ENST00000381180 | | CD99 | CD99 molecule |
| ENST00000229265 | | CDCA3 | Cell division cycle associated 3 |
| ENST00000336219 | | CDCA4_HUMAN | |
| ENST00000268794 | NM_004360 | CDH1 | Cadherin 1, type 1, E-cadherin (epithelial) |
| ENST00000382239 | NM_006727 | CDH10 | Cadherin 10, type 2 (T2-cadherin) |
| ENST00000268603 | NM_001797 | CDH11 | Cadherin 11, type 2, OB-cadherin (osteoblast) |
| ENST00000219789 | NM_006319 | CDIPT | CDP-diacylglycerol--inositol 3-phosphatidyltransferase (phosphatidylinositol synthase) |
| ENST00000361279 | | CDKN2A | Cyclin-dependent kinase inhibitor 2A (melanoma, p16, inhibits CDK4) |
| ENST00000262662 | | CDKN2C | Cyclin-dependent kinase inhibitor 2C (p18, inhibits CDK4) |
| ENST00000006724 | NM_006890 | CEACAM7 | Carcinoembryonic antigen-related cell adhesion molecule 7 |
| ENST00000331437 | NM_031890 | CECR6 | Cat eye syndrome chromosome region, candidate 6 |
| ENST00000379037 | NM_030649 | CENTB5 | Centaurin, beta 5 |
| ENST00000373855 | NM_007018 | CEP110 | Centrosomal protein 110 kDa |

TABLE 4-continued

All targets of miR-489.

| Transcript ID | RefSeq Accession Number | Target Name | Gene Name |
|---|---|---|---|
| ENST00000375002 | | CF010_HUMAN | |
| ENST00000370318 | | CF150_HUMAN | |
| ENST00000355693 | | CHCHD8 | Coiled-coil-helix-coiled-coil-helix domain containing 8 |
| ENST00000361293 | NM_004284 | CHD1L | Chromodomain helicase DNA binding protein 1-like |
| ENST00000309818 | NM_001042572.2 NM_001271 | CHD2 | Chromodomain helicase DNA binding protein 2 |
| ENST00000266880 | | CHFR | Checkpoint with forkhead and ring finger domains |
| ENST00000035307 | | CHGUT_HUMAN | |
| ENST00000342610 | | CHRD | Chordin |
| ENST00000263671 | NM_015424 | CHRDL2 | Chordin-like 2 |
| ENST00000276410 | NM_004198 | CHRNA6 | Cholinergic receptor, nicotinic, alpha 6 |
| ENST00000370397 | | CHUK | Conserved helix-loop-helix ubiquitous kinase |
| ENST00000381895 | | CI068_HUMAN | |
| ENST00000377773 | | CI105_HUMAN | |
| ENST00000317358 | | CJ055_HUMAN | |
| ENST00000342366 | NM_000084 | CLCN5 | Chloride channel 5 (nephrolithiasis 2, X-linked, Dent disease) |
| ENST00000328796 | NM_021195 | CLDN6 | Claudin 6 |
| ENST00000300107 | | CLPX | ClpX caseinolytic peptidase X homolog (*E. coli*) |
| ENST00000360535 | | CLR59_HUMAN | |
| ENST00000263200 | NM_007098.2 | CLTCL1 | Clathrin, heavy chain-like 1 |
| ENST00000380446 | NM_001831 NM_203339.1 | CLU | Clusterin |
| ENST00000338387 | NM_014410.4 NM_199167.1 | CLUL1 | Clusterin-like 1 (retinal) |
| ENST00000229329 | | CMAS | Cytidine monophosphate N-acetylneuraminic acid synthetase |
| ENST00000306954 | | CN142_HUMAN | |
| ENST00000303904 | | COPS6 | COP9 constitutive photomorphogenic homolog subunit 6 (*Arabidopsis*) |
| ENST00000229251 | NM_016319 | COPS7A | COP9 constitutive photomorphogenic homolog subunit 7A (*Arabidopsis*) |
| ENST00000300452 | | COQ4 | Coenzyme Q4 homolog (*S. cerevisiae*) |
| ENST00000314133 | NM_004074 | COX8A | Cytochrome c oxidase subunit 8A (ubiquitous) |
| ENST00000264613 | NM_000096 | CP | Ceruloplasmin (ferroxidase) |
| ENST00000296046 | NM_001870 | CPA3 | Carboxypeptidase A3 (mast cell) |
| ENST00000359703 | | CPE | Carboxypeptidase E |
| ENST00000266679 | NM_007007 | CPSF6 | Cleavage and polyadenylation specific factor 6, 68 kDa |
| ENST00000299529 | | CRABP1 | Cellular retinoic acid binding protein 1 |
| ENST00000354577 | | CRSP3 | |
| ENST00000353151 | NM_001891 | CSN2 | Casein beta |
| ENST00000361804 | | CSPG6 | |
| ENST00000370938 | NM_001902 NM_153742 | CTH | Cystathionase (cystathionine gamma-lyase) |
| ENST00000330295 | NM_138455 | CTHRC1 | Collagen triple helix repeat containing 1 |
| ENST00000375943 | | CTRC | Chymotrypsin C (caldecrin) |
| ENST00000217131 | NM_001336 | CTSZ | Cathepsin Z |
| ENST00000346329 | NM_005231.2 NM_138565 | CTTN | Cortactin |
| ENST00000382705 | | CU063_HUMAN | |
| ENST00000310513 | | CUGBP1 | CUG triplet repeat, RNA binding protein 1 |
| ENST00000310806 | | CV106_HUMAN | |
| ENST00000371594 | NM_022101 | CXorf56 | Chromosome X open reading frame 56 |
| ENST00000302517 | NM_016463.6 | CXXC5 | CXXC finger 5 |
| ENST00000371904 | NM_000778 | CYP4A11 | Cytochrome P450, family 4, subfamily A, polypeptide 11 |
| ENST00000250498 | NM_001344 | DAD1 | Defender against cell death 1 |

TABLE 4-continued

All targets of miR-489.

| Transcript ID | RefSeq Accession Number | Target Name | Gene Name |
|---|---|---|---|
| ENST00000264161 | NM_001349 | DARS | Aspartyl-tRNA synthetase |
| ENST00000369563 | NM_022836 | DCLRE1B | DNA cross-link repair 1B (PSO2 homolog, *S. cerevisiae*) |
| ENST00000263576 | NM_013264.2 | DDX25 | DEAD (Asp-Glu-Ala-Asp) box polypeptide 25 |
| ENST00000382697 | NM_001925 | DEFA4 | Defensin, alpha 4, corticostatin |
| ENST00000362033 | NM_004401 NM_213566 | DFFA | DNA fragmentation factor, 45 kDa, alpha polypeptide |
| ENST00000264057 | NM_003648.2 NM_152879 | DGKD | Diacylglycerol kinase, delta 130 kDa |
| ENST00000346603 | | DHRS7B | Dehydrogenase/reductase (SDR family) member 7B |
| ENST00000358290 | | DHRS8 | |
| ENST00000199320 | | DIMH_HUMAN | |
| ENST00000366636 | | DISC1 | Disrupted in schizophrenia 1 |
| ENST00000346964 | NM_001098424.1 NM_004087 | DLG1 | Discs, large homolog 1 (*Drosophila*) |
| ENST00000190165 | NM_021240 | DMRT3 | Doublesex and mab-3 related transcription factor 3 |
| ENST00000082259 | NM_020877 | DNAH2 | Dynein, axonemal, heavy chain 2 |
| ENST00000376795 | | DNAJC3 | DnaJ (Hsp40) homolog, subfamily C, member 3 |
| ENST00000359526 | NM_001379 | DNMT1 | DNA (cytosine-5-)-methyltransferase 1 |
| ENST00000382345 | | DOCK8_HUMAN | |
| ENST00000371403 | NM_018431 | DOK5 | Docking protein 5 |
| ENST00000382713 | | DOK6_HUMAN | |
| ENST00000268795 | | DPEP2 | Dipeptidase 2 |
| ENST00000360534 | NM_001935 | DPP4 | Dipeptidyl-peptidase 4 (CD26, adenosine deaminase complexing protein 2) |
| ENST00000342856 | NM_181787 | DPY19L4 | Dpy-19-like 4 (*C. elegans*) |
| ENST00000370192 | NM_000110 | DPYD | Dihydropyrimidine dehydrogenase |
| ENST00000338492 | NM_006426 | DPYSL4 | Dihydropyrimidinase-like 4 |
| ENST00000382465 | NM_000798 | DRD5 | Dopamine receptor D5 |
| ENST00000374395 | | DSCR1L2 | |
| ENST00000377846 | | DSTN | Destrin (actin depolymerizing factor) |
| ENST00000267837 | | DUOX2 | Dual oxidase 2 |
| ENST00000288943 | NM_004418 | DUSP2 | Dual specificity phosphatase 2 |
| ENST00000372199 | NM_032372 | DYDC2 | DPY30 domain containing 2 |
| ENST00000375735 | NM_001080463.1 | DYNC2H1 | Dynein, cytoplasmic 2, heavy chain 1 |
| ENST00000240343 | | DYNLL2 | Dynein, light chain, LC8-type 2 |
| ENST00000372497 | | EBNA1BP2 | EBNA1 binding protein 2 |
| ENST00000372979 | NM_007265 | ECD | Ecdysoneless homolog (*Drosophila*) |
| ENST00000253392 | NM_021783 | EDA2R | Ectodysplasin A2 receptor |
| ENST00000309311 | NM_001961 | EEF2 | Eukaryotic translation elongation factor 2 |
| ENST00000337611 | NM_001039348 NM_001039349 NM_004105 | EFEMP1 | EGF-containing fibulin-like extracellular matrix protein 1 |
| ENST00000382374 | | EFHA1 | EF-hand domain family, member A1 |
| ENST00000344838 | NM_144715 | EFHB | EF-hand domain family, member B |
| ENST00000250457 | NM_022073 | EGLN3 | Egl nine homolog 3 (*C. elegans*) |
| ENST00000253039 | NM_001415 | EIF2S3 | Eukaryotic translation initiation factor 2, subunit 3 gamma, 52 kDa |
| ENST00000380512 | | EIF4A1 | Eukaryotic translation initiation factor 4A, isoform 1 |
| ENST00000269466 | NM_018696 | ELAC1 | ElaC homolog 1 (*E. coli*) |
| ENST00000379498 | | ELF1 | E74-like factor 1 (ets domain transcription factor) |
| ENST00000163344 | NM_022821 | ELOVL1 | Elongation of very long chain fatty acids (FEN1/Elo2, SUR4/Elo3, yeast)-like 1 |
| ENST00000295206 | NM_001426 | EN1 | Engrailed homeobox 1 |
| ENST00000361674 | | ENK13_HUMAN | |
| ENST00000254928 | | ERAL1 | Era G-protein-like 1 (*E. coli*) |
| ENST00000376107 | | ERCC3 | Excision repair cross- |

TABLE 4-continued

All targets of miR-489.

| Transcript ID | RefSeq Accession Number | Target Name | Gene Name |
|---|---|---|---|
| | | | complementing rodent repair deficiency, complementation group 3 (xeroderma pigmentosum group B complementing) |
| ENST00000314992 | NM_152596 | EXDL1 | Exonuclease 3'-5' domain-like 1 |
| ENST00000381295 | NM_001024924 NM_018261 NM_178237 | EXOC1 | Exocyst complex component 1 |
| ENST00000300005 | NM_080663 | EXOD1 | Exonuclease domain containing 1 |
| ENST00000370880 | NM_016046 | EXOSC1 | Exosome component 1 |
| ENST00000319211 | NM_001992 | F2R | Coagulation factor II (thrombin) receptor |
| ENST00000371780 | NM_007051 | FAF1 | Fas (TNFRSF6) associated factor 1 |
| ENST00000306378 | | FALZ_HUMAN | |
| ENST00000373084 | | FAM102A | Family with sequence similarity 102, member A |
| ENST00000361723 | NM_022074 NM_198847 | FAM111A | Family with sequence similarity 111, member A |
| ENST00000264344 | | FAM13A1 | Family with sequence similarity 13, member A1 |
| ENST00000359943 | NM_001040020 NM_014888 | FAM3C | Family with sequence similarity 3, member C |
| ENST00000369796 | | FAM40A | Family with sequence similarity 40, member A |
| ENST00000380274 | NM_012135 | FAM50B | Family with sequence similarity 50, member B |
| ENST00000372570 | NM_173642 | FAM80A | Family with sequence similarity 80, member A |
| ENST00000297530 | | FASTK | Fas-activated serine/threonine kinase |
| ENST00000368178 | NM_030764 NM_138738 | FCRL2 | Fc receptor-like 2 |
| ENST00000359263 | NM_013451.2 NM_133337.1 | FER1L3 | Fer-1-like 3, myoferlin (*C. elegans*) |
| ENST00000373535 | NM_173558 | FGD2 | FYVE, RhoGEF and PH domain containing 2 |
| ENST00000228837 | NM_020996 | FGF6 | Fibroblast growth factor 6 |
| ENST00000382333 | NM_005130 | FGFBP1 | Fibroblast growth factor binding protein 1 |
| ENST00000344213 | | FHL2 | Four and a half LIM domains 2 |
| ENST00000325888 | NM_001458.3 | FLNC | Filamin C, gamma (actin binding protein 280) |
| ENST00000008553 | NM_001002294 NM_006894 | FMO3 | Flavin containing monooxygenase 3 |
| ENST00000343844 | NM_001014986 NM_004476 | FOLH1 | Folate hydrolase (prostate-specific membrane antigen) 1 |
| ENST00000263578 | | FOXRED1 | FAD-dependent oxidoreductase domain containing 1 |
| ENST00000305531 | NM_001017929 NM_001018071 NM_152428 | FRMPD2 | FERM and PDZ domain containing 2 |
| ENST00000287474 | NM_001013660 | FRRS1 | Ferric-chelate reductase 1 |
| ENST00000265825 | | FSCN3 | Fascin homolog 3, actin-bundling protein, testicular (*Strongylocentrotus purpuratus*) |
| ENST00000304421 | NM_000145 NM_181446 | FSHR | Follicle stimulating hormone receptor |
| ENST00000379164 | NM_020116 | FSTL5 | Follistatin-like 5 |
| ENST00000367586 | NM_032020 | FUCA2 | Fucosidase, alpha-L-2, plasma |
| ENST00000254108 | | FUS | Fusion (involved in t(12; 16) in malignant liposarcoma) |
| ENST00000303225 | NM_000149 NM_001097639.1 NM_001097640.1 NM_001097641.1 | FUT3 | Fucosyltransferase 3 (galactoside 3(4)-L-fucosyltransferase, Lewis blood group) |
| ENST00000286955 | NM_000150 NM_001040701.1 | FUT6 | Fucosyltransferase 6 (alpha (1,3) fucosyltransferase) |
| ENST00000326575 | NM_002035 | FVT1 | Follicular lymphoma variant translocation 1 |
| ENST00000259271 | | GAD2 | Glutamate decarboxylase 2 (pancreatic islets and brain, 65 kDa) |

TABLE 4-continued

All targets of miR-489.

| Transcript ID | RefSeq Accession Number | Target Name | Gene Name |
|---|---|---|---|
| ENST00000376665 | NM_002049 | GATA1 | GATA binding protein 1 (globin transcription factor 1) |
| ENST00000370545 | | GATA5 | GATA binding protein 5 |
| ENST00000233612 | NM_012198 | GCA | Grancalcin, EF-hand calcium binding protein |
| ENST00000255945 | NM_018326 | GIMAP4 | GTPase, IMAP family member 4 |
| ENST00000342280 | NM_002060 | GJA4 | Gap junction protein, alpha 4, 37 kDa |
| ENST00000377938 | | GKN1 | Gastrokine 1 |
| ENST00000306497 | | GLPK3_HUMAN | |
| ENST00000278400 | NM_005838 NM_201648 | GLYAT | Glycine-N-acyltransferase |
| ENST00000380251 | NM_002069 | GNAI1 | Guanine nucleotide binding protein (G protein), alpha inhibiting activity polypeptide 1 |
| ENST00000378609 | NM_002074 | GNB1 | Guanine nucleotide binding protein (G protein), beta polypeptide 1 |
| ENST00000261837 | NM_006578.3 NM_016194 | GNB5 | Guanine nucleotide binding protein (G protein), beta 5 |
| ENST00000335281 | NM_053064 | GNG2 | Guanine nucleotide binding protein (G protein), gamma 2 |
| ENST00000373062 | | GNL2 | Guanine nucleotide binding protein-like 2 (nucleolar) |
| ENST00000359187 | | GOG8A_HUMAN | |
| ENST00000381436 | NM_005288 | GPR12 | G protein-coupled receptor 12 |
| ENST00000367838 | | GPR161 | G protein-coupled receptor 161 |
| ENST00000335866 | NM_001001549.1 NM_001001550.1 NM_001001555.1 NM_005311.3 | GRB10 | Growth factor receptor-bound protein 10 |
| ENST00000381001 | NM_001098477.1 NM_002092.3 | GRSF1 | G-rich RNA sequence binding factor 1 |
| ENST00000341272 | | GSN | Gelsolin (amyloidosis, Finnish type) |
| ENST00000219627 | NM_002094.2 | GSPT1 | G1 to S phase transition 1 |
| ENST00000375981 | NM_018094 | GSPT2 | G1 to S phase transition 2 |
| ENST00000369831 | | GSTM2 | Glutathione S-transferase M2 (muscle) |
| ENST00000261195 | NM_021957 | GYS2 | Glycogen synthase 2 (liver) |
| ENST00000378789 | NM_017545 | HAO1 | Hydroxyacid oxidase (glycolate oxidase) 1 |
| ENST00000336133 | | HCC1_HUMAN | |
| ENST00000376800 | NM_005844 | HCG9 | HLA complex group 9 |
| ENST00000368632 | NM_001527.2 | HDAC2 | Histone deacetylase 2 |
| ENST00000264173 | | HEAT1_HUMAN | |
| ENST00000058691 | | HEBP2 | Heme binding protein 2 |
| ENST00000261609 | NM_004667 | HERC2 | Hect domain and RLD 2 |
| ENST00000296575 | NM_022475 | HHIP | Hedgehog interacting protein |
| ENST00000274787 | | HIGD2A | HIG1 domain family, member 2A |
| ENST00000377781 | NM_021063 NM_138720 | HIST1H2BD | Histone cluster 1, H2bd |
| ENST00000289352 | | HIST1H4D | Histone cluster 1, H4d |
| ENST00000361427 | NM_005517 | HMGN2 | High-mobility group nucleosomal binding domain 2 |
| ENST00000377575 | NM_006353 | HMGN4 | High mobility group nucleosomal binding domain 4 |
| ENST00000313093 | NM_012292 | HMHA1 | Histocompatibility (minor) HA-1 |
| ENST00000358715 | NM_012484 NM_012485 | HMMR | Hyaluronan-mediated motility receptor (RHAMM) |
| ENST00000313173 | | HOXD8 | Homeobox D8 |
| ENST00000375000 | NM_016287 | HP1BP3 | Heterochromatin protein 1, binding protein 3 |
| ENST00000370027 | NM_024747 | HPS6 | Hermansky-Pudlak syndrome 6 |
| ENST00000381418 | | HR | Hairless homolog (mouse) |
| ENST00000369413 | | HSD3B1 | Hydroxy-delta-5-steroid dehydrogenase, 3 beta- and steroid delta-isomerase 1 |
| ENST00000369416 | | HSD3B2 | Hydroxy-delta-5-steroid dehydrogenase, 3 beta- and steroid delta-isomerase 2 |
| ENST00000375650 | | HSPA1A | Heat shock 70 kDa protein 1A |
| ENST00000375653 | | HSPA1L | Heat shock 70 kDa protein 1-like |

TABLE 4-continued

All targets of miR-489.

| Transcript ID | RefSeq Accession Number | Target Name | Gene Name |
|---|---|---|---|
| ENST00000304298 | NM_080659 | HSPB2 | Heat shock 27 kDa protein 2 |
| ENST00000258400 | NM_000867 | HTR2B | 5-hydroxytryptamine (serotonin) receptor 2B |
| ENST00000223026 | NM_012269 | HYAL4 | Hyaluronoglucosaminidase 4 |
| ENST00000240652 | NM_000415 | IAPP | Islet amyloid polypeptide |
| ENST00000371580 | NM_004969 | IDE | Insulin-degrading enzyme |
| ENST00000368132 | NM_005531 | IFI16 | Interferon, gamma-inducible protein 16 |
| ENST00000380206 | NM_000605 | IFNA2 | Interferon, alpha 2 |
| ENST00000229135 | NM_000619 | IFNG | Interferon, gamma |
| ENST00000357896 | | IFT20 | Intraflagellar transport 20 homolog (*Chlamydomonas*) |
| ENST00000270800 | NM_021258 | IL22RA1 | Interleukin 22 receptor, alpha 1 |
| ENST00000254636 | | IMMT | Inner membrane protein, mitochondrial (mitofilin) |
| ENST00000193391 | NM_016247 | IMPG2 | Interphotoreceptor matrix proteoglycan 2 |
| ENST00000338450 | NM_005537 NM_198217 NM_198218 NM_198219 | ING1 | Inhibitor of growth family, member 1 |
| ENST00000372343 | NM_014652 | IPO13 | Importin 13 |
| ENST00000360635 | | ITBP1_HUMAN | |
| ENST00000320640 | NM_030790 | ITFG1 | Integrin alpha FG-GAP repeat containing 1 |
| ENST00000339307 | NM_000885.4 | ITGA4 | Integrin, alpha 4 (antigen CD49D, alpha 4 subunit of VLA-4 receptor) |
| ENST00000222573 | NM_002214 | ITGB8 | Integrin, beta 8 |
| ENST00000295321 | NM_017969 | IWS1 | IWS1 homolog (*S. cerevisiae*) |
| ENST00000327520 | | JHD2C_HUMAN | |
| ENST00000240874 | NM_001024660.2 NM_003947 NM_007064 | KALRN | Kalirin, RhoGEF kinase |
| ENST00000377843 | | KC1A_HUMAN | |
| ENST00000290310 | NM_172201 | KCNE2 | Potassium voltage-gated channel, Isk-related family, member 2 |
| ENST00000381593 | NM_002236 | KCNF1 | Potassium voltage-gated channel, subfamily F, member 1 |
| ENST00000366621 | | KCNK1 | Potassium channel, subfamily K, member 1 |
| ENST00000303015 | | KCNK9 | Potassium channel, subfamily K, member 9 |
| ENST00000372443 | NM_001014797.1 NM_002247 | KCNMA1 | Potassium large conductance calcium-activated channel, subfamily M, alpha member 1 |
| ENST00000359963 | | KCNMB3L | |
| ENST00000264773 | NM_021614 NM_170775.1 | KCNN2 | Potassium intermediate/small conductance calcium-activated channel, subfamily N, member 2 |
| ENST00000382267 | | KDELR2 | KDEL (Lys-Asp-Glu-Leu) endoplasmic reticulum protein retention receptor 2 |
| ENST00000335817 | NM_014656 | KIAA0040 | KIAA0040 |
| ENST00000264214 | NM_015047 | KIAA0090 | KIAA0090 |
| ENST00000297423 | NM_001080394.1 | KIAA0146 | KIAA0146 |
| ENST00000318709 | | KIAA0241 | KIAA0241 |
| ENST00000372442 | NM_031207 | KIAA0467 | KIAA0467 |
| ENST00000322335 | NM_015229.3 | KIAA0664 | KIAA0664 |
| ENST00000236980 | | KIAA0971 | |
| ENST00000242315 | NM_015297.1 | KIAA1045 | KIAA1045 |
| ENST00000297222 | NM_152748 | KIAA1324L | KIAA1324-like |
| ENST00000329923 | NM_138346 | KIAA2013 | KIAA2013 |
| ENST00000335044 | NM_022342 NM_182902 NM_182903 | KIF9 | Kinesin family member 9 |
| ENST00000367769 | NM_014970 | KIFAP3 | Kinesin-associated protein 3 |
| ENST00000381763 | | KKCC1_HUMAN | |
| ENST00000359358 | NM_020805 | KLHL14 | Kelch-like 14 (*Drosophila*) |
| ENST00000265023 | NM_000893 NM_001102416.1 | KNG1 | Kininogen 1 |
| ENST00000375773 | NM_001032998 NM_003937 | KYNU | Kynureninase (L-kynurenine hydrolase) |

TABLE 4-continued

All targets of miR-489.

| Transcript ID | RefSeq Accession Number | Target Name | Gene Name |
|---|---|---|---|
| ENST00000381167 | | LAPTM4A | Lysosomal-associated protein transmembrane 4 alpha |
| ENST00000368787 | NM_032563 | LCE3D | Late cornified envelope 3D |
| ENST00000368789 | NM_178435 | LCE3E | Late cornified envelope 3E |
| ENST00000368791 | NM_178438 | LCE5A | Late cornified envelope 5A |
| ENST00000371748 | NM_014564 NM_178138 | LHX3 | LIM homeobox 3 |
| ENST00000316300 | NM_005577.2 | LPA | Lipoprotein, Lp(a) |
| ENST00000306688 | NM_144999 | LRRC45 | Leucine rich repeat containing 45 |
| ENST00000269025 | | LRRC46 | Leucine rich repeat containing 46 |
| ENST00000260382 | NM_017691 | LRRC49 | Leucine rich repeat containing 49 |
| ENST00000343742 | | LRRK2_HUMAN | |
| ENST00000228740 | | LTA4H | Leukotriene A4 hydrolase |
| ENST00000264265 | NM_020169 | LXN | Latexin |
| ENST00000219345 | | LYPLA3 | Lysophospholipase 3 (lysosomal phospholipase A2) |
| ENST00000285879 | NM_005462 | MAGEC1 | Melanoma antigen family C, 1 |
| ENST00000347546 | NM_014599 NM_177433 NM_201222 | MAGED2 | Melanoma antigen family D, 2 |
| ENST00000354489 | NM_005906 | MAK | Male germ cell-associated kinase |
| ENST00000369293 | NM_024641 | MANEA | Mannosidase, endo-alpha |
| ENST00000373045 | NM_001031740.1 NM_152496 | MANEAL | Mannosidase, endo-alpha-like |
| ENST00000307102 | NM_002755 | MAP2K1 | Mitogen-activated protein kinase kinase 1 |
| ENST00000354570 | NM_003980 | MAP7 | Microtubule-associated protein 7 |
| ENST00000374189 | | MAPK8 | Mitogen-activated protein kinase 8 |
| ENST00000347470 | NM_002752 NM_139068.1 NM_139069.1 NM_139070 | MAPK9 | Mitogen-activated protein kinase 9 |
| ENST00000329421 | | MARCKSL1 | MARCKS-like 1 |
| ENST00000376973 | NM_006610 NM_139208 | MASP2 | Mannan-binding lectin serine peptidase 2 |
| ENST00000359787 | | MB | Myoglobin |
| ENST00000370578 | NM_001099855.1 NM_005369 | MCF2 | MCF.2 cell line derived transforming sequence |
| ENST00000265056 | NM_004526 | MCM2 | Minichromosome maintenance complex component 2 |
| ENST00000233114 | | MDH1 | Malate dehydrogenase 1, NAD (soluble) |
| ENST00000359803 | | MDK | Midkine (neurite growth-promoting factor 2) |
| ENST00000346108 | NM_005587.1 | MEF2A | Myocyte enhancer factor 2A |
| ENST00000298048 | NM_014791 | MELK | Maternal embryonic leucine zipper kinase |
| ENST00000381290 | NM_005926 | MFAP1 | Microfibrillar-associated protein 1 |
| ENST00000228938 | NM_000900 | MGP | Matrix Gla protein |
| ENST00000379614 | | MICAL2 | Microtubule associated monoxygenase, calponin and LIM domain containing 2 |
| ENST00000317552 | NM_000381 NM_001098624.1 NM_033290 | MID1 | Midline 1 (Opitz/BBB syndrome) |
| ENST00000296597 | | MIMIT_HUMAN | |
| ENST00000388758 | | MKLN1 | Muskelin 1, intracellular mediator containing kelch motifs |
| ENST00000377052 | | MLLT10 | Myeloid/lymphoid or mixed-lineage leukemia (trithorax homolog, Drosophila); translocated to, 10 |
| ENST00000374259 | | MLLT7 | |
| ENST00000264605 | NM_001042467.1 NM_024101 | MLPH | Melanophilin |
| ENST00000182377 | NM_018099 | MLSTD1 | Male sterility domain containing 1 |
| ENST00000246912 | | MLX | MAX-like protein X |
| ENST00000260227 | | MMP7 | Matrix metallopeptidase 7 (matrilysin, uterine) |

TABLE 4-continued

All targets of miR-489.

| Transcript ID | RefSeq Accession Number | Target Name | Gene Name |
|---|---|---|---|
| ENST00000370782 | | MMS19L | |
| ENST00000340556 | NM_194270 | MORN2 | MORN repeat containing 2 |
| ENST00000370778 | NM_019556 | MOSPD1 | Motile sperm domain containing 1 |
| ENST00000245959 | | MPIP2_HUMAN | |
| ENST00000332314 | | MRGPRG | MAS-related GPR, member G |
| ENST00000371785 | | MRPS2 | Mitochondrial ribosomal protein S2 |
| ENST00000310776 | | MRPS22 | Mitochondrial ribosomal protein S22 |
| ENST00000313608 | | MRPS23 | Mitochondrial ribosomal protein S23 |
| ENST00000272418 | | MRPS5 | Mitochondrial ribosomal protein S5 |
| ENST00000016913 | NM_017716 | MS4A12 | Membrane-spanning 4-domains, subfamily A, member 12 |
| ENST00000281047 | | MSGN1 | Mesogenin 1 |
| ENST00000360270 | NM_002444 | MSN | Moesin |
| ENST00000249442 | NM_001006635.1 NM_006554 | MTX2 | Metaxin 2 |
| ENST00000308110 | | MUS81 | MUS81 endonuclease homolog (S. cerevisiae) |
| ENST00000274813 | | MUT | Methylmalonyl Coenzyme A mutase |
| ENST00000301415 | NM_001077186.1 NM_024729.3 | MYH14 | Myosin, heavy chain 14 |
| ENST00000349606 | NM_013262 | MYLIP | Myosin regulatory light chain interacting protein |
| ENST00000358212 | NM_000259.2 | MYO5A | Myosin VA (heavy chain 12, myoxin) |
| ENST00000259021 | NM_007067 | MYST2 | MYST histone acetyltransferase 2 |
| ENST00000360149 | NM_018257 | MYT1 | Myelin transcription factor 1 |
| ENST00000202831 | | NCKX6_HUMAN | |
| ENST00000359003 | NM_014071 | NCOA6 | Nuclear receptor coactivator 6 |
| ENST00000274137 | | NDUFS6 | NADH dehydrogenase (ubiquinone) Fe—S protein 6, 13 kDa (NADH-coenzyme Q reductase) |
| ENST00000318388 | | NDUFV2 | NADH dehydrogenase (ubiquinone) flavoprotein 2, 24 kDa |
| ENST00000373599 | | NEK6 | NIMA (never in mitosis gene a)-related kinase 6 |
| ENST00000297142 | | NEUROD6 | Neurogenic differentiation 6 |
| ENST00000375724 | NM_005384 | NFIL3 | Nuclear factor, interleukin 3 regulated |
| ENST00000329043 | NM_152995 | NFXL1 | Nuclear transcription factor, X-box binding-like 1 |
| ENST00000265259 | | NIT2 | Nitrilase family, member 2 |
| ENST00000295886 | | NKX6-1 | NK6 homeobox 1 |
| ENST00000298087 | NM_007363 | NONO | Non-POU domain containing, octamer-binding |
| ENST00000367158 | NM_015718 | NOX3 | NADPH oxidase 3 |
| ENST00000361505 | | NP | Nucleoside phosphorylase |
| ENST00000378115 | | NP_001003702.1 | |
| ENST00000279907 | | NP_001006948.1 | |
| ENST00000370640 | | NP_001009997.1 | |
| ENST00000340967 | | NP_001010887.2 | |
| ENST00000335160 | | NP_001012735.1 | |
| ENST00000374884 | | NP_001012986.2 | |
| ENST00000344380 | | NP_001013646.1 | |
| ENST00000388936 | | NP_001013712.1 | |
| ENST00000378877 | | NP_001013726.1 | |
| ENST00000377957 | | NP_001019851.1 | |
| ENST00000374251 | | NP_001020436.1 | |
| ENST00000360388 | | NP_001025029.1 | |
| ENST00000021776 | | NP_001025037.1 | |
| ENST00000334306 | | NP_001025041.1 | |
| ENST00000343217 | | NP_001028747.1 | |
| ENST00000315313 | | NP_001028831.1 | |
| ENST00000332968 | | NP_001030177.1 | |
| ENST00000381078 | | NP_001034981.1 | |
| ENST00000382142 | | NP_001035536.1 | |
| ENST00000262498 | | NP_037374.1 | |

TABLE 4-continued

All targets of miR-489.

| Transcript ID | RefSeq Accession Number | Target Name | Gene Name |
|---|---|---|---|
| ENST00000361462 | | NP_055906.2 | |
| ENST00000381240 | | NP_056174.1 | |
| ENST00000358677 | | NP_056350.1 | |
| ENST00000367220 | | NP_056368.1 | |
| ENST00000226105 | | NP_057576.2 | |
| ENST00000344442 | | NP_057732.1 | |
| ENST00000288168 | | NP_060028.2 | |
| ENST00000310452 | | NP_060222.2 | |
| ENST00000354544 | | NP_060325.3 | |
| ENST00000264434 | | NP_060350.1 | |
| ENST00000372543 | | NP_060485.3 | |
| ENST00000252100 | | NP_060972.3 | |
| ENST00000285871 | | NP_065930.2 | |
| ENST00000297788 | | NP_073579.2 | |
| ENST00000292199 | | NP_078894.2 | |
| ENST00000306049 | | NP_078959.2 | |
| ENST00000281924 | | NP_112185.1 | |
| ENST00000317568 | | NP_114110.1 | |
| ENST00000325106 | | NP_114162.1 | |
| ENST00000329713 | | NP_115622.2 | |
| ENST00000367003 | | NP_116094.2 | |
| ENST00000375706 | | NP_443121.1 | |
| ENST00000319194 | | NP_588616.1 | |
| ENST00000295488 | | NP_598375.1 | |
| ENST00000370922 | | NP_659404.2 | |
| ENST00000280571 | | NP_659495.1 | |
| ENST00000357613 | | NP_660297.1 | |
| ENST00000309733 | | NP_689613.1 | |
| ENST00000329620 | | NP_689826.1 | |
| ENST00000323352 | | NP_694553.1 | |
| ENST00000257034 | | NP_710163.1 | |
| ENST00000321510 | | NP_775908.1 | |
| ENST00000295723 | | NP_775919.2 | |
| ENST00000383671 | | NP_776160.1 | |
| ENST00000357872 | | NP_776161.2 | |
| ENST00000374900 | | NP_777572.1 | |
| ENST00000333598 | | NP_777578.1 | |
| ENST00000354310 | | NP_778223.1 | |
| ENST00000379190 | | NP_787068.2 | |
| ENST00000318586 | | NP_848650.2 | |
| ENST00000307201 | | NP_937790.1 | |
| ENST00000331738 | | NP_937992.1 | |
| ENST00000338588 | | NP_995327.1 | |
| ENST00000320866 | | NP_997283.1 | |
| ENST00000367553 | | NPL | N-acetylneuraminate pyruvate lyase (dihydrodipicolinate synthase) |
| ENST00000296930 | | NPM1 | Nucleophosmin (nucleolar phosphoprotein B23, numatrin) |
| ENST00000342694 | NM_003995 | NPR2 | Natriuretic peptide receptor B/guanylate cyclase B (atrionatriuretic peptide receptor B) |
| ENST00000338566 | NM_006174 | NPY5R | Neuropeptide Y receptor Y5 |
| ENST00000290426 | | NPY6R | Neuropeptide Y receptor Y6 (pseudogene) |
| ENST00000374570 | | NR_003086.1 | |
| ENST00000374816 | NM_001024628 NM_001024629 NM_003873 | NRP1 | Neuropilin 1 |
| ENST00000355783 | NM_022455 NM_172349 | NSD1 | Nuclear receptor binding SET domain protein 1 |
| ENST00000293973 | NM_006181 | NTN2L | Netrin 2-like (chicken) |
| ENST00000361681 | | NU6M_HUMAN | |
| ENST00000309188 | NM_024815.3 | NUDT18 | Nudix (nucleoside diphosphate linked moiety X)-type motif 18 |
| ENST00000354226 | | NUP214 | Nucleoporin 214 kDa |
| ENST00000295119 | | NUP35 | Nucleoporin 35 kDa |
| ENST00000372788 | NM_032946 NM_033152 NM_033153 NM_033154 NM_033155 | NXF5 | Nuclear RNA export factor 5 |
| ENST00000357403 | NM_022463 | NXN | Nucleoredoxin |

TABLE 4-continued

All targets of miR-489.

| Transcript ID | RefSeq Accession Number | Target Name | Gene Name |
|---|---|---|---|
| ENST00000368845 | | OAT | Ornithine aminotransferase (gyrate atrophy) |
| ENST00000371226 | | OMA1 | OMA1 homolog, zinc metallopeptidase (*S. cerevisiae*) |
| ENST00000304646 | NM_012360 | OR1F1 | Olfactory receptor, family 1, subfamily F, member 1 |
| ENST00000259357 | NM_001004451 | OR1J1 | Olfactory receptor, family 1, subfamily J, member 1 |
| ENST00000359776 | NM_001005479 | OR5H6 | Olfactory receptor, family 5, subfamily H, member 6 |
| ENST00000368144 | NM_001005184 | OR6K6 | Olfactory receptor, family 6, subfamily K, member 6 |
| ENST00000339258 | NM_001005278 | OR6N2 | Olfactory receptor, family 6, subfamily N, member 2 |
| ENST00000319481 | | OSBPL1A | Oxysterol binding protein-like 1A |
| ENST00000372858 | | PABPC4 | Poly(A) binding protein, cytoplasmic 4 (inducible form) |
| ENST00000366889 | NM_001080378.1 NM_001080379.1 NM_152410 | PACRG | PARK2 co-regulated |
| ENST00000375481 | NM_007365 | PADI2 | Peptidyl arginine deiminase, type II |
| ENST00000290507 | NM_012387 | PADI4 | Peptidyl arginine deiminase, type IV |
| ENST00000221265 | NM_019088 | PAF1 | Paf1, RNA polymerase II associated factor, homolog (*S. cerevisiae*) |
| ENST00000376141 | NM_007003 | PAGE4 | P antigen family, member 4 (prostate associated) |
| ENST00000381543 | NM_006451 NM_182789.2 NM_183323 | PAIP1 | Poly(A) binding protein interacting protein 1 |
| ENST00000379568 | NM_017906 | PAK1IP1 | PAK1 interacting protein 1 |
| ENST00000370180 | | PALMD | Palmdelphin |
| ENST00000358107 | NM_018109 | PAPD1 | PAP associated domain containing 1 |
| ENST00000338639 | | PARK7 | Parkinson disease (autosomal recessive, early onset) 7 |
| ENST00000310366 | | PARP15 | Poly (ADP-ribose) polymerase family, member 15 |
| ENST00000377123 | NM_006192 | PAX1 | Paired box 1 |
| ENST00000368465 | NM_020524 | PBXIP1 | Pre-B-cell leukemia homeobox interacting protein 1 |
| ENST00000231173 | NM_018935 | PCDHB15 | Protocadherin beta 15 |
| ENST00000194155 | NM_018936 | PCDHB2 | Protocadherin beta 2 |
| ENST00000297529 | NM_006197.3 | PCM1 | Pericentriolar material 1 |
| ENST00000367384 | NM_005389 | PCMT1 | Protein-L-isoaspartate (D-aspartate) O-methyltransferase |
| ENST00000295992 | NM_013363 | PCOLCE2 | Procollagen C-endopeptidase enhancer 2 |
| ENST00000359062 | NM_000921 | PDE3A | Phosphodiesterase 3A, cGMP-inhibited |
| ENST00000358923 | | PDE4D | Phosphodiesterase 4D, cAMP-specific (phosphodiesterase E3 dunce homolog, *Drosophila*) |
| ENST00000266395 | | PDE6H | Phosphodiesterase 6H, cGMP-specific, cone, gamma |
| ENST00000354513 | | PDGFA | Platelet-derived growth factor alpha polypeptide |
| ENST00000329399 | | PDLIM1 | PDZ and LIM domain 1 (elfin) |
| ENST00000308354 | NM_021630 NM_176871 NM_198042 | PDLIM2 | PDZ and LIM domain 2 (mystique) |
| ENST00000369032 | NM_020381 | PDSS2 | Prenyl (decaprenyl) diphosphate synthase, subunit 2 |
| ENST00000344770 | NM_002614 | PDZK1 | PDZ domain containing 1 |
| ENST00000261313 | | PEBP1 | Phosphatidylethanolamine binding protein 1 |
| ENST00000263985 | | PET112L | PET112-like (yeast) |
| ENST00000225873 | NM_000286 | PEX12 | Peroxisomal biogenesis factor 12 |
| ENST00000367756 | NM_000288 | PEX7 | Peroxisomal biogenesis factor 7 |
| ENST00000374516 | | PHF1 | PHD finger protein 1 |
| ENST00000370800 | NM_001015877 | PHF6 | PHD finger protein 6 |

TABLE 4-continued

All targets of miR-489.

| Transcript ID | RefSeq Accession Number | Target Name | Gene Name |
|---|---|---|---|
| | NM_032335 | | |
| | NM_032458 | | |
| ENST00000378659 | NM_001037537.1 | PHYH | Phytanoyl-CoA 2-hydroxylase |
| | NM_006214 | | |
| ENST00000367728 | NM_002642 | PIGC | Phosphatidylinositol glycan anchor biosynthesis, class C |
| | NM_153747 | | |
| ENST00000372689 | NM_015937 | PIGT | Phosphatidylinositol glycan anchor biosynthesis, class T |
| ENST00000374147 | NM_017837 | PIGV | Phosphatidylinositol glycan anchor biosynthesis, class V |
| ENST00000262039 | | PIK3C3 | Phosphoinositide-3-kinase, class 3 |
| ENST00000380994 | | PITRM1 | Pitrilysin metallopeptidase 1 |
| ENST00000361478 | NM_001032396 | PJA1 | Praja 1 |
| | NM_022368 | | |
| | NM_145119 | | |
| ENST00000262304 | NM_000296.2 | PKD1 | Polycystic kidney disease 1 (autosomal dominant) |
| | NM_001009944 | | |
| ENST00000372675 | NM_013355 | PKN3 | Protein kinase N3 |
| ENST00000367324 | NM_000299 | PKP1 | Plakophilin 1 (ectodermal dysplasia/skin fragility syndrome) |
| | NM_001005337 | | |
| ENST00000367466 | NM_024420 | PLA2G4A | Phospholipase A2, group IVA (cytosolic, calcium-dependent) |
| ENST00000216446 | | PLEK2 | Pleckstrin 2 |
| ENST00000341590 | NM_006832 | PLEKHC1 | Pleckstrin homology domain containing, family C (with FERM domain) member 1 |
| ENST00000361349 | NM_001042663.1 | PLEKHG5 | Pleckstrin homology domain containing, family G (with RhoGef domain) member 5 |
| | NM_001042664.1 | | |
| | NM_001042665.1 | | |
| | NM_020631 | | |
| | NM_198681.2 | | |
| ENST00000223127 | NM_001084 | PLOD3 | Procollagen-lysine, 2-oxoglutarate 5-dioxygenase 3 |
| ENST00000252590 | NM_031310 | PLVAP | Plasmalemma vesicle associated protein |
| ENST00000277585 | NM_032812 | PLXDC2 | Plexin domain containing 2 |
| ENST00000368276 | | PMF1 | Polyamine-modulated factor 1 |
| ENST00000342075 | | PMS1 | PMS1 postmeiotic segregation increased 1 (S. cerevisiae) |
| ENST00000388753 | | PO210_HUMAN | |
| ENST00000382229 | | POK9_HUMAN | |
| ENST00000215960 | | POLR2F | Polymerase (RNA) II (DNA directed) polypeptide F |
| ENST00000275569 | | POMZP3 | POM (POM121 homolog, rat) and ZP3 fusion |
| ENST00000379747 | NM_006475 | POSTN | Periostin, osteoblast specific factor |
| ENST00000344265 | NM_000306 | POU1F1 | POU class 1 homeobox 1 |
| ENST00000373232 | | PPA1 | Pyrophosphatase (inorganic) 1 |
| ENST00000372561 | NM_001080850 | PPCS | Phosphopantothenoylcysteine synthetase |
| ENST00000319610 | NM_006240 | PPEF1 | Protein phosphatase, EF-hand calcium binding domain 1 |
| | NM_152226.1 | | |
| ENST00000372341 | NM_005729 | PPIF | Peptidylprolyl isomerase F (cyclophilin F) |
| ENST00000253329 | NM_139126 | PPIL4 | Peptidylprolyl isomerase (cyclophilin)-like 4 |
| ENST00000357726 | | PRA12_HUMAN | |
| ENST00000389488 | | PRIM2A | |
| ENST00000287878 | | PRKAG2 | Protein kinase, AMP-activated, gamma 2 non-catalytic subunit |
| ENST00000379066 | | PRKD3 | Protein kinase D3 |
| ENST00000234071 | NM_000312 | PROC | Protein C (inactivator of coagulation factors Va and VIIIa) |
| ENST00000257860 | NM_006262 | PRPH | Peripherin |
| ENST00000161006 | NM_022119 | PRSS22 | Protease, serine, 22 |
| ENST00000284885 | NM_002772 | PRSS7 | Protease, serine, 7 (enterokinase) |
| ENST00000376588 | NM_021154 | PSAT1 | Phosphoserine aminotransferase 1 |
| | NM_058179 | | |

TABLE 4-continued

All targets of miR-489.

| Transcript ID | RefSeq Accession Number | Target Name | Gene Name |
|---|---|---|---|
| ENST00000342601 | | PSIP1 | PC4 and SFRS1 interacting protein 1 |
| ENST00000261479 | | PSMA6 | Proteasome (prosome, macropain) subunit, alpha type, 6 |
| ENST00000275605 | | PSPH | Phosphoserine phosphatase |
| ENST00000331920 | | PTCH | |
| ENST00000372192 | NM_003738 | PTCH2 | Patched homolog 2 (*Drosophila*) |
| ENST00000370758 | NM_000959 NM_001039585 | PTGFR | Prostaglandin F receptor (FP) |
| ENST00000263708 | | PTPN4 | Protein tyrosine phosphatase, non-receptor type 4 (megakaryocyte) |
| ENST00000367364 | NM_002838 NM_080921 NM_080922 NM_080923.2 | PTPRC | Protein tyrosine phosphatase, receptor type, C |
| ENST00000295927 | NM_002852 | PTX3 | Pentraxin-related gene, rapidly induced by IL-1 beta |
| ENST00000373742 | NM_001020658.1 NM_014676 | PUM1 | Pumilio homolog 1 (*Drosophila*) |
| ENST00000216200 | NM_002854 | PVALB | Parvalbumin |
| ENST00000376902 | | Q16653-5 | |
| ENST00000371277 | | Q4TT42_HUMAN | |
| ENST00000377439 | | Q4V339_HUMAN | |
| ENST00000316733 | | Q5SWJ0_HUMAN | |
| ENST00000331562 | | Q5T6X4_HUMAN | |
| ENST00000371932 | | Q5VXJ0_HUMAN | |
| ENST00000320930 | | Q68DA7_HUMAN | |
| ENST00000359049 | | Q6AI40_HUMAN | |
| ENST00000340357 | | Q6NXN4_HUMAN | |
| ENST00000359425 | | Q6ZNB4_HUMAN | |
| ENST00000327804 | | Q6ZSN3_HUMAN | |
| ENST00000376812 | | Q6ZSR2_HUMAN | |
| ENST00000377722 | | Q6ZVM9_HUMAN | |
| ENST00000359074 | | Q7Z4R2_HUMAN | |
| ENST00000333898 | | Q86TS2_HUMAN | |
| ENST00000335624 | | Q86VR7_HUMAN | |
| ENST00000280876 | | Q8IXV1_HUMAN | |
| ENST00000341249 | | Q8N712_HUMAN | |
| ENST00000327979 | | Q8NF41_HUMAN | |
| ENST00000328798 | | Q8NI66_HUMAN | |
| ENST00000358148 | | Q8TEB0_HUMAN | |
| ENST00000254579 | | Q8TEE6_HUMAN | |
| ENST00000329244 | | Q96S36_HUMAN | |
| ENST00000272845 | | Q96SS0_HUMAN | |
| ENST00000343811 | | Q9H579-2 | |
| ENST00000382764 | | Q9H606_HUMAN | |
| ENST00000314272 | | Q9NT86_HUMAN | |
| ENST00000356397 | | Q9P1D0_HUMAN | |
| ENST00000380195 | | Q9Y6V0-3 | |
| ENST00000382282 | | QDPR | Quinoid dihydropteridine reductase |
| ENST00000367495 | | RAB32 | RAB32, member RAS oncogene family |
| ENST00000264158 | | RAB3GAP1 | RAB3 GTPase activating protein subunit 1 (catalytic) |
| ENST00000337311 | NM_001024647.2 NM_022456 NM_175623 NM_175624 NM_175625.2 | RAB3IP | RAB3A interacting protein (rabin3) |
| ENST00000251507 | | RABGAP1L | RAB GTPase activating protein 1-like |
| ENST00000251849 | NM_002880 | RAF1 | V-raf-1 murine leukemia viral oncogene homolog 1 |
| ENST00000389591 | NM_002271 | RANBP5 | RAN binding protein 5 |
| ENST00000383772 | | RARB_HUMAN | |
| ENST00000369523 | | RARSL | |
| ENST00000222145 | NM_017805 | RASIP1 | Ras interacting protein 1 |
| ENST00000319715 | NM_006910 NM_018703 | RBBP6 | Retinoblastoma binding protein 6 |
| ENST00000315658 | | RBED1 | RNA binding motif and ELMO/CED-12 domain 1 |
| ENST00000254105 | NM_005105 | RBM8A | RNA binding motif protein 8A |

TABLE 4-continued

All targets of miR-489.

| Transcript ID | RefSeq Accession Number | Target Name | Gene Name |
|---|---|---|---|
| ENST00000378415 | NM_001268 | RCBTB2 | Regulator of chromosome condensation (RCC1) and BTB (POZ) domain containing protein 2 |
| ENST00000265881 | | REXO2 | REX2, RNA exonuclease 2 homolog (S. cerevisiae) |
| ENST00000367669 | NM_001001740.2 NM_022457 | RFWD2 | Ring finger and WD repeat domain 2 |
| ENST00000372092 | | RGR | Retinal G protein coupled receptor |
| ENST00000367460 | NM_130782 | RGS18 | Regulator of G-protein signaling 18 |
| ENST00000371175 | NM_000324 | RHAG | Rh-associated glycoprotein |
| ENST00000378013 | | RHG26_HUMAN | |
| ENST00000303700 | | RHOH | Ras homolog gene family, member H |
| ENST00000257700 | NM_021930 | RINT1 | RAD50 interactor 1 |
| ENST00000296277 | | RL39L_HUMAN | |
| ENST00000311413 | NM_032015 | RNF26 | Ring finger protein 26 |
| ENST00000263808 | NM_002944 | ROS1 | V-ros UR2 sarcoma virus oncogene homolog 1 (avian) |
| ENST00000381209 | | RPAIN | RPA interacting protein |
| ENST00000359429 | NM_006916.1 NM_199229 | RPE | Ribulose-5-phosphate-3-epimerase |
| ENST00000361575 | NM_001000 | RPL39 | Ribosomal protein L39 |
| ENST00000315741 | | RPL5 | Ribosomal protein L5 |
| ENST00000378203 | NM_001097590.1 NM_006414 NM_183005 | RPP38 | Ribonuclease P/MRP 38 kDa subunit |
| ENST00000341844 | | RPS12 | Ribosomal protein S12 |
| ENST00000359364 | | RPS4X | Ribosomal protein S4, X-linked |
| ENST00000358328 | NM_031464 | RPS6KL1 | Ribosomal protein S6 kinase-like 1 |
| ENST00000246792 | | RRAS | Related RAS viral (r-ras) oncogene homolog |
| ENST00000260563 | | RTCD1 | RNA terminal phosphate cyclase domain 1 |
| ENST00000312295 | NM_153708 | RTP1 | Receptor (chemosensory) transporter protein 1 |
| ENST00000369724 | | RWDD2 | |
| ENST00000368738 | NM_002965 | S100A9 | S100 calcium binding protein A9 |
| ENST00000296370 | | S100P | S100 calcium binding protein P |
| ENST00000359674 | | S6A12_HUMAN | |
| ENST00000335556 | NM_182610 | SAMD7 | Sterile alpha motif domain containing 7 |
| ENST00000367469 | NM_015278 | SASH1 | SAM and SH3 domain containing 1 |
| ENST00000379253 | | SAT | |
| ENST00000341787 | | SBSN | Suprabasin |
| ENST00000255390 | NM_004589 | SCO1 | SCO cytochrome oxidase deficient homolog 1 (yeast) |
| ENST00000371514 | NM_001007098.1 NM_001007099.1 NM_001007100.1 NM_001007250 NM_002979 | SCP2 | Sterol carrier protein 2 |
| ENST00000327872 | | SDHA | Succinate dehydrogenase complex, subunit A, flavoprotein (Fp) |
| ENST00000236147 | NM_000655.3 | SELL | Selectin L (lymphocyte adhesion molecule 1) |
| ENST00000379122 | NM_020210.3 NM_198925.2 | SEMA4B | Sema domain, immunoglobulin domain (Ig), transmembrane domain (TM) and short cytoplasmic domain, (semaphorin) 4B |
| ENST00000357877 | NM_004263 | SEMA4F | Sema domain, immunoglobulin domain (Ig), transmembrane domain (TM) and short cytoplasmic domain, (semaphorin) 4F |
| ENST00000340912 | NM_145204 | SENP8 | SUMO/sentrin specific peptidase family member 8 |

TABLE 4-continued

All targets of miR-489.

| Transcript ID | RefSeq Accession Number | Target Name | Gene Name |
|---|---|---|---|
| ENST00000341584 | | SERPINA6 | Serpin peptidase inhibitor, clade A (alpha-1 antiproteinase, antitrypsin), member 6 |
| ENST00000258405 | | SERPINE2 | Serpin peptidase inhibitor, clade E (nexin, plasminogen activator inhibitor type 1), member 2 |
| ENST00000295777 | NM_005025 | SERPINI1 | Serpin peptidase inhibitor, clade I (neuroserpin), member 1 |
| ENST00000264677 | NM_006217 | SERPINI2 | Serpin peptidase inhibitor, clade I (pancpin), member 2 |
| ENST00000335508 | NM_001005526.1 NM_012433 | SF3B1 | Splicing factor 3b, subunit 1, 155 kDa |
| ENST00000330854 | | SFR14_HUMAN | |
| ENST00000376280 | | SFRS1 | Splicing factor, arginine/serine-rich 1 (splicing factor 2, alternate splicing factor) |
| ENST00000334121 | NM_001077199.1 NM_139168 | SFRS12 | Splicing factor, arginine/serine-rich 12 |
| ENST00000370201 | | SFXN3 | Sideroflexin 3 |
| ENST00000263753 | NM_001012409.1 NM_001012410 NM_001012413.1 NM_138484 | SGOL1 | Shugoshin-like 1 (*S. pombe*) |
| ENST00000379698 | NM_001024666 NM_031892 | SH3KBP1 | SH3-domain kinase binding protein 1 |
| ENST00000316341 | NM_005072 | SLC12A4 | Solute carrier family 12 (potassium/chloride transporters), member 4 |
| ENST00000321925 | | SLC14A1 | Solute carrier family 14 (urea transporter), member 1 (Kidd blood group) |
| ENST00000376494 | NM_005073 | SLC15A1 | Solute carrier family 15 (oligopeptide transporter), member 1 |
| ENST00000345033 | NM_003058 | SLC22A2 | Solute carrier family 22 (organic cation transporter), member 2 |
| ENST00000263255 | | SLC25A17 | Solute carrier family 25 (mitochondrial carrier; peroxisomal membrane protein, 34 kDa), member 17 |
| ENST00000338602 | NM_004213 NM_201651 | SLC28A1 | Solute carrier family 28 (sodium-coupled nucleoside transporter), member 1 |
| ENST00000335244 | NM_181776 | SLC36A2 | Solute carrier family 36 (proton/amino acid symporter), member 2 |
| ENST00000367714 | | SLC9A11 | Solute carrier family 9, member 11 |
| ENST00000350148 | NM_005905 | SMAD9 | SMAD family member 9 |
| ENST00000358026 | NM_003072 | SMARCA4 | SWI/SNF related, matrix associated, actin dependent regulator of chromatin, subfamily a, member 4 |
| ENST00000283131 | NM_003601 | SMARCA5 | SWI/SNF related, matrix associated, actin dependent regulator of chromatin, subfamily a, member 5 |
| ENST00000374785 | | SMC2L1 | |
| ENST00000379494 | | SMPX | Small muscle protein, X-linked |
| ENST00000308624 | NM_018968.2 | SNTG2 | Syntrophin, gamma 2 |
| ENST00000368982 | | SNX3 | Sorting nexin 3 |
| ENST00000371227 | | SORBS1 | Sorbin and SH3 domain containing 1 |
| ENST00000340356 | NM_018419 | SOX18 | SRY (sex determining region Y)-box 18 |
| ENST00000227135 | | SPA17 | Sperm autoantigenic protein 17 |
| ENST00000357804 | NM_003971 | SPAG9 | Sperm associated antigen 9 |
| ENST00000280191 | | SPATA4 | Spermatogenesis associated 4 |
| ENST00000372659 | NM_020398 NM_080827 NM_181502 | SPINLW1 | Serine peptidase inhibitor-like, with Kunitz and WAP domains 1 (eppin) |
| ENST00000371258 | NM_012444 NM_198265 | SPO11 | SPO11 meiotic protein covalently bound to DSB homolog (*S. cerevisiae*) |

TABLE 4-continued

All targets of miR-489.

| Transcript ID | RefSeq Accession Number | Target Name | Gene Name |
|---|---|---|---|
| ENST00000237623 | | SPP1 | Secreted phosphoprotein 1 (osteopontin, bone sialoprotein I, early T-lymphocyte activation 1) |
| ENST00000307122 | NM_005987 | SPRR1A | Small proline-rich protein 1A |
| ENST00000244891 | NM_032681 | SPRYD5 | SPRY domain containing 5 |
| ENST00000372739 | NM_003127 | SPTAN1 | Spectrin, alpha, non-erythrocytic 1 (alpha-fodrin) |
| ENST00000262554 | | SPTLC1 | Serine palmitoyltransferase, long chain base subunit 1 |
| ENST00000382562 | NM_001047 | SRD5A1 | Steroid-5-alpha-reductase, alpha polypeptide 1 (3-oxo-5 alpha-steroid delta 4-dehydrogenase alpha 1) |
| ENST00000336613 | NM_182691 NM_182692 | SRPK2 | SFRS protein kinase 2 |
| ENST00000371320 | NM_001009955 NM_018070 NM_145716 | SSBP3 | Single stranded DNA binding protein 3 |
| ENST00000320370 | | SSFA2 | Sperm specific antigen 2 |
| ENST00000278412 | NM_003146 | SSRP1 | Structure specific recognition protein 1 |
| ENST00000337768 | | ST65G_HUMAN | |
| ENST00000225276 | | ST6GALNAC2 | ST6 (alpha-N-acetyl-neuraminyl-2,3-beta-galactosyl-1,3)-N-acetylgalactosaminide alpha-2,6-sialyltransferase 2 |
| ENST00000388888 | NM_017564 | STAB2 | Stabilin 2 |
| ENST00000380854 | NM_003155 | STC1 | Stanniocalcin 1 |
| ENST00000375333 | NM_004197 NM_032454 | STK19 | Serine/threonine kinase 19 |
| ENST00000376541 | NM_001032296 NM_003576 | STK24 | Serine/threonine kinase 24 (STE20 homolog, yeast) |
| ENST00000378577 | | STOML2 | Stomatin (EPB72)-like 2 |
| ENST00000267540 | | STON2 | Stonin 2 |
| ENST00000222812 | NM_004603 | STX1A | Syntaxin 1A (brain) |
| ENST00000273666 | NM_014980.1 | STXBP5L | Syntaxin binding protein 5-like |
| ENST00000378631 | NM_003850 | SUCLA2 | Succinate-CoA ligase, ADP-forming, beta subunit |
| ENST00000369899 | NM_016169 | SUFU | Suppressor of fused homolog (*Drosophila*) |
| ENST00000377973 | | SUGT1 | SGT1, suppressor of G2 allele of SKP1 (*S. cerevisiae*) |
| ENST00000371001 | NM_014258 | SYCP2 | Synaptonemal complex protein 2 |
| ENST00000376303 | | SYPH_HUMAN | |
| ENST00000334568 | NM_001077503.1 NM_001077504.1 NM_001077505.1 NM_001077506.1 NM_170685.2 | TAC4 | Tachykinin 4 (hemokinin) |
| ENST00000357300 | | TAF12 | TAF12 RNA polymerase II, TATA box binding protein (TBP)-associated factor, 20 kDa |
| ENST00000337256 | NM_005681 NM_139352 | TAF1A | TATA box binding protein (TBP)-associated factor, RNA polymerase I, A, 48 kDa |
| ENST00000344095 | NM_005641 NM_139122.1 NM_139123.1 NM_139315 | TAF6 | TAF6 RNA polymerase II, TATA box binding protein (TBP)-associated factor, 80 kDa |
| ENST00000374699 | | TAL2 | T-cell acute lymphocytic leukemia 2 |
| ENST00000259075 | | TANK_HUMAN | |
| ENST00000355975 | NM_017714 | TASP1 | Taspase, threonine aspartase, 1 |
| ENST00000265393 | NM_001079864.1 NM_006024 | TAX1BP1 | Tax1 (human T-cell leukemia virus type I) binding protein 1 |
| ENST00000380377 | | TBCA | Tubulin folding cofactor A |
| ENST00000373296 | NM_016954 | TBX22 | T-box 22 |
| ENST00000372680 | | TCAL5_HUMAN | |
| ENST00000372671 | | TCEAL7 | Transcription elongation factor A (SII)-like 7 |
| ENST00000369397 | | TCF7L2 | Transcription factor 7-like 2 (T-cell specific, HMG-box) |
| ENST00000286956 | NM_153046 | TDRD9 | Tudor domain containing 9 |

TABLE 4-continued

All targets of miR-489.

| Transcript ID | RefSeq Accession Number | Target Name | Gene Name |
|---|---|---|---|
| ENST00000265993 | | TECT3_HUMAN | |
| ENST00000239462 | | TENN_HUMAN | |
| ENST00000374896 | NM_001032281 NM_006287 | TFPI | Tissue factor pathway inhibitor (lipoprotein-associated coagulation inhibitor) |
| ENST00000305126 | | TGFBI | Transforming growth factor, beta-induced, 68 kDa |
| ENST00000212355 | NM_003243 | TGFBR3 | Transforming growth factor, beta receptor III |
| ENST00000296736 | NM_030953 | TIGD6 | Tigger transposable element derived 6 |
| ENST00000296802 | | TIP1_HUMAN | |
| ENST00000279992 | | TIRAP_HUMAN | |
| ENST00000265284 | | TLE4_HUMAN | |
| ENST00000389469 | | TLN2 | Talin 2 |
| ENST00000260010 | | TLR2 | Toll-like receptor 2 |
| ENST00000370196 | | TLX1_HUMAN | |
| ENST00000261789 | NM_001014842.1 NM_006405 | TM9SF1 | Transmembrane 9 superfamily member 1 |
| ENST00000245361 | NM_004800 | TM9SF2 | Transmembrane 9 superfamily member 2 |
| ENST00000288025 | NM_144676 | TMED6 | Transmembrane emp24 protein transport domain containing 6 |
| ENST00000368671 | | TMEM12 | |
| ENST00000379828 | NM_198507 | TMEM157 | Transmembrane protein 157 |
| ENST00000292246 | NM_018075 | TMEM16K | Transmembrane protein 16K |
| ENST00000353948 | | TMEM20 | Transmembrane protein 20 |
| ENST00000383743 | | TMEM42 | Transmembrane protein 42 |
| ENST00000381964 | NM_006134 | TMEM50B | Transmembrane protein 50B |
| ENST00000310991 | NM_178545 | TMEM52 | Transmembrane protein 52 |
| ENST00000356838 | NM_144649 | TMEM71 | Transmembrane protein 71 |
| ENST00000264331 | NM_001068.2 | TOP2B | Topoisomerase (DNA) II beta 180 kDa |
| ENST00000329305 | | TPM2 | Tropomyosin 2 (beta) |
| ENST00000367471 | NM_003292.2 | TPR | Translocated promoter region (to activated MET oncogene) |
| ENST00000357819 | NM_001011658.1 NM_014563.3 | TRAPPC2 | Trafficking protein particle complex 2 |
| ENST00000373162 | | TRAPPC3 | Trafficking protein particle complex 3 |
| ENST00000297221 | | TRERF1 | Transcriptional regulating factor 1 |
| ENST00000336708 | | TRIM16 | Tripartite motif-containing 16 |
| ENST00000225583 | | TRIM16L | Tripartite motif-containing 16-like |
| ENST00000376674 | NM_003449 | TRIM26 | Tripartite motif-containing 26 |
| ENST00000272395 | NM_138800 | TRIM43 | Tripartite motif-containing 43 |
| ENST00000353317 | NM_033058 NM_184085 NM_184086 NM_184087 | TRIM55 | Tripartite motif-containing 55 |
| ENST00000251607 | NM_182916 | TRNT1 | TRNA nucleotidyl transferase, CCA-adding, 1 |
| ENST00000375041 | NM_001039705.1 NM_016157.2 NM_177556.1 | TRO | Trophinin |
| ENST00000379645 | NM_003305 | TRPC3 | Transient receptor potential cation channel, subfamily C, member 3 |
| ENST00000312449 | NM_017662 | TRPM6 | Transient receptor potential cation channel, subfamily M, member 6 |
| ENST00000339687 | | TRYA1_HUMAN | |
| ENST00000361875 | NM_014779 | TSC22D2 | TSC22 domain family, member 2 |
| ENST00000355053 | NM_025244 NM_182911 | TSGA10 | Testis specific, 10 |
| ENST00000322038 | NM_005786 | TSHZ1 | Teashirt zinc finger homeobox 1 |
| ENST00000381121 | | TSN32_HUMAN | |
| ENST00000377711 | NM_145003 | TSNARE1 | T-SNARE domain containing 1 |
| ENST00000315170 | | TSP50_HUMAN | |
| ENST00000372003 | NM_005727 | TSPAN1 | Tetraspanin 1 |
| ENST00000360913 | NM_032037 | TSSK6 | Testis-specific serine kinase 6 |
| ENST00000382320 | NM_001007795 | TTC6 | Tetratricopeptide repeat domain 6 |
| ENST00000369798 | NM_003318 | TTK | TTK protein kinase |
| ENST00000242261 | NM_000474 | TWIST1 | Twist homolog 1 |

TABLE 4-continued

All targets of miR-489.

| Transcript ID | RefSeq Accession Number | Target Name | Gene Name |
|---|---|---|---|
| | | | (acrocephalosyndactyly 3; Saethre-Chotzen syndrome) (*Drosophila*) |
| ENST00000380122 | | TXLNG_HUMAN | |
| ENST00000217515 | | TXNL1 | Thioredoxin-like 1 |
| ENST00000271469 | NM_003115 | UAP1 | UDP-N-acteylglucosamine pyrophosphorylase 1 |
| ENST00000222402 | | UBE2D4 | Ubiquitin-conjugating enzyme E2D 4 (putative) |
| ENST00000272930 | | UBE2F | |
| ENST00000371077 | NM_152489 | UBE2U | Ubiquitin-conjugating enzyme E2U (putative) |
| ENST00000232165 | NM_000462.2 NM_130838 NM_130839.1 | UBE3A | Ubiquitin protein ligase E3A (human papilloma virus E6-associated protein, Angelman syndrome) |
| ENST00000252108 | NM_004788 | UBE4A | Ubiquitination factor E4A (UFD2 homolog, yeast) |
| ENST00000343638 | NM_001076683.1 NM_001076684.1 NM_014233 | UBTF | Upstream binding transcription factor, RNA polymerase I |
| ENST00000265616 | NM_005671.2 | UBXD6 | UBX domain containing 6 |
| ENST00000337130 | | UGP2 | UDP-glucose pyrophosphorylase 2 |
| ENST00000305107 | NM_021139.2 | UGT2B4 | UDP glucuronosyltransferase 2 family, polypeptide B4 |
| ENST00000282507 | NM_174914 | UGT3A2 | UDP glycosyltransferase 3 family, polypeptide A2 |
| ENST00000257548 | NM_032663 | USP30 | Ubiquitin specific peptidase 30 |
| ENST00000258499 | NM_001042403.1 NM_032147 | USP44 | Ubiquitin specific peptidase 44 |
| ENST00000286428 | NM_003372 | VBP1 | Von Hippel-Lindau binding protein 1 |
| ENST00000251127 | | VGCNL1 | |
| ENST00000372207 | | VMD2L2 | |
| ENST00000355155 | | VP13B_HUMAN | |
| ENST00000300793 | NM_021729.4 | VPS11 | Vacuolar protein sorting 11 homolog (*S. cerevisiae*) |
| ENST00000354367 | NM_018668 | VPS33B | Vacuolar protein sorting 33 homolog B (yeast) |
| ENST00000381313 | NM_003385 | VSNL1 | Visinin-like 1 |
| ENST00000369277 | NM_198496 | VWA2 | Von Willebrand factor A domain containing 2 |
| ENST00000368938 | NM_001024934 NM_001024935 NM_001024936 NM_003931 | WASF1 | WAS protein family, member 1 |
| ENST00000299764 | NM_153210.3 | WDR16 | WD repeat domain 16 |
| ENST00000369965 | NM_014969 | WDR47 | WD repeat domain 47 |
| ENST00000262144 | NM_030581 | WDR59 | WD repeat domain 59 |
| ENST00000287380 | NM_145647 | WDR67 | WD repeat domain 67 |
| ENST00000278856 | | WDR74 | WD repeat domain 74 |
| ENST00000289953 | NM_130896 NM_181510 | WFDC8 | WAP four-disulfide core domain 8 |
| ENST00000265293 | NM_015238 | WWC1 | WW and C2 domain containing 1 |
| ENST00000297303 | NM_173683 | XKR6 | XK, Kell blood group complex subunit-related family, member 6 |
| ENST00000340777 | | XP_498354.2 | |
| ENST00000351427 | | XP_931530.1 | |
| ENST00000274299 | | XP_932027.1 | |
| ENST00000342036 | | XP_932444.1 | |
| ENST00000361410 | | XP_942995.1 | |
| ENST00000306716 | | XP_944511.1 | |
| ENST00000375128 | | XPA | Xeroderma pigmentosum, complementation group A |
| ENST00000311755 | | XR_000659.1 | |
| ENST00000262887 | | XRCC1 | X-ray repair complementing defective repair in Chinese hamster cells 1 |
| ENST00000325680 | | YLPM1_HUMAN | |
| ENST00000261749 | | ZA20D3 | |
| ENST00000373515 | | ZBTB8_HUMAN | |
| ENST00000375947 | | ZCCHC6 | Zinc finger, CCHC domain containing 6 |

TABLE 4-continued

All targets of miR-489.

| Transcript ID | RefSeq Accession Number | Target Name | Gene Name |
|---|---|---|---|
| ENST00000359775 | | ZDH14_HUMAN | |
| ENST00000341191 | | ZF36_HUMAN | |
| ENST00000370609 | NM_003413 | ZIC3 | Zic family member 3 heterotaxy 1 (odd-paired homolog, *Drosophila*) |
| ENST00000381591 | NM_006624 NM_212479 | ZMYND11 | Zinc finger, MYND domain containing 11 |
| ENST00000298585 | NM_138462 | ZMYND19 | Zinc finger, MYND-type containing 19 |
| ENST00000355114 | | ZN565_HUMAN | |
| ENST00000299871 | | ZNF211 | Zinc finger protein 211 |
| ENST00000263095 | NM_003417 | ZNF264 | Zinc finger protein 264 |
| ENST00000262990 | NM_014487 | ZNF330 | Zinc finger protein 330 |
| ENST00000335815 | NM_005649 | ZNF354A | Zinc finger protein 354A |
| ENST00000221315 | NM_014650 NM_025040 | ZNF432 | Zinc finger protein 432 |
| ENST00000372524 | NM_032772 | ZNF503 | Zinc finger protein 503 |
| ENST00000291598 | NM_152478 | ZNF583 | Zinc finger protein 583 |
| ENST00000248125 | | ZNF598 | Zinc finger protein 598 |
| ENST00000379365 | NM_152577 | ZNF645 | Zinc finger protein 645 |
| ENST00000357130 | NM_024733.3 | ZNF665 | Zinc finger protein 665 |
| ENST00000372503 | | ZNF691 | Zinc finger protein 691 |
| ENST00000295131 | NM_182521 | ZSWIM2 | Zinc finger, SWIM-type containing 2 |

TABLE 5 miR-489 targets identified by miRanda and L2L

| Target Gene | Accession No: | Gene Name |
|---|---|---|
| AHSG | NM_001622.2 GI: 156523969 | alpha-2-HS-glycoprotein |
| AMELY | NM_001143.1 GI: 4502072 | amelogenin, Y-linked |
| BMP7 | NM_001719.1 GI: 4502426 | bone morphogenetic protein 7 (osteogenic protein 1) |
| CDH11 | NM_001797.2 GI: 16306531 | cadherin 11, type 2, OB-cadherin (osteoblast) |
| CHRD | NM_003741.2 GI: 30089979 | chordin |
| CHRDL2 | NM_015424.3 GI: 40353768 | chordin-like 2 |
| EN1 | NM_001426.3 GI: 126090908 | engrailed homeobox 1 |
| MAPK8 | NM_002750.2 GI: 20986493 | mitogen-activated protein kinase 8 |
| MAPK8 | NM_139046.1 GI: 20986518 | mitogen-activated protein kinase 8 |
| MAPK8 | NM_139047.1 GI: 20986520 | mitogen-activated protein kinase 8 |
| MAPK8 | NM_139049.1 GI: 20986522 | mitogen-activated protein kinase 8 |
| MGP | NM_000900.2 GI: 49574513 | matrix Gla protein |
| PAX1 | NM_006192.3 GI: 153791841 | paired box gene 1 |
| PEX7 | NM_000288.1 GI: 4505730 | peroxisomal biogenesis factor 7 |
| POSTN | NM_006475.1 GI: 5453833 | periostin, osteoblast specific factor |
| SPP1 | NM_001040058.1 GI: 91206461 | secreted phosphoprotein 1 (osteopontin, bone sialoprotein I, early T-lymphocyte activation 1) |
| SPP1 | NM_000582.2 GI: 38146097 | secreted phosphoprotein 1 (osteopontin, bone sialoprotein I, early T-lymphocyte activation 1) |
| SPP1 | NM_001040060.1 GI: 91598938 | secreted phosphoprotein 1 (osteopontin, bone sialoprotein I, early T-lymphocyte activation 1) |
| SUFU | NM_016169.2 GI: 19923478 | suppressor of fused homolog (*Drosophila*) |
| TRAPPC2 | NM_001011658.1 GI: 58533178 | trafficking protein particle complex 2 |
| TRAPPC2 | NM_014563.3 GI: 58533177 | trafficking protein particle complex 2 |
| TWIST1 | NM_000474.3 GI: 68160957 | twist homolog 1 (acrocephalosyndactyly 3; Saethre-Chotzen syndrome) (*Drosophila*) |

TABLE 6

All Targets of miR-148b

| Transcript ID. | RefSeq Accession No. | Target Name | Gene |
|---|---|---|---|
| ENSG00000008311 | NM_005763 | AASS | Aminoadipate-semialdehyde synthase |
| | | ABCB7 | ATP-binding cassette, sub-family B (MDR/TAP), member 7 |

TABLE 6-continued

All Targets of miR-148b

| Transcript ID. | RefSeq Accession No. | Target Name | Gene |
|---|---|---|---|
| ENSG00000108846 | NM_003786 | ABCC3 | ATP-binding cassette, sub-family C (CFTR/MRP), member 3 |
| ENSG00000117528 | NM_002858 | ABCD3 | ATP-binding cassette, sub-family D (ALD), member 3 |
| ENSG00000100997 | NM_001042472.1 NM_015600 | ABHD12 | Abhydrolase domain containing 12 |
| ENSG00000112077 ENSG00000136754 | NM_000324 NM_001012750 NM_001012751 NM_001012752 NM_005470 | ABI1 | Abl-interactor 1 |
| ENSG00000108798 | NM_016428 | ABI3 | ABI gene family, member 3 |
| ENSG00000167315 | NM_006111 | ACAA2 | Acetyl-Coenzyme A acyltransferase 2 (mitochondrial 3-oxoacyl-Coenzyme A thiolase) |
| ENSG00000135847 | NM_032360 | ACBD6 | Acyl-Coenzyme A binding domain containing 6 |
| ENSG00000101473 | NM_005469 NM_183385 NM_183386 | ACOT8 | Acyl-CoA thioesterase 8 |
| ENSG00000102575 | NM_001611 | ACP5 | Acid phosphatase 5, tartrate resistant |
| ENSG00000187003 | NM_006687 | ACTL7A | Actin-like 7A |
| ENSG00000163485 | NM_000674 NM_001048230.1 | ADORA1 | Adenosine A1 receptor |
| ENSG00000150594 | NM_000681 | ADRA2A | Adrenergic, alpha-2A-, receptor |
| ENSG00000106688 ENSG00000141385 | NM_004170 NM_006796 | AFG3L2 | AFG3 ATPase family gene 3-like 2 (yeast) |
| ENSG00000166748 | NM_152336.2 | AGBL1 | ATP/GTP binding protein-like 1 |
| ENSG00000165923 | NM_024783 | AGBL2 | ATP/GTP binding protein-like 2 |
| ENSG00000144891 | NM_000685 NM_004835 NM_009585 NM_031850 NM_032049 | AGTR1 | Angiotensin II receptor, type 1 |
| ENSG00000134817 | NM_005161 | AGTRL1 | Angiotensin II receptor-like 1 |
| ENSG00000004455 | NM_001625 NM_013411 | AK2 | Adenylate kinase 2 |
|  |  | AK3L2 |  |
| ENSG00000121057 ENSG00000204689 ENSG00000206519 | NM_003488 | AKAP1 | A kinase (PRKA) anchor protein 1 |
| ENSG00000117020 | NM_005465 NM_181690 | AKT3 | V-akt murine thymoma viral oncogene homolog 3 (protein kinase B, gamma) |
| ENSG00000155749 | NM_139163 | ALS2CR12 | Amyotrophic lateral sclerosis 2 (juvenile) chromosome region, candidate 12 |
| ENSG00000082146 | NM_018571 | ALS2CR2 | Amyotrophic lateral sclerosis 2 (juvenile) chromosome region, candidate 2 |
|  |  | AMZ2_HUMAN |  |
| ENSG00000176248 | NM_013366 | ANAPC2 | Anaphase promoting complex subunit 2 |
| ENSG00000091879 | NM_001147 | ANGPT2 | Angiopoietin 2 |
|  |  | ANKRD10 | Ankyrin repeat domain 10 |
| ENSG00000133302 | NM_032290 | ANKRD32 | Ankyrin repeat domain 32 |
| ENSG00000168096 | NM_133450 | ANKS3 | Ankyrin repeat and sterile alpha motif domain containing 3 |
| ENSG00000163516 | NM_001042410.1 NM_018089.2 | ANKZF1 | Ankyrin repeat and zinc finger domain containing 1 |
| ENSG00000213983 | NM_003917 NM_080545 | AP1G2 | Adaptor-related protein complex 1, gamma 2 subunit |
| ENSG00000157823 | NM_005829 | AP3S2 | Adaptor-related protein complex 3, sigma 2 subunit |
| ENSG00000204305 ENSG00000206253 ENSG00000206320 | NM_001136 NM_172197 | APBA1 | Amyloid beta (A4) precursor protein-binding, family A, member 1 (X11) |
| ENSG00000166313 | NM_001164.2 NM_145689 | APBB1 | Amyloid beta (A4) precursor protein-binding, family B, member 1 (Fe65) |

TABLE 6-continued

All Targets of miR-148b

| Transcript ID. | RefSeq Accession No. | Target Name | Gene |
|---|---|---|---|
| ENSG00000110244 | NM_000482 | APOA4 | Apolipoprotein A-IV |
| ENSG00000111701 | NM_001644 | APOBEC1 | Apolipoprotein B mRNA editing enzyme, catalytic polypeptide 1 |
| ENSG00000204444 ENSG00000206304 ENSG00000206409 | NM_019101 | APOM | Apolipoprotein M |
| ENSG00000178301 | NM_173039 | AQP11 | Aquaporin 11 |
| ENSG00000165269 | NM_001170 | AQP7 | Aquaporin 7 |
| ENSG00000105127 | NM_005858 | ARF4 | ADP-ribosylation factor 4 |
| ENSG00000168374 | NM_001660 | | |
| ENSG00000066777 | NM_006421 | ARFGEF1 | ADP-ribosylation factor guanine nucleotide-exchange factor 1(brefeldin A-inhibited) |
| ENSG00000170540 | NM_015161 | ARL6IP1 | ADP-ribosylation factor-like 6 interacting protein 1 |
| ENSG00000140691 | NM_024742.1 | ARMC5 | Armadillo repeat containing 5 |
| ENSG00000133794 ENSG00000159423 | NM_001030272 NM_001030273.1 NM_001178 NM_003748 NM_170726 | ARNTL | Aryl hydrocarbon receptor nuclear translocator-like |
| | | ARPC4 | Actin related protein 2/3 complex, subunit 4, 20 kDa |
| ENSG00000136950 | NM_030978 | ARPC5L | Actin related protein 2/3 complex, subunit 5-like |
| ENSG00000157399 | NM_000047 | ARSE | Arylsulfatase E (chondrodysplasia punctata 1) |
| ENSG00000141337 | NM_014960 | ARSG | Arylsulfatase G |
| ENSG00000156219 | NM_001179 | ART3 | ADP-ribosyltransferase 3 |
| ENSG00000119778 | NM_017552.1 | ATAD2B | ATPase family, AAA domain containing 2B |
| ENSG00000107669 | NM_001001976 | ATE1 | Arginyltransferase 1 |
| ENSG00000153147 | NM_007041 NM_003601 | | |
| ENSG00000125703 | NM_032852 NM_178221 | ATG4C | ATG4 autophagy related 4 homolog C (*S. cerevisiae*) |
| ENSG00000130734 | NM_032885 | ATG4D | ATG4 autophagy related 4 homolog D (*S. cerevisiae*) |
| ENSG00000198925 | NM_001077198.1 NM_024085.3 | ATG9A | ATG9 autophagy related 9 homolog A (*S. cerevisiae*) |
| ENSG00000101280 | NM_015985 | ATP2A1 | ATPase, Ca++ transporting, cardiac muscle, fast twitch 1 |
| ENSG00000196296 | NM_004320.3 NM_173201 | | |
| | | ATP2A2 | ATPase, Ca++ transporting, cardiac muscle, slow twitch 2 |
| ENSG00000186009 | NM_000705 | ATP4B | ATPase, H+/K+ exchanging, beta polypeptide |
| ENSG00000182220 | NM_005765 | ATP6AP2 | ATPase, H+ transporting, lysosomal accessory protein 2 |
| ENSG00000159720 | NM_004691 | ATP6V0D1 | ATPase, H+ transporting, lysosomal 38 kDa, V0 subunit d1 |
| | | ATP6V1E2 | ATPase, H+ transporting, lysosomal 31 kDa, V1 subunit E2 |
| ENSG00000105193 | NM_001020 | ATP8A1 | ATPase, aminophospholipid transporter (APLT), class I, type 8A, member 1 |
| ENSG00000171953 | NM_145691 | ATPAF2 | ATP synthase mitochondrial F1 complex assembly factor 2 |
| ENSG00000149541 | NM_012200 | B3GAT3 | Beta-1,3-glucuronyltransferase 3 (glucuronosyltransferase I) |
| ENSG00000118276 | NM_004775 | B4GALT6 | UDP-Gal:betaGlcNAc beta 1,4-galactosyltransferase, polypeptide 6 |
| ENSG00000081014 | NM_007347 | BAG1 | BCL2-associated athanogene |
| ENSG00000106588 | NM_002787 | BAG3 | BCL2-associated athanogene 3 |
| ENSG00000206580 | NM_004722 | BAGE | B melanoma antigen |
| ENSG00000135298 | NM_001704 | BAI3 | Brain-specific angiogenesis inhibitor 3 |
| | | BAIAP2 | BAI1-associated protein 2 |
| ENSG00000011132 | NM_004886 | BARD1 | BRCA1 associated RING |

TABLE 6-continued

All Targets of miR-148b

| Transcript ID. | RefSeq Accession No. | Target Name | Gene |
|---|---|---|---|
| ENSG00000138376 | NM_000465 | | domain 1 |
| ENSG00000105327 | NM_014417 | BBC3 | BCL2 binding component 3 |
| | | BBS1 | Bardet-Biedl syndrome 1 |
| ENSG00000138686 | NM_018190.2 NM_176824 | BBS7 | Bardet-Biedl syndrome 7 |
| ENSG00000153094 | NM_006538.3 NM_138621 NM_138623 NM_207002 | BCL2L11 | BCL2-like 11 (apoptosis facilitator) |
| ENSG00000121380 | NM_030766 NM_138722 NM_138723 NM_138724 | BCL2L14 | BCL2-like 14 (apoptosis facilitator) |
| ENSG00000099385 | NM_004765 | BCL7C | B-cell CLL/lymphoma 7C |
| ENSG00000100739 | NM_000710 | BDKRB1 | Bradykinin receptor B1 |
| ENSG00000117133 | NM_025065 | BXDC5 | Brix domain containing 5 |
| | | C10orf130 | |
| ENSG00000165669 | NM_022063 | C10orf84 | Chromosome 10 open reading frame 84 |
| ENSG00000204856 | NM_013300 | C12orf24 | Chromosome 12 open reading frame 24 |
| ENSG00000180116 | NM_001031748.2 | C12orf40 | Chromosome 12 open reading frame 40 |
| ENSG00000179088 | NM_001099336.1 NM_198521.2 | C12orf42 | Chromosome 12 open reading frame 42 |
| ENSG00000153495 | NM_152324 | C13orf16 | Chromosome 13 open reading frame 16 |
| ENSG00000050130 | NM_001098625.1 NM_016475.3 | C14orf100 | Chromosome 14 open reading frame 100 |
| ENSG00000165555 | NM_138791 | C14orf148 | Chromosome 14 open reading frame 148 |
| ENSG00000108671 | NM_002815 | C14orf2 | Chromosome 14 open reading frame 2 |
| | | C14orf37 | Chromosome 14 open reading frame 37 |
| | | C14orf8 | |
| ENSG00000166920 | NM_032413 NM_197955 | C15orf48 | Chromosome 15 open reading frame 48 |
| ENSG00000125149 | NM_025187 | C16orf70 | Chromosome 16 open reading frame 70 |
| ENSG00000070761 | NM_013242 | C16orf80 | Chromosome 16 open reading frame 80 |
| ENSG00000101546 | NM_024805 | C18orf22 | Chromosome 18 open reading frame 22 |
| | | C18orf8 | |
| ENSG00000181392 | NM_001039876.1 NM_032878 | C19orf46 | Chromosome 19 open reading frame 46 |
| ENSG00000104979 | NM_014047 | C19orf53 | Chromosome 19 open reading frame 53 |
| ENSG00000106392 | NM_020156 | C1GALT1 | Core 1 synthase, glycoprotein-N-acetylgalactosamine 3-beta-galactosyltransferase, 1 |
| ENSG00000162384 | NM_017887 | C1orf123 | Chromosome 1 open reading frame 123 |
| ENSG00000160767 | NM_006589 NM_198264 | C1orf2 | Chromosome 1 open reading frame 2 |
| | | C1orf68 | Chromosome 1 open reading frame 68 |
| ENSG00000153363 | NM_032705.3 | C1orf97 | Chromosome 1 open reading frame 97 |
| ENSG00000165985 | NM_001010908 | C1QL3 | Complement component 1, q subcomponent-like 3 |
| ENSG00000213192 | NM_015645 | C1QTNF5 | C1q and tumor necrosis factor related protein 5 |
| ENSG00000133466 | NM_031910 NM_182486 | C1QTNF6 | C1q and tumor necrosis factor related protein 6 |
| ENSG00000186312 | | CA5BL | Carbonic anhydrase VB-like |
| ENSG00000157782 | NM_001033677 NM_004276 NM_031205 | CABP1 | Calcium binding protein 1 |
| ENSG00000153956 | NM_000722 | CACNA2D1 | Calcium channel, voltage-dependent, alpha 2/delta subunit 1 |

TABLE 6-continued

All Targets of miR-148b

| Transcript ID. | RefSeq Accession No. | Target Name | Gene |
|---|---|---|---|
| ENSG00000169136 | NM_012068 | CAD | Carbamoyl-phosphate synthetase 2, aspartate transcarbamylase, and dihydroorotase |
| ENSG00000092529 | NM_000070.2 NM_024344 NM_173087 NM_173088.1 NM_173089 NM_173090 NM_212464.2 NM_212465.2 NM_212467.2 | CAPN3 | Calpain 3, (p94) |
| ENSG00000180881 | NM_032606 | CAPS2 | Calcyphosine 2 |
| ENSG00000187796 | NM_052813 | CARD9 | Caspase recruitment domain family, member 9 |
| ENSG00000153113 | NM_001042440.1 NM_001042441.1 NM_001042442.1 NM_001042443.1 NM_001042444.1 NM_001042445.1 NM_001042446.1 NM_001750.5 NM_173060 NM_173061 NM_173063.1 | CAST | Calpastatin |
| ENSG00000175294 | NM_053054 | CATSPER1 | Cation channel, sperm associated 1 |
| ENSG00000100211 | NM_001002880 NM_015373 | CBY1 | Chibby homolog 1 (*Drosophila*) |
| ENSG00000004766 | NM_017667.2 NM_024553 | CCDC132 | Coiled-coil domain containing 132 |
| ENSG00000122483 | NM_206886.2 | CCDC18 | Coiled-coil domain containing 18 |
| ENSG00000188848 | NM_207406.2 | CCDC4 | Coiled-coil domain containing 4 |
| ENSG00000130783 | NM_032573 NM_201435 | CCDC62 | Coiled-coil domain containing 62 |
|  |  | CCDC71 | Coiled-coil domain containing 71 |
| ENSG00000105321 | NM_015603 | CCDC9 | Coiled-coil domain containing 9 |
| ENSG00000040275 | NM_017785 | CCDC99 | Coiled-coil domain containing 99 |
| ENSG00000110148 | NM_176875 | CCKBR | Cholecystokinin B receptor |
| ENSG00000118922 | NM_007249 NM_016285 | CCL1 | Chemokine (C-C motif) ligand 1 |
| ENSG00000146731 | NM_001009186 NM_001762 | CCT6A | Chaperonin containing TCP1, subunit 6A (zeta 1) |
| ENSG00000135624 | NM_001009570.1 NM_006429.2 | CCT7 | Chaperonin containing TCP1, subunit 7 (eta) |
| ENSG00000177697 | NM_001039490 NM_004357 NM_139029 NM_139030 | CD151 | CD151 molecule (Raph blood group) |
| ENSG00000161649 | NM_145273 | CD300LG | CD300 molecule-like family member g |
| ENSG00000137101 | NM_001782 | CD72 | CD72 molecule |
| ENSG00000151465 | NM_006023 | CDC123 | Cell division cycle 123 homolog (*S. cerevisiae*) |
| ENSG00000158571 | NM_002625 |  |  |
|  |  | CDK5 | Cyclin-dependent kinase 5 |
|  |  | CDK8 | Cyclin-dependent kinase 8 |
|  |  | CDY1_HUMAN |  |
|  |  | CELP | Carboxyl ester lipase pseudogene |
| ENSG00000183678 | NM_001327 | CENPI | Centromere protein I |
| ENSG00000184033 | NM_139250 |  |  |
| ENSG00000138092 | NM_024322 | CENPO | Centromere protein O |
| ENSG00000101639 | NM_032142 | CEP192 | Centrosomal protein 192 kDa |
| ENSG00000182923 | NM_001042383.1 NM_001042384.1 NM_001042400.1 NM_025180 | CEP63 | Centrosomal protein 63 kDa |
| ENSG00000101624 | NM_024899 | CEP76 | Centrosomal protein 76 kDa |

TABLE 6-continued

All Targets of miR-148b

| Transcript ID. | RefSeq Accession No. | Target Name | Gene |
|---|---|---|---|
| ENSG00000147869 | NM_005454 | CER1 | Cerberus 1, cysteine knot superfamily, homolog (*Xenopus laevis*) |
| ENSG00000152785 | NM_001201 | CETN3 | Centrin, EF-hand protein, 3 (CDC31 homolog, yeast) |
| ENSG00000112175 | NM_021073 | CFL1 | Cofilin 1 (non-muscle) |
| ENSG00000172757 | NM_005507 | | |
| ENSG00000153922 | NM_001270 | CHD1 | Chromodomain helicase DNA binding protein 1 |
| ENSG00000131778 | NM_004284 | CHD1L | Chromodomain helicase DNA binding protein 1-like |
| ENSG00000111642 | NM_001273 | CHD4 | Chromodomain helicase DNA binding protein 4 |
| ENSG00000152518 | NM_006887 | | |
| ENSG00000171316 | NM_017780.2 | CHD7 | Chromodomain helicase DNA binding protein 7 |
| | | CHD9 | Chromodomain helicase DNA binding protein 9 |
| | | CHMP4B | Chromatin modifying protein 4B |
| | | CHUK | Conserved helix-loop-helix ubiquitous kinase |
| | | CIR_HUMAN | |
| ENSG00000134825 | NM_014206 | CKS2 | CDC28 protein kinase regulatory subunit 2 |
| ENSG00000109572 | NM_001829 NM_173872 | CLCN3 | Chloride channel 3 |
| ENSG00000166527 | NM_080387 | CLEC4D | C-type lectin domain family 4, member D |
| ENSG00000172243 | NM_022570 NM_197947.2 NM_197948.2 NM_197950 NM_197954 | CLEC7A | C-type lectin domain family 7, member A |
| ENSG00000186222 | NM_018366 | CNO | Cappuccino homolog (mouse) |
| ENSG00000113300 | NM_015455 | CNOT6 | CCR4-NOT transcription complex, subunit 6 |
| ENSG00000144619 | NM_175607.1 NM_175612.1 NM_175613 | CNTN4 | Contactin 4 |
| ENSG00000155052 | NM_130773.2 | CNTNAP5 | Contactin associated protein-like 5 |
| ENSG00000084636 | NM_001856.3 | COL16A1 | Collagen, type XVI, alpha 1 |
| | | COL20A1 | Collagen, type XX, alpha 1 |
| ENSG00000139219 | NM_001844.4 NM_033150 | COL2A1 | Collagen, type II, alpha 1 (primary osteoarthritis, spondyloepiphyseal dysplasia, congenital) |
| | | COX5B | Cytochrome c oxidase subunit Vb |
| ENSG00000160111 | NM_015692.2 | CPAMD8 | C3 and PZP-like, alpha-2-macroglobulin domain containing 8 |
| ENSG00000110090 | NM_001031847 NM_001876 | CPT1A | Carnitine palmitoyltransferase 1A (liver) |
| ENSG00000060566 | NM_032607 | CREB3L3 | CAMP responsive element binding protein 3-like 3 |
| | | CRSP7 | |
| ENSG00000163254 | NM_020989 | CRYGC | Crystallin, gamma C |
| | | CSTL1 | Cystatin-like 1 |
| ENSG00000188234 | NM_133446 | CTGLF1 | Centaurin, gamma-like family, member 1 |
| ENSG00000163453 | NM_001553 | CTSA | Cathepsin A |
| ENSG00000117984 | NM_001909 | CTSD | Cathepsin D |
| ENSG00000173681 | NM_198279 | CXorf23 | Chromosome X open reading frame 23 |
| ENSG00000205666 | | CXorf28 | Chromosome X open reading frame 28 |
| ENSG00000101901 | NM_001099922.1 NM_018466 | CXorf45 | Chromosome X open reading frame 45 |
| ENSG00000176034 | NM_173695 | CXorf59 | Chromosome X open reading frame 59 |
| ENSG00000065615 | NM_016230 | CYB5R4 | Cytochrome b5 reductase 4 |
| ENSG00000108468 | NM_006807 | CYP3A7 | Cytochrome P450, family 3, subfamily A, polypeptide 7 |
| ENSG00000160870 | NM_000765 | | |

TABLE 6-continued

All Targets of miR-148b

| Transcript ID. | RefSeq Accession No. | Target Name | Gene |
|---|---|---|---|
| ENSG00000186529 | NM_000896 | CYP4F3 | Cytochrome P450, family 4, subfamily F, polypeptide 3 |
| ENSG00000180432 | NM_004391 | CYP8B1 | Cytochrome P450, family 8, subfamily B, polypeptide 1 |
| ENSG00000078725 | NM_014618 | DBC1 | Deleted in bladder cancer 1 |
|  |  | DCC | Deleted in colorectal carcinoma |
|  |  | DCTN3 | Dynactin 3 (p22) |
| ENSG00000153904 | NM_012137 | DDAH1 | Dimethylarginine dimethylaminohydrolase 1 |
| ENSG00000181418 | NM_015086 | DDN | Dendrin |
| ENSG00000174243 | NM_004818 | DDX23 | DEAD (Asp-Glu-Ala-Asp) box polypeptide 23 |
| ENSG00000108654 | NM_004396 | DDX5 | DEAD (Asp-Glu-Ala-Asp) box polypeptide 5 |
| ENSG00000110367 | NM_004397.3 | DDX6 | DEAD (Asp-Glu-Ala-Asp) box polypeptide 6 |
| ENSG00000144231 | NM_004805 | DEDD | Death effector domain containing |
| ENSG00000158796 | NM_001039711 NM_001039712 NM_032998 |  |  |
| ENSG00000119522 | NM_020946 NM_024820 | DENND1A | DENN/MADD domain containing 1A |
| ENSG00000145214 | NM_001347 | DGKQ | Diacylglycerol kinase, theta 110 kDa |
| ENSG00000167536 | NM_144683 | DHRS13 | Dehydrogenase/reductase (SDR family) member 13 |
| ENSG00000105808 | NM_006989 | DIP2A | DIP2 disco-interacting protein 2 homolog A (*Drosophila*) |
| ENSG00000107984 | NM_012242 | DKK1 | Dickkopf homolog 1 (*Xenopus laevis*) |
| ENSG00000155011 | NM_014421 | DKK2 | Dickkopf homolog 2 (*Xenopus laevis*) |
| ENSG00000161249 | NM_001035516.1 NM_033317 | DMKN | Dermokine |
| ENSG00000104936 | NM_001081560.1 NM_001081563.1 NM_004409 | DMPK | Dystrophia myotonica-protein kinase |
| ENSG00000142700 | NM_032110.1 | DMRTA2 | DMRT-like family A2 |
| ENSG00000172869 | NM_005509 | DMXL1 | Dmx-like 1 |
| ENSG00000105877 | NM_003777.3 | DNAH11 | Dynein, axonemal, heavy chain 11 |
| ENSG00000214594 | NM_018916.3 NM_032011.1 |  |  |
| ENSG00000137094 | NM_012266 | DNAJB5 | DnaJ (Hsp40) homolog, subfamily B, member 5 |
| ENSG00000169403 | NM_000952 | DNAJC8 | DnaJ (Hsp40) homolog, subfamily C, member 8 |
| ENSG00000197959 | NM_015569.2 | DNM3 | Dynamin 3 |
| ENSG00000129757 | NM_000076 | DNMT1 | DNA (cytosine-5-)-methyltransferase 1 |
| ENSG00000123992 | NM_012100.2 | DNPEP | Aspartyl aminopeptidase |
| ENSG00000130158 | NM_020812.1 | DOCK6 | Dedicator of cytokinesis 6 |
| ENSG00000108963 | NM_001383.3 | DPH1 | DPH1 homolog (*S. cerevisiae*) |
| ENSG00000170946 | NM_181706 | DPH4 | DPH4, JJJ3 homolog (*S. cerevisiae*) |
|  |  | DTYMK | Deoxythymidylate kinase (thymidylate kinase) |
| ENSG00000140254 | NM_144565 | DUOXA1 | Dual oxidase maturation factor 1 |
| ENSG00000188542 | NM_001033575 | DUSP28 | Dual specificity phosphatase 28 |
| ENSG00000121083 | NM_080677 | DYNLL2 | Dynein, light chain, LC8-type 2 |
| ENSG00000165169 | NM_006520 | DYNLT3 | Dynein, light chain, Tctex-type 3 |
| ENSG00000105204 | NM_004714 NM_006483.1 NM_006484 | DYRK1B | Dual-specificity tyrosine-(Y)-phosphorylation regulated kinase 1B |
| ENSG00000101412 | NM_005225 | E2F1 | E2F transcription factor 1 |
|  |  | ECEL1 | Endothelin converting enzyme-like 1 |
| ENSG00000170989 | NM_001400 | EDG1 | Endothelial differentiation, sphingolipid G-protein-coupled receptor, 1 |
| ENSG00000102189 | NM_003566 | EEA1 | Early endosome antigen 1 |
| ENSG00000153922 | NM_001270 | EEF1A1 | Eukaryotic translation |

TABLE 6-continued

All Targets of miR-148b

| Transcript ID. | RefSeq Accession No. | Target Name | Gene |
|---|---|---|---|
| ENSG00000156508 | NM_001402 NR_003586.1 | | elongation factor 1 alpha 1 |
| ENSG00000165487 | NM_152726 | EFHA1 | EF-hand domain family, member A1 |
| ENSG00000100842 | NM_005864 NM_032459 | EFS | Embryonal Fyn-associated substrate |
| | | EGLX_HUMAN | |
| ENSG00000134698 | NM_017629 | EIF2C4 | Eukaryotic translation initiation factor 2C, 4 |
| | | EIF4E3 | Eukaryotic translation initiation factor 4E family member 3 |
| ENSG00000141642 | NM_018696 | ELAC1 | ElaC homolog 1 (E. coli) |
| ENSG00000162374 | NM_021952 | ELAVL4 | ELAV (embryonic lethal, abnormal vision, Drosophila)-like 4 (Hu antigen D) |
| ENSG00000126749 | NM_006331.5 | EMG1 | EMG1 nucleolar protein homolog (S. cerevisiae) |
| | | EML5 | Echinoderm microtubule associated protein like 5 |
| ENSG00000174837 | NM_001974 | EMR1 | Egf-like module containing, mucin-like, hormone receptor-like 1 |
| ENSG00000145293 | NM_021204 | ENOPH1 | Enolase-phosphatase 1 |
| ENSG00000136960 | NM_001040092 NM_006209 | ENPP2 | Ectonucleotide pyrophosphatase/phosphodiesterase 2 (autotaxin) |
| ENSG00000176177 | NM_152512 | ENTHD1 | ENTH domain containing 1 |
| ENSG00000054179 | NM_001246 | ENTPD2 | Ectonucleoside triphosphate diphosphohydrolase 2 |
| ENSG00000143032 | NM_203468 NM_020063 | | |
| ENSG00000134873 | NM_006984 NM_182848 | EP300 | E1A binding protein p300 |
| ENSG00000113946 | NM_006580 | EPB41L2 | Erythrocyte membrane protein band 4.1-like 2 |
| | | EPS15L2 | |
| ENSG00000134899 | NM_000123 | ERCC5 | Excision repair cross-complementing rodent repair deficiency, complementation group 5 (xeroderma pigmentosum, complementation group G (Cockayne syndrome)) |
| ENSG00000143845 | NM_018208 | ETNK2 | Ethanolamine kinase 2 |
| ENSG00000182944 | NM_005243 NM_013986 | EWSR1 | Ewing sarcoma breakpoint region 1 |
| ENSG00000104313 | NM_000503 NM_172058 NM_172059 NM_172060.1 | EYA1 | Eyes absent homolog 1 (Drosophila) |
| ENSG00000124491 | NM_000129 | F13A1 | Coagulation factor XIII, A1 polypeptide |
| ENSG00000117525 | NM_001993 | F3 | Coagulation factor III (thromboplastin, tissue factor) |
| ENSG00000132259 | NM_001037329 | | |
| ENSG00000116473 | NM_001010935 NM_002884 | FARP2 | FERM, RhoGEF and pleckstrin domain protein 2 |
| ENSG00000124279 | NM_024091 | FASTKD3 | FAST kinase domains 3 |
| ENSG00000139219 | NM_001844.4 | FBN1 | Fibrillin 1 |
| ENSG00000166147 | NM_033150 NM_000138 | | |
| ENSG00000142449 | NM_032447 | FBN3 | Fibrillin 3 |
| ENSG00000165355 | NM_203301 | FBXO33 | F-box protein 33 |
| | | FBXO7 | F-box protein 7 |
| ENSG00000159069 | NM_018998 | FBXW5 | F-box and WD repeat domain containing 5 |
| | | FCMD | |
| ENSG00000107831 | NM_006119 NM_033163 NM_033164 NM_033165 | FGF8 | Fibroblast growth factor 8 (androgen-induced) |
| | | FHAD1 | Forkhead-associated (FHA) phosphopeptide binding domain 1 |
| ENSG00000145216 | NM_030917 | FIP1L1 | FIP1 like 1 (S. cerevisiae) |
| ENSG00000010932 | NM_002021 | FMO1 | Flavin containing |

TABLE 6-continued

All Targets of miR-148b

| Transcript ID. | RefSeq Accession No. | Target Name | Gene |
|---|---|---|---|
| ENSG00000119203 | NM_016207 | | monooxygenase 1 |
| ENSG00000115226 | NM_022823 | FNDC4 | Fibronectin type III domain containing 4 |
| ENSG00000145708 | NM_001882 | FPGS | Folylpolyglutamate synthase |
| ENSG00000151474 | NM_018027 | FRMD4A | FERM domain containing 4A |
| ENSG00000166225 | NM_001042555.1 NM_006654.3 | FRS2 | Fibroblast growth factor receptor substrate 2 |
| ENSG00000075618 | NM_003088 | FSCN1 | Fascin homolog 1, actin-bundling protein (*Strongylocentrotus purpuratus*) |
| ENSG00000150667 | NM_152597 | FSIP1 | Fibrous sheath interacting protein 1 |
| ENSG00000160282 | NM_006657 NM_206965 | FTCD | Formiminotransferase cyclodeaminase |
| ENSG00000179163 | NM_000147 | FUCA1 | Fucosidase, alpha-L-1, tissue |
| ENSG00000165060 | NM_000144 NM_181425.1 | FXN | Frataxin |
| ENSG00000137731 | NM_001680 NM_021603 | FXYD2 | FXYD domain containing ion transport regulator 2 |
| ENSG00000010810 | NM_002037 NM_153047 NM_153048 | FYN | FYN oncogene related to SRC, FGR, YES |
| ENSG00000111432 | NM_007197 | FZD10 | Frizzled homolog 10 (*Drosophila*) |
| ENSG00000116717 | NM_001924 | GADD45A | Growth arrest and DNA-damage-inducible, alpha |
| ENSG00000166573 | NM_001480 | GALR1 | Galanin receptor 1 |
| ENSG00000140505 | NM_000761 | GAP43 | Growth associated protein 43 |
| ENSG00000165219 | NM_015635 | GAPVD1 | GTPase activating protein and VPS9 domains 1 |
| ENSG00000177628 | NM_000157 NM_001005741 NM_001005742 NM_001005749 NM_001005750 | GBA | Glucosidase, beta; acid (includes glucosylceramidase) |
| | | GCLC | Glutamate-cysteine ligase, catalytic subunit |
| ENSG00000140297 | NM_004751 | GCNT3 | Glucosaminyl (N-acetyl) transferase 3, mucin type |
| ENSG00000146013 | NM_001496 | GFRA3 | GDNF family receptor alpha 3 |
| ENSG00000167657 | NM_001348 | | |
| ENSG00000167925 | NM_032484 | GHDC | GH3 domain containing |
| | | GHRHR | Growth hormone releasing hormone receptor |
| ENSG00000106560 | NM_015660 | GIMAP2 | GTPase, IMAP family member 2 |
| ENSG00000163026 | NM_025203 | | |
| ENSG00000188910 | NM_001005752 NM_024009 | GJB3 | Gap junction protein, beta 3, 31 kDa |
| ENSG00000198814 | NM_000167 NM_203391 | GK | Glycerol kinase |
| ENSG00000182512 | NM_016417 | GLRX5 | Glutaredoxin 5 |
| | | GOLT1A | Golgi transport 1 homolog A (*S. cerevisiae*) |
| ENSG00000150625 | NM_005277 NM_201591 NM_201592.1 | GPM6A | Glycoprotein M6A |
| | | GPR103 | G protein-coupled receptor 103 |
| ENSG00000069122 | NM_001098518.1 NM_015234 | GPR116 | G protein-coupled receptor 116 |
| ENSG00000152990 | NM_145290 | GPR125 | G protein-coupled receptor 125 |
| ENSG00000206294 | | GPR143 | G protein-coupled receptor 143 |
| | | GPR157 | G protein-coupled receptor 157 |
| ENSG00000143147 | NM_007369 NM_153832 | GPR161 | G protein-coupled receptor 161 |
| ENSG00000136267 | NM_004080.1 | GPR27 | G protein-coupled receptor 27 |
| ENSG00000170837 | NM_145695.1 NM_018971 | | |
| ENSG00000134830 | NM_018485 | GPR77 | G protein-coupled receptor 77 |

TABLE 6-continued

All Targets of miR-148b

| Transcript ID. | RefSeq Accession No. | Target Name | Gene |
|---|---|---|---|
| ENSG00000164199 | NM_032119.3 | GPR98 | G protein-coupled receptor 98 |
| ENSG00000132522 | NM_004489 | GPS2 | G protein pathway suppressor 2 |
| ENSG00000181019 | NM_000903 NM_001025433 NM_001025434 | | |
| ENSG00000211445 | NM_002084.3 | GPX3 | Glutathione peroxidase 3 (plasma) |
| | | GPX5 | Glutathione peroxidase 5 (epididymal androgen-related protein) |
| ENSG00000089351 | NM_020895.2 | GRAMD1A | GRAM domain containing 1A |
| ENSG00000162946 | NM_001012957.1 NM_001012958 NM_001012959 NM_018662.2 | GRB14 | Growth factor receptor-bound protein 14 |
| ENSG00000140307 | NM_004492 | GTF2A2 | General transcription factor IIA, 2, 12 kDa |
| ENSG00000167968 | NM_001374.2 | | |
| ENSG00000197265 | NM_002095 | GTF2E2 | General transcription factor IIE, polypeptide 2, beta 34 kDa |
| | | GTF3A | General transcription factor IIIA |
| | | GTPBP6 | GTP binding protein 6 (putative) |
| ENSG00000070019 | NM_004963 | GUCY2C | Guanylate cyclase 2C (heat stable enterotoxin receptor) |
| ENSG00000132518 | NM_000180 | GUCY2D | Guanylate cyclase 2D, membrane (retina-specific) |
| ENSG00000113088 | NM_002104 | GZMK | Granzyme K (granzyme 3; tryptase II) |
| ENSG00000128708 | NM_001033085.1 NM_003642 | HAT1 | Histone acetyltransferase 1 |
| ENSG00000185808 | NM_153681 | HBE1 | Hemoglobin, epsilon 1 |
| ENSG00000213931 | NM_153682 NM_005330 | | |
| ENSG00000004961 | NM_005333 | HCCS | Holocytochrome c synthase (cytochrome c heme-lyase) |
| | | hCG_1643692 | |
| ENSG00000143321 | NM_004494 | HDGF | Hepatoma-derived growth factor (high-mobility group protein 1-like) |
| ENSG00000169660 | NM_173620.2 | HEXDC | Hexosaminidase (glycosyl hydrolase family 20, catalytic domain) containing |
| ENSG00000161202 | NM_004423 | HHEX | Hematopoietically expressed homeobox |
| ENSG00000124440 | NM_022462.3 NM_152794 NM_152795 | HIF3A | Hypoxia inducible factor 3, alpha subunit |
| ENSG00000112727 ENSG00000124693 ENSG00000178458 ENSG00000182572 | NM_021018 NM_003537 NM_003534 NM_003533 NM_003531 NM_003532 NM_003535 NM_003530 NM_003529 NM_003536 | HIST1H3H | Histone cluster 1, H3h |
| ENSG00000204523 | NM_005514 | HLA-B | Major histocompatibility complex, class I, B |
| ENSG00000204525 | NM_002117 | HLA-C | Major histocompatibility complex, class I, C |
| | | HLA-DQB2 | |
| ENSG00000204632 ENSG00000206443 ENSG00000206506 | NM_002127 | HLA-G | HLA-G histocompatibility antigen, class I, G |
| | | HLA-J | |
| ENSG00000205581 | NM_004965 | HMGN1 | High-mobility group nucleosome binding domain 1 |
| ENSG00000103942 | NM_004839.2 NM_199330.1 | HOMER2 | Homer homolog 2 (*Drosophila*) |
| | | HOXA2 | Homeobox A2 |
| | | HOXA5 | Homeobox A5 |

TABLE 6-continued

All Targets of miR-148b

| Transcript ID. | RefSeq Accession No. | Target Name | Gene |
|---|---|---|---|
| ENSG00000127483 | NM_016287 | HP1BP3 | Heterochromatin protein 1, binding protein 3 |
| ENSG00000110756 | NM_007216 NM_181507 NM_181508 | HPS5 | Hermansky-Pudlak syndrome 5 |
| | | HSP90B1 | Heat shock protein 90 kDa beta (Grp94), member 1 |
| | | IBRDC1 | |
| | | IDH3G | Isocitrate dehydrogenase 3 (NAD+) gamma |
| ENSG00000127415 | NM_000203 | IDUA | Iduronidase, alpha-L- |
| ENSG00000188483 | NM_203434.2 | IER5L | Immediate early response 5-like |
| ENSG00000204869 | NM_001002923 | IGFL4 | IGF-like family member 4 |
| ENSG00000104365 | NM_001556 | IKBKB | Inhibitor of kappa light polypeptide gene enhancer in B-cells, kinase beta |
| ENSG00000077942 | NM_001996 NM_006485 NM_006486 NM_006487.2 | IL15 | Interleukin 15 |
| ENSG00000177663 | NM_014339 | IL17RA | Interleukin 17 receptor A |
| ENSG00000115602 | NM_003856 NM_016232 | IL1RL1 | Interleukin 1 receptor-like 1 |
| ENSG00000016402 | NM_014432 | IL20RA | Interleukin 20 receptor, alpha |
| ENSG00000182393 | NM_172140 | IL29 | Interleukin 29 (interferon, lambda 1) |
| ENSG00000162747 | | INDO | Indoleamine-pyrrole 2,3 dioxygenase |
| ENSG00000128908 | NM_017553 | INOC1 | INO80 complex homolog 1 (S. cerevisiae) |
| ENSG00000102786 | NM_001039937.1 NM_001039938.1 NM_012141 | INTS6 | Integrator complex subunit 6 |
| ENSG00000119509 | NM_014425 NM_183245 | INVS | Inversin |
| ENSG00000120645 | NM_015232 | IQSEC3 | IQ motif and Sec7 domain 3 |
| ENSG00000186895 | NM_005247 | ITGAD | Integrin, alpha D |
| ENSG00000075388 | NM_002007 | ITGAE | Integrin, alpha E (antigen CD103, human mucosal lymphocyte antigen 1; alpha polypeptide) |
| ENSG00000083457 | NM_002208 | | |
| ENSG00000160867 | NM_002011 NM_022963 NM_213647 | ITGB4 | Integrin, beta 4 |
| | | ITGB4BP | |
| ENSG00000198399 | NM_006277 NM_019595 NM_147152.1 | ITSN2 | Intersectin 2 |
| ENSG00000066135 | NM_014663 | JMJD2A | Jumonji domain containing 2A |
| | | K0256_HUMAN | |
| ENSG00000173473 | NM_003074 | KATNA1 | Katanin p60 (ATPase-containing) subunit A 1 |
| ENSG00000186625 | NM_007044 | | |
| ENSG00000143603 | NM_002249 NM_170782 | KCNN3 | Potassium intermediate/small conductance calcium-activated channel, subfamily N, member 3 |
| ENSG00000117245 | NM_020816 | KIF17 | Kinesin family member 17 |
| ENSG00000130294 | NM_004321.4 | KIF1A | Kinesin family member 1A |
| ENSG00000143412 | NM_003568 | | |
| ENSG00000165115 | NM_017576 | KIF27 | Kinesin family member 27 |
| ENSG00000104892 | NM_177417 | KLC3 | Kinesin light chain 3 |
| ENSG00000163884 | NM_014079 | KLF15 | Kruppel-like factor 15 |
| ENSG00000138814 | NM_000944 | KLF4 | Kruppel-like factor 4 (gut) |
| | | KLF8 | Kruppel-like factor 8 |
| ENSG00000187961 | NM_198317 | KLHL17 | Kelch-like 17 (Drosophila) |
| ENSG00000129451 | NM_001077500.1 NM_002776 NM_145888 | KLK10 | Kallikrein-related peptidase 10 |
| ENSG00000182481 | NM_002266 | KPNA2 | Karyopherin alpha 2 (RAG cohort 1, importin alpha 1) |
| ENSG00000215769 | | | |
| ENSG00000118162 | NM_007059.2 | KPTN | Kaptin (actin binding protein) |
| ENSG00000108417 | NM_003770 | KRT37 | Keratin 37 |

TABLE 6-continued

All Targets of miR-148b

| Transcript ID. | RefSeq Accession No. | Target Name | Gene |
|---|---|---|---|
| ENSG00000186860 | NM_031964 | KRTAP17-1 | Keratin associated protein 17-1 |
| ENSG00000172886 | NM_001012503.1 NM_021046.2 | KRTAP5-9 | Keratin associated protein 5-9 |
| ENSG00000141068 | NM_014238.1 | KSR1 | Kinase suppressor of ras 1 |
| ENSG00000087299 | NM_024884 | L2HGDH | L-2-hydroxyglutarate dehydrogenase |
| | | L3MBTL | |
| ENSG00000167531 | NM_002289 | LALBA | Lactalbumin, alpha- |
| ENSG00000112769 | NM_002290 | LAMA4 | Laminin, alpha 4 |
| ENSG00000172037 | NM_002292 | LAMB2 | Laminin, beta 2 (laminin S) |
| ENSG00000005893 | NM_002294 NM_013995 | LAMP2 | Lysosomal-associated membrane protein 2 |
| ENSG00000107929 | NM_015155 | LARP5 | La ribonucleoprotein domain family, member 5 |
| ENSG00000143815 | NM_002296 NM_194442 | LBR | Lamin B receptor |
| ENSG00000043462 | NM_005565.3 | LCP2 | Lymphocyte cytosolic protein 2 (SH2 domain containing leukocyte protein of 76 kDa) |
| | | LDOC1 | Leucine zipper, down-regulated in cancer 1 |
| ENSG00000136110 | NM_001011705.1 | LECT1 | Leukocyte cell derived chemotaxin 1 |
| ENSG00000165349 | NM_007015 NM_001048164.1 NM_032803 | | |
| ENSG00000186007 | NM_001001552 | LEMD1 | LEM domain containing 1 |
| ENSG00000166477 | NM_138792 | LEO1 | Leo1, Paf1/RNA polymerase II complex component, homolog (S. cerevisiae) |
| | | LETMD1 | LETM1 domain containing 1 |
| ENSG00000153902 | NM_139284 | LGI4 | Leucine-rich repeat LGI family, member 4 |
| | | LGP2_HUMAN | |
| ENSG00000070404 | NM_005860 | LHCGR | Luteinizing hormone/choriogonadotropin receptor |
| ENSG00000138039 | NM_000233 | | |
| ENSG00000143355 | NM_001014434 NM_020204 | LHX9 | LIM homeobox 9 |
| ENSG00000101670 | NM_006033 | LIPG | Lipase, endothelial |
| ENSG00000188992 | NM_198996 | LIPI | Lipase, member I |
| ENSG00000168216 | NM_018368 | LMBRD1 | LMBR1 domain containing 1 |
| ENSG00000160789 | NM_005572 NM_170707 NM_170708 | LMNA | Lamin A/C |
| ENSG00000072201 | NM_032622 | LNX1 | Ligand of numb-protein X 1 |
| ENSG00000110002 | NM_014622 | LOH11CR2A | Loss of heterozygosity, 11, chromosomal region 2, gene A |
| ENSG00000176920 | NM_198315 NM_000511 NM_001097638.1 | | |
| ENSG00000177595 | NM_145886 | LRDD | Leucine-rich repeats and death domain containing |
| ENSG00000081479 | NM_004525 | LRP2 | Low density lipoprotein-related protein 2 |
| ENSG00000125122 | NM_001004055 NM_012163 | LRRC29 | Leucine rich repeat containing 29 |
| ENSG00000132128 | NM_006369 | LRRC41 | Leucine rich repeat containing 41 |
| ENSG00000163221 | NM_005621 | LRRC44 | Leucine rich repeat containing 44 |
| ENSG00000197147 | NM_015350 | LRRC8B | Leucine rich repeat containing 8 family, member B |
| ENSG00000175928 | NM_020873 | LRRN1 | Leucine rich repeat neuronal 1 |
| ENSG00000149657 | | LSM14B | LSM14B, SCD6 homolog B (S. cerevisiae) |
| ENSG00000090006 | NM_001042544.1 NM_001042545.1 NM_003573.2 | LTBP4 | Latent transforming growth factor beta binding protein 4 |
| ENSG00000083099 | NM_020466 | LYRM2 | LYR motif containing 2 |
| ENSG00000140280 | NM_153374 | LYSMD2 | LysM, putative peptidoglycan-binding, domain containing 2 |
| ENSG00000163818 | NM_020347 | LZTFL1 | Leucine zipper transcription factor-like 1 |

TABLE 6-continued

All Targets of miR-148b

| Transcript ID. | RefSeq Accession No. | Target Name | Gene |
|---|---|---|---|
| ENSG00000179632 | NM_032272 | MAF1 | MAF1 homolog (*S. cerevisiae*) |
| | | MAFB | V-maf musculoaponeurotic fibrosarcoma oncogene homolog B (avian) |
| ENSG00000068990 | NM_001011548 | MAGEA4 | Melanoma antigen family A, 4 |
| ENSG00000147381 | NM_001011549 | | |
| ENSG00000198716 | NM_001011550 | | |
| ENSG00000205777 | NM_002362 | | |
| | NM_001475.1 | | |
| | NM_001477.1 | | |
| | NM_021123.2 | | |
| | NM_001040663.1 | | |
| | NM_001098406.1 | | |
| | NM_001098407.1 | | |
| | NM_001098408.1 | | |
| | NM_001098409.1 | | |
| | NM_001098410.1 | | |
| | NM_001098418.1 | | |
| | NM_001468 | | |
| | NM_001085441.1 | | |
| | NM_001098405.1 | | |
| | NM_001474.1 | | |
| | NM_001476.1 | | |
| ENSG00000177383 | NM_022149 | MAGEF1 | Melanoma antigen family F, 1 |
| ENSG00000135040 | NM_024635 | MAK10 | MAK10 homolog, amino-acid N-acetyltransferase subunit, (*S. cerevisiae*) |
| ENSG00000196782 | NM_018717.3 | MAML3 | Mastermind-like 3 (*Drosophila*) |
| ENSG00000130758 | NM_002446 | MAP3K10 | Mitogen-activated protein kinase kinase kinase 10 |
| ENSG00000085511 | NM_005922 | MAP3K4 | Mitogen-activated protein kinase kinase kinase 4 |
| | NM_006724 | | |
| ENSG00000100324 | NM_006116 | MAP3K7IP1 | Mitogen-activated protein kinase kinase kinase 7 interacting protein 1 |
| | NM_153497 | | |
| ENSG00000128310 | NM_003614 | MAP4 | Microtubule-associated protein 4 |
| ENSG00000104814 | NM_001042600.1 | MAP4K1 | Mitogen-activated protein kinase kinase kinase kinase 1 |
| | NM_007181.4 | | |
| ENSG00000164114 | NM_001039580 | MAP9 | Microtubule-associated protein 9 |
| ENSG00000116141 | NM_018650 | MARK1 | MAP/microtubule affinity-regulating kinase 1 |
| | | MBIP | MAP3K12 binding inhibitory protein 1 |
| ENSG00000160294 | NM_003906 | MCM3AP | Minichromosome maintenance complex component 3 associated protein |
| ENSG00000171314 | NM_002629 | | |
| ENSG00000112139 | NM_153487.3 | MDGA1 | MAM domain containing glycosylphosphatidylinositol anchor 1 |
| ENSG00000184634 | NM_005120.2 | MED12 | Mediator complex subunit 12 |
| ENSG00000144893 | NM_053002 | MED12L | Mediator complex subunit 12-like |
| ENSG00000156603 | NM_153450 | MED19 | Mediator complex subunit 19 |
| ENSG00000123600 | NM_024770 | METTL8 | Methyltransferase like 8 |
| ENSG00000135953 | NM_032718 | MFSD9 | Major facilitator superfamily domain containing 9 |
| ENSG00000198160 | NM_001077700.1 | MIER1 | Mesoderm induction early response 1 homolog (*Xenopus laevis*) |
| | NM_001077701.1 | | |
| | NM_001077702.1 | | |
| | NM_001077703.1 | | |
| | NM_001077704.1 | | |
| | NM_020948.2 | | |
| ENSG00000099964 | NM_002415 | MIF | Macrophage migration inhibitory factor (glycosylation-inhibiting factor) |
| ENSG00000099875 | NM_017572 | MKNK2 | MAP kinase interacting serine/threonine kinase 2 |
| | NM_199054 | | |

TABLE 6-continued

All Targets of miR-148b

| Transcript ID. | RefSeq Accession No. | Target Name | Gene |
|---|---|---|---|
| ENSG00000089693 | NM_005439 | MLF2 | Myeloid leukemia factor 2 |
| ENSG00000076242 | NM_000249 | MLH1 | MutL homolog 1, colon cancer, nonpolyposis type 2 (*E. coli*) |
| | | MLLT10 | Myeloid/lymphoid or mixed-lineage leukemia (trithorax homolog, *Drosophila*); translocated to, 10 |
| ENSG00000115648 | NM_001042467.1 NM_024101 | MLPH | Melanophilin |
| ENSG00000142606 | NM_033467 | MMEL1 | Membrane metallo-endopeptidase-like 1 |
| ENSG00000106571 | NM_000168 | MMP10 | Matrix metallopeptidase 10 (stromelysin 2) |
| ENSG00000137745 | NM_002427 | MMP13 | Matrix metallopeptidase 13 (collagenase 3) |
| | | MND1 | Meiotic nuclear divisions 1 homolog (*S. cerevisiae*) |
| ENSG00000138587 | NM_018365 | MNS1 | Meiosis-specific nuclear structural 1 |
| ENSG00000165943 | NM_022151 | MOAP1 | Modulator of apoptosis 1 |
| | | MOB2_HUMAN | |
| ENSG00000182890 | NM_012084 | MOBP | Myelin-associated oligodendrocyte basic protein |
| ENSG00000075643 | NM_017947 | MOCOS | Molybdenum cofactor sulfurase |
| ENSG00000172680 | NM_005372 | MOS | V-mos Moloney murine sarcoma viral oncogene homolog |
| ENSG00000107186 | NM_003829.3 | MPDZ | Multiple PDZ domain protein |
| ENSG00000158186 | NM_001085049.1 NM_012219 | MRAS | Muscle RAS oncogene homolog |
| ENSG00000134042 | NM_031939 | MRO | Maestro |
| ENSG00000086504 | NM_006428 | MRPL28 | Mitochondrial ribosomal protein L28 |
| ENSG00000055950 | NM_032112 NM_176792 NM_176793 NM_176794 | MRPL43 | Mitochondrial ribosomal protein L43 |
| ENSG00000143436 | NM_031420 | MRPL9 | Mitochondrial ribosomal protein L9 |
| ENSG00000048544 | NM_018141 | MRPS10 | Mitochondrial ribosomal protein S10 |
| ENSG00000163319 | NM_016067 | MRPS18C | Mitochondrial ribosomal protein S18C |
| ENSG00000144029 | NM_031902 | MRPS5 | Mitochondrial ribosomal protein S5 |
| ENSG00000095002 | NM_000251 | MSH2 | MutS homolog 2, colon cancer, nonpolyposis type 1 (*E. coli*) |
| ENSG00000172209 | NM_005295 | MSMB | Microseminoprotein, beta- |
| ENSG00000173531 | NM_020998 | MST1 | Macrophage stimulating 1 (hepatocyte growth factor-like) |
| ENSG00000188786 | NM_005955 | MTF1 | Metal-regulatory transcription factor 1 |
| | | MTHFD1L | Methylenetetrahydrofolate dehydrogenase (NADP+ dependent) 1-like |
| ENSG00000063601 | NM_003828 | MTMR1 | Myotubularin related protein 1 |
| ENSG00000163719 | NM_001077525.1 NM_001077526.1 NM_022485.3 | MTMR14 | Myotubularin related protein 14 |
| ENSG00000170873 | NM_014751 | MTSS1 | Metastasis suppressor 1 |
| ENSG00000063515 | NM_005315 | MYCN | V-myc myelocytomatosis viral related oncogene, neuroblastoma derived (avian) |
| ENSG00000134323 | NM_005378 | | |
| ENSG00000172428 | NM_138336 | MYEOV2 | Myeloma overexpressed 2 |
| | | MYH13 | |
| | | MYO15B | Myosin XVB pseudogene |
| ENSG00000041515 | NM_015011 | MYO16 | Myosin XVI |
| ENSG00000142661 | NM_152372.3 | MYOM3 | Myomesin family, member 3 |
| ENSG00000090971 | NM_020378 | NAT14 | N-acetyltransferase 14 |

TABLE 6-continued

All Targets of miR-148b

| Transcript ID. | RefSeq Accession No. | Target Name | Gene |
|---|---|---|---|
| ENSG00000144035 | NM_003960 | NAT8B | N-acetyltransferase 8B (gene/pseudogene) |
| | NM_016347.2 | NBR1 | Neighbor of BRCA1 gene 1 |
| ENSG00000215691 | | NCAPH2 | Non-SMC condensin II complex, subunit H2 |
| ENSG00000025770 | NM_014551.4 NM_152299 | | |
| ENSG00000198646 | NM_014071 | NCOA6 | Nuclear receptor coactivator 6 |
| ENSG00000166579 | NM_001025579 NM_030808 | NDEL1 | NudE nuclear distribution gene E homolog (*A. nidulans*)-like 1 |
| ENSG00000124479 | NM_000266 | NDP | Norrie disease (pseudoglioma) |
| ENSG00000158864 | NM_004550 | NDUFS2 | NADH dehydrogenase (ubiquinone) Fe—S protein 2, 49 kDa (NADH-coenzyme Q reductase) |
| ENSG00000109674 | NM_018248 | NEIL3 | Nei endonuclease VIII-like 3 (*E. coli*) |
| ENSG00000197168 | NM_199289 | NEK5 | NIMA (never in mitosis gene a)-related kinase 5 |
| ENSG00000072736 | NM_004555 NM_173163 NM_173164.1 NM_173165 | NFATC3 | Nuclear factor of activated T-cells, cytoplasmic, calcineurin-dependent 3 |
| ENSG00000050344 | NM_004289 | NFE2L3 | Nuclear factor (erythroid-derived 2)-like 3 |
| ENSG00000124212 | NM_000961 | | |
| ENSG00000124529 | NM_003544 | NFKBIE | Nuclear factor of kappa light polypeptide gene enhancer in B-cells inhibitor, epsilon |
| ENSG00000146232 | NM_004556 | | |
| ENSG00000158406 | NM_003543 | | |
| ENSG00000182217 | NM_001034077 NM_003548 NM_003539 NM_003538 NM_003542 NM_021968 NM_175054 NM_003541 NM_003540 NM_003495 NM_003545 NM_003546 | | |
| ENSG00000167984 | NM_178844.2 | NLRC3 | NLR family, CARD domain containing 3 |
| ENSG00000179873 | NM_145007 | NLRP11 | NLR family, pyrin domain containing 11 |
| ENSG00000160703 | NM_024618 NM_170722.1 | NLRX1 | NLR family member X1 |
| | | NME7 | |
| | — | NMI | N-myc (and STAT) interactor |
| ENSG00000183691 | NM_005450 | NOG | Noggin |
| ENSG00000130935 | NM_015462 | NOL11 | Nucleolar protein 11 |
| ENSG00000128731 | NM_004667 | NPHS1 | Nephrosis 1, congenital, Finnish type (nephrin) |
| ENSG00000187258 | NM_207172 NM_207173 | NPSR1 | Neuropeptide S receptor 1 |
| ENSG00000156642 | NM_012428 NM_017455 | NPTN | Neuroplastin |
| ENSG00000181019 | NM_000903 NM_001025433 NM_001025434 | NQO1 | NAD(P)H dehydrogenase, quinone 1 |
| | | NR_002593.1 | |
| ENSG00000148572 | NM_030759 | NRBF2 | Nuclear receptor binding factor 2 |
| ENSG00000169752 | NM_138573 | NRG4 | Neuregulin 4 |
| ENSG00000173566 | NM_024815.3 | NUDT18 | Nudix (nucleoside diphosphate linked moiety X)-type motif 18 |
| ENSG00000167799 | NM_181843 | NUDT8 | Nudix (nucleoside diphosphate linked moiety X)-type motif 8 |
| ENSG00000136243 | NM_007342 | NUPL2 | Nucleoporin like 2 |
| | | NXF3 O95431_HUMAN | Nuclear RNA export factor 3 |
| ENSG00000135114 | NM_003733 NM_198213 | OASL | 2'-5'-oligoadenylate synthetase-like |

TABLE 6-continued

All Targets of miR-148b

| Transcript ID. | RefSeq Accession No. | Target Name | Gene |
|---|---|---|---|
| ENSG00000132297 | NM_001080399.1 | OC90 | Otoconin 90 |
|  |  | ODZ3 | Odz, odd Oz/ten-m homolog 3 (*Drosophila*) |
| ENSG00000181355 | NM_153003 | OFCC1 | Orofacial cleft 1 candidate 1 |
| ENSG00000011083 | NM_014228 | OGFR | Opioid growth factor receptor |
| ENSG00000060491 | NM_007346 |  |  |
| ENSG00000162745 | NM_015441 | OLFML2B | Olfactomedin-like 2B |
|  |  | OPRM1 | Opioid receptor, mu 1 |
| ENSG00000198965 | NM_001004472 | OR10R2 | Olfactory receptor, family 10, subfamily R, member 2 |
| ENSG00000203662 | NR_002141.1 | OR2M1P | Olfactory receptor, family 2, subfamily M, member 1 pseudogene |
| ENSG00000177186 | NM_001004691 | OR2M7 | Olfactory receptor, family 2, subfamily M, member 7 |
| ENSG00000122718 | NM_019897 | OR2S2 | Olfactory receptor, family 2, subfamily S, member 2 |
| ENSG00000180934 | NM_001001917 | OR56A1 | Olfactory receptor, family 56, subfamily A, member 1 |
| ENSG00000148215 | NM_001001923 | OR5C1 | Olfactory receptor, family 5, subfamily C, member 1 |
| ENSG00000179420 | NR_002140.1 | OR6W1P | Olfactory receptor, family 6, subfamily W, member 1 pseudogene |
| ENSG00000144909 | NM_022776 | OSBPL11 | Oxysterol binding protein-like 11 |
| ENSG00000134996 | NM_012383 | OSTF1 | Osteoclast stimulating factor 1 |
| ENSG00000036473 | NM_000531 | OTC | Ornithine carbamoyltransferase |
| ENSG00000149948 | NM_003484 |  |  |
| ENSG00000068308 | NM_017602 | OTUD5 | OTU domain containing 5 |
| ENSG00000187950 | NM_183378.2 | OVCH1 | Ovochymase 1 |
| ENSG00000187848 | NM_012226 | P2RX2 | Purinergic receptor P2X, ligand-gated ion channel, 2 |
|  | NM_016318 |  |  |
|  | NM_170682 |  |  |
|  | NM_170683 |  |  |
|  | NM_174872 |  |  |
|  | NM_174873 |  |  |
| ENSG00000171631 | NM_004154 | P2RY6 | Pyrimidinergic receptor P2Y, G-protein coupled, 6 |
|  | NM_176796 |  |  |
|  | NM_176797 |  |  |
|  | NM_178798 |  |  |
| ENSG00000112530 | NM_001080378.1 | PACRG | PARK2 co-regulated |
|  | NM_001080379.1 |  |  |
|  | NM_152410 |  |  |
| ENSG00000198682 | NM_001015880.1 | PAPSS2 | 3'-phosphoadenosine 5'-phosphosulfate synthase 2 |
|  | NM_004670 |  |  |
| ENSG00000140694 | NM_002582.1 | PARN | Poly(A)-specific ribonuclease (deadenylation nuclease) |
| ENSG00000148600 | NM_033100 | PCDH21 | Protocadherin 21 |
| ENSG00000120265 | NM_005389 | PCMT1 | Protein-L-isoaspartate (D-aspartate) O-methyltransferase |
| ENSG00000135749 | NM_014801.3 | PCNXL2 | Pecanex-like 2 (*Drosophila*) |
| ENSG00000173282 |  | PCNXL3 | Pecanex-like 3 (*Drosophila*) |
| ENSG00000197136 |  |  |  |
| ENSG00000099783 | NM_005968 | PCSK6 | Proprotein convertase subtilisin/kexin type 6 |
| ENSG00000140479 | NM_031203 |  |  |
|  | NM_002570.3 |  |  |
|  | NM_138319.2 |  |  |
|  | NM_138320.1 |  |  |
|  | NM_138321.1 |  |  |
|  | NM_138322.2 |  |  |
|  | NM_138323.1 |  |  |
|  | NM_138324.1 |  |  |
|  | NM_138325.2 |  |  |
| ENSG00000102230 | NM_004845 | PCYT1B | Phosphate cytidylyltransferase 1, choline, beta |
| ENSG00000154678 | NM_005020 | PDE1C | Phosphodiesterase 1C, calmodulin-dependent 70 kDa |
| ENSG00000121905 | NM_002143 | PDE4D | Phosphodiesterase 4D, cAMP-specific (phosphodiesterase E3 dunce homolog, *Drosophila*) |

TABLE 6-continued

All Targets of miR-148b

| Transcript ID. | RefSeq Accession No. | Target Name | Gene |
|---|---|---|---|
| ENSG00000167004 | NM_005313 | PDIA3 | Protein disulfide isomerase family A, member 3 |
| | | PDK3 | Pyruvate dehydrogenase kinase, isozyme 3 |
| ENSG00000125430 | NM_006041 | PFAS | Phosphoribosylformylglycinamidine synthase (FGAR amidotransferase) |
| ENSG00000170525 | NM_004566 | PFKFB3 | 6-phosphofructo-2-kinase/fructose-2,6-biphosphatase 3 |
| ENSG00000025293 | NM_016436 | PHF20 | PHD finger protein 20 |
| ENSG00000172943 | NM_015107 | PHF8 | PHD finger protein 8 |
| ENSG00000144381 | NM_002156 | PHKG2 | Phosphorylase kinase, gamma 2 (testis) |
| ENSG00000156873 | NM_199440 NM_000294 | | |
| ENSG00000087111 | NM_033198 | PIGS | Phosphatidylinositol glycan anchor biosynthesis, class S |
| ENSG00000121879 | NM_006218.2 | PIK3CA | Phosphoinositide-3-kinase, catalytic, alpha polypeptide |
| | | PIK4CA | |
| ENSG00000107959 | NM_014889.2 | PITRM1 | Pitrilysin metallopeptidase 1 |
| ENSG00000197181 | NM_018068 | PIWIL2 | Piwi-like 2 (*Drosophila*) |
| ENSG00000118762 | NM_000297 | PKD2 | Polycystic kidney disease 2 (autosomal dominant) |
| ENSG00000143627 | NM_000298 NM_181871.2 | PKLR | Pyruvate kinase, liver and RBC |
| ENSG00000116711 | NM_024420 | PLA2G4A | Phospholipase A2, group IVA (cytosolic, calcium-dependent) |
| ENSG00000168907 | NM_213600 | PLA2G4F | Phospholipase A2, group IVF |
| ENSG00000127472 | NM_000929 | PLA2G5 | Phospholipase A2, group V |
| ENSG00000137055 | NM_001031689 NM_004253 | PLAA | Phospholipase A2-activating protein |
| | | PLEKHQ1 | |
| | | PLGB_HUMAN | |
| | | PLGLA1 | Plasminogen-like A1 |
| ENSG00000003147 | NM_004968 | PLGLB1 | Plasminogen-like B1 |
| ENSG00000125551 | NM_022307 | | |
| ENSG00000183281 | NM_002665 NM_001032392 | | |
| | | PLSCR5 | Phospholipid scramblase family, member 5 |
| ENSG00000127957 | NM_001003686 NM_005395 | PMS2L3 | Postmeiotic segregation increased 2-like 3 |
| ENSG00000146453 | NM_173516 | PNLDC1 | Poly(A)-specific ribonuclease (PARN)-like domain containing 1 |
| ENSG00000177666 | NM_020376 | PNPLA2 | Patatin-like phospholipase domain containing 2 |
| ENSG00000032444 | NM_006702 | PNPLA6 | Patatin-like phospholipase domain containing 6 |
| ENSG00000146278 | NM_006813 | PNRC1 | Proline-rich nuclear receptor coactivator 1 |
| ENSG00000189266 | NM_017761 | PNRC2 | Proline-rich nuclear receptor coactivator 2 |
| ENSG00000215700 | | | |
| ENSG00000047315 | NM_000938 | POLR2B | Polymerase (RNA) II (DNA directed) polypeptide B, 140 kDa |
| ENSG00000172336 | NM_005837 | POP7 | Processing of precursor 7, ribonuclease P/MRP subunit (*S. cerevisiae*) |
| | | PPAP2C | Phosphatidic acid phosphatase type 2C |
| | | PPIB | Peptidylprolyl isomerase B (cyclophilin B) |
| ENSG00000084072 | NM_006112 NM_203456 NM_203457.1 | PPIE | Peptidylprolyl isomerase E (cyclophilin E) |
| ENSG00000156475 | NM_004576 NM_181674 NM_181675 NM_181676 NM_181677.1 NM_181678.1 | PPP2R2B | Protein phosphatase 2 (formerly 2A), regulatory subunit B, beta isoform |

TABLE 6-continued

All Targets of miR-148b

| Transcript ID. | RefSeq Accession No. | Target Name | Gene |
|---|---|---|---|
| ENSG00000204481 | NM_001099854.1 | PRAMEF14 | PRAME family member 14 |
| ENSG00000106617 | NM_001040633.1 NM_016203 NM_024429.1 | PRKAG2 | Protein kinase, AMP-activated, gamma 2 non-catalytic subunit |
| ENSG00000067606 | NM_001033581.1 NM_001033582.1 NM_002744 | PRKCZ | Protein kinase C, zeta |
| ENSG00000138669 | NM_006259 | PRKG2 | Protein kinase, cGMP-dependent, type II |
|  |  | PROM1 | Prominin 1 |
| ENSG00000197746 | NM_001042465.1 NM_001042466.1 NM_002778 | PSAP | Prosaposin (variant Gaucher disease and variant metachromatic leukodystrophy) |
| ENSG00000100055 | NM_013385 | PSCD4 | Pleckstrin homology, Sec7 and coiled-coil domains 4 |
| ENSG00000142507 | NM_002798 | PSMB6 | Proteasome (prosome, macropain) subunit, beta type, 6 |
|  |  | PSMC3IP |  |
| ENSG00000173692 | NM_002807 | PSMD1 | Proteasome (prosome, macropain) 26S subunit, non-ATPase, 1 |
| ENSG00000095261 | NM_005047 | PSMD5 | Proteasome (prosome, macropain) 26S subunit, non-ATPase, 5 |
| ENSG00000121390 | NM_001042414.1 NR_003272.1 | PSPC1 | Paraspeckle component 1 |
| ENSG00000125384 | NM_000956 | PTGER2 | Prostaglandin E receptor 2 (subtype EP2), 53 kDa |
| ENSG00000175354 | NM_002828 NM_080422 NM_080423 | PTPN2 | Protein tyrosine phosphatase, non-receptor type 2 |
|  |  | PXMP2 | Peroxisomal membrane protein 2, 22 kDa |
| ENSG00000041353 | NM_004163 | RAB27B | RAB27B, member RAS oncogene family |
| ENSG00000109113 | NM_031934 | RAB34 | RAB34, member RAS oncogene family |
| ENSG00000179331 | NM_017516 | RAB39 | RAB39, member RAS oncogene family |
| ENSG00000172780 | NM_020701.2 NM_198490 | RAB43 | RAB43, member RAS oncogene family |
| ENSG00000137955 | NM_004582 | RABGGTB | Rab geranylgeranyltransferase, beta subunit |
|  |  | RAC2 | Ras-related C3 botulinum toxin substrate 2 (rho family, small GTP binding protein Rac2) |
| ENSG00000051180 | NM_002875 NM_133487.2 | RAD51 | RAD51 homolog (RecA homolog, E. coli) (S. cerevisiae) |
| ENSG00000185379 | NM_002878 NM_133629 | RAD51L3 | RAD51-like 3 (S. cerevisiae) |
| ENSG00000155918 | NM_130900 | RAET1L | Retinoic acid early transcript 1L |
| ENSG00000175097 | NM_000536 | RAG2 | Recombination activating gene 2 |
| ENSG00000080823 | NM_014226 | RAGE | Renal tumor antigen |
| ENSG00000124233 | NM_003007 | RAI2 | Retinoic acid induced 2 |
| ENSG00000131831 | NM_198139.1 NM_021785 |  |  |
| ENSG00000125970 | NM_007367 NM_016732 | RALY | RNA binding protein, autoantigenic (hnRNP-associated with lethal yellow homolog (mouse)) |
| ENSG00000076864 | NM_002885 | RAP1GAP | RAP1 GTPase activating protein |
| ENSG00000111344 | NM_004658 | RASAL1 | RAS protein activator like 1 (GAP1 like) |
| ENSG00000107551 | NM_032023 | RASSF4 | Ras association (RalGDS/AF-6) domain family 4 |
| ENSG00000122257 | NM_006910 NM_018703 | RBBP6 | Retinoblastoma binding protein 6 |

TABLE 6-continued

All Targets of miR-148b

| Transcript ID. | RefSeq Accession No. | Target Name | Gene |
|---|---|---|---|
| ENSG00000179051 | NM_018715 | RCC2 | Regulator of chromosome condensation 2 |
| ENSG00000160957 | NM_004260.2 | RECQL4 | RecQ protein-like 4 |
| | | RG9MTD1 | RNA (guanine-9-) methyltransferase domain containing 1 |
| ENSG00000158315 | NM_017821 | RHBDL2 | Rhomboid, veinlet-like 2 (*Drosophila*) |
| ENSG00000187010 | NM_016124 | RHD | Rh blood group, D antigen |
| | | RHOT2 | Ras homolog gene family, member T2 |
| ENSG00000176406 | NM_014677.3 | RIMS2 | Regulating synaptic membrane exocytosis 2 |
| ENSG00000153561 | NM_022780 | RMND5A | Required for meiotic nuclear division 5 homolog A (*S. cerevisiae*) |
| ENSG00000137075 | NM_022781 NM_194328 NM_194329 NM_194330 NM_194332 | RNF38 | Ring finger protein 38 |
| ENSG00000169855 | NM_002941.2 NM_133631.1 | ROBO1 | Roundabout, axon guidance receptor, homolog 1 (*Drosophila*) |
| ENSG00000161016 | NM_000973 NM_033301 | RPL8 | Ribosomal protein L8 |
| ENSG00000124614 | NM_001014 | RPS10 | Ribosomal protein S10 |
| ENSG00000177606 | NM_002228 | | |
| ENSG00000166133 | NM_152260 | RPUSD2 | RNA pseudouridylate synthase domain containing 2 |
| ENSG00000144580 | NM_005444 | RQCD1 | RCD1 required for cell differentiation1 homolog (*S. pombe*) |
| ENSG00000083750 | NM_006064 NM_016656 | RRAGB | Ras-related GTP binding B |
| | | RSBN1L | Round spermatid basic protein 1-like |
| | | RSHL2 | |
| ENSG00000115310 | NM_007008.2 NM_020532.4 NM_153828 NM_207520.1 NM_207521 | RTN4 | Reticulon 4 |
| ENSG00000133105 | NM_130806 | RXFP2 | Relaxin/insulin-like family peptide receptor 2 |
| ENSG00000188015 | NM_002960 | S100A3 | S100 calcium binding protein A3 |
| | | S100A7A | S100 calcium binding protein A7A |
| ENSG00000151835 | NM_014363 | SACS | Spastic ataxia of Charlevoix-Saguenay (sacsin) |
| ENSG00000203943 | NM_001010971 | SAMD13 | Sterile alpha motif domain containing 13 |
| ENSG00000161526 | NM_013260 | SAP30BP | SAP30 binding protein |
| ENSG00000189001 | NM_198538 | SBSN | Suprabasin |
| | | SCAMP2 | Secretory carrier membrane protein 2 |
| ENSG00000114650 | NM_012235 | SCAP | SREBF chaperone |
| ENSG00000173572 | NM_176810 | | |
| ENSG00000136448 | NM_021079 | SCG2 | Secretogranin II (chromogranin C) |
| ENSG00000171951 | NM_003469 | | |
| ENSG00000079689 | NM_006998 | SCGN | Secretagogin, EF-hand calcium binding protein |
| ENSG00000153253 | NM_006922 | | |
| ENSG00000102098 | NM_006089 | SCML2 | Sex comb on midleg-like 2 (*Drosophila*) |
| ENSG00000134419 | NM_001019 NM_001030009 | | |
| ENSG00000215767 | NM_012313.1 NM_014512.1 NM_014513.2 | SCN9A | Sodium channel, voltage-gated, type IX, alpha subunit |
| ENSG00000080293 | NM_002980 | SCTR | Secretin receptor |
| ENSG00000133116 | NM_004795 | | |
| ENSG00000140612 | NM_014300.2 | SEC11A | SEC11 homolog A (*S. cerevisiae*) |
| ENSG00000188404 | NM_000655.3 | SELL | Selectin L (lymphocyte adhesion molecule 1) |
| ENSG00000174175 | NM_003005 | SELP | Selectin P (granule membrane protein 140 kDa, antigen CD62) |

TABLE 6-continued

All Targets of miR-148b

| Transcript ID. | RefSeq Accession No. | Target Name | Gene |
|---|---|---|---|
| ENSG00000112701 | NM_001100409.1 | SENP6 | SUMO1/sentrin specific peptidase 6 |
| ENSG00000144659 | NM_015571.2 NM_017875 | | |
| | | SERPINE2 | Serpin peptidase inhibitor, clade E (nexin, plasminogen activator inhibitor type 1), member 2 |
| ENSG00000149212 | NM_144665 | SESN3 | Sestrin 3 |
| ENSG00000104897 | NM_007165 | SF3A2 | Splicing factor 3a, subunit 2, 66 kDa |
| ENSG00000116754 | NM_004768 | SFRS11 | Splicing factor, arginine/serine-rich 11 |
| ENSG00000139218 | NM_004719 | SFRS2IP | Splicing factor, arginine/serine-rich 2, interacting protein |
| | | SG494_HUMAN | |
| ENSG00000160410 | NM_138392 | SHKBP1 | SH3KBP1 binding protein 1 |
| ENSG00000112246 | NM_005068 | SIM1 | Single-minded homolog 1 (*Drosophila*) |
| ENSG00000135862 | NM_002293 | | |
| ENSG00000089163 | NM_012240 | SIRT4 | Sirtuin (silent mating type information regulation 2 homolog) 4 (*S. cerevisiae*) |
| ENSG00000164303 | NM_153343 | | |
| ENSG00000077463 | NM_016539 | SIRT6 | Sirtuin (silent mating type information regulation 2 homolog) 6 (*S. cerevisiae*) |
| ENSG00000187531 | NM_016538 | SIRT7 | Sirtuin (silent mating type information regulation 2 homolog) 7 (*S. cerevisiae*) |
| ENSG00000126903 | NM_019848 | SLC10A3 | Solute carrier family 10 (sodium/bile acid cotransporter family), member 3 |
| ENSG00000145283 | NM_197965 | SLC10A6 | Solute carrier family 10 (sodium/bile acid cotransporter family), member 6 |
| ENSG00000139370 | NM_145648 | SLC15A4 | Solute carrier family 15, member 4 |
| ENSG00000102743 | NM_014252 | SLC25A15 | Solute carrier family 25 (mitochondrial carrier; ornithine transporter) member 15 |
| ENSG00000125648 | NM_024103 | SLC25A23 | Solute carrier family 25 (mitochondrial carrier; phosphate carrier), member 23 |
| ENSG00000153046 | NM_004824 NM_170751.1 NM_170752 | SLC26A3 | Solute carrier family 26, member 3 |
| ENSG00000008300 | NM_001040454.1 NM_001407 NM_022911.2 NM_134263.2 NM_134426.2 | SLC26A6 | Solute carrier family 26, member 6 |
| ENSG00000169359 | NM_004733 | SLC33A1 | Solute carrier family 33 (acetyl-CoA transporter), member 1 |
| ENSG00000175782 | NM_018656.2 | SLC35E3 | Solute carrier family 35, member E3 |
| ENSG00000141424 | NM_001099406.1 NM_012319.3 | SLC39A6 | Solute carrier family 39 (zinc transporter), member 6 |
| | | SLC5A3 | |
| ENSG00000170920 | NM_001001958 | SMARCA5 | SWI/SNF related, matrix associated, actin dependent regulator of chromatin, subfamily a, member 5 |
| ENSG00000146830 | NM_022574 | SMC3 | Structural maintenance of chromosomes 3 |
| ENSG00000102172 | NM_004595 | SMS | Spermine synthase |
| | | SNAPAP | |
| ENSG00000205302 | NM_003100 | SNX2 | Sorting nexin 2 |
| | | SNX3 | Sorting nexin 3 |
| ENSG00000115904 | NM_005633 | SOS1 | Son of sevenless homolog 1 (*Drosophila*) |

TABLE 6-continued

All Targets of miR-148b

| Transcript ID. | RefSeq Accession No. | Target Name | Gene |
|---|---|---|---|
| | | SOS2 | Son of sevenless homolog 2 (*Drosophila*) |
| ENSG00000123352 | NM_023071 | SPATS2 | Spermatogenesis associated, serine-rich 2 |
| | | SPESP1 | |
| ENSG00000147059 | NM_019003 | SPIN2A | Spindlin family, member 2A |
| | | SPINT4 | Serine peptidase inhibitor, Kunitz type 4 |
| ENSG00000188766 | NM_001039616.1 NM_001042522.1 | SPRED3 | Sprouty-related, EVH1 domain containing 3 |
| ENSG00000070182 | NM_000347 NM_001024858 | SPTB | Spectrin, beta, erythrocytic (includes spherocytosis, clinical type I) |
| ENSG00000213523 | NM_001035235 | SRA1 | Steroid receptor RNA activator 1 |
| | | SRP9 | Signal recognition particle 9 kDa |
| ENSG00000135250 | NM_182691 NM_182692 | SRPK2 | SFRS protein kinase 2 |
| ENSG00000138385 | NM_003142 | SSB | Sjogren syndrome antigen B (autoantigen La) |
| ENSG00000160075 | NM_014188 | SSU72 | SSU72 RNA polymerase II CTD phosphatase homolog (*S. cerevisiae*) |
| ENSG00000117155 | NM_014021 | SSX2IP | Synovial sarcoma, X breakpoint 2 interacting protein |
| ENSG00000115525 | NM_001042437.1 NM_003896 | ST3GAL5 | ST3 beta-galactoside alpha-2,3-sialyltransferase 5 |
| ENSG00000177511 | NM_015879 | ST8SIA3 | ST8 alpha-N-acetyl-neuraminide alpha-2,8-sialyltransferase 3 |
| ENSG00000101972 | NM_001042749.1 NM_001042750.1 NM_001042751.1 NM_006603 | STAG2 | Stromal antigen 2 |
| ENSG00000066923 | NM_012447 | STAG3 | Stromal antigen 3 |
| | | STAP1_HUMAN | |
| ENSG00000124214 ENSG00000185022 | NM_001037328 NM_004602 NM_017452 NM_017453 NM_017454 NM_012323 NM_152878 | STAU1 | Staufen, RNA binding protein, homolog 1 (*Drosophila*) |
| ENSG00000117632 | NM_005563 NM_203399 NM_203401 | STMN1 | Stathmin 1/oncoprotein 18 |
| | | STRA13 | Stimulated by retinoic acid 13 homolog (mouse) |
| ENSG00000137868 | NM_022369 | STRA6 | Stimulated by retinoic acid gene 6 homolog (mouse) |
| | | STX4 | Syntaxin 4 |
| ENSG00000076944 | NM_006949 | STXBP2 | Syntaxin binding protein 2 |
| ENSG00000164506 | NM_139244 | STXBP5 | Syntaxin binding protein 5 (tomosyn) |
| | | SUCLG1 | Succinate-CoA ligase, GDP-forming, alpha subunit |
| ENSG00000088002 | NM_004605 NM_177973 | SULT2B1 | Sulfotransferase family, cytosolic, 2B, member 1 |
| ENSG00000106868 | NM_022486 | SUSD1 | Sushi domain containing 1 |
| ENSG00000179751 | NM_001080468.1 | SYCN | Syncollin |
| | | SYNC1 | Syncoilin, intermediate filament 1 |
| ENSG00000159082 | NM_003895 NM_203446 | SYNJ1 | Synaptojanin 1 |
| ENSG00000163630 | NM_144642.3 | SYNPR | Synaptoporin |
| ENSG00000006432 | NM_033141 | SYT5 | Synaptotagmin V |
| ENSG00000129990 | NM_003180 | | |
| ENSG00000134207 | NM_205848 | SYT6 | Synaptotagmin VI |
| ENSG00000176358 | NM_001077503.1 NM_001077504.1 NM_001077505.1 NM_001077506.1 NM_170685.2 | TAC4 | Tachykinin 4 (hemokinin) |

TABLE 6-continued

All Targets of miR-148b

| Transcript ID. | RefSeq Accession No. | Target Name | Gene |
|---|---|---|---|
| ENSG00000141384 | NM_005640.1 | TAF4B | TAF4b RNA polymerase II, TATA box binding protein (TBP)-associated factor, 105 kDa |
| ENSG00000206233 ENSG00000206297 | | TAP1 | Transporter 1, ATP-binding cassette, sub-family B (MDR/TAP) |
| ENSG00000179002 | NM_152232 | TAS1R2 | Taste receptor, type 1, member 2 |
| ENSG00000121318 | NM_023921 | TAS2R10 | Taste receptor, type 2, member 10 |
| ENSG00000106052 | NM_001079864.1 NM_006024 | TAX1BP1 | Tax1 (human T-cell leukemia virus type I) binding protein 1 |
| ENSG00000131374 | NM_014744 | TBC1D5 | TBC1 domain family, member 5 |
| ENSG00000132561 | NM_002380.3 NM_030583.2 | TBP | TATA box binding protein |
| ENSG00000136270 | NM_004749 NM_030900 NM_199122 | TBRG4 | Transforming growth factor beta regulator 4 |
| ENSG00000059377 | NM_001061 NM_030984 | TBXAS1 | Thromboxane A synthase 1 (platelet, cytochrome P450, family 5, subfamily A) |
| ENSG00000133142 | NM_001006935.1 NM_001006936.1 NM_001006937.1 NM_024863 | TCEAL4 | Transcription elongation factor A (SII)-like 4 |
| ENSG00000148737 | NM_030756 | TCF7L2 | Transcription factor 7-like 2 (T-cell specific, HMG-box) |
| ENSG00000120156 | NM_000459 | TEK | TEK tyrosine kinase, endothelial (venous malformations, multiple cutaneous and mucosal) |
| ENSG00000132604 | NM_005652 | TERF2 | Telomeric repeat binding factor 2 |
| ENSG00000100109 | NM_001008697 NM_012143 | TFIP11 | Tuftelin interacting protein 11 |
| ENSG00000092295 | NM_000359 | TGM1 | Transglutaminase 1 (K polypeptide epidermal type I, protein-glutamine-gamma-glutamyltransferase) |
| ENSG00000180176 | NM_000360 NM_199292 NM_199293 | TH | Tyrosine hydroxylase |
| ENSG00000143198 | NM_004528 | THOP1 | Thimet oligopeptidase 1 |
| ENSG00000172009 | NM_003249 | | |
| ENSG00000179886 | NM_032862 | TIGD5 | Tigger transposable element derived 5 |
| ENSG00000071242 | NM_001006932 | TIMM23 | Translocase of inner mitochondrial membrane 23 homolog (yeast) |
| ENSG00000138297 | NM_021135 NM_006327 | | |
| | | TLE4 | Transducin-like enhancer of split 4 (E(sp1) homolog, *Drosophila*) |
| ENSG00000162604 | NM_032027.2 | TM2D1 | TM2 domain containing 1 |
| ENSG00000136404 | NM_023003 | TM6SF1 | Transmembrane 6 superfamily member 1 |
| | | TMEM112B | |
| | | TMEM128 | Transmembrane protein 128 |
| ENSG00000161558 | NM_018273 | TMEM143 | Transmembrane protein 143 |
| ENSG00000168890 | NM_001031738 NM_153342 | TMEM150 | Transmembrane protein 150 |
| ENSG00000166822 | NM_145254 | TMEM170 | Transmembrane protein 170 |
| | | TMEM177 | Transmembrane protein 177 |
| ENSG00000177854 | NM_003492 | TMEM187 | Transmembrane protein 187 |
| | | TMEM49 | Transmembrane protein 49 |
| ENSG00000118600 | NM_014254 | TMEM5 | Transmembrane protein 5 |
| ENSG00000142188 | NM_006134 | TMEM50B | Transmembrane protein 50B |
| ENSG00000121900 | NM_033504 | TMEM54 | Transmembrane protein 54 |
| ENSG00000116857 | NM_016456 | TMEM9 | Transmembrane protein 9 |
| ENSG00000175348 | NM_020644 | TMEM9B | TMEM9 domain family, member B |
| ENSG00000178297 | NM_182973 | TMPRSS9 | Transmembrane protease, serine 9 |
| ENSG00000034510 | NM_021103 | TMSB10 | Thymosin, beta 10 |
| | | TMSL1 | Thymosin-like 1 |

TABLE 6-continued

All Targets of miR-148b

| Transcript ID. | RefSeq Accession No. | Target Name | Gene |
|---|---|---|---|
| ENSG00000026036 | NM_003823<br>NM_016434<br>NM_032945<br>NM_032957 | TNFRSF6B | Tumor necrosis factor receptor superfamily, member 6b, decoy |
| ENSG00000131165 | NM_001083314.1<br>NM_002768.2 | TNFSF14 | Tumor necrosis factor (ligand) superfamily, member 14 |
| ENSG00000168884 | NM_024309 | TNIP2<br>TNPO2 | TNFAIP3 interacting protein 2<br>Transportin 2 (importin 3, karyopherin beta 2b) |
| ENSG00000090905 | NM_014494 | TNRC6A | Trinucleotide repeat containing 6A |
| ENSG00000079308 | NM_022648 | TNS1 | Tensin 1 |
| ENSG00000196655 | NM_016146 | TRAPPC4 | Trafficking protein particle complex 4 |
|  |  | TRAV24<br>TRBV10-1<br>TRBV4-3 |  |
| ENSG00000213689 | NM_016381.3<br>NM_033627<br>NM_033628<br>NM_033629 | TREX1 | Three prime repair exonuclease 1 |
| ENSG00000137394<br>ENSG00000204613<br>ENSG00000206424 | NM_006778<br>NM_052828 | TRIM10 | Tripartite motif-containing 10 |
| ENSG00000134253 | NM_025188 | TRIM45 | Tripartite motif-containing 45 |
| ENSG00000163462 | NM_025058 | TRIM46 | Tripartite motif-containing 46 |
| ENSG00000070985 | NM_014555 | TRPM5 | Transient receptor potential cation channel, subfamily M, member 5 |
| ENSG00000104447 | NW_014112 | TRPS1 | Trichorhinophalangeal syndrome I |
| ENSG00000111199 | NM_021625<br>NM_147204 | TRPV4 | Transient receptor potential cation channel, subfamily V, member 4 |
| ENSG00000103197 | NM_000548<br>NM_021055 | TSC2 | Tuberous sclerosis 2 |
| ENSG00000074319 | NM_006292 | TSG101 | Tumor susceptibility gene 101 |
| ENSG00000171045 | NM_145003 | TSNARE1 | T-SNARE domain containing 1 |
| ENSG00000064201 | NM_005705.4<br>NM_139022 | TSPAN32 | Tetraspanin 32 |
| ENSG00000163728 | NM_001042601.1<br>NM_133462 | TTC14 | Tetratricopeptide repeat domain 14 |
| ENSG00000176014 | NM_032525 | TUBB6 | Tubulin, beta 6 |
| ENSG00000074935 | NM_016262 | TUBE1 | Tubulin, epsilon 1 |
| ENSG00000104723 | NM_006765<br>NM_178234 | TUSC3 | Tumor suppressor candidate 3 |
|  |  | U464_HUMAN |  |
| ENSG00000125976 | NM_006047 | UBAP2L | Ubiquitin associated protein 2-like |
| ENSG00000143569 | NM_152838<br>NM_014847 |  |  |
| ENSG00000170035 | NM_006357<br>NM_182678 | UBE2E4P | Ubiquitin-conjugating enzyme E2E 4 pseudogene |
| ENSG00000175564 | NM_003356<br>NM_022803.1 | UCP3 | Uncoupling protein 3 (mitochondrial, proton carrier) |
| ENSG00000102595 | NM_020121 | UGCGL2 | UDP-glucose ceramide glucosyltransferase-like 2 |
|  |  | UGT1A1 |  |
| ENSG00000135226 | NM_053039 | UGT2B28 | UDP glucuronosyltransferase 2 family, polypeptide B28 |
| ENSG00000147854 | NM_152896 | UHRF2 | Ubiquitin-like, containing PHD and RING finger domains, 2 |
| ENSG00000111981 | NM_025218 | ULBP1 | UL16 binding protein 1 |
| ENSG00000131015 | NM_025217 | ULBP2 | UL16 binding protein 2 |
| ENSG00000182168 | NM_003728 | UNC5C | Unc-5 homolog C (C. elegans) |
| ENSG00000164405 | NM_014402 | UQCRQ | Ubiquinol-cytochrome c reductase, complex III subunit VII, 9.5 kDa |
| ENSG00000159650 | NM_144639 | UROC1 | Urocanase domain containing 1 |
| ENSG00000158773 | NM_007122<br>NM_207005.1 | USF1 | Upstream transcription factor 1 |
| ENSG00000135093 | NM_032663 | USP30 | Ubiquitin specific peptidase 30 |

TABLE 6-continued

All Targets of miR-148b

| Transcript ID. | RefSeq Accession No. | Target Name | Gene |
|---|---|---|---|
| ENSG00000170185 | NM_032557 | USP38 | Ubiquitin specific peptidase 38 |
| ENSG00000168883 | NM_006590 | USP39 | Ubiquitin specific peptidase 39 |
| ENSG00000170242 | NM_017944.3 | USP47 | Ubiquitin specific peptidase 47 |
|  |  | USP7 | Ubiquitin specific peptidase 7 (herpes virus-associated) |
| ENSG00000198382 | NM_003369 | UVRAG | UV radiation resistance associated gene |
| ENSG00000103043 | NM_018052 | VAC14 | Vac14 homolog (S. cerevisiae) |
| ENSG00000111786 | NM_003769 | VAMP5 | Vesicle-associated membrane protein 5 (myobrevin) |
| ENSG00000168899 | NM_006634 |  |  |
| ENSG00000162692 | NM_001078 NM_080682 | VCAM1 | Vascular cell adhesion molecule 1 |
| ENSG00000147852 | NM_001018056 NM_003383 | VLDLR | Very low density lipoprotein receptor |
| ENSG00000197969 | NM_001018037.1 NM_001018038.1 NM_015186 NM_033305 | VPS13A | Vacuolar protein sorting 13 homolog A (S. cerevisiae) |
| ENSG00000104142 | NM_020857 | VPS18 | Vacuolar protein sorting 18 homolog (S. cerevisiae) |
| ENSG00000115561 | NM_001005753.1 NM_016079 | VPS24 | Vacuolar protein sorting 24 homolog (S. cerevisiae) |
|  |  | VPS37A | Vacuolar protein sorting 37 homolog A (S. cerevisiae) |
| ENSG00000073111 | NM_004526 | VPS72 | Vacuolar protein sorting 72 homolog (S. cerevisiae) |
| ENSG00000163159 | NM_005997 |  |  |
| ENSG00000100568 | NM_006370 | VTI1B | Vesicle transport through interaction with t-SNAREs homolog 1B (yeast) |
| ENSG00000167992 | NM_152718 | VWCE | Von Willebrand factor C and EGF domains |
| ENSG00000139668 | NM_052950 | WDFY2 | WD repeat and FYVE domain containing 2 |
| ENSG00000128815 |  | WDFY4 | WDFY family member 4 |
| ENSG00000157796 | NM_025132.3 | WDR19 | WD repeat domain 19 |
| ENSG00000163811 |  | WDR43 | WD repeat domain 43 |
| ENSG00000103091 | NM_030581 | WDR59 | WD repeat domain 59 |
|  |  | WDR85 | WD repeat domain 85 |
| ENSG00000166483 | NM_003390 | WEE1 | WEE1 homolog (S. pombe) |
| ENSG00000120662 | NM_004294 | WHSC2 | Wolf-Hirschhorn syndrome candidate 2 |
| ENSG00000185049 | NM_005663 |  |  |
| ENSG00000135925 | NM_025216 | WNT10A | Wingless-type MMTV integration site family, member 10A |
| ENSG00000169884 | NM_003394 | WNT10B | Wingless-type MMTV integration site family, member 10B |
| ENSG00000154767 | NM_004628.3 | XPC | Xeroderma pigmentosum, complementation group C |
|  |  | XR_016777.1 XR_019191.1 |  |
| ENSG00000015532 | NM_022167 | XYLT2 | Xylosyltransferase II |
|  |  | YPEL3 | Yippee-like 3 (Drosophila) |
| ENSG00000182223 | NM_175619 | ZAR1 | Zygote arrest 1 |
| ENSG00000160062 | NM_001040441 | ZBTB8 | Zinc finger and BTB domain containing 8 |
| ENSG00000215897 |  |  |  |
| ENSG00000100722 | NM_024824 NM_207660 NM_207661 NM_207662 | ZC3H14 | Zinc finger CCCH-type containing 14 |
| ENSG00000186908 | NM_015336.2 | ZDHHC17 | Zinc finger, DHHC-type containing 17 |
| ENSG00000180776 | NM_153251.2 | ZDHHC20 | Zinc finger, DHHC-type containing 20 |
|  |  | ZDHHC6 | Zinc finger, DHHC-type containing 6 |
| ENSG00000166140 | NM_001077268.1 | ZFYVE19 | Zinc finger, FYVE domain containing 19 |
| ENSG00000157077 | NM_004799 NM_007323 NM_007324 | ZFYVE9 | Zinc finger, FYVE domain containing 9 |

TABLE 6-continued

All Targets of miR-148b

| Transcript ID. | RefSeq Accession No. | Target Name | Gene |
|---|---|---|---|
| ENSG00000156925 | NM_003413 | ZIC3 | Zic family member 3 heterotaxy 1 (odd-paired homolog, *Drosophila*) |
| ENSG00000186272 | NM_006959.2 | ZNF17 | Zinc finger protein 17 |
| ENSG00000105497 | NM_007147 | ZNF175 | Zinc finger protein 175 |
| ENSG00000188629 | NM_003451 | ZNF177 | Zinc finger protein 177 |
| ENSG00000178386 | NM_013361 | ZNF223 | Zinc finger protein 223 |
| ENSG00000171606 | NM_016324.2 NM_016325.2 NM_133502.1 | ZNF274 | Zinc finger protein 274 |
| ENSG00000181315 | NM_024639 | ZNF322A | Zinc finger protein 322A |
| ENSG00000188801 | NM_199005 | ZNF322B | Zinc finger protein 322B |
| ENSG00000175213 | NM_024741 | ZNF408 | Zinc finger protein 408 |
| ENSG00000112200 | NM_001031623.2 NM_015555 | ZNF451 ZNF508 | Zinc finger protein 451 |
| ENSG00000144331 | NM_152520 | ZNF533 | Zinc finger protein 533 |
| ENSG00000188171 | NM_001076675.1 NM_145297 | ZNF626 | Zihc finger protein 626 |
| ENSG00000198551 | NM_145295.2 | ZNF627 | Zinc finger protein 627 |
| ENSG00000175809 | NM_152577 | ZNF645 | Zinc finger protein 645 |
| ENSG00000161914 | NM_138783 | ZNF653 | Zinc finger protein 653 |
| ENSG00000156853 | NM_138447 | ZNF689 | Zinc finger protein 689 |
| ENSG00000167766 | NM_018300 | ZNF83 | Zinc finger protein 83 |
| ENSG00000106400 | NM_006349 | ZNHIT1 | Zinc finger, HIT type 1 |

TABLE 7 miR-148b targets identified by miRanda and L2L

| Target Gene | Accession No: | Gene Name |
|---|---|---|
| ARSE | NM_000047.2 GI:157266308 | arylsulfatase E (chondrodysplasia punctata 1) |
| COL2A1 | NM_001844.4 GI:111118975 | collagen, type II, alpha 1 (primary osteoarthritis, spondyloepiphyseal dysplasia, congenital) |
| COL2A1 | NM_033150.2 GI:111118973 | collagen, type II, alpha 1 (primary osteoarthritis, spondyloepiphyseal dysplasia, congenital) |
| FBN1 | NM_000138.3 GI:93589095 | fibrillin 1 |
| GHRHR | NM_000823.2 GI:58530850 | growth hormone releasing hormone receptor |
| GHRHR | NM_001009824.1 GI:58530852 | growth hormone releasing hormone receptor |
| HOXA2 | NM_006735.3 GI:37596298 | homeobox A2 |
| HOXA5 | NM_019102.2 GI:24497516 | homeobox A5 |
| LECT1 | NM_007015.2 GI:59806341 | leukocyte cell derived chemotaxin 1 |
| LECT1 | NM_001011705.1 GI:59806342 | leukocyte cell derived chemotaxin 1 |
| NOG | NM_005450.2 GI:38788425 | Noggin |
| OSTF1 | NM_012383.3 GI:38257156 | osteoclast stimulating factor 1 |
| PAPSS2 | NM_001015880.1 GI:62912491 | 3'-phosphoadenosine 5'-phosphosulfate synthase 2 |
| PAPSS2 | NM_004670.3 GI:62912490 | 3'-phosphoadenosine 5'-phosphosulfate synthase 2 |
| TFIP11 | NM_012143.2 GI:56788354 | tuftelin interacting protein 11 |
| TFIP11 | NM_001008697.1 GI:56788355 | tuftelin interacting protein 11 |
| TRPS1 | NM_014112.2 GI:90652850 | trichorhinophalangeal syndrome I |

What is claimed is:

1. A method of promoting mesenchymal stem cell (MSC) differentiation toward an osteogenic cell fate, the method comprising introducing into a MSC an effective amount of a composition comprising at least one differentiation promoting agent that is a mimic of miR-148b and an effective amount of an inhibitor of miR-489, wherein the inhibitor of miR-489 comprises a sequence that is the same as SEQ ID NO: 2, and the mimic of miR-148b comprises an antisense strand that comprises the sequence of SEQ ID NO: 6.

* * * * *